United States Patent
Alroy et al.

(10) Patent No.: US 7,659,277 B2
(45) Date of Patent: Feb. 9, 2010

(54) UBIQUITIN LIGASE INHIBITORS AND METHODS RELATED THERETO

(75) Inventors: Iris Alroy, Ness-Ziona (IL); Shmuel Tuvia, Netanya (IL); Yuval Reiss, Kiriat-Ono (IL); Ofra Levi-Hacham, Petah Tiqwa (IL)

(73) Assignee: Proteologies, Ltd., Rehovot (IL)

( * ) Notice: Subject to any disclaimer, the term of this patent is extended or adjusted under 35 U.S.C. 154(b) by 0 days.

(21) Appl. No.: 11/330,500

(22) Filed: Jan. 11, 2006

(65) Prior Publication Data

US 2007/0015768 A1    Jan. 18, 2007

Related U.S. Application Data

(63) Continuation of application No. PCT/US2004/021900, filed on Jul. 9, 2004, and a continuation-in-part of application No. PCT/US03/35712, filed on Nov. 10, 2003.

(60) Provisional application No. 60/486,730, filed on Jul. 11, 2003, provisional application No. 60/489,795, filed on Jul. 24, 2003, provisional application No. 60/549,896, filed on Mar. 2, 2004.

(51) Int. Cl.
*A01N 43/60* (2006.01)
*A01N 43/54* (2006.01)

(52) U.S. Cl. .................. 514/255.03; 514/270

(58) Field of Classification Search ............ 514/255.03, 514/270, 376, 617, 425
See application file for complete search history.

(56) References Cited

U.S. PATENT DOCUMENTS

| 3,153,014 | A | * | 10/1964 | Fletcher et al. ............. 525/282 |
| 7,250,250 | B2 | | 7/2007 | Alroy et al. |
| 7,268,227 | B2 | | 9/2007 | Alroy et al. |
| 2004/0009613 | A1 | | 1/2004 | Zhou et al. |
| 2006/0035213 | A1 | | 2/2006 | Alroy et al. |
| 2008/0187538 | A1 | | 8/2008 | Alroy et al. |

FOREIGN PATENT DOCUMENTS

| CN | 1288667 | * | 3/2001 |
| EP | 1 389 461 | A | | 2/2004 |
| GB | 2 376 943 | A | | 12/2002 |
| JP | 62-53963 | | * | 3/1987 |
| WO | WO-00/10573 | A1 | | 3/2000 |
| WO | WO-01/77091 | A2 | | 10/2001 |

(Continued)

OTHER PUBLICATIONS

Figueroa, C. et al., "Akt2 Negatively Regulates Assembly of the POSH-MLK-JNK Signaling Complex", The J. Bio. Chemistry, vol. 278(48), pp. 47922-47927 (2003).

(Continued)

*Primary Examiner*—Maryam Monshipouri
(74) *Attorney, Agent, or Firm*—Ropes & Gray LLP

(57) ABSTRACT

The application discloses compounds that inhibit ubiquitin ligase activity. The application further discloses antiviral compounds, anticancer compounds, and compounds useful for the treatment of neurological disorders.

2 Claims, 24 Drawing Sheets

Human POSH Amino Acid Sequence (SEQ ID NO:2)

```
MDESALLDLLECPVCLERLDASAKVLPCQHTFCKRCLLGIVGSRNELRCPECRTLVGSGVEELPSNILLV
RLLDGIKQRPWKPGPGGGSGTNCTNALRSQSSTVANCSSKDLQSSQGGQQPRVQSWSPPVRGIPQLPCAK
ALYNYEGKEPGDLKFSKGDIIILRRQVDENWYHGEVNGIHGFFPTNFVQIIKPLPQPPPQCKALYDFEVK
DKEADKDCLPFAKDDVLTVIRRVDENWAEGMLADKIGIFPISYVEFNSAAKQLIEWDKPPVPGVDAGECS
SAAAQSSTAPKHSDTKKNTKKRHSFTSLTMANKSSQASQNRHSMEISPPVLISSSNPTAAARISELSGLS
CSAPSQVHISTTGLIVTPPPSSPVTTGPSFTFPSDVPYQAALGTLNPPLPPPPLLAATVLASTPPGATAA
AAAAGMGPRPMAGSTDQIAHLRPQTRPSVYVAIYPYTPRKEDELELRKGEMFLVFERCQDGWFKGTSMHT
SKIGVFPGNYVAPVTRAVTNASQAKVPMSTAGQTSRGVTMVSPSTAGGPAQKLQGNGVAGSPSVVPAAVV
SAAHIQTSPQAKVLLHMTGQMTVNQARNAVRTVAAHNQERPTAAVTPIQVQNAAGLSPASVGLSHHSLAS
PQPAPLMPGSATHTAAISISRASAPLACAAAAPLTSPSITSASLEAEPSGRIVTVLPGLPTSPDSASSAC
GNSSATKPDKDSKKEKKGLLKLLSGASTKRKPRVSPPASPTLEVELGSAELPLQGAVGPELPPGGGHGRA
GSCPVDGDGPVTTAVAGAALAQDAFHRKASSLDSAVPIAPPPRQACSSLGPVLNESRPVVCERHRVVVSY
PPQSEAELELKEGDIVFVHKKREDGWFKGTLQRNGKTGLFPGSFVENI
```

FOREIGN PATENT DOCUMENTS

| | | |
|---|---|---|
| WO | WO-01/79209 A2 | 10/2001 |
| WO | WO-01/93841 A2 | 12/2001 |
| WO | WO0250082 * | 6/2002 |
| WO | WO-02/062337 A1 | 8/2002 |
| WO | WO-03/055867 A1 | 7/2003 |
| WO | WO-03/074497 A1 | 9/2003 |
| WO | WO-03/103686 A1 | 12/2003 |
| WO | WO-2004/007491 A1 | 1/2004 |
| WO | WO-2004/078130 A2 | 9/2004 |
| WO | WO-2004/089302 A2 | 10/2004 |
| WO | WO-2004/098492 A2 | 11/2004 |

OTHER PUBLICATIONS

Ulrich, Protein-Protein Interactions within an E2-Ring Finger Complex, J. Biol. Chem. 278(9):7051-7058 (2003).

Xu, Z., et al., "POSH acts as a scaffold for a multiprotein complex and mediates JNK activation in apoptosis", J. EMBO Journal, vol. 22(2), pp. 252-261 (2003).

International Search Report for PCT/US2004/021900 dated Feb. 4, 2005.

* cited by examiner

Figure 1: Human POSH Coding Sequence (SEQ ID NO:1)

```
ATGGATGAATCAGCCTTGTTGGATCTTTTGGAGTGTCCGGTGTGTCTAGAGCGCCTTGATGCTTCTGCGA
AGGTCTTGCCTTGCCAGCATACGTTTTGCAAGCGATGTTTGCTGGGGATCGTAGGTTCTCGAAATGAACT
CAGATGTCCCGAGTGCAGGACTCTTGTTGGCTCGGGTGTCGAGGAGCTTCCCAGTAACATCTTGCTGGTC
AGACTTCTGGATGGCATCAAACAGAGGCCTTGGAAACCTGGTCCTGGTGGGGGAAGTGGGACCAACTGCA
CAAATGCATTAAGGTCTCAGAGCAGCACTGTGGCTAATTGTAGCTCAAAAGATCTGCAGAGCTCCCAGGG
CGGACAGCAGCCTCGGGTGCAATCCTGGAGCCCCCAGTGAGGGTATACCTCAGTTACCATGTGCCAAA
GCGTTATACAACTATGAAGGAAAAGAGCCTGGAGACCTTAAATTCAGCAAAGGCGACATCATCATTTTGC
GAAGACAAGTGGATGAAAATTGGTACCATGGGGAAGTCAATGGAATCCATGGCTTTTTCCCCACCAACTT
TGTGCAGATTATTAAACCGTTACCTCAGCCCCCACCTCAGTGCAAAGCACTTTATGACTTTGAAGTGAAA
GACAAGGAAGCAGACAAAGATTGCCTTCCATTTGCAAAGGATGATGTTCTGACTGTGATCCGAAGAGTGG
ATGAAAACTGGGCTGAAGGAATGCTGGCAGACAAAATAGGAATATTTCCAATTTCATATGTTGAGTTTAA
CTCGGCTGCTAAGCAGCTGATAGAATGGGATAAGCCTCCTGTGCCAGGAGTTGATGCTGGAGAATGTTCC
TCGGCAGCAGCCCAGAGCAGCACTGCCCCAAAGCACTCCGACACCAAGAAGAACACCAAAAAGCGGCACT
CCTTCACTTCCCTCACTATGGCCAACAAGTCCTCCCAGGCATCCCAGAACCGCCACTCCATGGAGATCAG
CCCCCCTGTCCTCATCAGCTCCAGCAACCCCACTGCTGCTGCACGGATCAGCGAGCTGTCTGGGCTCTCC
TGCAGTGCCCCTTCTCAGGTTCATATAAGTACCACCGGGTTAATTGTGACCCCGCCCCAAGCAGCCCAG
TGACAACTGGCCCCTCGTTTACTTTCCCATCAGATGTTCCCTACCAAGCTGCCCTTGGAACTTTGAATCC
TCCTCTTCCACCACCCCCTCTCCTGGCTGCCACTGTCCTTGCCTCCACACCACCAGGCGCCACCGCCGCC
GCTGCTGCTGGAATGGGACCGAGGCCCATGGCAGGATCCACTGACCAGATTGCACATTTACGGCCGC
AGACTCGCCCCAGTGTGTATGTTGCTATATATCCATACACTCCTCGGAAAGAGGATGAACTAGAGCTGAG
AAAAGGGGAGATGTTTTAGTGTTTGAGCGCTGCCAGGATGGCTGGTTCAAAGGGACATCCATGCATACC
AGCAAGATAGGGGTTTTCCCTGGCAATTATGTGGCACCAGTCACAAGGGCGGTGACAAATGCTTCCCAAG
CTAAAGTCCCTATGTCTACAGCTGGCCAGACAAGTCGGGGAGTGACCATGGTCAGTCCTTCCACGGCAGG
AGGGCCTGCCCAGAAGCTCCAGGGAAATGGCGTGGCTGGGAGTCCCAGTGTTGTCCCCGCAGCTGTGGTA
TCAGCAGCTCACATCCAGACAAGTCCTCAGGCTAAGGTCTTGTTGCACATGACGGGGCAAATGACAGTCA
ACCAGGCCCGCAATGCTGTGAGGACAGTTGCAGCGCACAACCAGGAACGCCCCACGGCAGCAGTGACACC
CATCCAGGTACAGAATGCCGCCGGCCTCAGCCCTGCATCTGTGGGCCTGTCCCATCACTCGCTGGCCTCC
CCACAACCTGCGCCTCTGATGCCAGGCTCAGCCACGCACACTGCTGCCATCAGTATCAGTCGAGCCAGTG
CCCCTCTGGCCTGTGCAGCAGCTGCTCCACTGACTTCCCCAAGCATCACCAGTGCTTCTCTGGAGGCTGA
GCCCAGTGGCCGGATAGTGACCGTTCTCCCTGGACTCCCCACATCTCCTGACAGTGCTTCATCAGCTTGT
GGGAACAGTTCAGCAACCAAACCAGACAAGGATAGCAAAAAAGAAAAAAAGGGTTTGTTGAAGTTGCTTT
CTGGCGCCTCCACTAAACGGAAGCCCCGCGTGTCTCCTCCAGCATCGCCCACCCTAGAAGTGGAGCTGGG
CAGTGCAGAGCTTCCTCTCCAGGGAGCGGTGGGGCCCGAACTGCCACCAGGAGGTGGCCATGGCAGGGCA
GGCTCCTGCCCTGTGGACGGGGACGGACCGGTCACGACTGCAGTGGCAGGAGCAGCCCTGGCCCAGGATG
CTTTTCATAGGAAGGCAAGTTCCCTGGACTCCGCAGTTCCCATCGCTCCACCTCCTCGCCAGGCCTGTTC
CTCCCTGGGTCCTGTCTTGAATGAGTCTAGACCTGTCGTTTGTGAAAGGCACAGGGTGGTGGTTTCCTAT
CCTCCTCAGAGTGAGGCAGAACTTGAACTTAAAGAAGGAGATATTGTGTTTGTTCATAAAAAACGAGAGG
ATGGCTGGTTCAAAGGCACATTACAACGTAATGGGAAAACTGGCCTTTTCCCAGGAAGCTTTGTGGAAAA
CATATGA
```

Figure 2: Human POSH Amino Acid Sequence (SEQ ID NO:2)

```
MDESALLDLLECPVCLERLDASAKVLPCQHTFCKRCLLGIVGSRNELRCPECRTLVGSGVEELPSNILLV
RLLDGIKQRPWKPGPGGGSGTNCTNALRSQSSTVANCSSKDLQSSQGGQQPRVQSWSPPVRGIPQLPCAK
ALYNYEGKEPGDLKFSKGDIIILRRQVDENWYHGEVNGIHGFFPTNFVQIIKPLPQPPPQCKALYDFEVK
DKEADKDCLPFAKDDVLTVIRRVDENWAEGMLADKIGIFPISYVEFNSAAKQLIEWDKPPVPGVDAGECS
SAAAQSSTAPKHSDTKKNTKKRHSFTSLTMANKSSQASQNRHSMEISPPVLISSSNPTAAARISELSGLS
CSAPSQVHISTTGLIVTPPPSSPVTTGPSFTFPSDVPYQAALGTLNPPLPPPPLLAATVLASTPPGATAA
AAAAGMGPRPMAGSTDQIAHLRPQTRPSVYVAIYPYTPRKEDELELRKGEMFLVFERCQDGWFKGTSMHT
SKIGVFPGNYVAPVTRAVTNASQAKVPMSTAGQTSRGVTMVSPSTAGGPAQKLQGNGVAGSPSVVPAAVV
SAAHIQTSPQAKVLLHMTGQMTVNQARNAVRTVAAHNQERPTAAVTPIQVQNAAGLSPASVGLSHHSLAS
PQPAPLMPGSATHTAAISISRASAPLACAAAAPLTSPSITSASLEAEPSGRIVTVLPGLPTSPDSASSAC
GNSSATKPDKDSKKEKKGLLKLLSGASTKRKPRVSPPASPTLEVELGSAELPLQGAVGPELPPGGGHGRA
GSCPVDGDGPVTTAVAGAALAQDAFHRKASSLDSAVPIAPPPRQACSSLGPVLNESRPVVCERHRVVVSY
PPQSEAELELKEGDIVFVHKKREDGWFKGTLQRNGKTGLFPGSFVENI
```

Figure 3: Human POSH cDNA Sequence (SEQ ID NO:3)

```
CTGAGAGACACTGCGAGCGGCGAGCGCGGTGGGGCCGCATCTGCATCAGCCGCCGCAGCCGCTGCGGGGC
CGCGAACAAAGAGGAGGAGCCGAGGCGCGAGAGCAAAGTCTGAAATGGATGTTACATGAGTCATTTTAAG
GGATGCACACAACTATGAACATTTCTGAAGATTTTTTCTCAGTAAAGTAGATAAAGATGGATGAATCAGC
CTTGTTGGATCTTTTGGAGTGTCCGGTGTGTCTAGAGCGCCTTGATGCTTCTGCGAAGGTCTTGCCTTGC
CAGCATACGTTTTGCAAGCGATGTTTGCTGGGGATCGTAGGTTCTCGAAATGAACTCAGATGTCCCGAGT
GCAGGACTCTTGTTGGCTCGGGTGTCGAGGAGCTTCCCAGTAACATCTTGCTGGTCAGACTTCTGATGG
CATCAAACAGAGGCCTTGGAAACCTGGTCCTGGTGGGGGAAGTGGGACCAACTGCACAAATGCATTAAGG
TCTCAGAGCAGCACTGTGGCTAATTGTAGCTCAAAAGATCTGCAGAGCTCCCAGGGCGGACAGCAGCCTC
GGGTGCAATCCTGGAGCCCCCCAGTGAGGGGTATACCTCAGTTACCATGTGCCAAAGCGTTATACAACTA
TGAAGGAAAAGAGCCTGGAGACCTTAAATTCAGCAAAGGCGACATCATCATTTTGCGAAGACAAGTGGAT
GAAAATTGGTACCATGGGGAAGTCAATGGAATCCATGGCTTTTTCCCCACCAACTTTGTGCAGATTATTA
AACCGTTACCTCAGCCCCCACCTCAGTGCAAAGCACTTTATGACTTTGAAGTGAAAGACAAGGAAGCAGA
CAAAGATTGCCTTCCATTTGCAAAGGATGATGTTCTGACTGTGATCCGAAGAGTGGATGAAAACTGGGCT
GAAGGAATGCTGGCAGACAAAATAGGAATATTTCCAATTTCATATGTTGAGTTTAACTCGGCTGCTAAGC
AGCTGATAGAATGGGATAAGCCTCCTGTGCCAGGAGTTGATGCTGGAGAATGTTCCTCGGCAGCAGCCCA
GAGCAGCACTGCCCAAAGCACTCCGACACCAAGAAGAACACCAAAAAGCGGCACTCCTTCACTTCCCTC
ACTATGGCCAACAAGTCCTCCCAGGCATCCCAGAACCGCCACTCCATGGAGATCAGCCCCCCTGTCCTCA
TCAGCTCCAGCAACCCCACTGCTGCTGCACGGATCAGCGAGCTGTCTGGGCTCTCCTGCAGTGCCCCTTC
TCAGGTTCATATAAGTACCACCGGGTTAATTGTGACCCCGCCCCAAGCAGCCCAGTGACAACTGGCCCC
TCGTTTACTTTCCCATCAGATGTTCCCTACCAAGCTGCCCTTGGAACTTTGAATCCTCCTCTTCCACCAC
CCCCTCTCCTGGCTGCCACTGTCCTTGCCTCCACACCACCAGGCGCCACCGCCGCCGCTGCTGCTGCTGG
AATGGGACCGAGGCCCATGGCAGGATCCACTGACCAGATTGCACATTTACGGCCGCAGACTCGCCCCAGT
GTGTATGTTGCTATATATCCATACACTCCTCGGAAAGAGGATGAACTAGAGCTGAGAAAAGGGGAGATGT
TTTTAGTGTTTGAGCGCTGCCAGGATGGCTGGTTCAAAGGGACATCCATGCATACCAGCAAGATAGGGGT
TTTCCCTGGCAATTATGTGGCACCAGTCACAAGGGCGGTGACAAATGCTTCCCAAGCTAAAGTCCCTATG
TCTACAGCTGGCCAGACAAGTCGGGGAGTGACCATGGTCAGTCCTTCCACGGCAGGAGGGCCTGCCCAGA
AGCTCCAGGGAAATGGCGTGGCTGGGAGTCCCAGTGTTGTCCCCGCAGCTGTGGTATCAGCAGCTCACAT
CCAGACAAGTCCTCAGGCTAAGGTCTTGTTGCACATGACGGGGCAAATGACAGTCAACCAGGCCCGCAAT
GCTGTGAGGACAGTTGCAGCGCACAACCAGGAACGCCCCACGGCAGCAGTGACACCCATCCAGGTACAGA
ATGCCGCCGGCCTCAGCCCTGCATCTGTGGGCCTGTCCCATCACTCGCTGGCCTCCCCACAACCTGCGCC
TCTGATGCCAGGCTCAGCCACGCACACTGCTGCCATCAGTATCAGTCGAGCCAGTGCCCCTCTGGCCTGT
GCAGCAGCTGCTCCACTGACTTCCCCAAGCATCACCAGTGCTTCTCTGGAGGCTGAGCCCAGTGGCCGGA
TAGTGACCGTTCTCCCTGGACTCCCCACATCTCCTGACAGTGCTTCATCAGCTTGTGGGAACAGTTCAGC
AACCAAACCAGACAAGGATAGCAAAAAAGAAAAAAAGGGTTTGTTGAAGTTGCTTTCTGGCGCCTCCACT
AAACGGAAGCCCCGCGTGTCTCCTCCAGCATCGCCCACCCTAGAAGTGGAGCTGGGCAGTGCAGAGCTTC
CTCTCCAGGGAGCGGTGGGGCCCGAACTGCCACCAGGAGGTGGCCATGGCAGGGCAGGCTCCTGCCCTGT
GGACGGGACGGACCGGTCACGACTGCAGTGGCAGGAGCAGCCCTGGCCCAGGATGCTTTTCATAGGAAG
GCAAGTTCCCTGGACTCCGCAGTTCCCATCGCTCCACCTCCTCGCCAGGCCTGTTCCTCCCTGGGTCCTG
TCTTGAATGAGTCTAGACCTGTCGTTTGTGAAAGGCACAGGGTGGTGGTTTCCTATCCTCCTCAGAGTGA
GGCAGAACTTGAACTTAAAGAAGGAGATATTGTGTTTGTTCATAAAAAACGAGAGGATGGCTGGTTCAAA
GGCACATTACAACGTAATGGGAAAACTGGCCTTTTCCCAGGAAGCTTTGTGGAAAACATATGAGGAGACT
GACACTGAAGAAGCTTAAAATCACTTCACACAACAAAGTAGCACAAAGCAGTTTAACAGAAAGAGCACAT
TTGTGGACTTCCAGATGGTCAGGAGATGAGCAAAGGATTGGTATGTGACTCTGATGCCCCAGCACAGTTA
CCCCAGCGAGCAGAGTGAAGAAGATGTTTGTGTGGGTTTTGTTAGTCTGGATTCGGATGTATAAGGTGTG
CCTTGTACTGTCTGATTTACTACACAGAGAAACTTTTTTTTTTTTTAAGATATATGACTAAAATGGACA
ATTGTTTACAAGGCTTAACTAATTTATTTGCTTTTTTAAACTTGAACTTTTCGTATAATAGATACGTTCT
TTGGATTATGATTTTAAGAAATTATTAATTTATGAAATGATAGGTAAGGAGAAGCTGGATTATCTCCTGT
TGAGAGCAAGAGATTCGTTTTGACATAGAGTGAATGCATTTTCCCCTCTCCTCCTCCCTGCTACCATTAT
ATTTTGGGGTTATGTTTTGCTTCTTTAAGATAGAAATCCCAGTTCTCTAATTTGGTTTTCTTCTTTGGGA
AACCAAACATACAAATGAATCAGTATCAATTAGGGCCTGGGGTAGAGAGACAGAAACTTGAGAGAAGAGA
AGTTAGTGATTCCCTCTCTTTCTAGTTTGGTAGGAATCACCCTGAAGACCTAGTCCTCAATTTAATTGTG
TGGGTTTTTAATTTTCCTAGAATGAAGTGACTGAAACAATGAGAAAGAATACAGCACAACCCTTGAACAA
AATGTATTTAGAAATATATTTAGTTTTATAGCAGAAGCAGCTCAATTGTTTGGTTGGAAAGTAGGGGAAA
TTGAAGTTGTAGTCACTGTCTGAGAATGGCTATGAAGCGTCATTTCACATTTTACCCCAACTGACCTGCA
TGCCCAGGACACAAGTAAAACATTTGTGAGATAGTGGTGGTAAGTGATGCACTCGTGTTAAGTCAAAGGC
TATAAGAAACACTGTGAAAAGTTCATATTCATCCATTGTGATTCTTTCCCCACGTCTTGCATGTATTACT
GGATTCCCACAGTAATATAGACTGTGCATGGTGTGTATATTTCATTGCGATTTCCTGTTAAGATGAGTTT
GTACTCAGAATTGACCAATTCAGGAGGTGTAAAAATAAACAGTGTTCTCTTCCTACCCCAAAGCCACTA
CTGACCAAGGTCTCTTCAGTGCACTCGCTCCCTCTCTGGCTAAGGCATGCATTAGCCACTACACAAGTCA
TTAGTGAAAGTGGTCTTTTATGTCCTCCCAGCAGACAGACATCAAGGATGAGTTAACCAGGAGACTACTC
CTGTGACTGTGGAGCTCTGGAAGGCTTGGTGGGAGTGAATTTGCCCACACCTTACAATTGTGGCAGGATC
CAGAAGAGCCTGTCTTTTTATATCCATTCCTTGATGTCATTGGCCTCTCCCACCGATTTCATTACGGTGC
CACGCAGTCATGGATCTGGGTAGTCCGGAAAACAAAAGGAGGGAAGACAGCCTGGTAATGAATAAGATCC
```

Figure 3: Human POSH cDNA Sequence (SEQ ID NO:3)(continued)
```
TTACCACAGTTTTCTCATGGGAAATACATAATAAACCCTTTCATCTTTTTTTTTTCCTTTAAGAATTAA
AACTGGGAAATAGAAACATGAACTGAAAAGTCTTGCAATGACAAGAGGTTTCATGGTCTTAAAAAGATAC
TTTATATGGTTGAAGATGAAATCATTCCTAAATTAACCTTTTTTTAAAAAAAAACAATGTATATTATGT
TCCTGTGTGTTGAATTTAAAAAAAAAAAATACTTTACTTGGATATTCATGTAATATATAAAGGTTTGGTG
AAATGAACTTTAGTTAGGAAAAAGCTGGCATCAGCTTTCATCTGTGTAAGTTGACACCAATGTGTCATAA
TATTCTTTATTTTGGGAAATTAGTGTATTTTATAAAAATTTTAAAAAGAAAAAAGACTACTACAGGTTAA
GATAATTTTTTTACCTGTCTTTTCTCCATATTTTAAGCTATGTGATTGAAGTACCTCTGTTCATAGTTTC
CTGGTATAAAGTTGGTTAAAATTTCATCTGTTAATAGATCATTAGGTAATATAATGTATGGGTTTTCTAT
TGGTTTTTTGCAGACAGTAGAGGGAGATTTTGTAACAAGGGCTTGTTACACAGTGATATGGTAATGATAA
AATTGCAATTTATCACTCCTTTTCATGTTAATAATTTGAGGACTGGATAAAAGGTTTCAAGATTAAAATT
TGATGTTCAAACCTTTGT
```

Figure 4: 5' cDNA fragment of human POSH (public gi:10432611; SEQ ID NO:4)

```
ctgagagacactgcgagcggcgagcgcggtggggccgcatctgcatcagccgccgcagccgctgcggggc
cgcgaacaaagaggaggagccgaggcgcgagagcaaagtctgaaatggatgttacatgagtcattttaag
gatgcacacaactatgaacatttctgaagatttttctcagtaaagtagataaagatggatgaatcagcc
ttgttggatcttttggagtgtccggtgtgtctagagcgccttgatgcttctgcgaaggtcttgccttgcc
agcatacgttttgcaagcgatgtttgctggggatcgtaggttctcgaaatgaactcagatgtcccgagtg
caggactcttgttggctcgggtgtcgaggagcttcccagtaacatcttgctggtcagacttctggatggc
atcaaacagaggccttggaaacctggtcctggtgggggaagtgggaccaactgcacaaatgcattaaggt
ctcagagcagcactgtggctaattgtagctcaaaagatctgcagagctcccagggcggacagcagcctcg
ggtgcaatcctggagcccccagtgaggggtatacctcagttaccatgtgccaaagcgttatacaactat
gaaggaaaagagcctggagaccttaaattcagcaaaggcgacatcatcattttgcgaagacaagtggatg
aaaattggtaccatggggaagtcaatggaatccatggctttttcccaccaactttgtgcagattattaa
accgttacctcagcccccacctcagtgcaaagcactttatgactttgaagtgaaagacaaggaagcagac
aaagattgccttccatttgcaaaggatgatgttctgactgtgatccgaagagtggatgaaaactgggctg
aaggaatgctggcagacaaaataggaatatttccaatttcatatgttgagtttaactcggctgctaagca
gctgatagaatgggataagcctcctgtgccaggagttgatgctggagaatgttcctcggcagcagccag
agcagcactgccccaaagcactccgacaccaagaagaacaccaaaaagcggcactccttcacttccctca
ctatggccaacaagtcctcccaggcatcccagaaccgccactccatggagatcagccccctgtcctcat
cagctccagcaacccactgctgctgcacggatcagcgagctgtctgggctctcctgcagtgcccttct
caggttcatataagtaccaccgggttaattgtgaccccgccccaagcagcccagtgacaactggcccct
cgtttactttcccatcagatgttccctaccaagctgcccttggaactttgaatcctcctcttccaccacc
ccctctcctggctgccactgtccttgcctccacaccaccaggcgccaccgccgccgctgctgctgctgga
atgggaccgaggcccatggcaggatccactgaccagattgcacatttacggccgcagactcgccccagtg
tgtatgttgctatatatccatacactcctcggaaagaggatgaactagagctgagaaaaggggagatgtt
tttagtgtttgagcgctgccaggatggctggttcaaagggacatccatgcataccagcaagatagggtt
ttccctggcaattatgtggcaccagtcacaagggcggtgacaaatgcttcccaagctaaagtccctatgt
ctacagctggccagacaagtcggggagtgaccatggtcagtccttccacggcaggagggcctgcccagaa
gctccagggaaatggcgtggctgggagtcccagtgttgtccccgcagctgtggtatcagcagctcacatc
cagacaagtcctcaggctaaggtcttgttgcacatgacggggcaaatgacagtcaaccaggcccgcaatg
ctgtgaggacagttgcagcgcacaaccaggaacgccccacggcagcagtgacacccatccaggtacagaa
tgccgccggcctcagccctgcatctgtgggcctgtccatcactcgctggcctccccacaacctgcgcct
ctgatgccaggctcagccacgcacactgctgccatcagtatcagtcgagccagtgcccctctggcctgtg
cagcagctgctccactgacttccccaagcatcaccagtgcttctctggaggctgagcccagtggccggat
agtgaccgttctccctggactccccacatctcctgacagtgcttcatcagcttgtgggaacagttcagca
accaaaccagacaaggatagc
```

Figure 5: N terminus protein fragment of hPOSH (public gi:10432612; SEQ ID NO:5)

```
MDESALLDLLECPVCLERLDASAKVLPCQHTFCKRCLLGIVGSRNELRCPECRTLVGSGVEELPSNILLV
RLLDGIKQRPWKPGPGGGSGTNCTNALRSQSSTVANCSSKDLQSSQGGQQPRVQSWSPPVRGIPQLPCAK
ALYNYEGKEPGDLKFSKGDIIILRRQVDENWYHGEVNGIHGFFPTNFVQIIKPLPQPPPQCKALYDFEVK
DKEADKDCLPFAKDDVLTVIRRVDENWAEGMLADKIGIFPISYVEFNSAAKQLIEWDKPPVPGVDAGECS
SAAAQSSTAPKHSDTKKNTKKRHSFTSLTMANKSSQASQNRHSMEISPPVLISSSNPTAAARISELSGLS
CSAPSQVHISTTGLIVTPPPSSPVTTGPSFTFPSDVPYQAALGTLNPPLPPPPLLAATVLASTPPGATAA
AAAAGMGPRPMAGSTDQIAHLRPQTRPSVYVAIYPYTPRKEDELELRKGEMFLVFERCQDGWFKGTSMHT
SKIGVFPGNYVAPVTRAVTNASQAKVPMSTAGQTSRGVTMVSPSTAGGPAQKLQGNGVAGSPSVVPAAVV
SAAHIQTSPQAKVLLHMTGQMTVNQARNAVRTVAAHNQERPTAAVTPIQVQNAAGLSPASVGLSHHSLAS
PQPAPLMPGSATHTAAISISRASAPLACAAAAPLTSPSITSASLEAEPSGRIVTVLPGLPTSPDSASSAC
GNSSATKPDKDS
```

Figure 6: 3' mRNA fragment of hPOSH (public gi:7959248; SEQ ID NO:6)

```
atttcatatgttgagtttaactcggctgctaagcagctgatagaatgggataagcctcctgtgccaggag
ttgatgctggagaatgttcctcggcagcagcccagagcagcactgccccaaagcactccgacaccaagaa
gaacaccaaaaagcggcactccttcacttccctcactatggccaacaagtcctcccaggcatcccagaac
cgccactccatggagatcagcccccctgtcctcatcagctccagcaacccactgctgctgcacggatca
gcgagctgtctgggctctcctgcagtgccccttctcaggttcatataagtaccaccgggttaattgtgac
cccgcccccaagcagcccagtgacaactggcccctcgtttactttcccatcagatgttccctaccaagct
gcccttggaactttgaatcctcctcttccaccacccctctcctggctgccactgtccttgcctccacac
caccaggcgccaccgccgctgctgctgctggaatgggaccgaggcccatggcaggatccactgacca
gattgcacatttacggccgcagactcgcccagtgtgtatgttgctatatatccatacactcctcggaaa
gaggatgaactagagctgagaaaaggggagatgttttagtgtttgagcgctgccaggatggctggttca
aagggacatccatgcataccagcaagatgggttttccctggcaattatgtggcaccagtcacaagggc
ggtgacaaatgcttcccaagctaaagtccctatgtctacagctggccagacaagtcggggagtgaccatg
gtcagtccttccacggcaggagggcctgcccagaagctccagggaaatggcgtggctgggagtcccagtg
ttgtccccgcagctgtggtatcagcagctcacatccagacaagtcctcaggctaaggtcttgttgcacat
gacggggcaaatgacagtcaaccaggcccgcaatgctgtgaggacagttgcagcgcacaaccaggaacgc
cccacggcagcagtgacacccatccaggtacagaatgccgccggcctcagccctgcatctgtgggcctgt
cccatcactcgctggcctccccacaacctgcgcctctgatgccaggctcagccacgcacactgctgccat
cagtatcagtcgagccagtgcccctctggcctgtgcagcagctgctccactgacttccccaagcatcacc
agtgcttctctggaggctgagcccagtggccggatagtgaccgttctccctggactccccacatctcctg
acagtgcttcatcagcttgtgggaacagttcagcaaccaaaccagacaaggatagcaaaaaagaaaaaaa
gggtttgttgaagttgctttctggcgcctccactaaacggaagccccgcgtgtctcctccagcatcgcc
accctagaagtggagctgggcagtgcagagcttcctctccagggagcggtggggcccgaactgccaccag
gaggtggccatggcagggcaggctcctgccctgtggacggggacggaccggtcacgactgcagtggcagg
agcagccctggcccaggatgcttttcataggaaggcaagttccctggactccgcagttcccatcgctcca
cctcctcgccaggcctgttcctccctgggtcctgtcttgaatgagtctagacctgtcgtttgtgaaggc
acagggtggtggtttcctatcctcctcagagtgaggcagaacttgaacttaaagaaggagatattgtgtt
tgttcataaaaaacgagaggatggctggttcaaaggcacattacaacgtaatgggaaaactggcctttc
ccaggaagctttgtggaaaacatatgaggagactgacactgaagaagcttaaaatcacttcacacaacaa
agtagcacaaagcagtttaacagaaagagcacatttgtggacttccagatggtcaggagatgagcaaagg
attggtatgtgactctgatgccccagcacagttaccccagcgagcagagtgaagaagatgtttgtgtggg
ttttgttagtctggattcggatgtataaggtgtgccttgtactgtctgatttactacacagagaaacttt
tttttttttttaagatatatgactaaaatggacaattgtttacaaggcttaactaatttatttgctttt
taaacttgaacttttcgtataatagatacgttctttggattatgattttaagaaattattaatttatgaa
atgataggtaaggagaagctggattatctcctgttgagagcaagagattcgtttgacatagagtgaatg
cattttcccctctcctcctccctgctaccattatattttggggttatgttttgcttctttaagatagaaa
tcccagttctctaatttggttttcttctttgggaaaccaaacatacaaatgaatcagtatcaattagggc
ctggggtagagagacagaaacttgagagaagagaagttagtgattccctctctttctagtttggtaggaa
tcaccctgaagacctagtcctcaatttaattgtgtgggttttaattttcctagaatgaagtgactgaaa
caatgagaaagaatacagcacaacccttgaacaaaatgtatttagaaatatatttagttttatagcagaa
gcagctcaattgtttggttggaaagtaggggaaattgaagttgtagtcactgtctgagaatggctatgaa
gcgtcatttcacattttaccccaactgacctgcatgcccaggacacaagtaaaacatttgtgagatagtg
gtggtaagtgatgcactcgtgttaagtcaaaggctataagaaacactgtgaaaagttcatattcatccat
tgtgattctttcccacgtcttgcatgtattactggattcccacagtaatatagactgtgcatggtgtgt
atatttcattgcgatttcctgttaagatgagtttgtactcagaattgaccaattcaggaggtgtaaaaat
aaacagtgttctcttctctacccccaaagccactactgaccaaggtctcttcagtgcactcgctccctctc
tggctaaggcatgcattagccactacacaagtcattagtgaaagtggtctttatgtcctcccagcagac
agacatcaaggatgagttaaccaggagactactcctgtgactgtggagctctggaaggcttggtgggagt
gaatttgcccacaccttacaattgtggcaggatccagaagagcctgtcttttatatccattccttgatg
tcattggcctctcccaccgatttcattacggtgccacgcagtcatggatctgggtagtccggaaaacaaa
aggagggaagacagcctggtaatgaataagatccttaccacagttttctcatgggaaatacataataaac
cctttcatctttttttttttcctttaagaattaaaactgggaaatagaaacatgaactgaaaagtcttgc
aatgacaagaggtttcatggtcttaaaagatactttatatggttgaagatgaaatcattcctaaattaa
ccttttttttaaaaaaaaacaatgtatattatgttcctgtgtgttgaatttaaaaaaaaaaaatacttta
cttggatattcatgtaatatataaaggtttggtgaaatgaactttagttaggaaaagctggcatcagct
ttcatctgtgtaagttgacaccaatgtgtcataatattctttattttgggaaattagtgtattttataaa
aattttaaaagaaaaagactactacaggttaagataattttttttacctgtcttttctccatatttaa
gctatgtgattgaagtacctctgttcatagtttcctggtataaagttggttaaaatttcatctgttaata
gatcattaggtaatataatgtatgggttttctattggttttttgcagacagtagagggagattttgtaac
aagggcttgttacacagtgatatggtaatgataaaattgcaatttatcactccttttcatgttaataatt
tgaggactggataaaaggtttcaagattaaaatttgatgttcaaacctttgt
```

Figure 7: C terminus protein fragment of hPOSH (public gi:7959249; SEQ ID NO:7)

```
ISYVEFNSAAKQLIEWDKPPVPGVDAGECSSAAAQSSTAPKHSDTKKNTKKRHSFTSLTMANKSSQASQN
RHSMEISPPVLISSSNPTAAARISELSGLSCSAPSQVHISTTGLIVTPPPSSPVTTGPSFTFPSDVPYQA
ALGTLNPPLPPPPLLAATVLASTPPGATAAAAAAGMGPRPMAGSTDQIAHLRPQTRPSVYVAIYPYTPRK
EDELELRKGEMFLVFERCQDGWFKGTSMHTSKIGVFPGNYVAPVTRAVTNASQAKVPMSTAGQTSRGVTM
VSPSTAGGPAQKLQGNGVAGSPSVVPAAVVSAAHIQTSPQAKVLLHMTGQMTVNQARNAVRTVAAHNQER
PTAAVTPIQVQNAAGLSPASVGLSHHSLASPQPAPLMPGSATHTAAISISRASAPLACAAAAPLTSPSIT
SASLEAEPSGRIVTVLPGLPTSPDSASSACGNSSATKPDKDSKKEKKGLLKLLSGASTKRKPRVSPPASP
TLEVELGSAELPLQGAVGPELPPGGGHGRAGSCPVDGDGPVTTAVAGAALAQDAFHRKASSLDSAVPIAP
PPRQACSSLGPVLNESRPVVCERHRVVVSYPPQSEAELELKEGDIVFVHKKREDGWFKGTLQRNGKTGLF
PGSFVENI
```

Figure 8: Human POSH full mRNA, Annotated Sequence

---- - gi|10432611|dbj|AK021429.1|AK021429 Homo sapiens cDNA
FLJ11367 fis, clone HEMBA1000303, highly similar to Mus musculus
Plenty of SH3s (POSH) mRNA ---- - gi|7959248|dbj|AB040927.1|AB040927 Homo sapiens mRNA for
KIAA1494 protein, partial cds ▓▓▓ - Both hPOSH and KIAA1495

▓▓▓ - Ring Domain

▓▓▓ - SH3 Domian

▓▓▓ - start codon and stop codon of predicted ORF

```
CTGAGAGACACTGCGAGCGGCGAGCGCGGTGGGGCCGCATCTGCATCAGCCGCCGCAGCCGCTGCGGGGC
CGCGAACAAAGAGGAGGAGCCGAGGCGCGAGAGCAAAGTCTGAAATGGATGTTACATGAGTCATTTTAAG
GGATGCACACAACTATGAACATTTCTGAAGATTTTTTCTCAGTAAAGTAGATAAAGATGGATGAATCAGC
CTTGTTGGATCTTTTGGAG▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓
▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓
GCAGGACTCTTGTTGGCTCGGGTGTCGAGGAGCTTCCCAGTAACATCTTGCTGGTCAGACTTCTGGATGG
CATCAAACAGAGGCCTTGGAAACCTGGTCCTGGTGGGGGAAGTGGGACCAACTGCACAAATGCATTAAGG
TCTCAGAGCAGCACTGTGGCTAATTGTAGCTCAAAAGATCTGCAGAGCTCCCAGGGCGGACAGCAGCCTC
GGGTGCAATCCTGGAGCCCCCCAGTGAGGGGTATACCTCAGTTA▓▓▓▓▓▓▓▓▓▓▓▓▓▓▓▓▓▓▓▓▓▓▓▓▓
▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓A
AACCGTTACCTCAGCCCCCA▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓
▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓TCGCGTGCTAAGC
AGCTGATACAATCGGATAAGCCTCCTGTGCCAGGAGTTGATGCTGGACAATGTTGCTCGGCAGCAGCCCA
GAGGCACCACTGCCCCAAAGCACTCCGACACGAAGCAGCCAAAAACCGGCACTCCTTCACTTCCGTC
ACTATGCCAACAAGTGCGTCCCAGGCGATCCCAGAACCGGCACTCCATCGACATCAGCGCCCTGTCCTCA
TCAGCTGCAGCAACGGCACTGCTGCTGCAGGCATCAGGCAGCTGTCTGGCTCTCGTCCAGTGCCCTTG
TCAGCTTCATATAACTAGCAGCCGGTTAATTGTCACCGGGGCGGCAAGCAGGCAGTGACAACTGGCGCC
TCGTTTACTTTCCCATCAGATGTTGCCTACCAAGCTGCCGTTCCAACTTCAATCCTCCTCTTCCACCAG
CCCCTCTCCTGCCTGCCAGTCTCCTTGCCTCACCACGACGCCGCACCGCCCGCGCTGCTGCTCCTGG
AATCGCACCGCACCGCCATCGCACGATCCACTCACCACATTGCACATTTACCGCCGCCACAGTCGCCGCC
▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓ACAAGCCCGTGACAAATGCTTCCCAAAGCTAAAGTCCCTATG
TCTACAGCTGCCCACAGACAAGTCGCCCGAGTGACCATGGTCAGTCCTTCCACGGCACGACGGCGTGCCGACA
AGCTCCACCGCAAATGGCGTCGCTGGGACTCGCAATGTTGTCCCCGGCACCTCTCCTATCAGCAGCTCACAT
CCAGACAACTGCCTCAGCGAAGCTGTTCTTCCACATCACCGGCGAAATGACACTCAACCAGCCCCGAAT
GCTGTGACGCACAGTTGCAGCGGCACAAGCCAACGCGCCCGGCAGCCGTCACACCCATCCAGTAGACA
ATGCCCGCGCCCTCAGCGGTGGACTGTCGCCGCTGTCGGATCACTCGGTCCGCTCGGCCAGAACGTGCGCC
TCTGATCGCACGGCTGCAGGAGGCACGACTGGTGCGATCAGTATCACTCGACCCAGTCGCCGTCTCGCCTCT
GCAGGACCTGGCTGCCACGACATTCCCAAGCATCAGCCAGCGTCTCTGCGACGGTCACGCCACGTGCGCCGA
TACACCCGTTCTGGCTGCAACTGCCCACACTCTGCTCAGCTGCTCATCAGCTTGTCGGAACAGTTCAGC
AACCAAAGCCACACGAAGCATAGCAAAAAAGAAAAAAGGGTTTGTTGAAGTTGCTTTCTGGCGCCTCCACT
AAACGGAAGCCCCGCGTGTCTCCTCCAGCATCGCCCACCCTAGAAGTGGAGCTGGGCAGTGCAGAGCTTC
CTCTCCAGGGAGCGGTGGGGCCCGAACTGCCACCAGGAGGTGGCCATGGCAGGGCAGGCTCCTGCCCTGT
GGACGGGGACGGACCGGTCACGACTGCAGTGGCAGGAGCAGCCCTGGCCCAGGATGCTTTTCATAGGAAG
GCAAGTTCCCTGGACTCCGCAGTTCCCATCGCTCCACCTCCTCGCCAGGCCTGTTCCTCCCTGGGTCCTG
TCTTGAATGAGTCTAGACCTGTCGTTTGT▓▓▓▓▓▓▓▓▓▓▓▓▓▓▓▓▓▓▓▓▓▓▓▓▓▓▓▓▓▓▓▓▓▓▓▓▓▓▓
▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓TGAGGAGACT
GACACTGAAGAAGCTTAAAATCACTTCACACAACAAAGTAGCACAAAGCAGTTTAACAGAAAGAGCACAT
TTGTGGACTTCCAGATGGTCAGGAGATGAGCAAAGGATTGGTATGTGACTCTGATGCCCCAGCACAGTTA
CCCCAGCGAGCAGAGTGAAGAAGATGTTTGTGTGGGTTTTGTTAGTCTGGATTCGGATGTATAAGGTGTG
CCTTGTACTGTCTGATTTACTACACAGAGAAACTTTTTTTTTTTTTTAAGATATATGACTAAAATGGACA
```

Figure 8: Human POSH full mRNA, Annotated Sequence (continued)

```
ATTGTTTACAAGGCTTAACTAATTTATTTGCTTTTTTAAACTTGAACTTTTCGTATAATAGATACGTTCT
TTGGATTATGATTTTAAGAAATTATTAATTTATGAAATGATAGGTAAGGAGAAGCTGGATTATCTCCTGT
TGAGAGCAAGAGATTCGTTTTGACATAGAGTGAATGCATTTTCCCCTCTCCTCCTCCCTGCTACCATTAT
ATTTTGGGGTTATGTTTTGCTTCTTTAAGATAGAAATCCCAGTTCTCTAATTTGGTTTTCTTCTTTGGGA
AACCAAACATACAAATGAATCAGTATCAATTAGGGCCTGGGGTAGAGAGACAGAAACTTGAGAGAAGAGA
AGTTAGTGATTCCCTCTCTTTCTAGTTTGGTAGGAATCACCCTGAAGACCTAGTCCTCAATTTAATTGTG
TGGGTTTTTAATTTTCCTAGAATGAAGTGACTGAAACAATGAGAAAGAATACAGCACAACCCTTGAACAA
AATGTATTTAGAAATATATTTAGTTTTATAGCAGAAGCAGCTCAATTGTTTGGTTGGAAAGTAGGGGAAA
TTGAAGTTGTAGTCACTGTCTGAGAATGGCTATGAAGCGTCATTTCACATTTTACCCCAACTGACCTGCA
TGCCCAGGACACAAGTAAAACATTTGTGAGATAGTGGTGGTAAGTGATGCACTCGTGTTAAGTCAAAGGC
TATAAGAAACACTGTGAAAAGTTCATATTCATCCATTGTGATTCTTTCCCCACGTCTTGCATGTATTACT
GGATTCCCACAGTAATATAGACTGTGCATGGTGTGTATATTTCATTGCGATTTCCTGTTAAGATGAGTTT
GTACTCAGAATTGACCAATTCAGGAGGTGTAAAAATAAACAGTGTTCTCTTCTCTACCCCAAAGCCACTA
CTGACCAAGGTCTCTTCAGTGCACTCGCTCCCTCTCTGGCTAAGGCATGCATTAGCCACTACACAAGTCA
TTAGTGAAAGTGGTCTTTTATGTCCTCCCAGCAGACAGACATCAAGGATGAGTTAACCAGGAGACTACTC
CTGTGACTGTGGAGCTCTGGAAGGCTTGGTGGGAGTGAATTTGCCCACACCTTACAATTGTGGCAGGATC
CAGAAGAGCCTGTCTTTTTATATCCATTCCTTGATGTCATTGGCCTCTCCCACCGATTTCATTACGGTGC
CACGCAGTCATGGATCTGGGTAGTCCGGAAAACAAAAGGAGGGAAGACAGCCTGGTAATGAATAAGATCC
TTACCACAGTTTTCTCATGGGAAATACATAATAAACCCTTTCATCTTTTTTTTTTCCTTTAAGAATTAA
AACTGGGAAATAGAAACATGAACTGAAAAGTCTTGCAATGACAAGAGGTTTCATGGTCTTAAAAAGATAC
TTTATATGGTTGAAGATGAAATCATTCCTAAATTAACCTTTTTTTTAAAAAAAAACAATGTATATTATGT
TCCTGTGTGTTGAATTTAAAAAAAAAAAAATACTTTACTTGGATATTCATGTAATATATAAAGGTTTGGTG
AAATGAACTTTAGTTAGGAAAAAGCTGGCATCAGCTTTCATCTGTGTAAGTTGACACCAATGTGTCATAA
TATTCTTTATTTTGGGAAATTAGTGTATTTTATAAAAATTTTAAAAAGAAAAAAGACTACTACAGGTTAA
GATAATTTTTTTACCTGTCTTTTCTCCATATTTTAAGCTATGTGATTGAAGTACCTCTGTTCATAGTTTC
CTGGTATAAAGTTGGTTAAAATTTCATCTGTTAATAGATCATTAGGTAATATAATGTATGGGTTTTCTAT
TGGTTTTTTGCAGACAGTAGAGGGAGATTTTGTAACAAGGGCTTGTTACACAGTGATATGGTAATGATAA
AATTGCAATTTATCACTCCTTTTCATGTTAATAATTTGAGGACTGGATAAAAGGTTTCAAGATTAAAATT
TGATGTTCAAACCTTTGT
```

Figure 9: Domain Analysis of Human POSH

| Domain Name | begin | end | E-value |
|---|---|---|---|
| RING | 12 | 52 | 1.06e-08 |
| SH3 | 137 | 192 | 2.76e-19 |
| SH3 | 199 | 258 | 4.84e-15 |
| low complexity | 366 | 384 | - |
| low complexity | 390 | 434 | - |
| SH3 | 448 | 505 | 2.40e-19 |
| low complexity | 547 | 563 | - |
| low complexity | 652 | 668 | - |
| low complexity | 705 | 729 | - |
| SH3 | 832 | 888 | 1.47e-14 |

Figure 10: Diagram of Human POSH Nucleic Acids
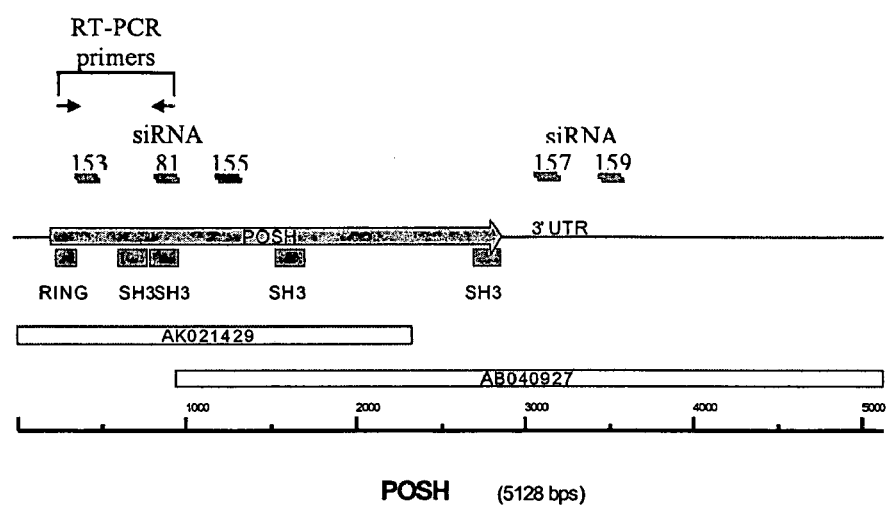

Figure 11: Mouse POSH mRNA sequence (public gi:10946921; SEQ ID NO: 8)

```
GGGCAGCGGGCTCGGCGGGGCTGCATCTACCAGCGCTGCGGGGCCGCGAACAAAGGCGAGCAGCGGAGGC
GCGAGAGCAAAGTCTGAAATGGATGTTACATGAATCACTTTAAGGGCTGCGCACAACTATGAACGTTCTG
AAGCCGTTTTCTCACTAAAGTCACTCAAGATGGATGAGTCTGCCTTGTTGGACCTTCTGGAGTGCCCTGT
GTGTCTAGAACGCCTGGATGCTTCCGCAAAGGTCTTACCCTGCCAGCATACCTTTTGCAAACGCTGTTTG
CTGGGGATTGTGGGTTCCCGGAATGAACTCAGATGTCCCGAATGCCGGACTCTTGTTGGCTCTGGGGTCG
ACGAGCTCCCCAGTAACATCCTACTGGTCAGACTTCTGGATGGCATCAAGCAGAGGCCTTGGAAACCCGG
CCCTGGTGGGGCGGCGGGACCACCTGCACAAACACATTAAGGGCGCAGGGCAGCACTGTGGTTAATTGT
GGCTCGAAAGATCTGCAGAGCTCCCAGTGTGGACAGCAGCCTCGGGTGCAAGCCTGGAGCCCCCAGTGA
GGGGAATACCTCAGTTACCGTGTGCCAAAGCATTATATAACTACGAAGGAAAAGAGCCCGGAGACCTTAA
GTTCAGCAAAGGCGACACCATCATTCTGCGCCGACAGGTGGATGAGAATTGGTACCACGGGGAAGTCAGC
GGGGTCCACGGCTTTTTCCCCACTAACTTCGTGCAGATCATCAAACCTTTACCTCAGCCCCCGCCTCAGT
GCAAAGCACTTTACGACTTTGAAGTGAAAGACAAGGAAGCTGACAAAGATTGCCTTCCCTTCGCAAAGGA
CGACGTACTGACCGTGATCCGCAGAGTGGATGAAAACTGGGCTGAAGGAATGCTGGCAGATAAAATAGGA
ATATTTCCAATTTCATACGTGGAGTTTAACTCAGCTGCCAAGCAGCTGATAGAGTGGGATAAGCCTCCCG
TGCCAGGAGTGGACACGGCAGAATGCCCCTCAGCGACGGCGCAGAGCACCTCTGCCTCAAAGCACCCCGA
CACCAAGAAGAACACCAGGAAGCGACACTCCTTCACCTCCCTCACCATGGCCAACAAGTCTTCCCAGGGG
TCCCAGAACCGCCACTCCATGGAGATCAGCCCTCCTGTGCTCATCAGTTCCAGCAACCCCACAGCCGCAG
CCCGCATCAGCGAACTGTCCGGGCTCTCCTGCAGCGCCCGTCTCAGGTCCATATAAGCACCACTGGGTT
AATTGTGACCCCACCCCTAGCAGCCGGTGACAACTGGCCCTGCGTTCACGTTCCCTTCAGATGTCCCC
TACCAAGCTGCCCTTGGAAGTATGAATCCTCCACTTCCCCCACCCCCTCTCCTGGCGGCCACCGTACTCG
CCTCCACCCCGTCAGGCGCTACTGCTGCTGTTGCTGCTGCTGCTGCCGCCGCCGCTGCTGGAATGGG
ACCCAGGCCTGTGATGGGGTCCTCTGAACAGATTGCACATTTACGGCCTCAGACTCGTCCCAGTGTATAT
GTTGCTATATATCCGTACACTCCCCGGAAGGAAGACGAACTGGAGCTGAGGAAAGGGGAGATGTTTTGG
TGTTTGAGCGTTGCCAGGACGGCTGGTACAAAGGGACATCGATGCATACCAGCAAGATAGGCGTTTTCCC
TGGCAACTATGTGGCGCCCGTCACAAGGGCGGTGACGAATGCCTCCCAAGCTAAAGTCTCTATGTCTACT
GCGGGTCAGGCAAGTCGCGGGGTGACCATGGTCAGCCCTTCCACTGCAGGAGGACCTACACAGAAGCCCC
AAGGAAACGGCGTGGCCGGAAATCCCAGCGTCGTCCCCACGGCTGTGGTGTCAGCAGCTCATATCCAGAC
AAGTCCTCAGGCTAAGGTCCTGCTGCACATGTCTGGGCAGATGACAGTCAATCAGGCCCGCAATGCTGTG
AGGACAGTTGCAGCACATAGCCAGGAACGCCCCACAGCAGCAGTGACTCCCATCCAGGTCCAGAATGCCG
CCTGCCTTGGTCCTGCATCCGTGGGCCTGCCCCATCATTCTCTGGCCTCCCAACCTCTGCCTCCAATGGC
GGGTCCTGCTGCCCACGGTGCTGCCGTCAGCATCAGTCGAACCAATGCCCCCATGGCCTGCGCTGCAGGG
GCTTCTCTGGCCTCCCCAAATATGACCAGTGCCATGTTGGAGACAGAGCCCAGTGGTCGCACAGTGACCA
TCCTCCCTGGACTCCCCACATCTCCAGAGAGTGCTGCATCAGCGTGTGGGAACAGTTCAGCTGGGAAACC
AGACAAGGACAGTAAGAAAGAAAAAAGGGCCTACTGAAGCTGCTTTCTGGTGCCTCCACCAAACGCAAG
CCCCGAGTCTCCCCTCCAGCATCACCTACCCTGGATGTGGAGCTGGGTGCTGGGAGGCTCCCTTGCAGG
GAGCAGTAGGTCCTGAGCTGCCGCTAGGGGCAGCCACGGCAGAGTGGGGTCATGCCCCACAGATGGTGA
TGGTCCAGTGGCCGCTGGAACAGCAGCCCTAGCCCAGGATGCCTTCCACCGCAAGACAAGCTCCCTGGAC
TCCGCAGTGCCCATTGCTCCACCACCTCGCCAGGCCTGCTCCTCCCTGGGCCCAGTCATGAATGAGGCCC
GGCCTGTTGTTTGTGAAAGGCACAGGGTGGTGGTTTCCTACCCTCCTCAGAGTGAGGCCGAACTTGAACT
CAAGGAAGGAGATATTGTGTTTGTTCATAAGAAACGAGAGGACGGCTGGTTCAAAGGCACGTTACAGAGG
AATGGGAAGACTGGCCTTTTCCCAGGGAGCTTTGTGGAAAACATCTGAGAAGACGGGACACGGAGAAAGC
TTATCATCACACCACGTGTGACTAAAGAGCACAAAGCAGTTTCATAGAAAGAGCACATCTGTGGACTTCC
AGATCTTCAAGAACCGAGCAGAAGATGGGCACCTGACTCCAGAGCCCCGGCCTGGTTACCCCAGGGGCAG
AGGGAAGGAGGACACACCTGTGTGGGTTCCGTCTCTCTGGGTTCTGATGTGTAAAGTGTGCCTTGTAATG
TCTAATGGACTTTACAGATAAATGTCTTTTTTTTTTAAGATGTATAACTAAAATGGACAATTGTTTACA
AGGCTTAACTAATTTATTTGCTTTTTTAAAACTTGAACTTTCTTGTAATAGCAAAT
```

Figure 12: Mouse POSH Protein sequence (Public gi: 10946922; SEQ ID NO: 9)

MDESALLDLLECPVCLERLDASAKVLPCQHTFCKRCLLGIVGSRNELRCPECRTLVGSGVDELPSNILLV
RLLDGIKQRPWKPGPGGGGGTTCTNTLRAQGSTVVNCGSKDLQSSQCGQQPRVQAWSPPVRGIPQLPCAK
ALYNYEGKEPGDLKFSKGDTIILRRQVDENWYHGEVSGVHGFFPTNFVQIIKPLPQPPPQCKALYDFEVK
DKEADKDCLPFAKDDVLTVIRRVDENWAEGMLADKIGIFPISYVEFNSAAKQLIEWDKPPVPGVDTAECP
SATAQSTSASKHPDTKKNTRKRHSFTSLTMANKSSQGSQNRHSMEISPPVLISSSNPTAAARISELSGLS
CSAPSQVHISTTGLIVTPPPSSPVTTGPAFTFPSDVPYQAALGSMNPPLPPPPLLAATVLASTPSGATAA
VAAAAAAAAAAGMGPRPVMGSSEQIAHLRPQTRPSVYVAIYPYTPRKEDELELRKGEMFLVFERCQDGWY
KGTSMHTSKIGVFPGNYVAPVTRAVTNASQAKVSMSTAGQASRGVTMVSPSTAGGPTQKPQGNGVAGNPS
VVPTAVVSAAHIQTSPQAKVLLHMSGQMTVNQARNAVRTVAAHSQERPTAAVTPIQVQNAACLGPASVGL
PHHSLASQPLPPMAGPAAHGAAVSISRTNAPMACAAGASLASPNMTSAMLETEPSGRTVTILPGLPTSPE
SAASACGNSSAGKPDKDSKKEKKGLLKLLSGASTKRKPRVSPPASPTLDVELGAGEAPLQGAVGPELPLG
GSHGRVGSCPTDGDGPVAAGTAALAQDAFHRKTSSLDSAVPIAPPPRQACSSLGPVMNEARPVVCERHRV
VVSYPPQSEAELELKEGDIVFVHKKREDGWFKGTLQRNGKTGLFPGSFVENI

Figure 13: Drosophila melanogaster POSH mRNA sequence (public gi:17737480; SEQ ID NO:10)

```
CATTTGTATCCGCTTGGCCACGAGCTTTGGCTGCACTTGGCAAACTTAATAAATTAAACATTGAATCCTG
CCTATTGCAACGATAATATAATCTGATTTAGTGCATTAAGAACGACAAGTAGCGATTATAATAGTAGATT
TTAGCATTTGAGCTAAATTTATTTCCCAACCGCGTCTTGGGATTGCGTATGCGTGAGCCAGTACCTGCAT
GTGTGTGTGTTTTGGAATGTGGCCCTGCACGAAATTCAAATAGTGACCATCCTTGAGATTTTGCATACTG
GCAAGATGGACGAGCACACGTTAAACGACCTGTTGGAGTGCTCCGTGTGTCTTGAGCGACTGGACACCAC
ATCGAAGGTGCTGCCATGCCAGCACACCTTCTGCCGCAAATGCTTGCAGGACATTGTGGCCAGTCAGCAC
AAGTTGCGATGCCCGGAGTGCCGCATCCTGGTCTCTTGCAAAATTGATGAGCTGCCTCCAAACGTCTTGC
TGATGCGAATCTTAGAAGGCATGAAACAAAATGCAGCAGCTGGCAAAGGAGAAGAAAAGGGAGAGGAGAC
TGAAACACAGCCGGAAAGGGCCAAACCTCAGCCGCCAGCGGAATCAGTGGCCCCGCCTGACAACCAACTA
CTCCAGCTGCAGTCACATCAGCAATCTCATCAGCCGGCTCGTCACAAGCAACGTCGATTTCTACTCCCCC
ACGCCTATGCCCTCTTTGACTTCGCCTCCGGTGAAGCCACCGATCTAAAGTTCAAGAAAGGGGATCTGAT
ACTGATCAAGCATCGCATCGACAACAACTGGTTTGTGGGTCAAGCGAATGGTCAGGAGGGCACATTTCCC
ATCAACTACGTCAAGGTATCGGTTCCGCTGCCCATGCCGCAGTGCATTGCCATGTATGACTTTAAGATGG
GGCCCAACGACGAGGAGGGATGCCTCGAATTTAAGAAAAGCACTGTAATACAGGTAATGCGCCGAGTTGA
TCATAATTGGGCAGAAGGACGAATTGGCCAGACCATCGGAATCTTTCCAATAGCATTCGTTGAGCTGAAT
GCAGCGGCCAAAAAGCTGTTGGACAGCGGGCTACACACCCATCCATTCTGCCATCCACCGAAGCAACAGG
GGCAGCGGGCCCTTCCTCCGGTTCCAGTTATTGATCCCACGGTGGTCACGGAATCCAGTTCGGGATCCTC
CAATTCCACGCCGGGCAGCAGCAATTCAAGCTCCACATCCAGCTCGAATAACTGCAGTCCGAATCACCAA
ATCTCACTGCCGAATACCCCCCAACATGTAGTAGCTTCCGGATCGGCGTCTGTTCGTTTCCGTGACAAGG
GAGCAAAGGAGAAACGCCACTCACTAAATGCTTTGCTGGGAGGAGGAGCTCCATTAAGTCTGCTGCAGAC
CAACCGCCATTCGGCTGAAATTCTTAGCCTGCCCCATGAACTAAGCCGCTTGGAAGTTTCCAGCTCAACA
GCTCTAAAACCCACGTCAGCCCCACAGACATCGCGTGTACTTAAGACCACTGTTCAGCAGCAGATGCAAC
CGAATTTACCCTGGGGATACTTAGCCCTGTTCCCATACAAACCACGCCAAACGGATGAGCTGGAATTAAA
AAAGGGTTGTGTTTACATTGTGACCGAACGATGTGTGGACGGTTGGTTCAAGGGAAAAAACTGGTTGGAC
ATCACTGGAGTGTTCCCGGGCAACTACCTGACGCCCCTGCGCGCCCGCGACCAGCAGCAGTTAATGCATC
AATGGAAATATGTTCCCCAAAATGCAGACGCCCAGATGGCACAAGTACAGCAGCATCCAGTTGCACCAGA
TGTGCGACTCAACAACATGCTGTCCATGCAACCGCCTGATTGCCACCTCGTCAGCAGCAGGCTACCGCC
ACGACCACCAGTTGCTCTGTGTGGTCGAAACCAGTGGAGGCGCTGTTCAGCAGAAAATCGGAGCCCAAGC
CTGAAACTGCCACAGCTTCGACTACGAGCAGCAGTTCCTCTGGAGCAGTGGGACTTATGAGGAGATTAAC
TCACATGAAAACACGCTCCAAATCTCCGGGAGCGTCCTTGCAGCAAGTTCCGAAAGAAGCTATTAGCACA
AATGTGGAATTTACAACAAACCCATCAGCTAAATTGCATCCAGTACATGTAAGATCCGGCTCGTGCCCCA
GTCAGCTGCAGCACAGTCAACCGCTCAATGAAACTCCAGCAGCCAAGACAGCGGCACAACAACAGCAGTT
CCTACCCAAGCAGCTGCCTTCCGCTTCTACGAACAGCGTTTCGTACGGATCGCAACGCGTGAAAGGAAGC
AAGGAACGTCCTCACTTGATTTGCGCGAGACAATCATTAGATGCAGCTACATTTCGCAGTATGTACAACA
ATGCCGCGTCGCCGCCGCCACCTACTACTTCCGTGGCCCCAGCTGTCTACGCCGGCGGTCAGCAACAGGT
GATTCCTGGAGGTGGAGCGCAATCCCAGTTGCATGCCAATATGATTATTGCACCCAGCCATCGGAAGTCG
CACAGCCTAGATGCGAGTCATGTGCTGAGTCCCAGCAGCAATATGATCACGGAGGCGGCCATTAAGGCCA
GCGCCACCACTAAGTCTCCTTACTGCACGAGGGAAAGTCGATTCCGCTGCATTGTGCCGTATCCACCAAA
CAGTGACATTGAACTAGAGCTACATTTGGGCGACATTATCTACGTCCAGCGGAAGCAGAAGAACGGCTGG
TATAAGGGCACCCATGCCCGTACCCACAAAACCGGGCTGTTCCCCGCCTCCTTTGTTGAACCGGATTGTT
AGGAAAGTTATGGTTCAAACTAGAATTTATTAAGCGAAATTCCAAATTACTTGTCTAAAAGGATTCAATC
GTCGGTCTATTCGGGCTTCCAAATACGCAATCTCATATTTCTCTTTTCAAAAAAGAAACCGTTTTGTACT
CTTCCAATCGAATGGGCAGCTCGCCGTTGTACTTTTTTATACAATGCTTGATCAAAATAGGCTAGCCATG
TAAGACTTAGGGAACAGTTACTTAAGCCTTAGCGATTAGTTAGCTAGAGAAATAATCTAACCGATCCTTG
TGCCCTCTACAAAGTTATTTGTAATATACGATACTCAGTAATAAAAAAAAAAAAAAAAAAAAAAAAAA
```

Figure 14: Drosophila melanogaster POSH protein sequence (public gi:17737481; SEQ ID NO:11)

```
MDEHTLNDLLECSVCLERLDTTSKVLPCQHTFCRKCLQDIVASQHKLRCPECRILVSCKIDELPPNVLLM
RILEGMKQNAAAGKGEEKGEETETQPERAKPQPPAESVAPPDNQLLQLQSHQQSHQPARHKQRRFLLPHA
YALFDFASGEATDLKFKKGDLILIKHRIDNNWFVGQANGQEGTFPINYVKVSVPLPMPQCIAMYDFKMGP
NDEEGCLEFKKSTVIQVMRRVDHNWAEGRIGQTIGIFPIAFVELNAAAKKLLDSGLHTHPFCHPPKQQGQ
RALPPVPVIDPTVVTESSSGSSNSTPGSSNSSSTSSSNNCSPNHQISLPNTPQHVVASGSASVRFRDKGA
KEKRHSLNALLGGGAPLSLLQTNRHSAEILSLPHELSRLEVSSSTALKPTSAPQTSRVLKTTVQQQMQPN
LPWGYLALFPYKPRQTDELELKKGCVYIVTERCVDGWFKGKNWLDITGVFPGNYLTPLRARDQQQLMHQW
KYVPQNADAQMAQVQQHPVAPDVRLNNMLSMQPPDLPPRQQQATATTTSCSVWSKPVEALFSRKSEPKPE
TATASTTSSSSSGAVGLMRRLTHMKTRSKSPGASLQQVPKEAISTNVEFTTNPSAKLHPVHVRSGSCPSQ
LQHSQPLNETPAAKTAAQQQQFLPKQLPSASTNSVSYGSQRVKGSKERPHLICARQSLDAATFRSMYNNA
ASPPPPTTSVAPAVYAGGQQQVIPGGGAQSQLHANMIIAPSHRKSHSLDASHVLSPSSNMITEAAIKASA
TTKSPYCTRESRFRCIVPYPPNSDIELELHLGDIIYVQRKQKNGWYKGTHARTHKTGLFPASFVEPDC
```

Figure 15: POSH Domain Analysis
hPOSH protein sequence :
N terminus protein fragment of hPOSH (public gi:10432612):
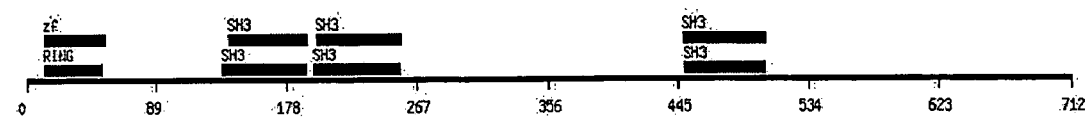
C terminus protein fragment of hPOSH (public gi:7959249):
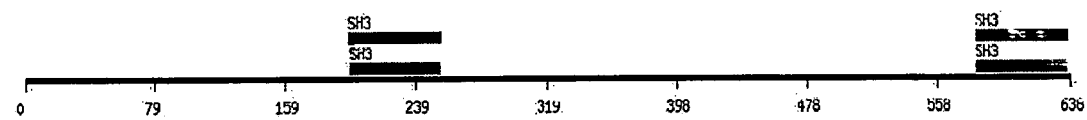
Mouse POSH Protein sequence (Public gi: 10946922):
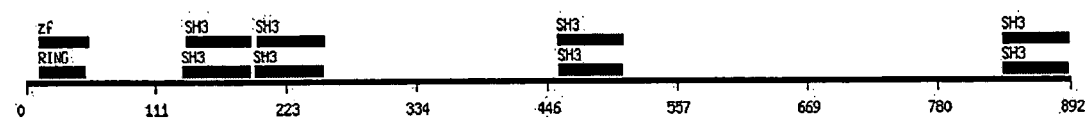
Drosophila melanogaster POSH protein sequence (public gi:17737481)
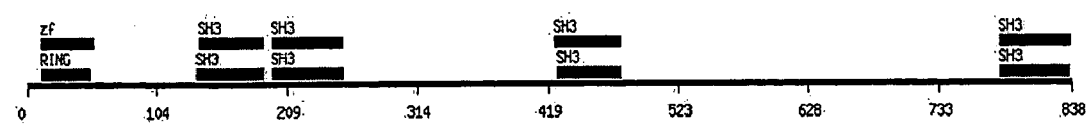

Figure 16: Human POSH has ubiquitin ligase activity
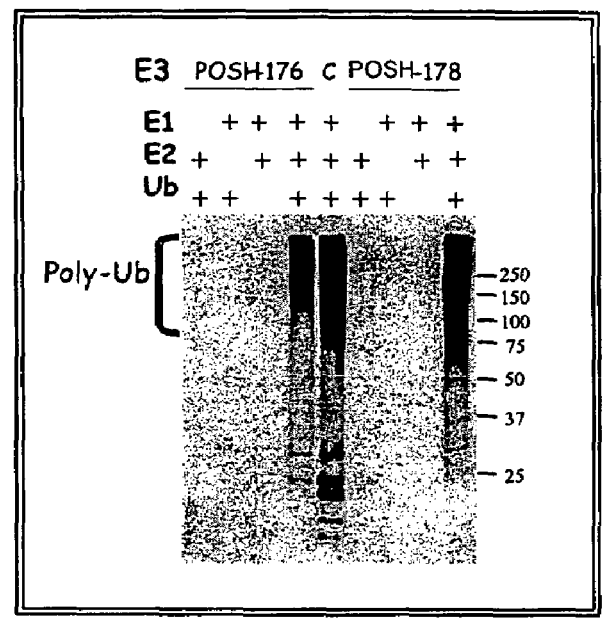

Figure 17A.
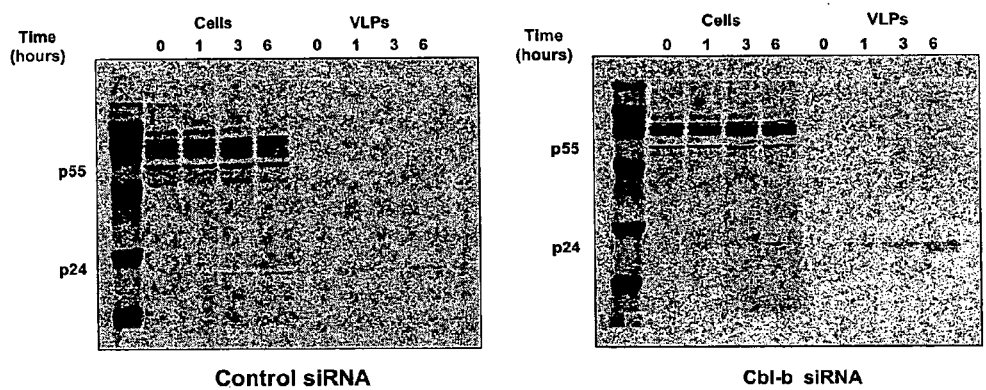
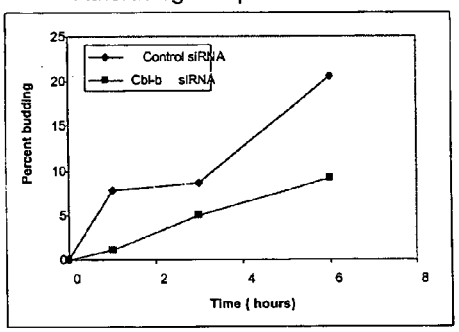
Immunoprecipitation of Cbi-b from siRNA-transfected cells
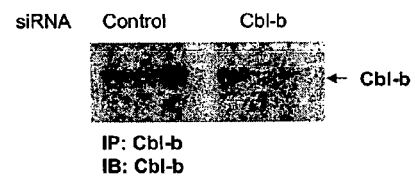
IP: Cbl-b
IB: Cbl-b a. Growth curve of HeLa SS cells as a function of time.
b. Levels of POSH expression as a function of time after POSH siRNA transfection.

RT activity in VLP secreted from cells treated with indicated siRNAs.

SEQUENCE LISTING

<160> NUMBER OF SEQ ID NOS: 58

<210> SEQ ID NO 1
<211> LENGTH: 2667
<212> TYPE: DNA
<213> ORGANISM: Homo sapiens

<400> SEQUENCE: 1

```
atggatgaat cagccttgtt ggatcttttg gagtgtccgg tgtgtctaga gcgccttgat      60
gcttctgcga aggtcttgcc ttgccagcat acgttttgca agcgatgttt gctggggatc     120
gtaggttctc gaaatgaact cagatgtccc gagtgcagga ctcttgttgg ctcgggtgtc     180
gaggagcttc ccagtaacat cttgctggtc agacttctgg atggcatcaa acagaggcct     240
tggaaacctg gtcctggtgg gggaagtggg accaactgca caaatgcatt aaggtctcag     300
agcagcactg tggctaattg tagctcaaaa gatctgcaga gctcccaggg cggacagcag     360
```

```
cctcgggtgc aatcctggag ccccccagtg aggggtatac ctcagttacc atgtgccaaa    420
gcgttataca actatgaagg aaaagagcct ggagacctta aattcagcaa aggcgacatc    480
atcattttgc gaagacaagt ggatgaaaat tggtaccatg gggaagtcaa tggaatccat    540 ggcttttttcc ccaccaactt tgtgcagatt attaaaccgt tacctcagcc cccacctcag    600
tgcaaagcac tttatgactt tgaagtgaaa gacaaggaag cagacaaaga ttgccttcca    660
tttgcaaagg atgatgttct gactgtgatc cgaagagtgg atgaaaactg gctgaagga    720 atgctggcag acaaaatagg aatatttcca atttcatatg ttgagtttaa ctcggctgct    780
aagcagctga tagaatggga taagcctcct gtgccaggag ttgatgctgg agaatgttcc    840
tcggcagcag cccagagcag cactgcccca aagcactccg acaccaagaa gaacaccaaa    900
aagcggcact ccttcacttc cctcactatg gccaacaagt cctcccaggc atcccagaac    960
cgccactcca tggagatcag ccccccctgtc ctcatcagct ccagcaaccc cactgctgct   1020
gcacggatca gcgagctgtc tgggctctcc tgcagtgccc cttctcaggt tcatataagt   1080
accaccgggt taattgtgac cccgccccca agcagcccag tgacaactgg cccctcgttt   1140
actttcccat cagatgttcc ctaccaagct gcccttggaa ctttgaatcc tcctcttcca   1200 ccacccccctc tcctggctgc cactgtcctt gcctccacac caccaggcgc caccgccgcc   1260
gctgctgctg ctggaatggg accgaggccc atggcaggat ccactgacca gattgcacat   1320
ttacggccgc agactcgccc cagtgtgtat gttgctatat atccatacac tcctcggaaa   1380
gaggatgaac tagagctgag aaaaggggag atgtttttag tgtttgagcg ctgccaggat   1440
ggctggttca aagggacatc catgcatacc agcaagatag gggttttccc tggcaattat   1500
gtggcaccag tcacaagggc ggtgacaaat gcttcccaag ctaaagtccc tatgtctaca   1560
gctggccaga caagtcgggg agtgaccatg gtcagtcctt ccacggcagg agggcctgcc   1620
cagaagctcc agggaaatgg cgtggctggg agtcccagtg ttgtcccccgc agctgtggta   1680 tcagcagctc acatccagac aagtcctcag gctaaggtct tgttgcacat gacggggcaa   1740
atgacagtca accaggcccg caatgctgtg aggacagttg cagcgcacaa ccaggaacgc   1800
cccacggcag cagtgacacc catccaggta cagaatgccg ccggcctcag ccctgcatct   1860
gtgggcctgt cccatcactc gctggcctcc ccacaacctg cgcctctgat gccaggctca   1920
gccacgcaca ctgctgccat cagtatcagt cgagccagtg cccctctggc ctgtgcagca   1980
gctgctccac tgacttcccc aagcatcacc agtgcttctc tggaggctga gcccagtggc   2040
cggatagtga ccgttctccc tggactcccc acatctcctg acagtgcttc atcagcttgt   2100
gggaacagtt cagcaaccaa accagacaag gatagcaaaa aagaaaaaaa gggtttgttg   2160
aagttgcttt ctggcgcctc cactaaacgg aagccccgcg tgtctcctcc agcatcgccc   2220
accctagaag tggagctggg cagtgcagag cttcctctcc agggagcggt ggggcccgaa   2280
ctgccaccag gaggtggcca tggcaggca ggctcctgcc ctgtggacgg ggacggaccg   2340
gtcacgactg cagtggcagg agcagccctg gcccaggatg cttttcatag gaaggcaagt   2400
tccctggact ccgcagttcc catcgctcca cctcctcgcc aggcctgttc ctccctgggt   2460
cctgtcttga atgagtctag acctgtcgtt tgtgaaaggc acagggtggt ggtttcctat   2520
cctcctcaga gtgaggcaga acttgaactt aaagaaggag atattgtgtt tgttcataaa   2580
aaacgagagg atggctggtt caaaggcaca ttacaacgta atgggaaaac tggccttttc   2640
ccaggaagct ttgtggaaaa catatga                                       2667
```

```
<210> SEQ ID NO 2
<211> LENGTH: 888
<212> TYPE: PRT
<213> ORGANISM: Homo sapiens

<400> SEQUENCE: 2

Met Asp Glu Ser Ala Leu Leu Asp Leu Leu Glu Cys Pro Val Cys Leu
 1               5                  10                  15

Glu Arg Leu Asp Ala Ser Ala Lys Val Leu Pro Cys Gln His Thr Phe
            20                  25                  30

Cys Lys Arg Cys Leu Leu Gly Ile Val Gly Ser Arg Asn Glu Leu Arg
        35                  40                  45

Cys Pro Glu Cys Arg Thr Leu Val Gly Ser Gly Val Glu Glu Leu Pro
    50                  55                  60

Ser Asn Ile Leu Leu Val Arg Leu Leu Asp Gly Ile Lys Gln Arg Pro
 65                  70                  75                  80

Trp Lys Pro Gly Pro Gly Gly Ser Gly Thr Asn Cys Thr Asn Ala
                85                  90                  95

Leu Arg Ser Gln Ser Ser Thr Val Ala Asn Cys Ser Ser Lys Asp Leu
               100                 105                 110

Gln Ser Ser Gln Gly Gly Gln Gln Pro Arg Val Gln Ser Trp Ser Pro
           115                 120                 125

Pro Val Arg Gly Ile Pro Gln Leu Pro Cys Ala Lys Ala Leu Tyr Asn
       130                 135                 140

Tyr Glu Gly Lys Glu Pro Gly Asp Leu Lys Phe Ser Lys Gly Asp Ile
145                 150                 155                 160

Ile Ile Leu Arg Arg Gln Val Asp Glu Asn Trp Tyr His Gly Glu Val
                165                 170                 175

Asn Gly Ile His Gly Phe Phe Pro Thr Asn Phe Val Gln Ile Ile Lys
            180                 185                 190

Pro Leu Pro Gln Pro Pro Pro Gln Cys Lys Ala Leu Tyr Asp Phe Glu
        195                 200                 205

Val Lys Asp Lys Glu Ala Asp Lys Asp Cys Leu Pro Phe Ala Lys Asp
    210                 215                 220

Asp Val Leu Thr Val Ile Arg Arg Val Asp Glu Asn Trp Ala Glu Gly
225                 230                 235                 240

Met Leu Ala Asp Lys Ile Gly Ile Phe Pro Ile Ser Tyr Val Glu Phe
                245                 250                 255

Asn Ser Ala Ala Lys Gln Leu Ile Glu Trp Asp Lys Pro Pro Val Pro
            260                 265                 270

Gly Val Asp Ala Gly Glu Cys Ser Ala Ala Ala Gln Ser Ser Thr
        275                 280                 285

Ala Pro Lys His Ser Asp Thr Lys Lys Asn Thr Lys Lys Arg His Ser
    290                 295                 300

Phe Thr Ser Leu Thr Met Ala Asn Lys Ser Ser Gln Ala Ser Gln Asn
305                 310                 315                 320

Arg His Ser Met Glu Ile Ser Pro Pro Val Leu Ile Ser Ser Ser Asn
                325                 330                 335

Pro Thr Ala Ala Ala Arg Ile Ser Glu Leu Ser Gly Leu Ser Cys Ser
            340                 345                 350

Ala Pro Ser Gln Val His Ile Ser Thr Thr Gly Leu Ile Val Thr Pro
        355                 360                 365

Pro Pro Ser Ser Pro Val Thr Thr Gly Pro Ser Phe Thr Phe Pro Ser
    370                 375                 380
```

```
Asp Val Pro Tyr Gln Ala Ala Leu Gly Thr Leu Asn Pro Pro Leu Pro
385                 390                 395                 400

Pro Pro Pro Leu Leu Ala Ala Thr Val Leu Ala Ser Thr Pro Pro Gly
                405                 410                 415

Ala Thr Ala Ala Ala Ala Ala Gly Met Gly Pro Arg Pro Met Ala
            420                 425                 430

Gly Ser Thr Asp Gln Ile Ala His Leu Arg Pro Gln Thr Arg Pro Ser
            435                 440                 445

Val Tyr Val Ala Ile Tyr Pro Tyr Thr Pro Arg Lys Glu Asp Glu Leu
        450                 455                 460

Glu Leu Arg Lys Gly Glu Met Phe Leu Val Phe Glu Arg Cys Gln Asp
465                 470                 475                 480

Gly Trp Phe Lys Gly Thr Ser Met His Thr Ser Lys Ile Gly Val Phe
                485                 490                 495

Pro Gly Asn Tyr Val Ala Pro Val Thr Arg Ala Val Thr Asn Ala Ser
            500                 505                 510

Gln Ala Lys Val Pro Met Ser Thr Ala Gly Gln Thr Ser Arg Gly Val
        515                 520                 525

Thr Met Val Ser Pro Ser Thr Ala Gly Gly Pro Ala Gln Lys Leu Gln
        530                 535                 540

Gly Asn Gly Val Ala Gly Ser Pro Ser Val Val Pro Ala Ala Val Val
545                 550                 555                 560

Ser Ala Ala His Ile Gln Thr Ser Pro Gln Ala Lys Val Leu Leu His
                565                 570                 575

Met Thr Gly Gln Met Thr Val Asn Gln Ala Arg Asn Ala Val Arg Thr
                580                 585                 590

Val Ala Ala His Asn Gln Glu Arg Pro Thr Ala Ala Val Thr Pro Ile
            595                 600                 605

Gln Val Gln Asn Ala Ala Gly Leu Ser Pro Ala Ser Val Gly Leu Ser
        610                 615                 620

His His Ser Leu Ala Ser Pro Gln Pro Ala Pro Leu Met Pro Gly Ser
625                 630                 635                 640

Ala Thr His Thr Ala Ala Ile Ser Ile Ser Arg Ala Ser Ala Pro Leu
                645                 650                 655

Ala Cys Ala Ala Ala Ala Pro Leu Thr Ser Pro Ser Ile Thr Ser Ala
            660                 665                 670

Ser Leu Glu Ala Glu Pro Ser Gly Arg Ile Val Thr Val Leu Pro Gly
        675                 680                 685

Leu Pro Thr Ser Pro Asp Ser Ala Ser Ser Ala Cys Gly Asn Ser Ser
        690                 695                 700

Ala Thr Lys Pro Asp Lys Asp Ser Lys Lys Glu Lys Lys Gly Leu Leu
705                 710                 715                 720

Lys Leu Leu Ser Gly Ala Ser Thr Lys Arg Lys Pro Arg Val Ser Pro
                725                 730                 735

Pro Ala Ser Pro Thr Leu Glu Val Glu Leu Gly Ser Ala Glu Leu Pro
            740                 745                 750

Leu Gln Gly Ala Val Gly Pro Glu Leu Pro Pro Gly Gly His Gly
        755                 760                 765

Arg Ala Gly Ser Cys Pro Val Asp Gly Asp Gly Pro Val Thr Thr Ala
        770                 775                 780

Val Ala Gly Ala Ala Leu Ala Gln Asp Ala Phe His Arg Lys Ala Ser
785                 790                 795                 800

Ser Leu Asp Ser Ala Val Pro Ile Ala Pro Pro Arg Gln Ala Cys
```

|     |     |     |     |     |     |
| --- | --- | --- | --- | --- | --- |
|     | 805 |     | 810 |     | 815 |
| Ser | Ser | Leu | Gly | Pro | Val | Leu | Asn | Glu | Ser | Arg | Pro | Val | Val | Cys | Glu |
|     |     |     | 820 |     |     |     | 825 |     |     |     | 830 |     |     |     |     |

Ser Ser Leu Gly Pro Val Leu Asn Glu Ser Arg Pro Val Val Cys Glu
            820                 825                 830

Arg His Arg Val Val Ser Tyr Pro Pro Gln Ser Glu Ala Glu Leu
            835                 840                 845

Glu Leu Lys Glu Gly Asp Ile Val Phe Val His Lys Lys Arg Glu Asp
            850                 855                 860

Gly Trp Phe Lys Gly Thr Leu Gln Arg Asn Gly Lys Thr Gly Leu Phe
865                 870                 875                 880

Pro Gly Ser Phe Val Glu Asn Ile
            885

<210> SEQ ID NO 3
<211> LENGTH: 5128
<212> TYPE: DNA
<213> ORGANISM: Homo sapiens

<400> SEQUENCE: 3

| | | | | | |
|---|---|---|---|---|---|
| ctgagagaca | ctgcgagcgg | cgagcgcggt | ggggccgcat | ctgcatcagc | cgccgcagcc | 60 |
| gctgcgggc | cgcgaacaaa | gaggaggagc | cgaggcgcga | gagcaaagtc | tgaaatggat | 120 |
| gttacatgag | tcattttaag | ggatgcacac | aactatgaac | atttctgaag | attttttctc | 180 |
| agtaaagtag | ataagatgg | atgaatcagc | cttgttggat | cttttggagt | gtccggtgtg | 240 |
| tctagagcgc | cttgatgctt | ctgcgaaggt | cttgccttgc | cagcatacgt | tttgcaagcg | 300 |
| atgtttgctg | gggatcgtag | gttctcgaaa | tgaactcaga | tgtcccgagt | gcaggactct | 360 |
| tgttggctcg | ggtgtcgagg | agcttcccag | taacatcttg | ctggtcagac | ttctggatgg | 420 |
| catcaaacag | aggccttgga | aacctggtcc | tggtgggggga | agtgggacca | actgcacaaa | 480 |
| tgcattaagg | tctcagagca | gcactgtggc | taattgtagc | tcaaaagatc | tgcagagctc | 540 |
| ccagggcgga | cagcagcctc | gggtgcaatc | ctggagcccc | ccagtgaggg | gtatacctca | 600 |
| gttaccatgt | gccaaagcgt | tatacaacta | tgaaggaaaa | gagcctggag | accttaaatt | 660 |
| cagcaaaggc | gacatcatca | ttttgcgaag | acaagtggat | gaaaattggt | accatggggga | 720 |
| agtcaatgga | atccatggct | ttttccccac | caactttgtg | cagattatta | aaccgttacc | 780 |
| tcagccccca | cctcagtgca | aagcacttta | tgactttgaa | gtgaaagaca | aggaagcaga | 840 |
| caaagattgc | cttccatttg | caaaggatga | tgttctgact | gtgatccgaa | gagtggatga | 900 |
| aaactgggct | gaaggaatgc | tggcagacaa | aataggaata | tttccaattt | catatgttga | 960 |
| gtttaactcg | gctgctaagc | agctgataga | atgggataag | cctcctgtgc | caggagttga | 1020 |
| tgctggagaa | tgttcctcgg | cagcagccca | gagcagcact | gccccaaagc | actccgacac | 1080 |
| caagaagaac | accaaaaagc | ggcactcctt | cacttccctc | actatggcca | acaagtcctc | 1140 |
| ccaggcatcc | cagaaccgcc | actccatgga | gatcagcccc | cctgtcctca | tcagctccag | 1200 |
| caacccact | gctgctgcac | ggatcagcga | gctgtctggg | ctctcctgca | gtgcccttc | 1260 |
| tcaggttcat | ataagtacca | ccgggttaat | tgtgaccccg | cccccaagca | gcccagtgac | 1320 |
| aactggcccc | tcgtttactt | tcccatcaga | tgttccctac | caagctgccc | ttggaacttt | 1380 |
| gaatcctcct | cttccaccac | cccctctcct | ggctgccact | gtccttgcct | ccacaccacc | 1440 |
| aggcgccacc | gccgccgctg | ctgctgctgg | aatgggaccg | aggcccatgg | caggatccac | 1500 |
| tgaccagatt | gcacatttac | ggccgcagac | tcgccccagt | gtgtatgttg | ctatatatcc | 1560 |
| atacactcct | cggaaagagg | atgaactaga | gctgagaaaa | ggggagatgt | ttttagtgtt | 1620 |

```
tgagcgctgc caggatggct ggttcaaagg gacatccatg cataccagca agatagsgggt    1680 tttccctggc aattatgtgg caccagtcac aagggcggtg acaaatgctt cccaagctaa    1740
agtccctatg tctacagctg ccagacaag tcggggagtg accatggtca gtccttccac     1800
ggcaggaggg cctgcccaga agctccaggg aaatggcgtg gctgggagtc ccagtgttgt    1860
ccccgcagct gtggtatcag cagctcacat ccagacaagt cctcaggcta aggtcttgtt    1920
gcacatgacg gggcaaatga cagtcaacca ggcccgcaat gctgtgagga cagttgcagc    1980
gcacaaccag gaacgcccca cggcagcagt gacacccatc caggtacaga atgccgccgg    2040
cctcagccct gcatctgtgg gcctgtccca tcactcgctg gcctcccac aacctgcgcc     2100 tctgatgcca ggctcagcca cgcacactgc tgccatcagt atcagtcgag ccagtgcccc    2160
tctggcctgt gcagcagctg ctccactgac ttccccaagc atcaccagtg cttctctgga    2220
ggctgagccc agtggccgga tagtgaccgt ctccctgga ctccccacat tcctgacag      2280 tgcttcatca gcttgtggga acagttcagc aaccaaacca gacaaggata gcaaaaaga     2340 aaaaagggt ttgttgaagt tgctttctgg cgcctccact aaacggaagc cccgcgtgtc     2400
tcctccagca tcgcccaccc tagaagtgga gctgggcagt gcagagcttc ctctccaggg    2460
agcggtgggg cccgaactgc caccaggagg tggccatggc agggcaggct cctgccctgt    2520
ggacggggac ggaccggtca cgactgcagt ggcaggagca gccctggccc aggatgcttt    2580
tcataggaag gcaagttccc tggactccgc agttcccatc gctccacctc ctcgccaggc    2640
ctgttcctcc ctgggtcctg tcttgaatga gtctagacct gtcgtttgtg aaaggcacag    2700
ggtggtggtt tcctatcctc ctcagagtga ggcagaactt gaacttaaag aaggagatat    2760
tgtgtttgtt cataaaaaac gagaggatgg ctggttcaaa ggcacattac aacgtaatgg    2820
gaaaactggc cttttcccag gaagctttgt ggaaaacata tgaggagact gacactgaag    2880
aagcttaaaa tcacttcaca caacaaagta gcacaaagca gtttaacaga aagagcacat    2940
ttgtggactt ccagatggtc aggagatgag caaaggattg gtatgtgact ctgatgcccc    3000
agcacagtta ccccagcgag cagagtgaag aagatgtttg tgtgggtttt gttagtctgg    3060
attcggatgt ataaggtgtg ccttgtactg tctgatttac tacacagaga aactttttt     3120 ttttttttaag atatatgact aaaatggaca attgttaca aggcttaact aatttatttg     3180
cttttttaaa cttgaacttt tcgtataata gatacgttct ttggattatg attttaagaa    3240
attattaatt tatgaaatga taggtaagga gaagctggat tatctcctgt tgagagcaag    3300
agattcgttt tgacatagag tgaatgcatt ttcccctctc ctcctccctg ctaccattat    3360 attttgggt tatgtttgc ttctttaaga tagaaatccc agttctctaa tttggttttc       3420
ttctttggga aaccaaacat acaaatgaat cagtatcaat tagggcctgg ggtagagaga    3480
cagaaacttg agagaagaga agttagtgat tccctctctt tctagtttgg taggaatcac    3540
cctgaagacc tagtcctcaa tttaattgtg tgggtttta attttcctag aatgaagtga     3600
ctgaaacaat gagaaagaat acagcacaac ccttgaacaa aatgtattta gaaatatatt    3660 tagtttata gcagaagcag ctcaattgtt tggttggaaa gtaggggaaa ttgaagttgt      3720
agtcactgtc tgagaatggc tatgaagcgt catttcacat tttaccccaa ctgacctgca    3780
tgcccaggac acaagtaaaa catttgtgag atagtggtgg taagtgatgc actcgtgtta    3840
agtcaaaggc tataagaaac actgtgaaaa gttcatattc atccattgtg attctttccc    3900
cacgtcttgc atgtattact ggattcccac agtaatatag actgtgcatg gtgtgtatat    3960
ttcattgcga tttcctgtta agatgagttt gtactcagaa ttgaccaatt caggaggtgt    4020
```

```
aaaaataaac agtgttctct tctctacccc aaagccacta ctgaccaagg tctcttcagt      4080
gcactcgctc cctctctggc taaggcatgc attagccact acacaagtca ttagtgaaag      4140
tggtctttta tgtcctccca gcagacagac atcaaggatg agttaaccag agactactc      4200 ctgtgactgt ggagctctgg aaggcttggt gggagtgaat ttgcccacac cttacaattg      4260
tggcaggatc cagaagagcc tgtctttta tatccattcc ttgatgtcat tggcctctcc      4320
caccgatttc attacggtgc cacgcagtca tggatctggg tagtccggaa acaaaagga      4380 gggaagacag cctggtaatg aataagatcc ttaccacagt tttctcatgg gaaatacata      4440 ataaacccctt tcatctttt ttttttcctt taagaattaa aactgggaaa tagaaacatg      4500
aactgaaaag tcttgcaatg acaagaggtt tcatggtctt aaaaagatac tttatatggt      4560
tgaagatgaa atcattccta aattaacctt tttttttaaaa aaaaacaatg tatattatgt      4620
tcctgtgtgt tgaatttaaa aaaaaaaaat actttacttg gatattcatg taatatataa      4680
aggtttggtg aaatgaactt tagttaggaa aaagctggca tcagctttca tctgtgtaag      4740
ttgacaccaa tgtgtcataa tattctttat tttgggaaat tagtgtattt tataaaaatt      4800
ttaaaaagaa aaaagactac tacaggttaa gataattttt ttacctgtct tttctccata      4860
ttttaagcta tgtgattgaa gtacctctgt tcatagtttc ctggtataaa gttggttaaa      4920
atttcatctg ttaatagatc attaggtaat ataatgtatg ggttttctat tggttttttg      4980
cagacagtag agggagattt tgtaacaagg gcttgttaca cagtgatatg gtaatgataa      5040
aattgcaatt tatcactcct tttcatgtta ataatttgag gactggataa aaggtttcaa      5100
gattaaaatt tgatgttcaa acctttgt                                        5128

<210> SEQ ID NO 4
<211> LENGTH: 2331
<212> TYPE: DNA
<213> ORGANISM: Homo sapiens

<400> SEQUENCE: 4
ctgagagaca ctgcgagcgg cgagcgcggt ggggccgcat ctgcatcagc cgccgcagcc        60 gctgcgggc cgcgaacaaa gaggaggagc cgaggcgcga gagcaaagtc tgaaatggat       120
gttacatgag tcattttaag gatgcacaca actatgaaca tttctgaaga tttttttctca      180 gtaaagtaga taaagatgga tgaatcagcc ttgttggatc ttttggagtg tccggtgtgt      240
ctagagcgcc ttgatgcttc tgcgaaggtc ttgccttgcc agcatacgtt ttgcaagcga      300
tgtttgctgg ggatcgtagg ttctcgaaat gaactcagat gtcccgagtg caggactctt      360
gttggctcgg gtgtcgagga gcttccccagt aacatcttgc tggtcagact tctggatggc      420
atcaaacaga ggccttggaa acctggtcct ggtggggaa gtgggaccaa ctgcacaaat      480
gcattaaggt ctcagagcag cactgtggct aattgtagct caaagatct gcagagctcc      540 cagggcggac agcagcctcg ggtgcaatcc tggagccccc cagtgagggg tatacctcag       600
ttaccatgtg ccaaagcgtt atacaactat gaaggaaaag agcctggaga ccttaaattc       660
agcaaaggcg acatcatcat tttgcgaaga caagtggatg aaaattggta ccatgggga       720 gtcaatggaa tccatggctt tttccccacc aactttgtgc agattattaa accgttacct       780 cagccccacac ctcagtgcaa agcactttat gactttgaag tgaaagacaa ggaagcagac       840
aaagattgcc ttccatttgc aaaggatgat gttctgactg tgatccgaag agtggatgaa       900
aactgggctg aaggaatgct ggcagacaaa ataggaatat ttccaattc atatgttgag      960
```

-continued

```
tttaactcgg ctgctaagca gctgatagaa tgggataagc ctcctgtgcc aggagttgat      1020
gctggagaat gttcctcggc agcagcccag agcagcactg ccccaaagca ctccgacacc      1080
aagaagaaca ccaaaaagcg gcactccttc acttccctca ctatggccaa caagtcctcc      1140
caggcatccc agaaccgcca ctccatggag atcagccccc ctgtcctcat cagctccagc      1200
aaccccactg ctgctgcacg gatcagcgag ctgtctgggc tctcctgcag tgcccttct       1260 caggttcata taagtaccac cgggttaatt gtgaccccgc ccccaagcag cccagtgaca      1320
actggcccct cgtttacttt cccatcagat gttccctacc aagctgccct tggaactttg      1380
aatcctcctc ttccaccacc ccctctcctg gctgccactg tccttgcctc cacaccacca      1440
ggcgccaccg ccgccgctgc tgctgctgga atgggaccga ggcccatggc aggatccact      1500
gaccagattg cacatttacg gccgcagact cgccccagtg tgtatgttgc tatatatcca      1560
tacactcctc ggaaagagga tgaactagag ctgagaaaag gggagatgtt tttagtgttt      1620
gagcgctgcc aggatggctg gttcaaaggg acatccatgc ataccagcaa gatagggggtt    1680 ttccctggca attatgtggc accagtcaca agggcggtga caaatgcttc ccaagctaaa      1740
gtccctatgt ctacagctgg ccagacaagt cggggagtga ccatggtcag tccttccacg      1800
gcaggagggc ctgcccagaa gctccaggga atggcgtgg ctgggagtcc cagtgttgtc       1860
cccgcagctg tggtatcagc agctcacatc cagacaagtc ctcaggctaa ggtcttgttg      1920
cacatgacgg ggcaaatgac agtcaaccag gcccgcaatg ctgtgaggac agttgcagcg      1980
cacaaccagg aacgcccac ggcagcagtg acacccatcc aggtacagaa tgccgccggc       2040
ctcagccctg catctgtggg cctgtcccat cactcgctgg cctccccaca acctgcgcct      2100
ctgatgccag gctcagccac gcacactgct gccatcagta tcagtcgagc cagtgccct      2160 ctggcctgtg cagcagctgc tccactgact tccccaagca tcaccagtgc ttctctggag      2220
gctgagccca gtggccggat agtgaccgtt ctccctggac tccccacatc tcctgacagt      2280
gcttcatcag cttgtgggaa cagttcagca accaaaccag acaaggatag c               2331
```

<210> SEQ ID NO 5
<211> LENGTH: 712
<212> TYPE: PRT
<213> ORGANISM: Homo sapiens

<400> SEQUENCE: 5

```
Met Asp Glu Ser Ala Leu Leu Asp Leu Leu Glu Cys Pro Val Cys Leu
 1               5                  10                  15

Glu Arg Leu Asp Ala Ser Ala Lys Val Leu Pro Cys Gln His Thr Phe
            20                  25                  30

Cys Lys Arg Cys Leu Leu Gly Ile Val Gly Ser Arg Asn Glu Leu Arg
        35                  40                  45

Cys Pro Glu Cys Arg Thr Leu Val Gly Ser Gly Val Glu Glu Leu Pro
    50                  55                  60

Ser Asn Ile Leu Leu Val Arg Leu Leu Asp Gly Ile Lys Gln Arg Pro
65                  70                  75                  80

Trp Lys Pro Gly Pro Gly Gly Ser Gly Thr Asn Cys Thr Asn Ala
                85                  90                  95

Leu Arg Ser Gln Ser Ser Thr Val Ala Asn Cys Ser Ser Lys Asp Leu
            100                 105                 110

Gln Ser Ser Gln Gly Gly Gln Gln Pro Arg Val Gln Ser Trp Ser Pro
        115                 120                 125

Pro Val Arg Gly Ile Pro Gln Leu Pro Cys Ala Lys Ala Leu Tyr Asn
```

-continued

```
                130                 135                 140
Tyr Glu Gly Lys Glu Pro Gly Asp Leu Lys Phe Ser Lys Gly Asp Ile
145                 150                 155                 160

Ile Ile Leu Arg Arg Gln Val Asp Glu Asn Trp Tyr His Gly Glu Val
                165                 170                 175

Asn Gly Ile His Gly Phe Phe Pro Thr Asn Phe Val Gln Ile Ile Lys
                180                 185                 190

Pro Leu Pro Gln Pro Pro Gln Cys Lys Ala Leu Tyr Asp Phe Glu
            195                 200                 205

Val Lys Asp Lys Glu Ala Asp Lys Asp Cys Leu Pro Phe Ala Lys Asp
    210                 215                 220

Asp Val Leu Thr Val Ile Arg Arg Val Asp Glu Asn Trp Ala Glu Gly
225                 230                 235                 240

Met Leu Ala Asp Lys Ile Gly Ile Phe Pro Ile Ser Tyr Val Glu Phe
                245                 250                 255

Asn Ser Ala Ala Lys Gln Leu Ile Glu Trp Asp Lys Pro Pro Val Pro
                260                 265                 270

Gly Val Asp Ala Gly Glu Cys Ser Ser Ala Ala Gln Ser Ser Thr
            275                 280                 285

Ala Pro Lys His Ser Asp Thr Lys Lys Asn Thr Lys Lys Arg His Ser
            290                 295                 300

Phe Thr Ser Leu Thr Met Ala Asn Lys Ser Ser Gln Ala Ser Gln Asn
305                 310                 315                 320

Arg His Ser Met Glu Ile Ser Pro Pro Val Leu Ile Ser Ser Ser Asn
                325                 330                 335

Pro Thr Ala Ala Ala Arg Ile Ser Glu Leu Ser Gly Leu Ser Cys Ser
                340                 345                 350

Ala Pro Ser Gln Val His Ile Ser Thr Thr Gly Leu Ile Val Thr Pro
            355                 360                 365

Pro Pro Ser Ser Pro Val Thr Thr Gly Pro Ser Phe Thr Phe Pro Ser
            370                 375                 380

Asp Val Pro Tyr Gln Ala Ala Leu Gly Thr Leu Asn Pro Pro Leu Pro
385                 390                 395                 400

Pro Pro Pro Leu Leu Ala Ala Thr Val Leu Ala Ser Thr Pro Gly
                405                 410                 415

Ala Thr Ala Ala Ala Ala Ala Gly Met Gly Pro Arg Pro Met Ala
            420                 425                 430

Gly Ser Thr Asp Gln Ile Ala His Leu Arg Pro Gln Thr Arg Pro Ser
            435                 440                 445

Val Tyr Val Ala Ile Tyr Pro Tyr Thr Pro Arg Lys Glu Asp Glu Leu
    450                 455                 460

Glu Leu Arg Lys Gly Glu Met Phe Leu Val Phe Glu Arg Cys Gln Asp
465                 470                 475                 480

Gly Trp Phe Lys Gly Thr Ser Met His Thr Ser Lys Ile Gly Val Phe
                485                 490                 495

Pro Gly Asn Tyr Val Ala Pro Val Thr Arg Ala Val Thr Asn Ala Ser
            500                 505                 510

Gln Ala Lys Val Pro Met Ser Thr Ala Gly Gln Thr Ser Arg Gly Val
            515                 520                 525

Thr Met Val Ser Pro Ser Thr Ala Gly Gly Pro Ala Gln Lys Leu Gln
    530                 535                 540

Gly Asn Gly Val Ala Gly Ser Pro Ser Val Val Pro Ala Ala Val Val
545                 550                 555                 560
```

```
Ser Ala Ala His Ile Gln Thr Ser Pro Gln Ala Lys Val Leu Leu His
                565                 570                 575

Met Thr Gly Gln Met Thr Val Asn Gln Ala Arg Asn Ala Val Arg Thr
            580                 585                 590

Val Ala Ala His Asn Gln Glu Arg Pro Thr Ala Ala Val Thr Pro Ile
        595                 600                 605

Gln Val Gln Asn Ala Ala Gly Leu Ser Pro Ala Ser Val Gly Leu Ser
    610                 615                 620

His His Ser Leu Ala Ser Pro Gln Pro Ala Pro Leu Met Pro Gly Ser
625                 630                 635                 640

Ala Thr His Thr Ala Ala Ile Ser Ile Ser Arg Ala Ser Ala Pro Leu
                645                 650                 655

Ala Cys Ala Ala Ala Ala Pro Leu Thr Ser Pro Ser Ile Thr Ser Ala
            660                 665                 670

Ser Leu Glu Ala Glu Pro Ser Gly Arg Ile Val Thr Val Leu Pro Gly
        675                 680                 685

Leu Pro Thr Ser Pro Asp Ser Ala Ser Ser Ala Cys Gly Asn Ser Ser
    690                 695                 700

Ala Thr Lys Pro Asp Lys Asp Ser
705                 710
```

```
<210> SEQ ID NO 6
<211> LENGTH: 4182
<212> TYPE: DNA
<213> ORGANISM: Homo sapiens

<400> SEQUENCE: 6
atttcatatg ttgagtttaa ctcggctgct aagcagctga tagaatggga taagcctcct      60
gtgccaggag ttgatgctgg agaatgttcc tcggcagcag cccagagcag cactgcccca     120
aagcactccg acaccaagaa gaacaccaaa aagcggcact ccttcacttc cctcactatg     180
gccaacaagt cctcccaggc atcccagaac cgccactcca tggagatcag ccccctgtc     240 ctcatcagct ccagcaaccc cactgctgct gcacggatca gcgagctgtc tgggctctcc     300
tgcagtgccc cttctcaggt tcatataagt accaccgggt taattgtgac cccgccccca     360
agcagcccag tgacaactgg cccctcgttt actttcccat cagatgttcc ctaccaagct     420
gcccttggaa ctttgaatcc tcctcttcca ccacccctc tcctggctgc cactgtcctt     480
gcctccacac caccaggcgc caccgccgct gctgctgctg ctggaatggg accgaggccc     540
atggcaggat ccactgacca gattgcacat ttacggccgc agactcgccc cagtgtgtat     600
gttgctatat atccatacac tcctcggaaa gaggatgaac tagagctgag aaaaggggag     660 atgttttag tgtttgagcg ctgccaggat ggctggttca aagggacatc catgcatacc     720
agcaagatag gggttttccc tggcaattat gtggcaccag tcacaagggc ggtgacaaat     780
gcttcccaag ctaaagtccc tatgtctaca gctggccaga caagtcgggg agtgaccatg     840
gtcagtcctt ccacggcagg agggcctgcc cagaagctcc agggaaatgg cgtggctggg     900
agtcccagtg ttgtccccgc agctgtggta tcagcagctc acatccagac aagtcctcag     960
gctaaggtct tgttgcacat gacggggcaa atgacagtca accaggcccg caatgctgtg    1020
aggacagttg cagcgcacaa ccaggaacgc cccacggcag cagtgacacc catccaggta    1080
cagaatgccg ccggcctcag ccctgcatct gtgggcctgt ccatcactc gctggcctcc    1140 ccacaacctg cgcctctgat gccaggctca gccacgcaca ctgctgccat cagtatcagt    1200
```

```
cgagccagtg cccctctggc ctgtgcagca gctgctccac tgacttcccc aagcatcacc   1260
agtgcttctc tggaggctga gcccagtggc cggatagtga ccgttctccc tggactccca   1320
acatctcctg acagtgcttc atcagcttgt gggaacagtt cagcaaccaa accagacaag   1380
gatagcaaaa aagaaaaaaa gggtttgttg aagttgcttt ctggcgcctc cactaaacgg   1440
aagccccgcg tgtctcctcc agcatcgccc accctagaag tggagctggg cagtgcagag   1500
cttcctctcc agggagcggt ggggcccgaa ctgccaccag gaggtggcca tggcagggca   1560
ggctcctgcc ctgtggacgg ggacggaccg gtcacgactg cagtggcagg agcagccctg   1620
gcccaggatg cttttcatag gaaggcaagt tccctggact ccgcagttcc catcgctcca   1680
cctcctcgcc aggcctgttc ctccctgggt cctgtcttga atgagtctag acctgtcgtt   1740
tgtgaaaggc acagggtggt ggtttcctat cctcctcaga gtgaggcaga acttgaactt   1800
aaagaaggag atattgtgtt tgttcataaa aaacgagagg atggctggtt caaaggcaca   1860
ttacaacgta atgggaaaac tggccttttc ccaggaagct tgtgaaaaa catatgagga   1920 gactgacact gaagaagctt aaaatcactt cacacaacaa agtagcacaa agcagtttaa   1980
cagaaagagc acatttgtgg acttccagat ggtcaggaga tgagcaaagg attggtatgt   2040
gactctgatg ccccagcaca gttaccccag cgagcagagt gaagaagatg tttgtgtggg   2100
ttttgttagt ctggattcgg atgtataagg tgtgccttgt actgtctgat ttactacaca   2160
gagaaacttt ttttttttt taagatatat gactaaaatg gacaattgtt tacaaggctt   2220
aactaattta tttgcttttt taaacttgaa cttttcgtat aatagatacg ttctttggat   2280
tatgatttta agaaattatt aatttatgaa atgataggta aggagaagct ggattatctc   2340
ctgttgagag caagagattc gttttgacat agagtgaatg cattttcccc tctcctcctc   2400
cctgctacca ttatattttg gggttatgtt ttgcttcttt aagatagaaa tcccagttct   2460
ctaatttggt tttcttcttt gggaaaccaa acatacaaat gaatcagtat caattagggc   2520
ctggggtaga gagacagaaa cttgagagaa gagaagttag tgattccctc tctttctagt   2580
ttggtaggaa tcaccctgaa gacctagtcc tcaatttaat tgtgtgggtt tttaattttc   2640
ctagaatgaa gtgactgaaa caatgagaaa gaatacagca caaccccttga acaaaatgta   2700 tttagaaata tatttagttt tatagcagaa gcagctcaat tgtttggttg gaaagtaggg   2760
gaaattgaag ttgtagtcac tgtctgagaa tggctatgaa gcgtcatttc acattttacc   2820
ccaactgacc tgcatgccca ggacacaagt aaaacatttg tgagatagtg gtggtaagtg   2880
atgcactcgt gttaagtcaa aggctataag aaacactgtg aaaagttcat attcatccat   2940
tgtgattctt tccccacgtc ttgcatgtat tactggattc ccacagtaat atagactgtg   3000
catggtgtgt atatttcatt gcgatttcct gttaagatga gtttgtactc agaattgacc   3060
aattcaggag gtgtaaaaat aaacagtgtt ctcttctcta ccccaaagcc actactgacc   3120
aaggtctctt cagtgcactc gctccctctc tggctaaggc atgcattagc cactacacaa   3180
gtcattagtg aaagtggtct tttatgtcct cccagcagac agacatcaag gatgagttaa   3240
ccaggagact actcctgtga ctgtggagct ctggaaggct tggtgggagt gaatttgccc   3300
acaccttaca attgtggcag gatccagaag agcctgtctt tttatatcca ttccttgatg   3360
tcattggcct ctcccaccga tttcattacg gtgccacgca gtcatggatc tgggtagtcc   3420
ggaaaacaaa aggagggaag acagcctggt aatgaataag atccttacca cagttttctc   3480
atgggaaata cataataaac cctttcatct ttttttttt cctttaagaa ttaaaactgg   3540
gaaatagaaa catgaactga aaagtcttgc aatgacaaga ggtttcatgg tcttaaaaag   3600
```

-continued

```
atactttata tggttgaaga tgaaatcatt cctaaattaa cctttttttt aaaaaaaaac    3660
aatgtatatt atgttcctgt gtgttgaatt taaaaaaaaa aaatacttta cttggatatt    3720 catgtaaatat ataaaggttt ggtgaaatga actttagtta ggaaaaagct ggcatcagct    3780
ttcatctgtg taagttgaca ccaatgtgtc ataatattct ttattttggg aaattagtgt    3840
attttataaa aattttaaaa agaaaaaaga ctactacagg ttaagataat ttttttacct    3900
gtcttttctc catattttaa gctatgtgat tgaagtacct ctgttcatag tttcctggta    3960
taaagttggt taaaatttca tctgttaata gatcattagg taatataatg tatgggtttt    4020
ctattggttt tttgcagaca gtagagggag attttgtaac aagggcttgt tacacagtga    4080
tatggtaatg ataaaattgc aatttatcac tccttttcat gttaataatt tgaggactgg    4140
ataaaaggtt tcaagattaa aatttgatgt tcaaaccttt gt                       4182
```

<210> SEQ ID NO 7
<211> LENGTH: 638
<212> TYPE: PRT
<213> ORGANISM: Homo sapiens

<400> SEQUENCE: 7

```
Ile Ser Tyr Val Glu Phe Asn Ser Ala Ala Lys Gln Leu Ile Glu Trp
  1               5                  10                  15

Asp Lys Pro Pro Val Pro Gly Val Asp Ala Gly Glu Cys Ser Ser Ala
             20                  25                  30

Ala Ala Gln Ser Ser Thr Ala Pro Lys His Ser Asp Thr Lys Lys Asn
         35                  40                  45

Thr Lys Lys Arg His Ser Phe Thr Ser Leu Thr Met Ala Asn Lys Ser
 50                  55                  60

Ser Gln Ala Ser Gln Asn Arg His Ser Met Glu Ile Ser Pro Pro Val
 65                  70                  75                  80

Leu Ile Ser Ser Asn Pro Thr Ala Ala Arg Ile Ser Glu Leu
             85                  90                  95

Ser Gly Leu Ser Cys Ser Ala Pro Ser Gln Val His Ile Ser Thr Thr
            100                 105                 110

Gly Leu Ile Val Thr Pro Pro Ser Ser Pro Val Thr Thr Gly Pro
        115                 120                 125

Ser Phe Thr Phe Pro Ser Asp Val Pro Tyr Gln Ala Ala Leu Gly Thr
    130                 135                 140

Leu Asn Pro Pro Leu Pro Pro Pro Leu Leu Ala Ala Thr Val Leu
145                 150                 155                 160

Ala Ser Thr Pro Pro Gly Ala Thr Ala Ala Ala Ala Ala Gly Met
                165                 170                 175

Gly Pro Arg Pro Met Ala Gly Ser Thr Asp Gln Ile Ala His Leu Arg
                180                 185                 190

Pro Gln Thr Arg Pro Ser Val Tyr Val Ala Ile Tyr Pro Tyr Thr Pro
            195                 200                 205

Arg Lys Glu Asp Glu Leu Glu Leu Arg Lys Gly Glu Met Phe Leu Val
        210                 215                 220

Phe Glu Arg Cys Gln Asp Gly Trp Phe Lys Gly Thr Ser Met His Thr
225                 230                 235                 240

Ser Lys Ile Gly Val Phe Pro Gly Asn Tyr Val Ala Pro Val Thr Arg
                245                 250                 255

Ala Val Thr Asn Ala Ser Gln Ala Lys Val Pro Met Ser Thr Ala Gly
                260                 265                 270
```

```
Gln Thr Ser Arg Gly Val Thr Met Val Ser Pro Ser Thr Ala Gly Gly
        275                 280                 285

Pro Ala Gln Lys Leu Gln Gly Asn Gly Val Ala Gly Ser Pro Ser Val
    290                 295                 300

Val Pro Ala Ala Val Val Ser Ala Ala His Ile Gln Thr Ser Pro Gln
305                 310                 315                 320

Ala Lys Val Leu Leu His Met Thr Gly Gln Met Thr Val Asn Gln Ala
                325                 330                 335

Arg Asn Ala Val Arg Thr Val Ala Ala His Asn Gln Glu Arg Pro Thr
            340                 345                 350

Ala Ala Val Thr Pro Ile Gln Val Gln Asn Ala Ala Gly Leu Ser Pro
        355                 360                 365

Ala Ser Val Gly Leu Ser His Ser Leu Ala Ser Pro Gln Pro Ala
    370                 375                 380

Pro Leu Met Pro Gly Ser Ala Thr His Thr Ala Ala Ile Ser Ile Ser
385                 390                 395                 400

Arg Ala Ser Ala Pro Leu Ala Cys Ala Ala Ala Pro Leu Thr Ser
                405                 410                 415

Pro Ser Ile Thr Ser Ala Ser Leu Glu Ala Glu Pro Ser Gly Arg Ile
            420                 425                 430

Val Thr Val Leu Pro Gly Leu Pro Thr Ser Pro Asp Ser Ala Ser Ser
        435                 440                 445

Ala Cys Gly Asn Ser Ser Ala Thr Lys Pro Asp Lys Asp Ser Lys Lys
    450                 455                 460

Glu Lys Lys Gly Leu Leu Lys Leu Leu Ser Gly Ala Ser Thr Lys Arg
465                 470                 475                 480

Lys Pro Arg Val Ser Pro Pro Ala Ser Pro Thr Leu Glu Val Glu Leu
                485                 490                 495

Gly Ser Ala Glu Leu Pro Leu Gln Gly Ala Val Gly Pro Glu Leu Pro
            500                 505                 510

Pro Gly Gly Gly His Gly Arg Ala Gly Ser Cys Pro Val Asp Gly Asp
        515                 520                 525

Gly Pro Val Thr Thr Ala Val Ala Gly Ala Ala Leu Ala Gln Asp Ala
    530                 535                 540

Phe His Arg Lys Ala Ser Ser Leu Asp Ser Ala Val Pro Ile Ala Pro
545                 550                 555                 560

Pro Pro Arg Gln Ala Cys Ser Ser Leu Gly Pro Val Leu Asn Glu Ser
                565                 570                 575

Arg Pro Val Val Cys Glu Arg His Arg Val Val Val Ser Tyr Pro Pro
            580                 585                 590

Gln Ser Glu Ala Glu Leu Glu Leu Lys Glu Gly Asp Ile Val Phe Val
        595                 600                 605

His Lys Lys Arg Glu Asp Gly Trp Phe Lys Gly Thr Leu Gln Arg Asn
    610                 615                 620

Gly Lys Thr Gly Leu Phe Pro Gly Ser Phe Val Glu Asn Ile
625                 630                 635
```

<210> SEQ ID NO 8
<211> LENGTH: 3206
<212> TYPE: DNA
<213> ORGANISM: Mouse

<400> SEQUENCE: 8
gggcagcggg ctcggcgggg ctgcatctac cagcgctgcg gggccgcgaa caaaggcgag    60

-continued

| | | | | |
|---|---|---|---|---|
| cagcggaggc | gcgagagcaa | agtctgaaat | ggatgttaca | tgaatcactt | taagggctgc | 120 |
| gcacaactat | gaacgttctg | aagccgtttt | ctcactaaag | tcactcaaga | tggatgagtc | 180 |
| tgccttgttg | gaccttctgg | agtgccctgt | gtgtctagaa | cgcctggatg | cttccgcaaa | 240 |
| ggtcttaccc | tgccagcata | ccttttgcaa | acgctgtttg | ctggggattg | tgggttcccg | 300 |
| gaatgaactc | agatgtcccg | aatgccggac | tcttgttggc | tctggggtcg | acgagctccc | 360 |
| cagtaacatc | ctactggtca | gacttctgga | tggcatcaag | cagaggcctt | ggaaacccgg | 420 |
| ccctggtggg | ggcggcggga | ccacctgcac | aaacacatta | agggcgcagg | gcagcactgt | 480 |
| ggttaattgt | ggctcgaaag | atctgcagag | ctcccagtgt | ggacagcagc | ctcgggtgca | 540 |
| agcctggagc | cccccagtga | ggggaatacc | tcagttaccg | tgtgccaaag | cattatataa | 600 |
| ctacgaagga | aaagagcccg | gagaccttaa | gttcagcaaa | ggcgacacca | tcattctgcg | 660 |
| ccgacaggtg | gatgagaatt | ggtaccacgg | ggaagtcagc | ggggtccacg | gcttttttccc | 720 |
| cactaacttc | gtgcagatca | tcaaacctttt | acctcagccc | ccgcctcagt | gcaaagcact | 780 |
| ttacgacttt | gaagtgaaag | acaaggaagc | tgacaaagat | tgccttccct | tcgcaaagga | 840 |
| cgacgtactg | accgtgatcc | gcagagtgga | tgaaaactgg | gctgaaggaa | tgctggcaga | 900 |
| taaaatagga | atatttccaa | tttcatacgt | ggagtttaac | tcagctgcca | agcagctgat | 960 |
| agagtgggat | aagcctcccg | tgccaggagt | ggacacggca | gaatgcccct | cagcgacggc | 1020 |
| gcagagcacc | tctgcctcaa | agcaccccga | caccaagaag | aacaccagga | agcgacactc | 1080 |
| cttcacctcc | ctcaccatgg | ccaacaagtc | ttcccagggg | tcccagaacc | gccactccat | 1140 |
| ggagatcagc | cctcctgtgc | tcatcagttc | cagcaacccc | acagccgcag | cccgcatcag | 1200 |
| cgaactgtcc | gggctctcct | gcagcgcccc | gtctcaggtc | catataagca | ccactggggtt | 1260 |
| aattgtgacc | ccaccccta | gcagcccggt | gacaactggc | cctgcgttca | cgttcccttc | 1320 |
| agatgtcccc | taccaagctg | cccttggaag | tatgaatcct | ccacttcccc | cacccccctct | 1380 |
| cctggcggcc | accgtactcg | cctccacccc | gtcaggcgct | actgctgctg | ttgctgctgc | 1440 |
| tgctgccgcc | gccgccgctg | ctggaatggg | acccaggcct | gtgatggggt | cctctgaaca | 1500 |
| gattgcacat | ttacggcctc | agactcgtcc | cagtgtatat | gttgctatat | atccgtacac | 1560 |
| tccccggaag | gaagacgaac | tggagctgag | gaaaggggag | atgttttttgg | tgtttgagcg | 1620 |
| ttgccaggac | ggctggtaca | aagggacatc | gatgcatacc | agcaagatag | gcgttttccc | 1680 |
| tggcaactat | gtggcgcccg | tcacaagggc | ggtgacgaat | gcctcccaag | ctaaagtctc | 1740 |
| tatgtctact | gcgggtcagg | caagtcgcgg | ggtgaccatg | gtcagcccttt | ccactgcagg | 1800 |
| aggacctaca | cagaagcccc | aaggaaacgg | cgtggccgga | atcccagcg | tcgtccccac | 1860 |
| ggctgtggtg | tcagcagctc | atatccagac | aagtcctcag | gctaaggtcc | tgctgcacat | 1920 |
| gtctgggcag | atgacagtca | atcaggcccg | caatgctgtg | aggacagttg | cagcacatag | 1980 |
| ccaggaacgc | cccacagcag | cagtgactcc | catccaggtc | cagaatgccg | cctgccttgg | 2040 |
| tcctgcatcc | gtgggcctgc | ccatcattc | tctggcctcc | caacctctgc | tccaatggc | 2100 |
| gggtcctgct | gcccacggtg | ctgccgtcag | catcagtcga | accaatgccc | ccatggcctg | 2160 |
| cgctgcaggg | gcttctctgg | cctccccaaa | tatgaccagt | gccatgttgg | agacagagcc | 2220 |
| cagtggtcgc | acagtgacca | tcctccctgg | actccccaca | tctccagaga | gtgctgcatc | 2280 |
| agcgtgtggg | aacagttcag | ctgggaaacc | agacaaggac | agtaagaaag | aaaaaaaggg | 2340 |
| cctactgaag | ctgctttctg | gtgcctccac | caaacgcaag | ccccgagtct | cccctccagc | 2400 |

-continued

```
atcacctacc ctggatgtgg agctgggtgc tggggaggct cccttgcagg gagcagtagg    2460
tcctgagctg ccgctagggg gcagccacgg cagagtgggg tcatgcccca cagatggtga    2520
tggtccagtg gccgctggaa cagcagccct agcccaggat gccttccacc gcaagacaag    2580
ctccctggac tccgcagtgc ccattgctcc accacctcgc caggcctgct cctccctggg    2640
cccagtcatg aatgaggccc ggcctgttgt ttgtgaaagg cacagggtgg tggtttccta    2700
ccctcctcag agtgaggccg aacttgaact caaggaagga gatattgtgt ttgttcataa    2760
gaaacgagag gacggctggt tcaaaggcac gttacagagg aatgggaaga ctggcctttt    2820
cccagggagc tttgtggaaa acatctgaga agacgggaca cggagaaagc ttatcatcac    2880
accacgtgtg actaaagagc acaaagcagt tcatagaaa gagcacatct gtggacttcc     2940
agatcttcaa gaaccgagca gaagatgggc acctgactcc agagcccgg cctggttacc      3000 ccaggggcag agggaaggag gacacacctg tgtgggttcc gtctctctgg gttctgatgt    3060
gtaaagtgtg cctgtaatg tctaatggac tttacagata aatgtctttt tttttttaag     3120
atgtataact aaaatggaca attgtttaca aggcttaact aatttatttg cttttttaaa    3180
acttgaactt tcttgtaata gcaaat                                          3206
```

<210> SEQ ID NO 9
<211> LENGTH: 892
<212> TYPE: PRT
<213> ORGANISM: Mouse

<400> SEQUENCE: 9

```
Met Asp Glu Ser Ala Leu Leu Asp Leu Leu Glu Cys Pro Val Cys Leu
  1               5                  10                  15

Glu Arg Leu Asp Ala Ser Ala Lys Val Leu Pro Cys Gln His Thr Phe
             20                  25                  30

Cys Lys Arg Cys Leu Leu Gly Ile Val Gly Ser Arg Asn Glu Leu Arg
         35                  40                  45

Cys Pro Glu Cys Arg Thr Leu Val Gly Ser Gly Val Asp Glu Leu Pro
     50                  55                  60

Ser Asn Ile Leu Leu Val Arg Leu Leu Asp Gly Ile Lys Gln Arg Pro
 65                  70                  75                  80

Trp Lys Pro Gly Pro Gly Gly Gly Gly Thr Thr Cys Thr Asn Thr
             85                  90                  95

Leu Arg Ala Gln Gly Ser Thr Val Val Asn Cys Gly Ser Lys Asp Leu
            100                 105                 110

Gln Ser Ser Gln Cys Gly Gln Gln Pro Arg Val Gln Ala Trp Ser Pro
        115                 120                 125

Pro Val Arg Gly Ile Pro Gln Leu Pro Cys Ala Lys Ala Leu Tyr Asn
    130                 135                 140

Tyr Glu Gly Lys Glu Pro Gly Asp Leu Lys Phe Ser Lys Gly Asp Thr
145                 150                 155                 160

Ile Ile Leu Arg Arg Gln Val Asp Glu Asn Trp Tyr His Gly Glu Val
                165                 170                 175

Ser Gly Val His Gly Phe Phe Pro Thr Asn Phe Val Gln Ile Ile Lys
            180                 185                 190

Pro Leu Pro Gln Pro Pro Pro Gln Cys Lys Ala Leu Tyr Asp Phe Glu
        195                 200                 205

Val Lys Asp Lys Glu Ala Asp Lys Asp Cys Leu Pro Phe Ala Lys Asp
    210                 215                 220

Asp Val Leu Thr Val Ile Arg Arg Val Asp Glu Asn Trp Ala Glu Gly
```

-continued

```
            225                 230                 235                 240
Met Leu Ala Asp Lys Ile Gly Ile Phe Pro Ile Ser Tyr Val Glu Phe
                245                 250                 255
Asn Ser Ala Ala Lys Gln Leu Ile Glu Trp Asp Lys Pro Pro Val Pro
                260                 265                 270
Gly Val Asp Thr Ala Glu Cys Pro Ser Ala Thr Ala Gln Ser Thr Ser
                275                 280                 285
Ala Ser Lys His Pro Asp Thr Lys Lys Asn Thr Arg Lys Arg His Ser
            290                 295                 300
Phe Thr Ser Leu Thr Met Ala Asn Lys Ser Ser Gln Gly Ser Gln Asn
305                 310                 315                 320
Arg His Ser Met Glu Ile Ser Pro Pro Val Leu Ile Ser Ser Ser Asn
                325                 330                 335
Pro Thr Ala Ala Ala Arg Ile Ser Glu Leu Ser Gly Leu Ser Cys Ser
                340                 345                 350
Ala Pro Ser Gln Val His Ile Ser Thr Thr Gly Leu Ile Val Thr Pro
                355                 360                 365
Pro Pro Ser Ser Pro Val Thr Thr Gly Pro Ala Phe Thr Phe Pro Ser
            370                 375                 380
Asp Val Pro Tyr Gln Ala Ala Leu Gly Ser Met Asn Pro Pro Leu Pro
385                 390                 395                 400
Pro Pro Pro Leu Leu Ala Ala Thr Val Leu Ala Ser Thr Pro Ser Gly
                405                 410                 415
Ala Thr Ala Ala Val Ala Ala Ala Ala Ala Ala Ala Ala Ala Ala Gly
                420                 425                 430
Met Gly Pro Arg Pro Val Met Gly Ser Ser Glu Gln Ile Ala His Leu
            435                 440                 445
Arg Pro Gln Thr Arg Pro Ser Val Tyr Val Ala Ile Tyr Pro Tyr Thr
            450                 455                 460
Pro Arg Lys Glu Asp Glu Leu Glu Leu Arg Lys Gly Glu Met Phe Leu
465                 470                 475                 480
Val Phe Glu Arg Cys Gln Asp Gly Trp Tyr Lys Gly Thr Ser Met His
                485                 490                 495
Thr Ser Lys Ile Gly Val Phe Pro Gly Asn Tyr Val Ala Pro Val Thr
                500                 505                 510
Arg Ala Val Thr Asn Ala Ser Gln Ala Lys Val Ser Met Ser Thr Ala
                515                 520                 525
Gly Gln Ala Ser Arg Gly Val Thr Met Val Ser Pro Ser Thr Ala Gly
            530                 535                 540
Gly Pro Thr Gln Lys Pro Gln Gly Asn Gly Val Ala Gly Asn Pro Ser
545                 550                 555                 560
Val Val Pro Thr Ala Val Val Ser Ala Ala His Ile Gln Thr Ser Pro
                565                 570                 575
Gln Ala Lys Val Leu Leu His Met Ser Gly Gln Met Thr Val Asn Gln
            580                 585                 590
Ala Arg Asn Ala Val Arg Thr Val Ala Ala His Ser Gln Glu Arg Pro
            595                 600                 605
Thr Ala Ala Val Thr Pro Ile Gln Val Gln Asn Ala Ala Cys Leu Gly
            610                 615                 620
Pro Ala Ser Val Gly Leu Pro His His Ser Leu Ala Ser Gln Pro Leu
625                 630                 635                 640
Pro Pro Met Ala Gly Pro Ala Ala His Gly Ala Ala Val Ser Ile Ser
                645                 650                 655
```

```
Arg Thr Asn Ala Pro Met Ala Cys Ala Ala Gly Ala Ser Leu Ala Ser
            660                 665                 670

Pro Asn Met Thr Ser Ala Met Leu Glu Thr Glu Pro Ser Gly Arg Thr
        675                 680                 685

Val Thr Ile Leu Pro Gly Leu Pro Thr Ser Pro Glu Ser Ala Ala Ser
    690                 695                 700

Ala Cys Gly Asn Ser Ser Ala Gly Lys Pro Asp Lys Asp Ser Lys Lys
705                 710                 715                 720

Glu Lys Lys Gly Leu Leu Lys Leu Leu Ser Gly Ala Ser Thr Lys Arg
                725                 730                 735

Lys Pro Arg Val Ser Pro Pro Ala Ser Pro Thr Leu Asp Val Glu Leu
            740                 745                 750

Gly Ala Gly Glu Ala Pro Leu Gln Gly Ala Val Gly Pro Glu Leu Pro
        755                 760                 765

Leu Gly Gly Ser His Gly Arg Val Gly Ser Cys Pro Thr Asp Gly Asp
    770                 775                 780

Gly Pro Val Ala Ala Gly Thr Ala Ala Leu Ala Gln Asp Ala Phe His
785                 790                 795                 800

Arg Lys Thr Ser Ser Leu Asp Ser Ala Val Pro Ile Ala Pro Pro Pro
                805                 810                 815

Arg Gln Ala Cys Ser Ser Leu Gly Pro Val Met Asn Glu Ala Arg Pro
            820                 825                 830

Val Val Cys Glu Arg His Arg Val Val Ser Tyr Pro Pro Gln Ser
        835                 840                 845

Glu Ala Glu Leu Glu Leu Lys Glu Gly Asp Ile Val Phe Val His Lys
    850                 855                 860

Lys Arg Glu Asp Gly Trp Phe Lys Gly Thr Leu Gln Arg Asn Gly Lys
865                 870                 875                 880

Thr Gly Leu Phe Pro Gly Ser Phe Val Glu Asn Ile
                885                 890

<210> SEQ ID NO 10
<211> LENGTH: 3149
<212> TYPE: DNA
<213> ORGANISM: Drosophila

<400> SEQUENCE: 10
catttgtatc cgcttggcca cgagctttgg ctgcacttgg caaacttaat aaattaaaca       60
ttgaatcctg cctattgcaa cgataatata atctgattta gtgcattaag aacgacaagt      120
agcgattata atagtagatt ttagcatttg agctaaattt atttcccaac cgcgtcttgg      180
gattgcgtat gcgtgagcca gtacctgcat gtgtgtgtgt tttggaatgt ggccctgcac      240
gaaattcaaa tagtgaccat ccttgagatt ttgcatactg gcaagatgga cgagcacacg      300
ttaaacgacc tgttggagtg ctccgtgtgt cttgagcgac tggacaccac atcgaaggtg      360
ctgccatgcc agcacacctt ctgccgcaaa tgcttgcagg acattgtggc cagtcagcac      420
aagttgcgat gccggagtg ccgcatcctg gtctcttgca aaattgatga gctgcctcca      480
aacgtcttgc tgatgcgaat cttagaaggc atgaaacaaa atgcagcagc tggcaaagga      540
gaagaaaagg gagaggagac tgaaacacag ccggaaaggg ccaaacctca gccgccagcg      600
gaatcagtgg ccccgcctga caaccaacta ctccagctgc agtcacatca gcaatctcat      660
cagccggctc gtcacaagca acgtcgattt ctactccccc acgcctatgc cctctttgac      720
ttcgcctccg gtgaagccac cgatctaaag ttcaagaaag gggatctgat actgatcaag      780
```

```
catcgcatcg acaacaactg gtttgtgggt caagcgaatg gtcaggaggg cacatttccc    840
atcaactacg tcaaggtatc ggttccgctg cccatgccgc agtgcattgc catgtatgac    900
tttaagatgg ggcccaacga cgaggaggga tgcctcgaat ttaagaaaag cactgtaata    960
caggtaatgc gccgagttga tcataattgg gcagaaggac gaattggcca gaccatcgga   1020
atctttccaa tagcattcgt tgagctgaat gcagcggcca aaaagctgtt ggacagcggg   1080
ctacacaccc atccattctg ccatccaccg aagcaacagg ggcagcgggc ccttcctccg   1140
gttccagtta ttgatcccac ggtggtcacg gaatccagtt cgggatcctc caattccacg   1200
ccgggcagca gcaattcaag ctccacatcc agctcgaata actgcagtcc gaatcaccaa   1260
atctcactgc cgaataccc ccaacatgta gtagcttccg gatcggcgtc tgttcgtttc    1320
cgtgacaagg gagcaaagga gaaacgccac tcactaaatg ctttgctggg aggaggagct   1380
ccattaagtc tgctgcagac caaccgccat tcggctgaaa ttcttagcct gccccatgaa   1440
ctaagccgct tggaagtttc cagctcaaca gctctaaaac ccacgtcagc cccacagaca   1500
tcgcgtgtac ttaagaccac tgttcagcag cagatgcaac cgaatttacc ctggggatac   1560
ttagccctgt tcccatacaa accacgccaa acggatgagc tggaattaaa aaagggttgt   1620
gtttacattg tgaccgaacg atgtgtggac ggttggttca agggaaaaaa ctggttggac   1680
atcactggag tgttcccggg caactacctg acgcccctgc gcgcccgcga ccagcagcag   1740
ttaatgcatc aatggaaata tgttccccaa aatgcagacg cccagatggc acaagtacag   1800
cagcatccag ttgcaccaga tgtgcgactc aacaacatgc tgtccatgca accgcctgat   1860
ttgccacctc gtcagcagca ggctaccgcc acgaccacca gttgctctgt gtggtcgaaa   1920
ccagtggagg cgctgttcag cagaaaatcg gagcccaagc ctgaaactgc cacagcttcg   1980
actacgagca gcagttcctc tggagcagtg ggacttatga ggagattaac tcacatgaaa   2040
acacgctcca atctccgggg agcgtccttg cagcaagttc cgaaagaagc tattagcaca   2100
aatgtggaat ttacaacaaa cccatcagct aaattgcatc cagtacatgt aagatccggc   2160
tcgtgcccca gtcagctgca gcacagtcaa ccgctcaatg aaactccagc agccaagaca   2220
gcggcacaac aacagcagtt cctacccaag cagctgcctt ccgcttctac gaacagcgtt   2280
tcgtacggat cgcaacgcgt gaaaggaagc aaggaacgtc ctcacttgat ttgcgcgaga   2340
caatcattag atgcagctac atttcgcagt atgtacaaca atgccgcgtc gccgccgcca   2400
cctactactt ccgtggcccc agctgtctac gccggcggtc agcaacaggt gattcctgga   2460
ggtggagcgc aatcccagtt gcatgccaat atgattattg cacccagcca tcggaagtcg   2520
cacagcctag atgcgagtca tgtgctgagt cccagcagca atatgatcac ggaggcggcc   2580
attaaggcca gcgccaccac taagtctcct tactgcacga gggaaagtcg attccgctgc   2640
attgtgccgt atccaccaaa cagtgacatt gaactagagc tacatttggg cgacattatc   2700
tacgtccagc ggaagcagaa gaacggctgg tataagggca cccatgcccg tacccacaaa   2760
accgggctgt tccccgcctc ctttgttgaa ccggattgtt aggaaagtta tggttcaaac   2820
tagaatttat taagcgaaat tccaaattac ttgtctaaaa ggattcaatc gtcggtctat   2880
tcgggcttcc aaatacgcaa tctcatattt ctcttttcaa aaaagaaacc gttttgtact   2940
cttccaatcg aatgggcagc tcgccgttgt acttttttat acaatgcttg atcaaaatag   3000
gctagccatg taagacttag ggaacagtta cttaagcctt agcgattagt tagctagaga   3060
aataatctaa ccgatccttg tgccctctac aaagttattt gtaatatacg atactcagta   3120
```
ataaaaaaaa aaaaaaaaaa aaaaaaaaa                                    3149

<210> SEQ ID NO 11
<211> LENGTH: 838
<212> TYPE: PRT
<213> ORGANISM: Drosophila

<400> SEQUENCE: 11

Met Asp Glu His Thr Leu Asn Asp Leu Leu Glu Cys Ser Val Cys Leu
1               5                   10                  15

Glu Arg Leu Asp Thr Thr Ser Lys Val Leu Pro Cys Gln His Thr Phe
            20                  25                  30

Cys Arg Lys Cys Leu Gln Asp Ile Val Ala Ser Gln His Lys Leu Arg
        35                  40                  45

Cys Pro Glu Cys Arg Ile Leu Val Ser Cys Lys Ile Asp Glu Leu Pro
    50                  55                  60

Pro Asn Val Leu Met Arg Ile Leu Glu Gly Met Lys Gln Asn Ala
65                  70                  75                  80

Ala Ala Gly Lys Gly Glu Glu Lys Gly Glu Thr Glu Thr Gln Pro
                85                  90                  95

Glu Arg Ala Lys Pro Gln Pro Pro Ala Glu Ser Val Ala Pro Pro Asp
            100                 105                 110

Asn Gln Leu Leu Gln Leu Gln Ser His Gln Gln Ser His Gln Pro Ala
        115                 120                 125

Arg His Lys Gln Arg Arg Phe Leu Leu Pro His Ala Tyr Ala Leu Phe
    130                 135                 140

Asp Phe Ala Ser Gly Glu Ala Thr Asp Leu Lys Phe Lys Lys Gly Asp
145                 150                 155                 160

Leu Ile Leu Ile Lys His Arg Ile Asp Asn Asn Trp Phe Val Gly Gln
                165                 170                 175

Ala Asn Gly Gln Glu Gly Thr Phe Pro Ile Asn Tyr Val Lys Val Ser
            180                 185                 190

Val Pro Leu Pro Met Pro Gln Cys Ile Ala Met Tyr Asp Phe Lys Met
        195                 200                 205

Gly Pro Asn Asp Glu Glu Gly Cys Leu Glu Phe Lys Lys Ser Thr Val
    210                 215                 220

Ile Gln Val Met Arg Arg Val Asp His Asn Trp Ala Glu Gly Arg Ile
225                 230                 235                 240

Gly Gln Thr Ile Gly Ile Phe Pro Ile Ala Phe Val Glu Leu Asn Ala
                245                 250                 255

Ala Ala Lys Lys Leu Leu Asp Ser Gly Leu His Thr His Pro Phe Cys
            260                 265                 270

His Pro Pro Lys Gln Gln Gly Gln Arg Ala Leu Pro Val Pro Val
        275                 280                 285

Ile Asp Pro Thr Val Val Thr Glu Ser Ser Gly Ser Ser Asn Ser
    290                 295                 300

Thr Pro Gly Ser Ser Asn Ser Ser Thr Ser Ser Ser Asn Asn Cys
305                 310                 315                 320

Ser Pro Asn His Gln Ile Ser Leu Pro Asn Thr Pro Gln His Val Val
                325                 330                 335

Ala Ser Gly Ser Ala Ser Val Arg Phe Arg Asp Lys Gly Ala Lys Glu
            340                 345                 350

Lys Arg His Ser Leu Asn Ala Leu Leu Gly Gly Gly Ala Pro Leu Ser
        355                 360                 365

-continued

```
Leu Leu Gln Thr Asn Arg His Ser Ala Glu Ile Leu Ser Leu Pro His
    370                 375                 380

Glu Leu Ser Arg Leu Glu Val Ser Ser Thr Ala Leu Lys Pro Thr
385                 390                 395                 400

Ser Ala Pro Gln Thr Ser Arg Val Leu Lys Thr Thr Val Gln Gln
                405                 410                 415

Met Gln Pro Asn Leu Pro Trp Gly Tyr Leu Ala Leu Phe Pro Tyr Lys
                420                 425                 430

Pro Arg Gln Thr Asp Glu Leu Glu Leu Lys Lys Gly Cys Val Tyr Ile
                435                 440                 445

Val Thr Glu Arg Cys Val Asp Gly Trp Phe Lys Gly Lys Asn Trp Leu
    450                 455                 460

Asp Ile Thr Gly Val Phe Pro Gly Asn Tyr Leu Thr Pro Leu Arg Ala
465                 470                 475                 480

Arg Asp Gln Gln Gln Leu Met His Gln Trp Lys Tyr Val Pro Gln Asn
                485                 490                 495

Ala Asp Ala Gln Met Ala Gln Val Gln Gln His Pro Val Ala Pro Asp
                500                 505                 510

Val Arg Leu Asn Asn Met Leu Ser Met Gln Pro Pro Asp Leu Pro Pro
            515                 520                 525

Arg Gln Gln Gln Ala Thr Ala Thr Thr Thr Ser Cys Ser Val Trp Ser
    530                 535                 540

Lys Pro Val Glu Ala Leu Phe Ser Arg Lys Ser Glu Pro Lys Pro Glu
545                 550                 555                 560

Thr Ala Thr Ala Ser Thr Thr Ser Ser Ser Ser Gly Ala Val Gly
                565                 570                 575

Leu Met Arg Arg Leu Thr His Met Lys Thr Arg Ser Lys Ser Pro Gly
            580                 585                 590

Ala Ser Leu Gln Gln Val Pro Lys Glu Ala Ile Ser Thr Asn Val Glu
            595                 600                 605

Phe Thr Thr Asn Pro Ser Ala Lys Leu His Pro Val His Val Arg Ser
    610                 615                 620

Gly Ser Cys Pro Ser Gln Leu Gln His Ser Gln Pro Leu Asn Glu Thr
625                 630                 635                 640

Pro Ala Ala Lys Thr Ala Ala Gln Gln Gln Phe Leu Pro Lys Gln
                645                 650                 655

Leu Pro Ser Ala Ser Thr Asn Ser Val Ser Tyr Gly Ser Gln Arg Val
            660                 665                 670

Lys Gly Ser Lys Glu Arg Pro His Leu Ile Cys Ala Arg Gln Ser Leu
    675                 680                 685

Asp Ala Ala Thr Phe Arg Ser Met Tyr Asn Asn Ala Ser Pro Pro
690                 695                 700

Pro Pro Thr Thr Ser Val Ala Pro Ala Val Tyr Ala Gly Gly Gln Gln
705                 710                 715                 720

Gln Val Ile Pro Gly Gly Ala Gln Ser Gln Leu His Ala Asn Met
                725                 730                 735

Ile Ile Ala Pro Ser His Arg Lys Ser His Ser Leu Asp Ala Ser His
                740                 745                 750

Val Leu Ser Pro Ser Ser Asn Met Ile Thr Glu Ala Ala Ile Lys Ala
            755                 760                 765

Ser Ala Thr Thr Lys Ser Pro Tyr Cys Thr Arg Glu Ser Arg Phe Arg
    770                 775                 780

Cys Ile Val Pro Tyr Pro Pro Asn Ser Asp Ile Glu Leu Glu Leu His
```

```
                785                 790                 795                 800
Leu Gly Asp Ile Ile Tyr Val Gln Arg Lys Gln Lys Asn Gly Trp Tyr
                805                 810                 815

Lys Gly Thr His Ala Arg Thr His Lys Thr Gly Leu Phe Pro Ala Ser
            820                 825                 830

Phe Val Glu Pro Asp Cys
        835

<210> SEQ ID NO 12
<211> LENGTH: 4
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 2
<223> OTHER INFORMATION: Xaa= Thr or Ser

<400> SEQUENCE: 12

Pro Xaa Ala Pro
 1

<210> SEQ ID NO 13
<211> LENGTH: 5
<212> TYPE: PRT
<213> ORGANISM: Artificial Sequence
<220> FEATURE:
<223> OTHER INFORMATION: consensus sequence

<400> SEQUENCE: 13

Pro Phe Arg Asp Tyr
 1               5

<210> SEQ ID NO 14
<211> LENGTH: 7
<212> TYPE: PRT
<213> ORGANISM: Artificial Sequence
<220> FEATURE:
<223> OTHER INFORMATION: consensus sequence

<400> SEQUENCE: 14

Arg Pro Glu Pro Thr Ala Pro
 1               5

<210> SEQ ID NO 15
<211> LENGTH: 7
<212> TYPE: PRT
<213> ORGANISM: Artificial Sequence
<220> FEATURE:
<223> OTHER INFORMATION: consensus sequence

<400> SEQUENCE: 15

Arg Gln Gly Pro Lys Glu Pro
 1               5

<210> SEQ ID NO 16
<211> LENGTH: 8
<212> TYPE: PRT
<213> ORGANISM: Artificial Sequence
<220> FEATURE:
<223> OTHER INFORMATION: consensus sequence

<400> SEQUENCE: 16

Arg Gln Gly Pro Lys Glu Pro Phe
 1               5
```

-continued

<210> SEQ ID NO 17
<211> LENGTH: 9
<212> TYPE: PRT
<213> ORGANISM: Artificial Sequence
<220> FEATURE:
<223> OTHER INFORMATION: consensus sequence

<400> SEQUENCE: 17

Arg Pro Glu Pro Thr Ala Pro Glu Glu
 1               5

<210> SEQ ID NO 18
<211> LENGTH: 7
<212> TYPE: PRT
<213> ORGANISM: Artificial Sequence
<220> FEATURE:
<223> OTHER INFORMATION: consensus sequence

<400> SEQUENCE: 18

Arg Pro Leu Pro Val Ala Pro
 1               5

<210> SEQ ID NO 19
<211> LENGTH: 3381
<212> TYPE: DNA
<213> ORGANISM: Homo sapiens

<400> SEQUENCE: 19

| | | | | | |
|---|---|---|---|---|---|
| agaggaggag | gaccggtcgt | cgctgctgct | gctgtcgccg | cccgcggcca | ccgcctctca | 60 |
| gacccagcag | atcccaggcg | ggtccctggg | gtctgtgctg | ctgccagccg | ccaggttcga | 120 |
| tgcccgggga | gcggcggccg | cggcggcggc | ggcgggggtg | ctgtacggag | gggacgatgc | 180 |
| ccagggcatg | atggcggcga | tgctgtccca | cgcctacggc | ccggcggtt | gtggggcggc | 240 |
| ggcggccgcc | ctgaacgggg | agcaggcggc | cctgctccgg | agaaagagcg | tcaacaccac | 300 |
| cgagtgcgtc | ccggtgccca | gctccgagca | cgtcgccgag | atcgtcggcc | gccagggttg | 360 |
| taaaattaaa | gcactgagag | ccaagacaaa | cacgtatatc | aagactcctg | ttcgtggtga | 420 |
| agagcccatt | tttgttgtca | ctggaaggaa | agaagatgtt | gccatggcca | aaagagagat | 480 |
| cctctcagct | gcagagcact | tctccatgat | tcgtgcatct | cgaaacaaaa | atgggcctgc | 540 |
| cctgggagga | ttatcatgta | gtcctaatct | gcccggtcaa | accaccgtcc | aagtcagggt | 600 |
| cccttatcgt | gtggtaggat | tagtggttgg | acccaaagga | gcaactatta | aaagaattca | 660 |
| gcagcagacc | cacacctaca | gtaactcc | gagcagagat | aaggaacctg | tctttgaagt | 720 |
| gacagggatg | cctgaaaatg | ttgaccgagc | acgggaagaa | atagaaatgc | atattgccat | 780 |
| gcgtacagga | aactatatag | agctcaatga | agagaatgat | ttccattaca | atggtaccga | 840 |
| tgtaagcttt | gaaggtggca | ctcttggctc | tgcgtggctc | cctccaatc | ctgttcctcc | 900 |
| tagccgcgca | agaatgatat | ccaattatcg | aaatgatagt | tccagttctc | taggaagtgg | 960 |
| ctctacagat | tcctactttg | gaagcaatag | gctggctgac | tttagtccaa | caagcccatt | 1020 |
| tagcacagga | aacttctggt | tggagatac | actaccatct | gtaggctcag | aagacctagc | 1080 |
| agttgactct | cctgcctttg | actctttacc | aacatctgct | caaactatct | ggactccatt | 1140 |
| tgaaccagtt | aacccactct | ctggctttgg | gagtgatcct | tctggtaaca | tgaagactca | 1200 |
| gcgcagagga | agtcagccat | ctactcctcg | tctgtctcct | acatttcctg | agagcataga | 1260 |
| acatccactt | gctcggaggg | ttaggagcga | cccacctagt | acaggcaacc | atgttggcct | 1320 |

```
tccaatatat atccctgctt tttctaatgg taccaatagt tactcctctt ccaatggtgg    1380
ttccacctct agctcacctc cagaatcaag acgaaagcat gactgtgtga tttgctttga    1440
gaatgaggtt attgctgccc tagttccatg tggccacaac ctcttctgca tggaatgtgc    1500
caacaagatc tgtgaaaaga gaacgccatc atgtccagtt tgccagacag ctgttactca    1560
ggcaatccaa attcactctt aactatatat atatacataa atactatatc tctatatgga    1620
ctcgtaaagg catgggtata atggtacccc ccagtaaact tcctaatgat ttcttatgac    1680
tgttatcagg ctttattggg attaggctaa agttgttagt aaacttataa aaggctgcta    1740
tggtaacact aaacctaagt ggtctcttgt ctattagttt ggtttgaatt attagtacta    1800
tcctgtagac ccagagacat agtttatata agaattgcta agctgaagt tcaacttggc     1860 tgagtgaaga taatcatagg ttgtgtgagc ctatgaaaaa gtgtatacgt ctaagatttc    1920
aaaacaatgg gtcccaaagc ctaaccactt taagagttta tggagggtac ttggcattac    1980
agacgattca tacacttcca gtgctgcctt ctttacactg ccagttttga caaaacaggt    2040 ttgttttta ttttacaaca acatatgcct aattctgcag gattgcaagt aactttttaa     2100
tgcattgtga ttacttattg gtaatgatag ggctgatggc agtttactag atcactggtt    2160
ataatttggg acaaaaactg ctacatcaac tttcatctcg cccagagtgc tcaaggctgg    2220
tatgatcagt ggatcaggaa tgcaattgtg aattcctgcc cattgcctct cttggtgaat    2280
gtggaaatgg ccacctgggt tttcccatat caggaagggc tttgggatgg cacctatatt    2340
ggctgataat tgaggatgca acattccat tcattagtgt gatcgagctg ttaattttta     2400
gactatagat caaaatgtga acatttat gttcaatcca tatttgtctt gcacattata      2460
aatatatttt tatttttag taatttaggg gagggaggag ggagaaaggg ataatgatgc     2520
ccttggcata attcacaaaa acagctgtga caacctccaa tcagtttact tcatttcaaa    2580
actatttcca atcacaagga aagatttatt taaaatatac tcgtacattt cacctgtgga    2640
tgtctataac ttcatcctca gtatgttccc aaatctgtgc tggcattgaa aggacaaaac    2700
attatactag tgggttttc tactaattat tttttgaagc attattttcc caacacaaaa     2760 gagcttttt ctcggtataa tgaaaattga atcctatgt gtattcaata gtaaatagac      2820 aaatttatt ttttatttcc acttgaagag ttacatttcg tataaaagtt tacaaataac     2880 ggttttatt ttgattttt cagtataaaa aaagttgcct tgatggcata ttatgatgta      2940
atgctaattg cttgtaggat agtaaatggt cagtattgaa acctaatctc tagctgccgt    3000
cttgtagata tgaacgaatg ttcaccaagc atgtattttg tattttgttg cattgtacac    3060
tgcaactaat aagccaagga atcgacatat attaggtgcg tgtactgttt ctaaaaacca    3120
caaactaaga atgataaatt atcaatatag tttagtattt gctaatttta ctacactctt    3180
ttgttatgta tatgtaggga agtcataggg attataaatt caatttgagt aaaatttaaa    3240
accatatatt ttatgataaa gggcctttaa cttaagatgg ccaaagcact gatattatat    3300
atttgctgta aagagaatta taagagtttt attttttctga tattaaaagt tacttaataa   3360
agacttgttt ccattaactt g                                              3381
```

<210> SEQ ID NO 20
<211> LENGTH: 464
<212> TYPE: PRT
<213> ORGANISM: Homo sapiens

<400> SEQUENCE: 20

Met Met Ala Ala Met Leu Ser His Ala Tyr Gly Pro Gly Gly Cys Gly

-continued

```
  1               5              10              15
Ala Ala Ala Ala Ala Leu Asn Gly Glu Gln Ala Leu Leu Arg Arg
             20              25              30
Lys Ser Val Asn Thr Thr Glu Cys Val Pro Val Pro Ser Ser Glu His
             35              40              45
Val Ala Glu Ile Val Gly Arg Gln Gly Cys Lys Ile Lys Ala Leu Arg
             50              55              60
Ala Lys Thr Asn Thr Tyr Ile Lys Thr Pro Val Arg Gly Glu Glu Pro
 65              70              75              80
Ile Phe Val Val Thr Gly Arg Lys Glu Asp Val Ala Met Ala Lys Arg
             85              90              95
Glu Ile Leu Ser Ala Ala Glu His Phe Ser Met Ile Arg Ala Ser Arg
            100             105             110
Asn Lys Asn Gly Pro Ala Leu Gly Gly Leu Ser Cys Ser Pro Asn Leu
            115             120             125
Pro Gly Gln Thr Thr Val Gln Val Arg Val Pro Tyr Arg Val Val Gly
            130             135             140
Leu Val Val Gly Pro Lys Gly Ala Thr Ile Lys Arg Ile Gln Gln Gln
145             150             155             160
Thr His Thr Tyr Ile Val Thr Pro Ser Arg Asp Lys Glu Pro Val Phe
            165             170             175
Glu Val Thr Gly Met Pro Glu Asn Val Asp Arg Ala Arg Glu Glu Ile
            180             185             190
Glu Met His Ile Ala Met Arg Thr Gly Asn Tyr Ile Glu Leu Asn Glu
            195             200             205
Glu Asn Asp Phe His Tyr Asn Gly Thr Asp Val Ser Phe Glu Gly Gly
            210             215             220
Thr Leu Gly Ser Ala Trp Leu Ser Ser Asn Pro Val Pro Pro Ser Arg
225             230             235             240
Ala Arg Met Ile Ser Asn Tyr Arg Asn Asp Ser Ser Ser Ser Leu Gly
            245             250             255
Ser Gly Ser Thr Asp Ser Tyr Phe Gly Ser Asn Arg Leu Ala Asp Phe
            260             265             270
Ser Pro Thr Ser Pro Phe Ser Thr Gly Asn Phe Trp Phe Gly Asp Thr
            275             280             285
Leu Pro Ser Val Gly Ser Glu Asp Leu Ala Val Asp Ser Pro Ala Phe
            290             295             300
Asp Ser Leu Pro Thr Ser Ala Gln Thr Ile Trp Thr Pro Phe Glu Pro
305             310             315             320
Val Asn Pro Leu Ser Gly Phe Gly Ser Asp Pro Ser Gly Asn Met Lys
            325             330             335
Thr Gln Arg Arg Gly Ser Gln Pro Ser Thr Pro Arg Leu Ser Pro Thr
            340             345             350
Phe Pro Glu Ser Ile Glu His Pro Leu Ala Arg Arg Val Arg Ser Asp
            355             360             365
Pro Pro Ser Thr Gly Asn His Val Gly Leu Pro Ile Tyr Ile Pro Ala
            370             375             380
Phe Ser Asn Gly Thr Asn Ser Tyr Ser Ser Asn Gly Gly Ser Thr
385             390             395             400
Ser Ser Ser Pro Pro Glu Ser Arg Arg Lys His Asp Cys Val Ile Cys
            405             410             415
Phe Glu Asn Glu Val Ile Ala Ala Leu Val Pro Cys Gly His Asn Leu
            420             425             430
```

Phe Cys Met Glu Cys Ala Asn Lys Ile Cys Glu Lys Arg Thr Pro Ser
    435                 440                 445

Cys Pro Val Cys Gln Thr Ala Val Thr Gln Ala Ile Gln Ile His Ser
    450                 455                 460

<210> SEQ ID NO 21
<211> LENGTH: 3022
<212> TYPE: DNA
<213> ORGANISM: Homo sapiens

<400> SEQUENCE: 21

```
caagacaaac acgtatatca agactcctgt tcgtggtgaa gagcccattt ttgttgtcac      60
tggaaggaaa gaagatgttg ccatggccaa aagagagatc ctctcagctg cagagcactt     120
ctccatgatt cgtgcatctc gaaacaaaaa tgggcctgcc ctgggaggat tatcatgtag     180
tcctaatctg cccggtcaaa ccaccgtcca agtcagggtc ccttatcgtg tggtaggatt     240
agtggttgga cccaaaggag caactattaa aagaattcag cagcagaccc acacctacat     300
agtaactccg agcagagata aggaacctgt ctttgaagtg acaggatgc  ctgaaaatgt     360
tgaccgagca cgggaagaaa tagaaatgca tattgccatg cgtacaggaa actatataga     420
gctcaatgaa gagaatgatt tccattacaa tggtaccgat gtaagctttg aaggtggcac     480
tcttggctct gcgtggctct cctccaatcc tgttcctcct agccgcgcaa gaatgatatc     540
caattatcga aatgatagtt ccagttctct aggaagtggc tctacagatt cctactttgg     600
aagcaatagg ctggctgact ttagtccaac aagcccattt agcacaggaa acttctggtt     660
tggagataca ctaccatctg taggctcaga agacctagca gttgactctc ctgcctttga     720
ctctttacca acgtctgctc aaactatctg gactccattt gaaccagtta cccactctc      780
tggctttggg agtgatcctt ctggtaacat gaagactcag cgcagaggaa gtcagccatc     840
tactcctcgt ctgtctccta catttcctga gagcatagaa catccacttg ctcggagggt     900
taggagcgac ccacctagta caggcaacca tgttggcctt ccaatatata tccctgcttt     960
ttctaatggt accaatagtt actcctcttc caatggtggt tccacctcta gctcacctcc    1020
agaatcaaga cgaaagcacg actgtgtgat ttgctttgag aatgaggtta ttgctgccct    1080
agttccatgt ggccacaacc tcttctgcat ggaatgtgcc aacaagatct gtgaaaagag    1140
aacgccatca tgtccagttt gccagacagc tgttactcag gcaatccaaa ttcactctta    1200
actatatata tatacataaa tactatatct ctatatggac tcgtaaaggc atgggtataa    1260
tggtacccc cagtaaactt cctaatgatt tcttatgact gttatcaggc tttattggga     1320
ttaggctaaa gttgttagta aacttataaa aggctgctat ggtaacacta aacctaagtg    1380
gtctcttgtc tattagtttg gtttgaatta ttagtactat cctgtagacc cagagacata    1440
gtttatataa gaattgctaa agctgaagtt caacttggct gagtgaagat aatcataggt    1500
tgtgtgagcc tatgaaaaag tgtatacgtc taagatttca aaacaatggg tcccaaagcc    1560
taaccacttt aagagtttat ggagggtact tggcattaca gacgattcat acacttccag    1620
tgctgccttc tttacactgc cagttttgac aaaacaggtt tgtttttat  tttacaacaa    1680
catatgccta attctgcagg attgcaagta acttttttaat gcattgtgat tacttattgg    1740
taatgatagg gctgatggca gtttactaga tcactggtta taatttggga caaaaactgc    1800
tacatcaact ttcatctcgc ccagagtgct caaggctggt atgatcagtg gatcaggaat    1860
gcaattgtga attcctgccc attgcctctc ttggtgaatg tggaaatggc cacctgggtt    1920
```

-continued

```
ttcccatatc aggaagggct tgggatggc acctatattg gctgataatt gaggatgcaa    1980
acattccatt cattagtgtg atcgagctgt taattttttag actatagatc aaaatgtgaa    2040
acattttatg ttcaatccat atttgtcttg cacattataa atatattttt attttttagt    2100
aatttagggg agggaggagg gagaaaggga taatgatgcc cttggcataa ttcacaaaag    2160
cagctgtgac aacctccaat cagtttactt catttcaaaa ctatttccaa tcacaaggaa    2220
agatttattt aaaatatact cgtacatttc acctgtggat gtctataact tcatcctcag    2280
tatgttccca aatctgtgct ggcattgaaa ggacaaaaca ttatactagt gggttttctct   2340 actaattatt ttttgaagca ttattttccc aacacaaaag agctttttc tcggtataat     2400 gaaaattgaa atcctatgtg tattcaatag taaatagaca aattttattt tttatttcca    2460
cttgaagagt tacatttcgt ataaaagttt acaataacg gttttattt tgatttttc       2520 agtataaaaa aagttgcctt gatggcatat tatgatgtaa tgctaattgc ttgtaggata    2580
gtaaatggtc agtattgaaa cctaatctct agctgccgtc ttgtagatat gaacgaatgt    2640
tcaccaagca tgtattttgt attttgttgc attgtacact gcaactaata agccaaggaa    2700
tcgacatata ttaggtgcgt gtactgtttc taaaaaccac aaactaagaa tgataaatta    2760
tcaatatagt ttagtatttg ctaattttac tacactcttt tgttatgtat atgtagggaa    2820
gtcataggga ttataaattc aatttgagta aaatttaaaa ccatatattt tatgataaag    2880
ggcctttaac ttaagatggc caaagcactg atattatata tttgctgtaa agagaattat    2940
aagagtttta ttttctgat attaaaagtt acttgataaa gacttgtttc cattaacttg     3000
aaaaaaaaaa aaaaaaaaaa aa                                             3022
```

<210> SEQ ID NO 22
<211> LENGTH: 372
<212> TYPE: PRT
<213> ORGANISM: Homo sapiens

<400> SEQUENCE: 22

```
Met Ala Lys Arg Glu Ile Leu Ser Ala Ala Glu His Phe Ser Met Ile
  1               5                  10                  15

Arg Ala Ser Arg Asn Lys Asn Gly Pro Ala Leu Gly Gly Leu Ser Cys
                 20                  25                  30

Ser Pro Asn Leu Pro Gly Gln Thr Thr Val Gln Val Arg Val Pro Tyr
             35                  40                  45

Arg Val Val Gly Leu Val Val Gly Pro Lys Gly Ala Thr Ile Lys Arg
         50                  55                  60

Ile Gln Gln Gln Thr His Thr Tyr Ile Val Thr Pro Ser Arg Asp Lys
 65                  70                  75                  80

Glu Pro Val Phe Glu Val Thr Gly Met Pro Glu Asn Val Asp Arg Ala
                 85                  90                  95

Arg Glu Glu Ile Glu Met His Ile Ala Met Arg Thr Gly Asn Tyr Ile
            100                 105                 110

Glu Leu Asn Glu Glu Asn Asp Phe His Tyr Asn Gly Thr Asp Val Ser
        115                 120                 125

Phe Glu Gly Gly Thr Leu Gly Ser Ala Trp Leu Ser Ser Asn Pro Val
    130                 135                 140

Pro Pro Ser Arg Ala Arg Met Ile Ser Asn Tyr Arg Asn Asp Ser Ser
145                 150                 155                 160

Ser Ser Leu Gly Ser Gly Ser Thr Asp Ser Tyr Phe Gly Ser Asn Arg
                165                 170                 175
```

```
Leu Ala Asp Phe Ser Pro Thr Ser Pro Phe Thr Gly Asn Phe Trp
            180                 185                 190
Phe Gly Asp Thr Leu Pro Ser Val Gly Ser Glu Asp Leu Ala Val Asp
        195                 200                 205
Ser Pro Ala Phe Asp Ser Leu Pro Thr Ser Ala Gln Thr Ile Trp Thr
    210                 215                 220
Pro Phe Glu Pro Val Asn Pro Leu Ser Gly Phe Gly Ser Asp Pro Ser
225                 230                 235                 240
Gly Asn Met Lys Thr Gln Arg Arg Gly Ser Gln Pro Ser Thr Pro Arg
                245                 250                 255
Leu Ser Pro Thr Phe Pro Glu Ser Ile Glu His Pro Leu Ala Arg Arg
            260                 265                 270
Val Arg Ser Asp Pro Pro Ser Thr Gly Asn His Val Gly Leu Pro Ile
        275                 280                 285
Tyr Ile Pro Ala Phe Ser Asn Gly Thr Asn Ser Tyr Ser Ser Ser Asn
    290                 295                 300
Gly Gly Ser Thr Ser Ser Ser Pro Pro Glu Ser Arg Arg Lys His Asp
305                 310                 315                 320
Cys Val Ile Cys Phe Glu Asn Glu Val Ile Ala Ala Leu Val Pro Cys
                325                 330                 335
Gly His Asn Leu Phe Cys Met Glu Cys Ala Asn Lys Ile Cys Glu Lys
            340                 345                 350
Arg Thr Pro Ser Cys Pro Val Cys Gln Thr Ala Val Thr Gln Ala Ile
        355                 360                 365
Gln Ile His Ser
    370

<210> SEQ ID NO 23
<211> LENGTH: 1513
<212> TYPE: DNA
<213> ORGANISM: Homo sapiens

<400> SEQUENCE: 23
cctgaacggg gagcaggcgg ccctgctccg gagaaagagc gtcaacacca ccgagtgcgt    60
cccggtgccc agctccgagc acgtcgccga gatcgtcggc cgccagggtt gtaaaattaa   120
agcactgaga gccaagacaa acacgtatat caagactcct gttcgtggtg aagagcccat   180
ttttgttgtc actggaagga agaagatgt tgccatggcc aaaagagaga tcctctcagc   240
tgcagagcac ttctccatga ttcgtgcatc tcgaaacaaa aatgggcctg ccctgggagg   300
attatcatgt agtcctaatc tgcccggtca accaccgtc caagtcaggg tcccttatcg   360
tgtggtagga ttagtggttg gacccaaagg agcaactatt aaaagaattc agcagcagac   420
ccacacctac atagtaactc cgagcagaga taaggaacct gtctttgaag tgacagggat   480
gcctgaaaat gttgaccgag cacgggaaga aatagaaatg catattgcca tgcgtacagg   540
aaactatata gagctcaatg aagagaatga tttccattac aatggtaccg atgtaagctt   600
tgaaggtggc actcttggct ctgcgtggct ctcctccaat cctgttcctc ctagccgcgc   660
aagaatgata tccaattatc gaaatgatag ttccagttct ctaggaagtg gctctacaga   720
ttcctacttt ggaagcaata ggctggctga ctttagtcca acaagcccat ttagcacagg   780
aaacttctgg tttggagata cactaccatc tgtaggctca gaagacctag cagttgactc   840
tcctgccttt gactctttac caacatctgc tcaaactatc tggactccat ttgaaccagt   900
taacccactc tctggctttg ggagtgatcc ttctggtaac atgaagactc agcgcagagg   960
```

-continued

```
aagtcagcca tctactcctc gtctgtctcc tacatttcct gagagcatag aacatccact    1020
tgctcggagg gttaggagcg acccaccTag tacaggcaac catgttggcc ttccaatata    1080
tatccctgct ttttctaatg gtaccaatag ttactcctct tccaatggtg gttccacctc    1140
tagctcacct ccagaatcaa gacgaaagca cgactgtgtg atttgctttg agaatgaggt    1200
tattgctgcc ctagttccat gtggccacaa cctcttctgc atggaatgtg ccaacaagat    1260
ctgtgaaaag agaacgccat catgtccagt ttgccagaca gctgttactc aggcaatcca    1320
aattcactct taactatata tatatacata aatactatat ctctatatgg actcgtaaag    1380
gcatgggtat aatggtaccc cccagtaaac ttcctaatga tttcttatga ctgttatcag    1440
gctttattgg gattaggcta aagttgttag taaacttata aaaggctgct atggtaacac    1500
taaaaaaaaa aaa                                                       1513
```

<210> SEQ ID NO 24
<211> LENGTH: 372
<212> TYPE: PRT
<213> ORGANISM: Homo sapiens

<400> SEQUENCE: 24

```
Met Ala Lys Arg Glu Ile Leu Ser Ala Ala Glu His Phe Ser Met Ile
 1               5                  10                  15

Arg Ala Ser Arg Asn Lys Asn Gly Pro Ala Leu Gly Gly Leu Ser Cys
            20                  25                  30

Ser Pro Asn Leu Pro Gly Gln Thr Thr Val Gln Val Arg Val Pro Tyr
        35                  40                  45

Arg Val Val Gly Leu Val Val Gly Pro Lys Gly Ala Thr Ile Lys Arg
    50                  55                  60

Ile Gln Gln Gln Thr His Thr Tyr Ile Val Thr Pro Ser Arg Asp Lys
65                  70                  75                  80

Glu Pro Val Phe Glu Val Thr Gly Met Pro Glu Asn Val Asp Arg Ala
                85                  90                  95

Arg Glu Glu Ile Glu Met His Ile Ala Met Arg Thr Gly Asn Tyr Ile
            100                 105                 110

Glu Leu Asn Glu Glu Asn Asp Phe His Tyr Asn Gly Thr Asp Val Ser
        115                 120                 125

Phe Glu Gly Gly Thr Leu Gly Ser Ala Trp Leu Ser Ser Asn Pro Val
    130                 135                 140

Pro Pro Ser Arg Ala Arg Met Ile Ser Asn Tyr Arg Asn Asp Ser Ser
145                 150                 155                 160

Ser Ser Leu Gly Ser Gly Ser Thr Asp Ser Tyr Phe Gly Ser Asn Arg
                165                 170                 175

Leu Ala Asp Phe Ser Pro Thr Ser Pro Phe Ser Thr Gly Asn Phe Trp
            180                 185                 190

Phe Gly Asp Thr Leu Pro Ser Val Gly Ser Glu Asp Leu Ala Val Asp
        195                 200                 205

Ser Pro Ala Phe Asp Ser Leu Pro Thr Ser Ala Gln Thr Ile Trp Thr
    210                 215                 220

Pro Phe Glu Pro Val Asn Pro Leu Ser Gly Phe Gly Ser Asp Pro Ser
225                 230                 235                 240

Gly Asn Met Lys Thr Gln Arg Arg Gly Ser Gln Pro Ser Thr Pro Arg
                245                 250                 255

Leu Ser Pro Thr Phe Pro Glu Ser Ile Glu His Pro Leu Ala Arg Arg
            260                 265                 270
```

```
Val Arg Ser Asp Pro Pro Ser Thr Gly Asn His Val Gly Leu Pro Ile
    275                 280                 285

Tyr Ile Pro Ala Phe Ser Asn Gly Thr Asn Ser Tyr Ser Ser Ser Asn
    290                 295                 300

Gly Gly Ser Thr Ser Ser Ser Pro Pro Glu Ser Arg Arg Lys His Asp
305                 310                 315                 320

Cys Val Ile Cys Phe Glu Asn Glu Val Ile Ala Ala Leu Val Pro Cys
                325                 330                 335

Gly His Asn Leu Phe Cys Met Glu Cys Ala Asn Lys Ile Cys Glu Lys
                340                 345                 350

Arg Thr Pro Ser Cys Pro Val Cys Gln Thr Ala Val Thr Gln Ala Ile
                355                 360                 365

Gln Ile His Ser
    370

<210> SEQ ID NO 25

<400> SEQUENCE: 25

000

<210> SEQ ID NO 26
<211> LENGTH: 41
<212> TYPE: PRT
<213> ORGANISM: Homo sapiens

<400> SEQUENCE: 26

Cys Pro Val Cys Leu Glu Arg Leu Asp Ala Ser Ala Lys Val Leu Pro
1               5                   10                  15

Cys Gln His Thr Phe Cys Lys Arg Cys Leu Leu Gly Ile Val Gly Ser
                20                  25                  30

Arg Asn Glu Leu Arg Cys Pro Glu Cys
            35                  40

<210> SEQ ID NO 27
<211> LENGTH: 56
<212> TYPE: PRT
<213> ORGANISM: Homo sapiens

<400> SEQUENCE: 27

Pro Cys Ala Lys Ala Leu Tyr Asn Tyr Glu Gly Lys Glu Pro Gly Asp
1               5                   10                  15

Leu Lys Phe Ser Lys Gly Asp Ile Ile Ile Leu Arg Arg Gln Val Asp
                20                  25                  30

Glu Asn Trp Tyr His Gly Glu Val Asn Gly Ile His Gly Phe Phe Pro
            35                  40                  45

Thr Asn Phe Val Gln Ile Ile Lys
    50                  55

<210> SEQ ID NO 28
<211> LENGTH: 60
<212> TYPE: PRT
<213> ORGANISM: Homo sapiens

<400> SEQUENCE: 28

Pro Gln Cys Lys Ala Leu Tyr Asp Phe Glu Val Lys Asp Lys Glu Ala
1               5                   10                  15

Asp Lys Asp Cys Leu Pro Phe Ala Lys Asp Asp Val Leu Thr Val Ile
                20                  25                  30
```

```
Arg Arg Val Asp Glu Asn Trp Ala Glu Gly Met Leu Ala Asp Lys Ile
        35                  40                  45

Gly Ile Phe Pro Ile Ser Tyr Val Glu Phe Asn Ser
 50                  55                  60

<210> SEQ ID NO 29
<211> LENGTH: 58
<212> TYPE: PRT
<213> ORGANISM: Homo sapiens

<400> SEQUENCE: 29

Ser Val Tyr Val Ala Ile Tyr Pro Tyr Thr Pro Arg Lys Glu Asp Glu
 1               5                  10                  15

Leu Glu Leu Arg Lys Gly Glu Met Phe Leu Val Phe Glu Arg Cys Gln
            20                  25                  30

Asp Gly Trp Phe Lys Gly Thr Ser Met His Thr Ser Lys Ile Gly Val
        35                  40                  45

Phe Pro Gly Asn Tyr Val Ala Pro Val Thr
 50                  55

<210> SEQ ID NO 30
<211> LENGTH: 57
<212> TYPE: PRT
<213> ORGANISM: Homo sapiens

<400> SEQUENCE: 30

Glu Arg His Arg Val Val Ser Tyr Pro Pro Gln Ser Gly Ala Glu
 1               5                  10                  15

Leu Glu Leu Lys Glu Gly Asp Ile Val Phe Val His Lys Lys Arg Glu
            20                  25                  30

Asp Gly Trp Phe Lys Gly Thr Leu Gln Arg Asn Gly Lys Thr Gly Leu
        35                  40                  45

Phe Pro Gly Ser Phe Val Glu Asn Ile
 50                  55

<210> SEQ ID NO 31
<211> LENGTH: 121
<212> TYPE: DNA
<213> ORGANISM: Homo sapiens

<400> SEQUENCE: 31
tgtccggtgt gtctagagcg ccttgatgct tctgcgaagg tcttgccttg ccagcatacg      60
ttttgcaagc gatgtttgct ggggatcgta ggttctcgaa atgaactcag atgtcccgag     120
t                                                                    121

<210> SEQ ID NO 32
<211> LENGTH: 165
<212> TYPE: DNA
<213> ORGANISM: Homo sapiens

<400> SEQUENCE: 32
ccatgtgcca aagcgttata caactatgaa ggaaaagagc ctggagacct taaattcagc      60
aaaggcgaca tcatcatttt gcgaagacaa gtggatgaaa attggtacca tggggaagtc     120
aatggaatcc atggcttttt ccccaccaac tttgtgcaga ttatt                     165

<210> SEQ ID NO 33
<211> LENGTH: 177
<212> TYPE: DNA
<213> ORGANISM: Homo sapiens
```

<400> SEQUENCE: 33

| | |
|---|---|
| cctcagtgca aagcacttta tgactttgaa gtgaaagaca aggaagcaga caaagattgc | 60 |
| cttccatttg caaaggatga tgttctgact gtgatccgaa gagtggatga aaactgggct | 120 |
| gaaggaatgc tggcagacaa ataggaata tttccaattt catatgttga gtttaac | 177 |

<210> SEQ ID NO 34
<211> LENGTH: 171
<212> TYPE: DNA
<213> ORGANISM: Homo sapiens

<400> SEQUENCE: 34

| | |
|---|---|
| agtgtgtatg ttgctatata tccatacact cctcggaaag aggatgaact agagctgaga | 60 |
| aaaggggaga tgttttagt gtttgagcgc tgccaggatg gctggttcaa agggacatcc | 120 |
| atgcatacca gcaagatagg ggttttccct ggcaattatg tggcaccagt c | 171 |

<210> SEQ ID NO 35
<211> LENGTH: 169
<212> TYPE: DNA
<213> ORGANISM: Homo sapiens

<400> SEQUENCE: 35

| | |
|---|---|
| gaaaggcaca gggtggtggt ttcctatcct cctcagagtg aggcagaact gaacttaaa | 60 |
| gaaggagata ttgtgtttgt tcataaaaaa cgagaggatg gctggttcaa aggcacatta | 120 |
| caacgtaatg ggaaaactgg cctttttccca ggaagctttg tggaaaaca | 169 |

<210> SEQ ID NO 36

<400> SEQUENCE: 36

000

<210> SEQ ID NO 37
<211> LENGTH: 3354
<212> TYPE: DNA
<213> ORGANISM: Homo sapiens

<400> SEQUENCE: 37

| | |
|---|---|
| ctgggtcctg tgtgtgccac aggggtgggg tgtccagcga gcggtctcct cctcctgcta | 60 |
| gtgctgctgc ggcgtcccgc ggcctccccg agtcgggcgg gaggggagag cgggtgtgga | 120 |
| tttgtcttga cggtaattgt tgcgtttcca cgtctcggag gcctgcgcgc tgggttgctc | 180 |
| cttcttcggg agcagctgt tctcagcgat cccactccca gccggggctc cccacacaca | 240 |
| ctgggctgcg tgcgtgtgga gtgggacccg cgcacacgcg tgtctctgga cagctacggc | 300 |
| gccgaaagaa ctaaaattcc agatggcaaa ctcaatgaat ggcagaaacc tggtggtcg | 360 |
| aggaggaaat ccccgaaaag gtcgaatttt gggtattatt gatgctattc aggatgcagt | 420 |
| tggaccccct aagcaagctg ccgcagatcg caggaccgtg gagaagactt ggaagctcat | 480 |
| ggacaaagtg gtaagactgt gccaaaatcc caaacttcag ttgaaaaata gcccaccata | 540 |
| tatacttgat attttgcctg atacatatca gcatttacga cttatattga gtaaatatga | 600 |
| tgacaaccag aaacttgccc aactcagtga gaatgagtac tttaaaatct acattgatag | 660 |
| ccttatgaaa aagtcaaaac gggcaataag actctttaaa gaaggcaagg agagaatgta | 720 |
| tgaagaacag tcacaggaca gacgaaatct cacaaaactg tcccttatct tcagtcacat | 780 |
| gctggcagaa atcaaagcaa tctttcccaa tggtcaattc cagggagata actttcgtat | 840 |

```
cacaaaagca gatgctgctg aattctggag aaagtttttt ggagacaaaa ctatcgtacc    900
atggaaagta ttcagacagt gccttcatga ggtccaccag attagctcta gcctggaagc    960
aatggctcta aaatcaacaa ttgatttaac ttgcaatgat tacatttcag tttttgaatt   1020
tgatattttt accaggctgt ttcagccttg gggctctatt ttgcggaatt ggaatttctt   1080
agctgtgaca catccaggtt acatggcatt tctcacatat gatgaagtta aagcacgact   1140
acagaaatat agcaccaaac ccggaagcta tattttccgg ttaagttgca ctcgattggg   1200
acagtgggcc attggctatg tgactgggga tgggaatatc ttacagacca tacctcataa   1260
caagccctta tttcaagccc tgattgatgg cagcagggaa ggattttatc tttatcctga   1320
tgggaggagt tataatcctg atttaactgg attatgtgaa cctacacctc atgaccatat   1380
aaaagttaca caggaacaat atgaattata ttgtgaaatg gctccactt ttcagctctg   1440
taagatttgt gcagagaatg acaaagatgt caagattgag ccttgtgggc atttgatgtg   1500
cacctcttgc cttacggcat ggcaggagtc ggatggtcag ggctgccctt tctgtcgttg   1560
tgaaataaaa ggaactgagc ccataatcgt ggacccctt gatccaagag atgaaggctc   1620
caggtgttgc agcatcattg ccccctttgg catgccgatg ctagacttgg acgacgatga   1680
tgatcgtgag gagtccttga tgatgaatcg gttggcaaac gtccgaaagt gcactgacag   1740
gcagaactca ccagtcacat caccaggatc ctctcccctt gcccagagaa gaaagccaca   1800
gcctgaccca ctccagatcc cacatctaag cctgccaccc gtgcctcctc gcctggatct   1860
aattcagaaa ggcatagtta gatctccctg tggcagccca acaggttcac caaagtcttc   1920
tccttgcatg gtgagaaaac aagataaacc actcccagca ccacctcctc ccttaagaga   1980
tcctcctcca ccgccacctg aaagacctcc accaatccca ccagacaata gactgagtag   2040
acacatccat catgtggaaa gcgtgccttc cagagacccg ccaatgcctc ttgaagcatg   2100
gtgccctcgg gatgtgtttg ggactaatca gcttgtggga tgtcgactcc taggggaggg   2160
ctctccaaaa cctggaatca gcgagttc aaatgtcaat ggaaggcaca gtagagtggg   2220
ctctgaccca gtgcttatgc ggaaacacag acgccatgat ttgcctttag aaggagctaa   2280
ggtcttttcc aatggtcacc ttggaagtga agaatatgat gttcctcccc ggctttctcc   2340
tcctcctcca gttaccaccc tcctccctag cataaagtgt actggtccgt tagcaaattc   2400
tctttcagag aaaacaagag acccagtaga ggaagatgat gatgaataca agattccttc   2460
atcccaccct gtttccctga attcacaacc atctcattgt cataatgtaa aacctcctgt   2520
tcggtcctgt gataatggtc actgtatgct gaatggaaca catggtccat cttcagagaa   2580
gaaatcaaac atccctgact taagcatata tttaaagggt acgtatagaa tataatttcc   2640
tttgtgatgt acatcttaat ggtcagaatt taaaggcaaa atttcatgcc attgtactga   2700
aaatacatta aggttttgtg ttatcctcta ggagatgttt ttgattcagc ctctgatccc   2760
gtgccattac cacctgccag gcctccaact cgggacaatc caaagcatgg ttcttcactc   2820
aacaggacgc cctctgatta tgatcttctc atccctccat taggttgaaa cctttaaaaa   2880
agttttgaac aacccacccc tccttctttt aatttcagaa ttttcagaat tcagagttca   2940
gtataacaca gactcactgg gttgtgaatt tgcctgaaat ttgaatgggt tctccaggtg   3000
ccggtgactc ccaagttcac gagaccatta ctccatgtag atgattaagg tagtagtgta   3060
gtagttgggc atcagtcagg ttttaagcaa gttgttttgt ccatactaaa tgtagtctaa   3120
aaacacatga gagctttgtg ctctagtagt tttgaagtga tgacttgaag tgttgagatt   3180
```

| | |
|---|---:|
| ttctttaagt ataataattc ttaataaata tgaacttgct tttccttgcag catgagcacc | 3240 |
| agttccactt acgctaatta aattatgcaa aattaaatag ttgtatgtag agaactgata | 3300 |
| ataaattctg ttttattcta atcattacaa ctgtaacaca ttcaaaaaaa aaaa | 3354 |

<210> SEQ ID NO 38
<211> LENGTH: 3928
<212> TYPE: DNA
<213> ORGANISM: Homo sapiens

<400> SEQUENCE: 38

| | |
|---|---:|
| agcggagtgc tgctgcggcg tcccgcggcc tccccgagtc gggcgggagg ggagagcggg | 60 |
| tgtggatttg tcttgacggt aattgttgcg tttccacgtc tcggaggcct gcgcgctggg | 120 |
| ttgctccttc ttcgggagcg agctgttctc agcgatccca ctcccagccg gggctcccca | 180 |
| cacacactgg gctgcgtgcg tgtggagtgg gacccgcgca cacgcgtgtc tctggacagc | 240 |
| tacggcgccg aaagaactaa aattccagat ggcaaactca atgaatgca gaaaccctgg | 300 |
| tggtcgagga ggaaatcccc gaaaaggtcg aattttgggt attattgatg ctattcagga | 360 |
| tgcagttgga cccctaagc aagctgccgc agatcgcagg accgtggaga agacttggaa | 420 |
| gctcatggac aaagtggtaa gactgtgcca aaatcccaaa cttcagttga aaaatagccc | 480 |
| accatatata cttgatattt tgcctgatac atatcagcat ttacgactta tattgagtaa | 540 |
| atatgatgac aaccagaaac ttgcccaact cagtgagaat gagtacttta aaatctacat | 600 |
| tgatagcctt atgaaaaagt caaaacgggc aataagactc tttaaagaag gcaaggagag | 660 |
| aatgtatgaa gaacagtcac aggacagacg aaatctcaca aaactgtccc ttatcttcag | 720 |
| tcacatgctg gcagaaatca agcaatcctt tcccaatggt caattccagg agataactt | 780 |
| tcgtatcaca aaagcagatg ctgctgaatt ctggagaaag tttttttggag acaaaactat | 840 |
| cgtaccatgg aaagtattca gacagtgcct tcatgaggtc caccagatta gctctggcct | 900 |
| ggaagcaatg gctctaaaat caacaattga tttaacttgc aatgattaca tttcagtttt | 960 |
| tgaatttgat attttttacca ggctgtttca gccttgggc tctatttgc ggaattggaa | 1020 |
| tttcttagct gtgacacatc caggttacat ggcatttctc acatatgatg aagttaaagc | 1080 |
| acgactacag aaatatagca ccaaacccgg aagctatatt ttccggttaa gttgcactcg | 1140 |
| attgggacag tgggccattg ctatgtgac tggggatggg aatatcttac agaccatacc | 1200 |
| tcataacaag cccttatttc aagccctgat tgatggcagc agggaaggat tttatctta | 1260 |
| tcctgatggg aggagttata atcctgattt aactggatta tgtgaaccta cacctcatga | 1320 |
| ccatataaaa gttacacagg acaatatga attatattgt gaaatgggct ccacttttca | 1380 |
| gctctgtaag atttgtgcag agaatgacaa agatgtcaag attgagcctt gtgggcattt | 1440 |
| gatgtgcacc tcttgcctta cggcatggca ggagtcggat ggtcagggct gcccttctg | 1500 |
| tcgttgtgaa ataaaaggaa ctgagcccat aatcgtggat ccctttgatc caagagatga | 1560 |
| aggctccagg tgttgcagca tcattgaccc ctttggcatg ccgatgctcg acttggacga | 1620 |
| cgatgatgat cgtgaggagt ccttgatgat gaatcggttg gcaaacgtcc gaaagtgcac | 1680 |
| tgacaggcag aactcaccag tcacatcacc aggatcctct ccccttgccc agagaagaaa | 1740 |
| gccacagcct gacccactcc agatcccaca tctaagcctg ccaccgtgc ctcctcgcct | 1800 |
| ggatctaatt cagaaaggca tagttagatc tccctgtggc agcccaacgg gttcaccaaa | 1860 |
| gtcttctcct tgcatggtga aaaacaaga taaccactc ccagcaccac ctcctcccctt | 1920 |
| aagagatcct cctccaccgc cacctgaaag acctccacca atcccaccag acaatagact | 1980 |

```
gagtagacac atccatcatg tggaaagcgt gccttccaaa gacccgccaa tgcctcttga    2040
agcatggtgc cctcgggatg tgtttgggac taatcagctt gtgggatgtc gactcctagg    2100
ggagggctct ccaaaacctg gaatcacagc gagttcaaat gtcaatggaa ggcacagtag    2160
agtgggctct gacccagtgc ttatgcggaa acacagacgc catgatttgc ctttagaagg    2220
agctaaggtc ttttccaatg gtcaccttgg aagtgaagaa tatgatgttc ctccccggct    2280
ttctcctcct cctccagtta ccaccctcct ccctagcata aagtgtactg gtccgttagc    2340
aaattctctt tcagagaaaa caagagaccc agtagaggaa gatgatgatg aatacaagat    2400
tccttcatcc caccctgttt ccctgaattc acaaccatct cattgtcata atgtaaaacc    2460
tcctgttcgg tcttgtgata atggtcactg tatgctgaat ggaacacatg gtccatcttc    2520
agagaagaaa tcaaacatcc ctgacttaag catatattta aagggagatg ttttgattc     2580 agcctctgat cccgtgccat taccacctgc caggcctcca actcgggaca atccaaagca    2640
tggttcttca ctcaacagga cgccctctga ttatgatctt ctcatccctc cattaggtga    2700
agatgctttt gatgccctcc ctccatctct cccacctccc ccacctcctg caaggcatag    2760
tctcattgaa cattcaaaac tcctggctc cagtagccgg ccatcctcag gacaggatct     2820 tttcttctt ccttcagatc cctttgttga tctagcaagt ggccaagttc ctttgcctcc     2880
cgctagaagg ttaccaggtg aaaatgtcaa aactaacaga acatcacagg actatgatca    2940
gcttccttca tgttcagatg gttcacaggc accagccaga cccctaaac cacgaccgcg     3000 caggactgca ccagaaattc accacagaaa acccatggg cctgaggcgg cattggaaaa     3060
tgtcgatgca aaaattgcaa aactcatggg agagggttat gcctttgaag aggtgaagag    3120
agccttagag atagcccaga ataatgtcga agttgcccgg agcatcctcc gagaatttgc    3180
cttccctcct ccagtatccc cacgtctaaa tctatagcag ccagaactgt agacaccaaa    3240
atggaaagca atcgatgtat ccaagagtg tggaaataaa gagaactgag atggaattca    3300
agagagaagt gtctcctcct cgtgtagcag cttgagaaga ggcttgggag tgcagcttct    3360
caaaggagac cgatgcttgc tcaggatgtc gacagctgtg gcttccttgt ttttgctagc    3420
catattttta aatcagggtt gaactgacaa aaataattta aagacgttta cttcccttga    3480
actttgaacc tgtgaaatgc tttaccttgt ttacaatttg gcaaagttgc agtttgttct    3540 tgttttagt ttagttttgt tttggtgttt tgatacctgt actgtgttct tcacagaccc     3600
tttgtagcgt ggtcaggtct gctgtaacat ttcccaccaa ctctcttgct gtccacatca    3660
acagctaaat catttattca tatggatctc taccatcccc atgccttgcc caggtccagt    3720
tccatttctc tcattcacaa gatgctttga aggttctgat tttcaactga tcaaactaat    3780
gcaaaaaaaa aagtatgtat tcttcactac tgagtttctt cttttggaaac catcactatt    3840 gagagatggg aaaacctga atgtataaag catttatttg tcaataaact gccttttgta    3900
aggggttttc acaaaaaaaa aaaaaaa                                        3928

<210> SEQ ID NO 39
<211> LENGTH: 3982
<212> TYPE: DNA
<213> ORGANISM: Homo sapiens

<400> SEQUENCE: 39
ctgggtcctg tgtgtgccac aggggtgggg tgtccagcga gcggtctcct cctcctgcta      60
gtgctgctgc ggcgtcccgc ggcctccccg agtcgggcgg gaggggagag cgggtgtgga     120
```

```
tttgtcttga cggtaattgt tgcgtttcca cgtctcggag gcctgcgcgc tggggttgctc    180
cttcttcggg agcgagctgt tctcagcgat cccactccca gccggggctc cccacacaca    240
ctgggctgcg tgcgtgtgga gtgggacccg cgcacacgcg tgtctctgga cagctacggc    300
gccgaaagaa ctaaaattcc agatggcaaa ctcaatgaat ggcagaaacc ctggtggtcg    360
aggaggaaat ccccgaaaag gtcgaatttt gggtattatt gatgctattc aggatgcagt    420
tggaccccct aagcaagctg ccgcagatcg caggaccgtg gagaagactt ggaagctcat    480
ggacaaagtg gtaagactgt gccaaaatcc caaacttcag ttgaaaaata gcccaccata    540
tatacttgat attttgcctg atacatatca gcatttacga cttatattga gtaaatatga    600
tgacaaccag aaacttgccc aactcagtga gaatgagtac tttaaaatct acattgatag    660
ccttatgaaa aagtcaaaac gggcaataag actcttaaa gaaggcaagg agagaatgta     720
tgaagaacag tcacaggaca gacgaaatct cacaaaactg tcccttatct tcagtcacat    780
gctggcagaa atcaaagcaa tcttttcccaa tggtcaattc cagggagata actttcgtat   840
cacaaaagca gatgctgctg aattctggag aaagtttttt ggagacaaaa ctatcgtacc    900
atggaaagta ttcagacagt gccttcatga ggtccaccag attagctcta gcctggaagc    960
aatggctcta aaatcaacaa ttgatttaac ttgcaatgat tacatttcag ttttgaatt    1020
tgatatttt accaggctgt ttcagccttg gggctctatt ttgcggaatt ggaatttctt    1080
agctgtgaca catccaggtt acatggcatt tctcacatat gatgaagtta agcacgact    1140
acagaaatat agcaccaaac ccggaagcta tattttccgg ttaagttgca ctcgattggg    1200
acagtgggcc attggctatg tgactgggga tgggaatatc ttacagacca tacctcataa    1260
caagcccta tttcaagccc tgattgatgg cagcagggaa ggattttatc tttatcctga    1320
tgggaggagt tataatcctg atttaactgg attatgtgaa cctacacctc atgaccatat    1380
aaaagttaca caggaacaat atgaattata ttgtgaaatg ggctccactt ttcagctctg    1440
taagatttgt gcagagaatg acaaagatgt caagattgag ccttgtgggc atttgatgtg    1500
cacctcttgc cttacggcat ggcaggagtc ggatggtcag ggctgccctt tctgtcgttg    1560
tgaaataaaa ggaactgagc ccataatcgt ggacccctttt gatccaagag atgaaggctc    1620
caggtgttgc agcatcattg accccttggg catgccgatg ctagacttgg acgacgatga    1680
tgatcgtgag gagtccttga tgatgaatcg gttggcaaac gtccgaaagt gcactgacag    1740
gcagaactca ccagtcacat caccaggatc ctctcccctt gcccagagaa gaaagccaca    1800
gcctgaccca ctccagatcc cacatctaag cctgccaccc gtgcctcctc gcctggatct    1860
aattcagaaa ggcatagtta gatctcctg tggcagccca acaggttcac caaagtcttc    1920
tccttgcatg gtgagaaaac aagataaacc actcccagca ccacctcctc ccttaagaga    1980
tcctcctcca ccgccacctg aaagacctcc accaatccca ccagacaata gactgagtag    2040
acacatccat catgtggaaa gcgtgccttc cagagacccg ccaatgcctc ttgaagcatg    2100
gtgccctcgg gatgtgtttg ggactaatca gcttgtggga tgtcgactcc taggggaggg    2160
ctctccaaaa cctggaatca cagcgagttc aaatgtcaat ggaaggcaca gtagagtggg    2220
ctctgaccca gtgcttatgc ggaaacacag acgccatgat ttgcctttag aaggagctaa    2280
ggtcttttcc aatggtcacc ttggaagtga agaatatgat gttcctcccc ggcttttctcc   2340
tcctcctcca gttaccaccc tcctcctag cataaagtgt actggtccgt tagcaaattc    2400
tcttttcagag aaaacaagag acccagtaga ggaagatgat gatgaataca agattccttc    2460
atcccacccct gtttccctga attcacaacc atctcattgt cataatgtaa aacctcctgt    2520
```

```
tcggtcctgt gataatggtc actgtatgct gaatggaaca catggtccat cttcagagaa        2580
gaaatcaaac atccctgact taagcatata tttaaaggga gatgttttg attcagcctc         2640 tgatcccgtg ccattaccac ctgccaggcc tccaactcgg acaatccaa agcatggttc         2700 ttcactcaac aggacgccct ctgattatga tcttctcatc cctccattag gtgaagatgc        2760 tttgatgcc ctccctccat ctctcccacc tcccccacct cctgcaaggc atagtctcat         2820
tgaacattca aaacctcctg ctccagtag ccggccatcc tcaggacagg atcttttct          2880 tcttccttca gatccctttg ttgatctagc aagtggccaa gttcctttgc ctcctgctag        2940
aaggttacca ggtgaaaatg tcaaaactaa cagaacatca caggactatg atcagcttcc       3000
ttcatgttca gatggttcac aggcaccagc cagaccccct aaaccacgac cgcgcaggac       3060
tgcaccagaa attcaccaca gaaaacccca tgggcctgag gcggcattgg aaaatgtcga      3120
tgcaaaaatt gcaaaactca tgggagaggg ttatgccttt gaagaggtga agagagcctt      3180
agagatagcc cagaataatg tcgaagttgc ccggagcatc ctccgagaat ttgccttccc      3240
tcctccagta tccccacgtc taaatctata gcagccagaa ctgtagacac caaaatggaa     3300
agcaatcgat gtattccaag agtgtggaaa taaagagaac tgagatggaa ttcaagagag      3360
aagtgtctcc tcctcgtgta gcagcttgag aagaggcttg ggagtgcagc ttctcaaagg     3420
agaccgatgc ttgctcagga tgtcgacagc tgtggcttcc ttgttttgc tagccatatt      3480 tttaaatcag ggttgaactg acaaaaataa tttaaagacg tttacttccc ttgaactttg     3540
aacctgtgaa atgctttacc ttgtttacaa tttggcaaag ttgcagtttg ttcttgtttt    3600
tagtttagtt ttgttttggt gttttgatac ctgtactgtg ttcttcacag acccttgta      3660 gcgtggtcag gtctgctgta acatttccca ccaactctct tgctgtccac atcaacagct    3720
aaatcattta ttcatatgga tctctaccat ccccatgcct tgcccaggtc cagttccatt    3780
tctctcattc acaagatgct tgaaggttc tgattttcaa ctgatcaaac taatgcaaaa     3840
aaaaaaagta tgtattcttc actactgagt ttcttctttg gaaaccatca ctattgagag    3900
atgggaaaaa cctgaatgta taagcatttt atttgtcaat aaactgcctt ttgtaagggg    3960
ttttcacata aaaaaaaaaa aa                                              3982
```

<210> SEQ ID NO 40
<211> LENGTH: 3241
<212> TYPE: DNA
<213> ORGANISM: Homo sapiens

<400> SEQUENCE: 40

```
ctgggtcctg tgtgtgccac aggggtgggg tgtccagcga gcggtctcct cctcctgcta         60
gtgctgctgc ggcgtcccgc ggcctccccg agtcgggcgg gaggggagag cgggtgtgga       120
tttgtcttga cggtaattgt tgcgtttcca cgtctcggag gcctgcgcgc tgggttgctc       180
cttcttcggg agcgagctgt tctcagcgat cccactccca gccggggctc cccacacaca       240
ctgggctgcg tgcgtgtgga gtgggacccg cgcacgcgcg tgtctctgga cagctacggc       300
gccgaaagaa ctaaaattcc agatggcaaa ctcaatgaat ggcagaaacc ctggtggtcg       360
aggaggaaat ccccgaaaag gtcgaatttt gggtattatt gatgctattc aggatgcagt       420
tggaccccct aagcaagctg ccgcagatcg caggaccgtg gagaagactt ggaagctcat       480
ggacaaagtg gtaagactgt gccaaaatcc caaacttcag ttgaaaaata gcccaccata       540
tatacttgat attttgcctg atacatatca gcatttacga cttatattga gtaaatatga       600
```

-continued

```
tgacaaccag aaacttgccc aactcagtga gaatgagtac tttaaaatct acattgatag    660
ccttatgaaa aagtcaaaac gggcaataag actcttaaa gaaggcaagg agagaatgta    720
tgaagaacag tcacaggaca gacgaaatct cacaaaactg tcccttatct tcagtcacat    780
gctggcagaa atcaaagcaa tctttcccaa tggtcaattc cagggagata actttcgtat    840
cacaaaagca gatgctgctg aattctggag aaagtttttt ggagacaaaa ctatcgtacc    900
atggaaagta ttcagacagt gccttcatga ggtccaccag attagctcta gcctggaagc    960
aatggctcta aaatcaacaa ttgatttaac ttgcaatgat tacatttcag ttttttgaatt   1020
tgatattttt accaggctgt ttcagccttg gggctctatt ttgcggaatt ggaatttctt   1080
agctgtgaca catccaggtt acatggcatt tctcacatat gatgaagtta aagcacgact   1140
acagaaatat agcaccaaac ccggaagcta tattttccgg ttaagttgca ctcgattggg   1200
acagtgggcc attggctatg tgactgggga tgggaatatc ttacagacca tacctcataa   1260
caagcccta tttcaagccc tgattgatgg cagcagggaa ggattttatc tttatcctga   1320
tgggaggagt tataatcctg atttaactgg attatgtgaa cctacacctc atgaccatat   1380
aaaagttaca caggaacaat atgaattata ttgtgaaatg ggctccactt ttcagctctg   1440
taagatttgt gcagagaatg acaaagatgt caagattgag ccttgtgggc atttgatgtg   1500
cacctcttgc cttacggcat ggcaggagtc ggatggtcag ggctgccctt tctgtcgttg   1560
tgaaataaaa ggaactgagc ccataatcgt ggacccsctttt gatccaagag atgaaggctc   1620
caggtgttgc agcatcattg accccttggg catgccgatg ctagacttgg acgacgatga   1680
tgatcgtgag gagtccttga tgatgaatcg gttggcaaac gtccgaaagt gcactgacag   1740
gcagaactca ccagtcacat caccaggatc ctctccccct gcccagagaa gaaagccaca   1800
gcctgaccca ctccagatcc cacatctaag cctgccaccc gtgcctcctc gcctggatct   1860
aattcagaaa ggcatagtta gatctcccctg tggcagccca acaggttcac caaagtcttc   1920
tccttgcatg gtgagaaaac aagataaacc actcccagca ccacctcctc ccttaagaga   1980
tcctcctcca ccgccacctg aaagacctcc accaatccca ccagacaata gactgagtag   2040
acacatccat catgtggaaa gcgtgccttc cagagacccg ccaatgcctc ttgaagcatg   2100
gtgccctcgg gatgtgtttg ggactaatca gcttgtggga tgtcgactcc taggggaggg   2160
ctctccaaaa cctggaatca cagcgagttc aaatgtcaat ggaaggcaca gtagagtggg   2220
ctctgaccca gtgcttatgc ggaaacacag acgccatgat ttgcctttag aaggagctaa   2280
ggtcttttcc aatggtcacc ttggaagtga agaatatgat gttcctcccc ggctttctcc   2340
tcctcctcca gttaccaccc tcctccctag cataaagtgt actggtccgt tagcaaattc   2400
tctttcagag aaaacaagag acccagtaga ggaagatgat gatgaataca agattccttc   2460
atcccaccct gtttccctga attcacaacc atctcattgt cataatgtaa aacctcctgt   2520
tcggtcctgt gataatggtc actgtatgct gaatggaaca catggtccat cttcagagaa   2580
gaaatcaaac atccctgact taagcatata tttaaaggga gatgttttg attcagcctc   2640
tgatcccgtg ccattaccac ctgccaggcc tccaactcgg gacaatccaa agcatggttc   2700
ttcactcaac aggacgcct ctgattatga tcttctcatc cctccattag gttgaaacct   2760
ttaaaaaagt tttgaacaac ccaccctctcc ttcttttaat ttcagaattt tcagaattca   2820
gagttcagta taacacagac tcactggggtt gtgaatttgc ctgaaatttg aatgggttct   2880
ccaggtgccg tgactcccca agttcacgag accattactc catgtagatg attaaggtag   2940
tagtgtagta gttgggcatc agtcaggttt taagcaagtt gttttgtcca tactaaatgt   3000
```

| | |
|---|---|
| agtctaaaaa cacatgagag ctttgtgctc tagtagtttt gaagtgatga cttgaagtgt | 3060 |
| tgagattttc tttaagtata ataattctta ataaatatga acttgctttt cttgcagcat | 3120 |
| gagcaccagt tccacttacg ctaattaaat tatgcaaaat taaatagttg tatgtagaga | 3180 |
| actgataata aattctgttt tattctaatc attacaactg taacacattc aaaaaaaaaa | 3240 |
| a | 3241 |

<210> SEQ ID NO 41
<211> LENGTH: 3354
<212> TYPE: DNA
<213> ORGANISM: Homo sapiens

<400> SEQUENCE: 41

| | |
|---|---|
| ctgggtcctg tgtgtgccac aggggtgggg tgtccagcga gcggtctcct cctcctgcta | 60 |
| gtgctgctgc ggcgtcccgc ggcctccccg agtcgggcgg gaggggagag cgggtgtgga | 120 |
| tttgtcttga cggtaattgt tgcgtttcca cgtctcggag gcctgcgcgc tgggttgctc | 180 |
| cttcttcggg agcgagctgt tctcagcgat cccactccca gccggggctc cccacacaca | 240 |
| ctgggctgcg tgcgtgtgga gtgggacccg cgcacacgcg tgtctctgga cagctacggc | 300 |
| gccgaaagaa ctaaaattcc agatggcaaa ctcaatgaat ggcagaaacc ctggtggtcg | 360 |
| aggaggaaat ccccgaaaag gtcgaatttt gggtattatt gatgctattc aggatgcagt | 420 |
| tggaccccct aagcaagctg ccgcagatcg caggaccgtg gagaagactt ggaagctcat | 480 |
| ggacaaagtg gtaagactgt gccaaaatcc caaacttcag ttgaaaaata gcccaccata | 540 |
| tacttgat attttgcctg atacatatca gcatttacga cttatattga gtaaatatga | 600 |
| tgacaaccag aaacttgccc aactcagtga gaatgagtac tttaaaatct acattgatag | 660 |
| ccttatgaaa aagtcaaaac gggcaataag actctttaaa gaaggcaagg agagaatgta | 720 |
| tgaagaacag tcacaggaca gacgaaatct cacaaaactg tcccttatct tcagtcacat | 780 |
| gctggcagaa atcaaagcaa tcttttcccaa tggtcaattc cagggagata actttcgtat | 840 |
| cacaaaagca gatgctgctg aattctggag aaagtttttt ggagacaaaa ctatcgtacc | 900 |
| atggaaagta ttcagacagt gccttcatga ggtccaccag attagctcta gcctggaagc | 960 |
| aatggctcta aaatcaacaa ttgatttaac ttgcaatgat tacatttcag ttttgaattt | 1020 |
| tgatattttt accaggctgt ttcagccttg gggctctatt ttgcggaatt ggaatttctt | 1080 |
| agctgtgaca catccaggtt acatggcatt tctcacatat gatgaagtta aagcacgact | 1140 |
| acagaaatat agcaccaaac ccggaagcta tattttccgg ttaagttgca ctcgattggg | 1200 |
| acagtggggcc attggctatg tgactgggga tgggaatatc ttacagacca tacctcataa | 1260 |
| caagccctta tttcaagccc tgattgatgg cagcagggaa ggatttttatc tttatcctga | 1320 |
| tgggaggagt tataatcctg atttaactgg attatgtgaa cctacacctc atgaccatat | 1380 |
| aaaagttaca caggaacaat atgaattata ttgtgaaatg ggctccactt ttcagctctg | 1440 |
| taagatttgt gcagagaatg acaaagatgt caagattgag ccttgtgggc atttgatgtg | 1500 |
| cacctcttgc cttacggcat ggcaggagtc ggatggtcag ggctgccctt tctgtcgttg | 1560 |
| tgaaataaaa ggaactgagc ccataatcgt ggacccctttt gatccaagag atgaaggctc | 1620 |
| caggtgttgc agcatcattg accccttttgg catgccgatg ctagacttgg acgacgatga | 1680 |
| tgatcgtgag gagtccttga tgatgaatcg gttggcaaac gtccgaaagt gcactgacag | 1740 |
| gcagaactca ccagtcacat caccaggatc ctctcccctt gcccagagaa gaaagccaca | 1800 |

| | |
|---|---|
| gcctgaccca ctccagatcc cacatctaag cctgccaccc gtgcctcctc gcctggatct | 1860 |
| aattcagaaa ggcatagtta gatctccctg tggcagccca acaggttcac caaagtcttc | 1920 |
| tccttgcatg gtgagaaaac aagataaacc actcccagca ccacctcctc ccttaagaga | 1980 |
| tcctcctcca ccgccacctg aaagacctcc accaatccca ccagacaata gactgagtag | 2040 |
| acacatccat catgtggaaa gcgtgccttc cagagacccg ccaatgcctc ttgaagcatg | 2100 |
| gtgccctcgg gatgtgtttg ggactaatca gcttgtggga tgtcgactcc taggggaggg | 2160 |
| ctctccaaaa cctggaatca cagcgagttc aaatgtcaat ggaaggcaca gtagagtggg | 2220 |
| ctctgaccca gtgcttatgc ggaaacacag acgccatgat ttgcctttag aaggagctaa | 2280 |
| ggtcttttcc aatggtcacc ttggaagtga agaatatgat gttcctcccc ggctttctcc | 2340 |
| tcctcctcca gttaccaccc tcctccctag cataaagtgt actggtccgt tagcaaattc | 2400 |
| tctttcagag aaaacaagag acccagtaga ggaagatgat gatgaataca agattccttc | 2460 |
| atcccaccct gtttccctga attcacaacc atctcattgt cataatgtaa aacctcctgt | 2520 |
| tcggtcctgt gataatggtc actgtatgct gaatggaaca catggtccat cttcagagaa | 2580 |
| gaaatcaaac atccctgact taagcatata tttaaagggt acgtatagaa tataatttcc | 2640 |
| tttgtgatgt acatcttaat ggtcagaatt taaaggcaaa atttcatgcc attgtactga | 2700 |
| aaatacatta aggttttgtg ttatcctcta ggagatgttt ttgattcagc ctctgatccc | 2760 |
| gtgccattac cacctgccag gcctccaact cgggacaatc caaagcatgg ttcttcactc | 2820 |
| aacaggacgc cctctgatta tgatcttctc atccctccat taggttgaaa cctttaaaaa | 2880 |
| agttttgaac aacccacccc tccttctttt aatttcagaa ttttcagaat tcagagttca | 2940 |
| gtataacaca gactcactgg gttgtgaatt tgcctgaaat ttgaatgggt tctccaggtg | 3000 |
| ccggtgactc ccaagttcac gagaccatta ctccatgtag atgattaagg tagtagtgta | 3060 |
| gtagttgggc atcagtcagg ttttaagcaa gttgttttgt ccatactaaa tgtagtctaa | 3120 |
| aaacacatga gagctttgtg ctctagtagt tttgaagtga tgacttgaag tgttgagatt | 3180 |
| ttctttaagt ataataattc ttaataaata tgaacttgct tttcttgcag catgagcacc | 3240 |
| agttccactt acgctaatta aattatgcaa aattaaatag ttgtatgtag agaactgata | 3300 |
| ataaattctg ttttattcta atcattacaa ctgtaacaca ttcaaaaaaa aaaa | 3354 |

<210> SEQ ID NO 42
<211> LENGTH: 2088
<212> TYPE: DNA
<213> ORGANISM: Homo sapiens

<400> SEQUENCE: 42

| | |
|---|---|
| agtgctgctg cggcgtcccg cggcctcccc gagtcgggcg ggaggggaga gcgggtgtgg | 60 |
| atttgtcttg acggtaattg ttgcgtttcc acgtctcgga ggcctgcgcg ctgggttgct | 120 |
| ccttcttcgg gagcgagctg ttctcagcga tcccactccc agccggggct ccccacacac | 180 |
| actgggctgc gtgcgtgtgg agtgggaccc gcgcacacgc gtgtctctgg acagctacgg | 240 |
| cgccgaaaga actaaaattc cagatggcaa actcaatgaa tggcagaaac cctggtggtc | 300 |
| gaggaggaaa tccccgaaaa ggtcgaattt tgggtattat tgatgctatt caggatgcag | 360 |
| ttggaccccc taagcaagct gccgcagatc gcaaaacctg gaatcacagc gagttcaaat | 420 |
| gtcaatggaa ggcacagtag agtgggctct gacccagtgc ttatgcggaa acacagacgc | 480 |
| catgatttgc ctttagaagg agctaaggtc ttttccaatg gtcacttgg aagtgaagaa | 540 |
| tatgatgttc ctccccggct ttctcctcct cctccagtta ccaccctcct ccctagcata | 600 |

-continued

```
aagtgtactg gtccgttagc aaattctctt tcagagaaaa caagagaccc agtagaggaa      660
gatgatgatg aatacaagat tccttcatcc caccctgttt ccctgaattc acaaccatct      720
cattgtcata atgtaaaacc tcctgttcgg tcttgtgata atggtcactg tatgctgaat      780
ggaacacatg gtccatcttc agagaagaaa tcaaacatcc ctgacttaag catatattta      840
aagggagatg ttttttgattc agcctctgat cccgtgccat taccacctgc caggcctcca     900
actcgggaca atccaaagca tggttcttca ctcaacagga cgccctctga ttatgatctt      960
ctcatccctc cattaggtga agatgctttt gatgccctcc ctccatctct cccacctccc     1020
ccacctcctg caaggcatag tctcattgaa cattcaaaac ctcctggctc cagtagccgg     1080
ccatcctcag gacaggatct ttttcttctt ccttcagatc cctttgttga tctagcaagt     1140
ggccaagttc ctttgcctcc tgctagaagg ttaccaggtg aaaatgtcaa aactaacaga     1200
acatcacagg actatgatca gcttccttca tgttcagatg gttcacaggc atcagccaga     1260 cccctaaac cacgaccgcg caggactgca ccagaaattc accacagaaa accccatggg      1320
cctgaggcgg cattggaaaa tgtcgatgca aaaattgcaa aactcatggg agagggttat     1380
gcctttgaag aggtgaagag agccttagag atagcccaga ataatgtcga agttgcccgg     1440
agcatcctcc gagaatttgc cttccctcct ccagtatccc cacgtctaaa tctatagcag     1500
ccagaactgt agacaccaaa atggaaagca atcgatgtat tccaagagtg tggaaataaa     1560
gagaactgag atggaattca agagagaagt gtctcctcct cgtgtagcag cttgagaaga     1620
ggcttgggag tgcagcttct caaaggagac cgatgcttgc tcaggatgtc gacagctgtg     1680
gcttccttgt ttttgctagc catatttttta aatcagggtt gaactgacaa aaataattta     1740
aagacgttta cttcccttga actttgaacc tgtgaaatgc tttaccttgt ttacagtttg     1800
gcaaagttgc agtttgttct tgtttttagt ttagttttgt tttggtgttt tgtacctgta     1860
ctgtgttctt cacagaccct ttgtagcgtg gtcaggtctg ctgtaacatt tcccaccaac     1920
tctcttgctg tccacatcaa cagctaaatc atttattcat atggatctct accatcccca     1980
tgccttgccc aggtccagtt ccatttctct cattcacaag atgctttgaa ggttctgatt     2040
ttcaactgat caaactaatg caaaaaaaaa aaaaaaaaa aaaaaaag               2088
```

```
<210> SEQ ID NO 43
<211> LENGTH: 770
<212> TYPE: PRT
<213> ORGANISM: Homo sapiens

<400> SEQUENCE: 43
```

Met Ala Asn Ser Met Asn Gly Arg Asn Pro Gly Gly Arg Gly Asn
1               5                   10                  15

Pro Arg Lys Gly Arg Ile Leu Gly Ile Ile Asp Ala Ile Gln Asp Ala
            20                  25                  30

Val Gly Pro Pro Lys Gln Ala Ala Asp Arg Arg Thr Val Glu Lys
        35                  40                  45

Thr Trp Lys Leu Met Asp Lys Val Val Arg Leu Cys Gln Asn Pro Lys
    50                  55                  60

Leu Gln Leu Lys Asn Ser Pro Pro Tyr Ile Leu Asp Ile Leu Pro Asp
65                  70                  75                  80

Thr Tyr Gln His Leu Arg Leu Ile Leu Ser Lys Tyr Asp Asp Asn Gln
                85                  90                  95

Lys Leu Ala Gln Leu Ser Glu Asn Glu Tyr Phe Lys Ile Tyr Ile Asp
            100                 105                 110

```
Ser Leu Met Lys Lys Ser Lys Arg Ala Ile Arg Leu Phe Lys Glu Gly
        115                 120                 125

Lys Glu Arg Met Tyr Glu Glu Gln Ser Gln Asp Arg Arg Asn Leu Thr
    130                 135                 140

Lys Leu Ser Leu Ile Phe Ser His Met Leu Ala Glu Ile Lys Ala Ile
145                 150                 155                 160

Phe Pro Asn Gly Gln Phe Gln Gly Asp Asn Phe Arg Ile Thr Lys Ala
                165                 170                 175

Asp Ala Ala Glu Phe Trp Arg Lys Phe Phe Gly Asp Lys Thr Ile Val
            180                 185                 190

Pro Trp Lys Val Phe Arg Gln Cys Leu His Glu Val His Gln Ile Ser
        195                 200                 205

Ser Ser Leu Glu Ala Met Ala Leu Lys Ser Thr Ile Asp Leu Thr Cys
    210                 215                 220

Asn Asp Tyr Ile Ser Val Phe Glu Phe Asp Ile Phe Thr Arg Leu Phe
225                 230                 235                 240

Gln Pro Trp Gly Ser Ile Leu Arg Asn Trp Asn Phe Leu Ala Val Thr
                245                 250                 255

His Pro Gly Tyr Met Ala Phe Leu Thr Tyr Asp Glu Val Lys Ala Arg
            260                 265                 270

Leu Gln Lys Tyr Ser Thr Lys Pro Gly Ser Tyr Ile Phe Arg Leu Ser
        275                 280                 285

Cys Thr Arg Leu Gly Gln Trp Ala Ile Gly Tyr Val Thr Gly Asp Gly
    290                 295                 300

Asn Ile Leu Gln Thr Ile Pro His Asn Lys Pro Leu Phe Gln Ala Leu
305                 310                 315                 320

Ile Asp Gly Ser Arg Glu Gly Phe Tyr Leu Tyr Pro Asp Gly Arg Ser
                325                 330                 335

Tyr Asn Pro Asp Leu Thr Gly Leu Cys Glu Pro Thr Pro His Asp His
            340                 345                 350

Ile Lys Val Thr Gln Glu Gln Tyr Glu Leu Tyr Cys Glu Met Gly Ser
        355                 360                 365

Thr Phe Gln Leu Cys Lys Ile Cys Ala Glu Asn Asp Lys Asp Val Lys
    370                 375                 380

Ile Glu Pro Cys Gly His Leu Met Cys Thr Ser Cys Leu Thr Ala Trp
385                 390                 395                 400

Gln Glu Ser Asp Gly Gln Gly Cys Pro Phe Cys Arg Cys Glu Ile Lys
                405                 410                 415

Gly Thr Glu Pro Ile Ile Val Asp Pro Phe Asp Pro Arg Asp Glu Gly
            420                 425                 430

Ser Arg Cys Cys Ser Ile Ile Asp Pro Phe Gly Met Pro Met Leu Asp
        435                 440                 445

Leu Asp Asp Asp Asp Arg Glu Glu Ser Leu Met Met Asn Arg Leu
    450                 455                 460

Ala Asn Val Arg Lys Cys Thr Asp Arg Gln Asn Ser Pro Val Thr Ser
465                 470                 475                 480

Pro Gly Ser Ser Pro Leu Ala Gln Arg Arg Lys Pro Gln Pro Asp Pro
                485                 490                 495

Leu Gln Ile Pro His Leu Ser Leu Pro Pro Val Pro Pro Arg Leu Asp
            500                 505                 510

Leu Ile Gln Lys Gly Ile Val Arg Ser Pro Cys Gly Ser Pro Thr Gly
        515                 520                 525
```

```
Ser Pro Lys Ser Ser Pro Cys Met Val Arg Lys Gln Asp Lys Pro Leu
            530                 535                 540

Pro Ala Pro Pro Pro Leu Arg Asp Pro Pro Pro Pro Pro Pro Pro Glu
545                 550                 555                 560

Arg Pro Pro Pro Ile Pro Pro Asp Asn Arg Leu Ser Arg His Ile His
                565                 570                 575

His Val Glu Ser Val Pro Ser Arg Asp Pro Pro Met Pro Leu Glu Ala
            580                 585                 590

Trp Cys Pro Arg Asp Val Phe Gly Thr Asn Gln Leu Val Gly Cys Arg
            595                 600                 605

Leu Leu Gly Glu Gly Ser Pro Lys Pro Gly Ile Thr Ala Ser Ser Asn
    610                 615                 620

Val Asn Gly Arg His Ser Arg Val Gly Ser Asp Pro Val Leu Met Arg
625                 630                 635                 640

Lys His Arg Arg His Asp Leu Pro Leu Glu Gly Ala Lys Val Phe Ser
                645                 650                 655

Asn Gly His Leu Gly Ser Glu Glu Tyr Asp Val Pro Pro Arg Leu Ser
            660                 665                 670

Pro Pro Pro Pro Val Thr Thr Leu Leu Pro Ser Ile Lys Cys Thr Gly
            675                 680                 685

Pro Leu Ala Asn Ser Leu Ser Glu Lys Thr Arg Asp Pro Val Glu Glu
690                 695                 700

Asp Asp Asp Glu Tyr Lys Ile Pro Ser Ser His Pro Val Ser Leu Asn
705                 710                 715                 720

Ser Gln Pro Ser His Cys His Asn Val Lys Pro Pro Val Arg Ser Cys
                725                 730                 735

Asp Asn Gly His Cys Met Leu Asn Gly Thr His Gly Pro Ser Ser Glu
            740                 745                 750

Lys Lys Ser Asn Ile Pro Asp Leu Ser Ile Tyr Leu Lys Gly Thr Tyr
            755                 760                 765

Arg Ile
770

<210> SEQ ID NO 44
<211> LENGTH: 982
<212> TYPE: PRT
<213> ORGANISM: Homo sapiens

<400> SEQUENCE: 44

Met Ala Asn Ser Met Asn Gly Arg Asn Pro Gly Gly Arg Gly Gly Asn
1               5                   10                  15

Pro Arg Lys Gly Arg Ile Leu Gly Ile Ile Asp Ala Ile Gln Asp Ala
                20                  25                  30

Val Gly Pro Pro Lys Gln Ala Ala Asp Arg Arg Thr Val Glu Lys
            35                  40                  45

Thr Trp Lys Leu Met Asp Lys Val Val Arg Leu Cys Gln Asn Pro Lys
50                  55                  60

Leu Gln Leu Lys Asn Ser Pro Pro Tyr Ile Leu Asp Ile Leu Pro Asp
65                  70                  75                  80

Thr Tyr Gln His Leu Arg Leu Ile Leu Ser Lys Tyr Asp Asp Asn Gln
                85                  90                  95

Lys Leu Ala Gln Leu Ser Glu Asn Glu Tyr Phe Lys Ile Tyr Ile Asp
            100                 105                 110

Ser Leu Met Lys Lys Ser Lys Arg Ala Ile Arg Leu Phe Lys Glu Gly
            115                 120                 125
```

-continued

```
Lys Glu Arg Met Tyr Glu Glu Gln Ser Gln Asp Arg Arg Asn Leu Thr
    130                 135                 140
Lys Leu Ser Leu Ile Phe Ser His Met Leu Ala Glu Ile Lys Ala Ile
145                 150                 155                 160
Phe Pro Asn Gly Gln Phe Gln Gly Asp Asn Phe Arg Ile Thr Lys Ala
                165                 170                 175
Asp Ala Ala Glu Phe Trp Arg Lys Phe Phe Gly Asp Lys Thr Ile Val
            180                 185                 190
Pro Trp Lys Val Phe Arg Gln Cys Leu His Glu Val His Gln Ile Ser
        195                 200                 205
Ser Gly Leu Glu Ala Met Ala Leu Lys Ser Thr Ile Asp Leu Thr Cys
    210                 215                 220
Asn Asp Tyr Ile Ser Val Phe Glu Phe Asp Ile Phe Thr Arg Leu Phe
225                 230                 235                 240
Gln Pro Trp Gly Ser Ile Leu Arg Asn Trp Asn Phe Leu Ala Val Thr
                245                 250                 255
His Pro Gly Tyr Met Ala Phe Leu Thr Tyr Asp Glu Val Lys Ala Arg
            260                 265                 270
Leu Gln Lys Tyr Ser Thr Lys Pro Gly Ser Tyr Ile Phe Arg Leu Ser
        275                 280                 285
Cys Thr Arg Leu Gly Gln Trp Ala Ile Gly Tyr Val Thr Gly Asp Gly
    290                 295                 300
Asn Ile Leu Gln Thr Ile Pro His Asn Lys Pro Leu Phe Gln Ala Leu
305                 310                 315                 320
Ile Asp Gly Ser Arg Glu Gly Phe Tyr Leu Tyr Pro Asp Gly Arg Ser
                325                 330                 335
Tyr Asn Pro Asp Leu Thr Gly Leu Cys Glu Pro Thr Pro His Asp His
            340                 345                 350
Ile Lys Val Thr Gln Glu Gln Tyr Glu Leu Tyr Cys Glu Met Gly Ser
        355                 360                 365
Thr Phe Gln Leu Cys Lys Ile Cys Ala Glu Asn Asp Lys Asp Val Lys
    370                 375                 380
Ile Glu Pro Cys Gly His Leu Met Cys Thr Ser Cys Leu Thr Ala Trp
385                 390                 395                 400
Gln Glu Ser Asp Gly Gln Gly Cys Pro Phe Cys Arg Cys Glu Ile Lys
                405                 410                 415
Gly Thr Glu Pro Ile Ile Val Asp Pro Phe Asp Pro Arg Asp Glu Gly
            420                 425                 430
Ser Arg Cys Cys Ser Ile Ile Asp Pro Phe Gly Met Pro Met Leu Asp
        435                 440                 445
Leu Asp Asp Asp Asp Arg Glu Glu Ser Leu Met Met Asn Arg Leu
    450                 455                 460
Ala Asn Val Arg Lys Cys Thr Asp Arg Gln Asn Ser Pro Val Thr Ser
465                 470                 475                 480
Pro Gly Ser Ser Pro Leu Ala Gln Arg Arg Lys Pro Gln Pro Asp Pro
                485                 490                 495
Leu Gln Ile Pro His Leu Ser Leu Pro Pro Val Pro Pro Arg Leu Asp
            500                 505                 510
Leu Ile Gln Lys Gly Ile Val Arg Ser Pro Cys Gly Ser Pro Thr Gly
        515                 520                 525
Ser Pro Lys Ser Ser Pro Cys Met Val Arg Lys Gln Asp Lys Pro Leu
    530                 535                 540
```

-continued

```
Pro Ala Pro Pro Pro Leu Arg Asp Pro Pro Pro Pro Glu
545                 550                 555                 560

Arg Pro Pro Pro Ile Pro Pro Asp Asn Arg Leu Ser Arg His Ile His
                565                 570                 575

His Val Glu Ser Val Pro Ser Lys Asp Pro Pro Met Pro Leu Glu Ala
            580                 585                 590

Trp Cys Pro Arg Asp Val Phe Gly Thr Asn Gln Leu Val Gly Cys Arg
                595                 600                 605

Leu Leu Gly Glu Gly Ser Pro Lys Pro Gly Ile Thr Ala Ser Ser Asn
        610                 615                 620

Val Asn Gly Arg His Ser Arg Val Gly Ser Asp Pro Val Leu Met Arg
625                 630                 635                 640

Lys His Arg Arg His Asp Leu Pro Leu Glu Gly Ala Lys Val Phe Ser
                645                 650                 655

Asn Gly His Leu Gly Ser Glu Glu Tyr Asp Val Pro Pro Arg Leu Ser
            660                 665                 670

Pro Pro Pro Pro Val Thr Thr Leu Leu Pro Ser Ile Lys Cys Thr Gly
                675                 680                 685

Pro Leu Ala Asn Ser Leu Ser Glu Lys Thr Arg Asp Pro Val Glu Glu
        690                 695                 700

Asp Asp Asp Glu Tyr Lys Ile Pro Ser Ser His Pro Val Ser Leu Asn
705                 710                 715                 720

Ser Gln Pro Ser His Cys His Asn Val Lys Pro Pro Val Arg Ser Cys
                725                 730                 735

Asp Asn Gly His Cys Met Leu Asn Gly Thr His Gly Pro Ser Ser Glu
            740                 745                 750

Lys Lys Ser Asn Ile Pro Asp Leu Ser Ile Tyr Leu Lys Gly Asp Val
        755                 760                 765

Phe Asp Ser Ala Ser Asp Pro Val Pro Leu Pro Pro Ala Arg Pro Pro
770                 775                 780

Thr Arg Asp Asn Pro Lys His Gly Ser Ser Leu Asn Arg Thr Pro Ser
785                 790                 795                 800

Asp Tyr Asp Leu Leu Ile Pro Pro Leu Gly Glu Asp Ala Phe Asp Ala
                805                 810                 815

Leu Pro Pro Ser Leu Pro Pro Pro Pro Pro Ala Arg His Ser Leu
        820                 825                 830

Ile Glu His Ser Lys Pro Pro Gly Ser Ser Arg Pro Ser Ser Gly
        835                 840                 845

Gln Asp Leu Phe Leu Leu Pro Ser Asp Pro Phe Val Asp Leu Ala Ser
850                 855                 860

Gly Gln Val Pro Leu Pro Pro Ala Arg Arg Leu Pro Gly Glu Asn Val
865                 870                 875                 880

Lys Thr Asn Arg Thr Ser Gln Asp Tyr Asp Gln Leu Pro Ser Cys Ser
                885                 890                 895

Asp Gly Ser Gln Ala Pro Ala Arg Pro Pro Lys Pro Arg Pro Arg Arg
            900                 905                 910

Thr Ala Pro Glu Ile His His Arg Lys Pro His Gly Pro Glu Ala Ala
        915                 920                 925

Leu Glu Asn Val Asp Ala Lys Ile Ala Lys Leu Met Gly Glu Gly Tyr
        930                 935                 940

Ala Phe Glu Glu Val Lys Arg Ala Leu Glu Ile Ala Gln Asn Asn Val
945                 950                 955                 960

Glu Val Ala Arg Ser Ile Leu Arg Glu Phe Ala Phe Pro Pro Pro Val
```

Ser Pro Arg Leu Asn Leu
            980

<210> SEQ ID NO 45
<211> LENGTH: 982
<212> TYPE: PRT
<213> ORGANISM: Homo sapiens

<400> SEQUENCE: 45

Met Ala Asn Ser Met Asn Gly Arg Asn Pro Gly Gly Arg Gly Gly Asn
1               5                   10                  15

Pro Arg Lys Gly Arg Ile Leu Gly Ile Ile Asp Ala Ile Gln Asp Ala
            20                  25                  30

Val Gly Pro Pro Lys Gln Ala Ala Asp Arg Arg Thr Val Glu Lys
            35                  40                  45

Thr Trp Lys Leu Met Asp Lys Val Val Arg Leu Cys Gln Asn Pro Lys
50                  55                  60

Leu Gln Leu Lys Asn Ser Pro Pro Tyr Ile Leu Asp Ile Leu Pro Asp
65                  70                  75                  80

Thr Tyr Gln His Leu Arg Leu Ile Leu Ser Lys Tyr Asp Asp Asn Gln
                85                  90                  95

Lys Leu Ala Gln Leu Ser Glu Asn Glu Tyr Phe Lys Ile Tyr Ile Asp
            100                 105                 110

Ser Leu Met Lys Lys Ser Lys Arg Ala Ile Arg Leu Phe Lys Glu Gly
            115                 120                 125

Lys Glu Arg Met Tyr Glu Glu Gln Ser Gln Asp Arg Arg Asn Leu Thr
130                 135                 140

Lys Leu Ser Leu Ile Phe Ser His Met Leu Ala Glu Ile Lys Ala Ile
145                 150                 155                 160

Phe Pro Asn Gly Gln Phe Gln Gly Asp Asn Phe Arg Ile Thr Lys Ala
                165                 170                 175

Asp Ala Ala Glu Phe Trp Arg Lys Phe Phe Gly Asp Lys Thr Ile Val
            180                 185                 190

Pro Trp Lys Val Phe Arg Gln Cys Leu His Glu Val His Gln Ile Ser
            195                 200                 205

Ser Ser Leu Glu Ala Met Ala Leu Lys Ser Thr Ile Asp Leu Thr Cys
210                 215                 220

Asn Asp Tyr Ile Ser Val Phe Glu Phe Asp Ile Phe Thr Arg Leu Phe
225                 230                 235                 240

Gln Pro Trp Gly Ser Ile Leu Arg Asn Trp Asn Phe Leu Ala Val Thr
                245                 250                 255

His Pro Gly Tyr Met Ala Phe Leu Thr Tyr Asp Glu Val Lys Ala Arg
            260                 265                 270

Leu Gln Lys Tyr Ser Thr Lys Pro Gly Ser Tyr Ile Phe Arg Leu Ser
            275                 280                 285

Cys Thr Arg Leu Gly Gln Trp Ala Ile Gly Tyr Val Thr Gly Asp Gly
            290                 295                 300

Asn Ile Leu Gln Thr Ile Pro His Asn Lys Pro Leu Phe Gln Ala Leu
305                 310                 315                 320

Ile Asp Gly Ser Arg Glu Gly Phe Tyr Leu Tyr Pro Asp Gly Arg Ser
                325                 330                 335

Tyr Asn Pro Asp Leu Thr Gly Leu Cys Glu Pro Thr Pro His Asp His
            340                 345                 350

-continued

```
Ile Lys Val Thr Gln Glu Gln Tyr Glu Leu Tyr Cys Glu Met Gly Ser
        355                 360                 365
Thr Phe Gln Leu Cys Lys Ile Cys Ala Glu Asn Asp Lys Asp Val Lys
    370                 375                 380
Ile Glu Pro Cys Gly His Leu Met Cys Thr Ser Cys Leu Thr Ala Trp
385                 390                 395                 400
Gln Glu Ser Asp Gly Gln Gly Cys Pro Phe Cys Arg Cys Glu Ile Lys
                405                 410                 415
Gly Thr Glu Pro Ile Ile Val Asp Pro Phe Asp Pro Arg Asp Glu Gly
                420                 425                 430
Ser Arg Cys Cys Ser Ile Ile Asp Pro Phe Gly Met Pro Met Leu Asp
        435                 440                 445
Leu Asp Asp Asp Asp Arg Glu Glu Ser Leu Met Met Asn Arg Leu
    450                 455                 460
Ala Asn Val Arg Lys Cys Thr Asp Arg Gln Asn Ser Pro Val Thr Ser
465                 470                 475                 480
Pro Gly Ser Ser Pro Leu Ala Gln Arg Arg Lys Pro Gln Pro Asp Pro
                485                 490                 495
Leu Gln Ile Pro His Leu Ser Leu Pro Val Pro Pro Arg Leu Asp
            500                 505                 510
Leu Ile Gln Lys Gly Ile Val Arg Ser Pro Cys Gly Ser Pro Thr Gly
        515                 520                 525
Ser Pro Lys Ser Ser Pro Cys Met Val Arg Lys Gln Asp Lys Pro Leu
    530                 535                 540
Pro Ala Pro Pro Pro Leu Arg Asp Pro Pro Pro Pro Pro Glu
545                 550                 555                 560
Arg Pro Pro Pro Ile Pro Pro Asp Asn Arg Leu Ser Arg His Ile His
                565                 570                 575
His Val Glu Ser Val Pro Ser Arg Asp Pro Pro Met Pro Leu Glu Ala
            580                 585                 590
Trp Cys Pro Arg Asp Val Phe Gly Thr Asn Gln Leu Val Gly Cys Arg
        595                 600                 605
Leu Leu Gly Glu Gly Ser Pro Lys Pro Gly Ile Thr Ala Ser Ser Asn
    610                 615                 620
Val Asn Gly Arg His Ser Arg Val Gly Ser Asp Pro Val Leu Met Arg
625                 630                 635                 640
Lys His Arg Arg His Asp Leu Pro Leu Glu Gly Ala Lys Val Phe Ser
                645                 650                 655
Asn Gly His Leu Gly Ser Glu Glu Tyr Asp Val Pro Pro Arg Leu Ser
            660                 665                 670
Pro Pro Pro Pro Val Thr Thr Leu Leu Pro Ser Ile Lys Cys Thr Gly
        675                 680                 685
Pro Leu Ala Asn Ser Leu Ser Glu Lys Thr Arg Asp Pro Val Glu Glu
    690                 695                 700
Asp Asp Asp Glu Tyr Lys Ile Pro Ser Ser His Pro Val Ser Leu Asn
705                 710                 715                 720
Ser Gln Pro Ser His Cys His Asn Val Lys Pro Pro Val Arg Ser Cys
                725                 730                 735
Asp Asn Gly His Cys Met Leu Asn Gly Thr His Gly Pro Ser Ser Glu
            740                 745                 750
Lys Lys Ser Asn Ile Pro Asp Leu Ser Ile Tyr Leu Lys Gly Asp Val
        755                 760                 765
Phe Asp Ser Ala Ser Asp Pro Val Pro Leu Pro Pro Ala Arg Pro Pro
```

-continued

```
              770                 775                 780
Thr Arg Asp Asn Pro Lys His Gly Ser Ser Leu Asn Arg Thr Pro Ser
785                 790                 795                 800

Asp Tyr Asp Leu Leu Ile Pro Pro Leu Gly Glu Asp Ala Phe Asp Ala
                805                 810                 815

Leu Pro Pro Ser Leu Pro Pro Pro Pro Ala Arg His Ser Leu
            820                 825                 830

Ile Glu His Ser Lys Pro Pro Gly Ser Ser Arg Pro Ser Ser Gly
            835                 840                 845

Gln Asp Leu Phe Leu Leu Pro Ser Asp Pro Phe Val Asp Leu Ala Ser
850                 855                 860

Gly Gln Val Pro Leu Pro Pro Ala Arg Arg Leu Pro Gly Glu Asn Val
865                 870                 875                 880

Lys Thr Asn Arg Thr Ser Gln Asp Tyr Asp Gln Leu Pro Ser Cys Ser
                885                 890                 895

Asp Gly Ser Gln Ala Pro Ala Arg Pro Pro Lys Pro Arg Pro Arg Arg
                900                 905                 910

Thr Ala Pro Glu Ile His His Arg Lys Pro His Gly Pro Glu Ala Ala
                915                 920                 925

Leu Glu Asn Val Asp Ala Lys Ile Ala Lys Leu Met Gly Glu Gly Tyr
            930                 935                 940

Ala Phe Glu Glu Val Lys Arg Ala Leu Glu Ile Ala Gln Asn Asn Val
945                 950                 955                 960

Glu Val Ala Arg Ser Ile Leu Arg Glu Phe Ala Phe Pro Pro Pro Val
                965                 970                 975

Ser Pro Arg Leu Asn Leu
            980

<210> SEQ ID NO 46
<211> LENGTH: 810
<212> TYPE: PRT
<213> ORGANISM: Homo sapiens

<400> SEQUENCE: 46

Met Ala Asn Ser Met Asn Gly Arg Asn Pro Gly Gly Arg Gly Gly Asn
1               5                   10                  15

Pro Arg Lys Gly Arg Ile Leu Gly Ile Ile Asp Ala Ile Gln Asp Ala
            20                  25                  30

Val Gly Pro Pro Lys Gln Ala Ala Ala Asp Arg Arg Thr Val Glu Lys
        35                  40                  45

Thr Trp Lys Leu Met Asp Lys Val Val Arg Leu Cys Gln Asn Pro Lys
50                  55                  60

Leu Gln Leu Lys Asn Ser Pro Pro Tyr Ile Leu Asp Ile Leu Pro Asp
65                  70                  75                  80

Thr Tyr Gln His Leu Arg Leu Ile Leu Ser Lys Tyr Asp Asp Asn Gln
                85                  90                  95

Lys Leu Ala Gln Leu Ser Glu Asn Glu Tyr Phe Lys Ile Tyr Ile Asp
            100                 105                 110

Ser Leu Met Lys Lys Ser Lys Arg Ala Ile Arg Leu Phe Lys Glu Gly
        115                 120                 125

Lys Glu Arg Met Tyr Glu Glu Gln Ser Gln Asp Arg Arg Asn Leu Thr
    130                 135                 140

Lys Leu Ser Leu Ile Phe Ser His Met Leu Ala Glu Ile Lys Ala Ile
145                 150                 155                 160
```

-continued

```
Phe Pro Asn Gly Gln Phe Gln Gly Asp Asn Phe Arg Ile Thr Lys Ala
                165                 170                 175

Asp Ala Ala Glu Phe Trp Arg Lys Phe Phe Gly Asp Lys Thr Ile Val
            180                 185                 190

Pro Trp Lys Val Phe Arg Gln Cys Leu His Glu Val His Gln Ile Ser
        195                 200                 205

Ser Ser Leu Glu Ala Met Ala Leu Lys Ser Thr Ile Asp Leu Thr Cys
    210                 215                 220

Asn Asp Tyr Ile Ser Val Phe Glu Phe Asp Ile Phe Thr Arg Leu Phe
225                 230                 235                 240

Gln Pro Trp Gly Ser Ile Leu Arg Asn Trp Asn Phe Leu Ala Val Thr
                245                 250                 255

His Pro Gly Tyr Met Ala Phe Leu Thr Tyr Asp Glu Val Lys Ala Arg
            260                 265                 270

Leu Gln Lys Tyr Ser Thr Lys Pro Gly Ser Tyr Ile Phe Arg Leu Ser
        275                 280                 285

Cys Thr Arg Leu Gly Gln Trp Ala Ile Gly Tyr Val Thr Gly Asp Gly
    290                 295                 300

Asn Ile Leu Gln Thr Ile Pro His Asn Lys Pro Leu Phe Gln Ala Leu
305                 310                 315                 320

Ile Asp Gly Ser Arg Glu Gly Phe Tyr Leu Tyr Pro Asp Gly Arg Ser
                325                 330                 335

Tyr Asn Pro Asp Leu Thr Gly Leu Cys Glu Pro Thr Pro His Asp His
            340                 345                 350

Ile Lys Val Thr Gln Glu Gln Tyr Glu Leu Tyr Cys Glu Met Gly Ser
        355                 360                 365

Thr Phe Gln Leu Cys Lys Ile Cys Ala Glu Asn Asp Lys Asp Val Lys
    370                 375                 380

Ile Glu Pro Cys Gly His Leu Met Cys Thr Ser Cys Leu Thr Ala Trp
385                 390                 395                 400

Gln Glu Ser Asp Gly Gln Gly Cys Pro Phe Cys Arg Cys Glu Ile Lys
                405                 410                 415

Gly Thr Glu Pro Ile Ile Val Asp Pro Phe Asp Pro Arg Asp Glu Gly
            420                 425                 430

Ser Arg Cys Cys Ser Ile Ile Asp Pro Phe Gly Met Pro Met Leu Asp
        435                 440                 445

Leu Asp Asp Asp Asp Asp Arg Glu Glu Ser Leu Met Met Asn Arg Leu
    450                 455                 460

Ala Asn Val Arg Lys Cys Thr Asp Arg Gln Asn Ser Pro Val Thr Ser
465                 470                 475                 480

Pro Gly Ser Ser Pro Leu Ala Gln Arg Arg Lys Pro Gln Pro Asp Pro
                485                 490                 495

Leu Gln Ile Pro His Leu Ser Leu Pro Pro Val Pro Pro Arg Leu Asp
            500                 505                 510

Leu Ile Gln Lys Gly Ile Val Arg Ser Pro Cys Gly Ser Pro Thr Gly
        515                 520                 525

Ser Pro Lys Ser Ser Pro Cys Met Val Arg Lys Gln Asp Lys Pro Leu
    530                 535                 540

Pro Ala Pro Pro Pro Leu Arg Asp Pro Pro Pro Pro Pro Pro Pro Glu
545                 550                 555                 560

Arg Pro Pro Pro Ile Pro Pro Asp Asn Arg Leu Ser Arg His Ile His
                565                 570                 575

His Val Glu Ser Val Pro Ser Arg Asp Pro Pro Met Pro Leu Glu Ala
```

```
                     580                 585                 590
Trp Cys Pro Arg Asp Val Phe Gly Thr Asn Gln Leu Val Gly Cys Arg
            595                 600                 605
Leu Leu Gly Glu Gly Ser Pro Lys Pro Gly Ile Thr Ala Ser Ser Asn
            610                 615                 620
Val Asn Gly Arg His Ser Arg Val Gly Ser Asp Pro Val Leu Met Arg
625                 630                 635                 640
Lys His Arg Arg His Asp Leu Pro Leu Glu Gly Ala Lys Val Phe Ser
                645                 650                 655
Asn Gly His Leu Gly Ser Glu Glu Tyr Asp Val Pro Pro Arg Leu Ser
            660                 665                 670
Pro Pro Pro Val Thr Thr Leu Leu Pro Ser Ile Lys Cys Thr Gly
            675                 680                 685
Pro Leu Ala Asn Ser Leu Ser Glu Lys Thr Arg Asp Pro Val Glu Glu
            690                 695                 700
Asp Asp Asp Glu Tyr Lys Ile Pro Ser Ser His Pro Val Ser Leu Asn
705                 710                 715                 720
Ser Gln Pro Ser His Cys His Asn Val Lys Pro Val Arg Ser Cys
                725                 730                 735
Asp Asn Gly His Cys Met Leu Asn Gly Thr His Gly Pro Ser Ser Glu
            740                 745                 750
Lys Lys Ser Asn Ile Pro Asp Leu Ser Ile Tyr Leu Lys Gly Asp Val
            755                 760                 765
Phe Asp Ser Ala Ser Asp Pro Val Pro Leu Pro Ala Arg Pro Pro
            770                 775                 780
Thr Arg Asp Asn Pro Lys His Gly Ser Ser Leu Asn Arg Thr Pro Ser
785                 790                 795                 800
Asp Tyr Asp Leu Leu Ile Pro Pro Leu Gly
                805                 810

<210> SEQ ID NO 47
<211> LENGTH: 3373
<212> TYPE: DNA
<213> ORGANISM: Rat

<400> SEQUENCE: 47
cgggcgggcg tggagctgtc tgcacgaaag gactaagatt ccagatggca aattctatga     60
atggcagaaa tcctggtggt cgaggaggaa acccccgcaa aggtcgaatt ttggggatta    120
ttgatgccat tcaggatgca gttggacccc caaagcaagc tgcagctgac cgcaggacag    180
tggagaagac ttggaaactc atggacaaag tggtaagact gtgccaaaat ccgaaacttc    240
agttgaaaaa cagcccacca tatatcctcg acattttacc tgatacgtat cagcatttgc    300
ggcttatatt gagtaagtat gacgacaacc agaagctggc tcaactgagc gagaatgagt    360
actttaaaat ctacatcgac agtctcatga gaagtcaaaa gcgagcgatc cggctcttca    420
aagaaggcaa ggagaggatg tacgaggagc agtcgcagga cagacggaat ctcacaaagc    480
tgtcccttat cttcagtcac atgctggcag aaatcaaggc gatctttccc aatggccagt    540
tccagggaga taacttccgg atcaccaaag cagatgctgc cgaattctgg aggaagtttt    600
ttggagacaa aactatcgta ccatggaaag tcttcagaca gtgcctgcat gaggtccatc    660
agatcagctc tggcctggag gccatggctc tgaagtcaac cattgactta acttgtaatg    720
attacatctc cgtgtttgaa tttgatattt taccaggct atttcagccc tggggctcta    780
ttttacggaa ttggaacttc ttagctgtga cacacccggg gtacatggca tttctcacat    840
```

```
atgatgaagt taaagctcga ctacagaaat acagcaccaa gcctggaagc tacattttcc      900
ggttaagctg cactcggctg ggacaatggg ccattggcta tgtgactggg gacggcaata      960
tcctacagac catacctcat aacaagcccc tgttccaagc cctgattgat ggtagcaggg     1020
aaggctttta cctttatcca gatggacgaa gctataaccc tgatttaacc ggattatgtg     1080
aacctacacc tcatgatcat ataaaagtta cacaggagca atatgaactg tattgtgaaa     1140
tgggctccac ttttcagctg tgcaagatct gtgcagagaa tgacaaagat gtcaagatcg     1200
agccttgtgg gcatctcatg tgcacttcgt gccttaccgc gtggcaggag tctgatggcc     1260
aaggctgccc cttctgtcgc tgtgagataa aaggaaccga acctatcatc gtggatccct     1320
ttgaccccag agacgaaggc tccaggtgct gcagcatcat cgacccttc agcatcccca     1380
tgctcgactt ggatgatgac gatgatcgag aggagtctct gatgatgaac cggctggcga     1440
gtgttcgcaa gtgcacagac aggcagaact cgccagtcac atcgccagga tcctcacccc     1500
ttgcccagag aagaaagcct cagccagacc ctctccagat cccccacctc agcctgccac     1560
cagtgcctcc ccgcctggac ctcattcaga aaggcatcgt gcgctctccc tgtggcagcc     1620
ccacgggctc cccgaagtct tctccatgca tggttagaaa acaagacaaa ccactcccag     1680
cacccctcc tcccttgcga gatcctccgc ctccaccaga gcggcctccg ccaatcccgc     1740
ctgacagtag actgagcaga cacttccacc acggagagag tgtgccttcc agggaccagc     1800
caatgcctct tgaagcctgg tgccctcggg atgccttcgg gactaatcag gtgatgggat     1860
gtcgcatcct aggggatggc tctccaaagc ctggcgtcac agcaaactcc aacttaaatg     1920
gacgtcacag tcgaatgggc tctgaccagg ttcttatgag gaaacacaga cgccacgatt     1980
tgccttcaga aggcgccaag gtcttttcca atggacacct tgcccctgaa gaatacgacg     2040
ttcctcctcg gctttcccct cctcctccag tcactgccct tctccctagc ataaagtgta     2100
ctggtccaat agcaaattgt ctctccgaga aaacaagaga cacagtagaa gaagatgatg     2160
atgaatacaa gattccttca tcccatcctg tttccctgaa ttcacaacca tctcattgtc     2220
ataatgtcaa acctcctgtt cggtcttgtg ataatggtca ctgtatactg aatggaactc     2280
atggtacgcc ttcagagatg aagaaatcaa acatcccaga tttaggcatc tatttgaagg     2340
gtgaagatgc ttttgatgcc ctccccccat cccttcctcc tccccacct cctgcaagac     2400
atagtctcat cgagcattca aaacctccag gctccagtag ccggccttcc tcaggacagg     2460
acctttcct tcttccttca gatcccttt ttgacccagc aagtggccaa gttccattgc     2520
ctccggccag gagagcacca ggagatggtg tcaaatccaa cagagcctcc caggactatg     2580
accagctccc ttcatcttcc gatggttcgc aagcaccagc tagaccccc aaaccacgac     2640
cccgaaggac tgcaccagaa attcatcaca gaaagcccca tgggcccgag gcggcactgg     2700
aaaatgtgga tgcgaaaatt gcaaaactca tgggagaggg gtatgccttt gaagaggtga     2760
agagagcctt agagatcgcc cagaataacc tggaagtggc caggagcata cttcgagaat     2820
tcgccttccc tcctcccgtc tcgccacgtc tcaatctata gcagcccaga ctgcaaacac     2880
caaagggtaa aacagttaac aaatattcca ggagtatggg acagaaggac tgagagggaa     2940
tgcaggagcc atggtgtctt ttcatgtggc gtctccagaa ggcagccttg agtccagctt     3000
ctctggtacc acagctccct gaggatgccc acgctgcagc ttctgtgttt gtgctagcca     3060
tacttttaaa tcagggttga actgagaaaa taatttaaag acgtttactc cccccttgaac    3120
tttgaatctg tgaaatgctt tccttgttta cacgttggca gaattgcagt ttgtctctgt     3180
```

```
tttgattcc tgtactgtgt tcctgacagg cccttggcag agttggtcag gtctgctgta    3240
agtttgtcca tgcccaccct gctgcccaca ttggcagcta aagcatctct tcgtgttgct    3300
gtctatccgg gccccacctc atgtgtccac gtccagttca tttctctcat tcacacagca    3360
tgctagtctg agg                                                        3373
```

<210> SEQ ID NO 48
<211> LENGTH: 938
<212> TYPE: PRT
<213> ORGANISM: Rat

<400> SEQUENCE: 48

```
Met Ala Asn Ser Met Asn Gly Arg Asn Pro Gly Gly Arg Gly Gly Asn
 1               5                  10                  15

Pro Arg Lys Gly Arg Ile Leu Gly Ile Ile Asp Ala Ile Gln Asp Ala
             20                  25                  30

Val Gly Pro Pro Lys Gln Ala Ala Ala Asp Arg Arg Thr Val Glu Lys
         35                  40                  45

Thr Trp Lys Leu Met Asp Lys Val Val Arg Leu Cys Gln Asn Pro Lys
 50                  55                  60

Leu Gln Leu Lys Asn Ser Pro Pro Tyr Ile Leu Asp Ile Leu Pro Asp
65                  70                  75                  80

Thr Tyr Gln His Leu Arg Leu Ile Leu Ser Lys Tyr Asp Asp Asn Gln
                 85                  90                  95

Lys Leu Ala Gln Leu Ser Glu Asn Glu Tyr Phe Lys Ile Tyr Ile Asp
            100                 105                 110

Ser Leu Met Lys Lys Ser Lys Arg Ala Ile Arg Leu Phe Lys Glu Gly
        115                 120                 125

Lys Glu Arg Met Tyr Glu Glu Gln Ser Gln Asp Arg Arg Asn Leu Thr
    130                 135                 140

Lys Leu Ser Leu Ile Phe Ser His Met Leu Ala Glu Ile Lys Ala Ile
145                 150                 155                 160

Phe Pro Asn Gly Gln Phe Gln Gly Asp Asn Phe Arg Ile Thr Lys Ala
                165                 170                 175

Asp Ala Ala Glu Phe Trp Arg Lys Phe Phe Gly Asp Lys Thr Ile Val
            180                 185                 190

Pro Trp Lys Val Phe Arg Gln Cys Leu His Glu Val His Gln Ile Ser
        195                 200                 205

Ser Gly Leu Glu Ala Met Ala Leu Lys Ser Thr Ile Asp Leu Thr Cys
    210                 215                 220

Asn Asp Tyr Ile Ser Val Phe Glu Phe Asp Ile Phe Thr Arg Leu Phe
225                 230                 235                 240

Gln Pro Trp Gly Ser Ile Leu Arg Asn Trp Asn Phe Leu Ala Val Thr
                245                 250                 255

His Pro Gly Tyr Met Ala Phe Leu Thr Tyr Asp Glu Val Lys Ala Arg
            260                 265                 270

Leu Gln Lys Tyr Ser Thr Lys Pro Gly Ser Tyr Ile Phe Arg Leu Ser
        275                 280                 285

Cys Thr Arg Leu Gly Gln Trp Ala Ile Gly Tyr Val Thr Gly Asp Gly
    290                 295                 300

Asn Ile Leu Gln Thr Ile Pro His Asn Lys Pro Leu Phe Gln Ala Leu
305                 310                 315                 320

Ile Asp Gly Ser Arg Glu Gly Phe Tyr Leu Tyr Pro Asp Gly Arg Ser
                325                 330                 335
```

-continued

```
Tyr Asn Pro Asp Leu Thr Gly Leu Cys Glu Pro Thr Pro His Asp His
            340                 345                 350

Ile Lys Val Thr Gln Glu Gln Tyr Glu Leu Tyr Cys Glu Met Gly Ser
            355                 360                 365

Thr Phe Gln Leu Cys Lys Ile Cys Ala Glu Asn Asp Lys Asp Val Lys
            370                 375                 380

Ile Glu Pro Cys Gly His Leu Met Cys Thr Ser Cys Leu Thr Ala Trp
385                 390                 395                 400

Gln Glu Ser Asp Gly Gln Gly Cys Pro Phe Cys Arg Cys Glu Ile Lys
            405                 410                 415

Gly Thr Glu Pro Ile Ile Val Asp Pro Phe Asp Pro Arg Asp Glu Gly
            420                 425                 430

Ser Arg Cys Cys Ser Ile Ile Asp Pro Phe Ser Ile Pro Met Leu Asp
            435                 440                 445

Leu Asp Asp Asp Asp Asp Arg Glu Glu Ser Leu Met Met Asn Arg Leu
        450                 455                 460

Ala Ser Val Arg Lys Cys Thr Asp Arg Gln Asn Ser Pro Val Thr Ser
465                 470                 475                 480

Pro Gly Ser Ser Pro Leu Ala Gln Arg Arg Lys Pro Gln Pro Asp Pro
            485                 490                 495

Leu Gln Ile Pro His Leu Ser Leu Pro Pro Val Pro Pro Arg Leu Asp
            500                 505                 510

Leu Ile Gln Lys Gly Ile Val Arg Ser Pro Cys Gly Ser Pro Thr Gly
            515                 520                 525

Ser Pro Lys Ser Ser Pro Cys Met Val Arg Lys Gln Asp Lys Pro Leu
            530                 535                 540

Pro Ala Pro Pro Pro Leu Arg Asp Pro Pro Pro Pro Pro Pro Glu Arg
545                 550                 555                 560

Pro Pro Pro Ile Pro Pro Asp Ser Arg Leu Ser Arg His Phe His His
            565                 570                 575

Gly Glu Ser Val Pro Ser Arg Asp Gln Pro Met Pro Leu Glu Ala Trp
            580                 585                 590

Cys Pro Arg Asp Ala Phe Gly Thr Asn Gln Val Met Gly Cys Arg Ile
            595                 600                 605

Leu Gly Asp Gly Ser Pro Lys Pro Gly Val Thr Ala Asn Ser Asn Leu
            610                 615                 620

Asn Gly Arg His Ser Arg Met Gly Ser Asp Gln Val Leu Met Arg Lys
625                 630                 635                 640

His Arg Arg His Asp Leu Pro Ser Glu Gly Ala Lys Val Phe Ser Asn
            645                 650                 655

Gly His Leu Ala Pro Glu Glu Tyr Asp Val Pro Arg Leu Ser Pro
            660                 665                 670

Pro Pro Pro Val Thr Ala Leu Leu Pro Ser Ile Lys Cys Thr Gly Pro
            675                 680                 685

Ile Ala Asn Cys Leu Ser Glu Lys Thr Arg Asp Thr Val Glu Glu Asp
            690                 695                 700

Asp Asp Glu Tyr Lys Ile Pro Ser Ser His Pro Val Ser Leu Asn Ser
705                 710                 715                 720

Gln Pro Ser His Cys His Asn Val Lys Pro Pro Val Arg Ser Cys Asp
            725                 730                 735

Asn Gly His Cys Ile Leu Asn Gly Thr His Gly Thr Pro Ser Glu Met
            740                 745                 750

Lys Lys Ser Asn Ile Pro Asp Leu Gly Ile Tyr Leu Lys Gly Glu Asp
```

```
                    755                 760                 765
Ala Phe Asp Ala Leu Pro Pro Ser Leu Pro Pro Pro Pro Pro Ala
    770                 775                 780

Arg His Ser Leu Ile Glu His Ser Lys Pro Pro Gly Ser Ser Arg
785                 790                 795                 800

Pro Ser Ser Gly Gln Asp Leu Phe Leu Leu Pro Ser Asp Pro Phe Phe
            805                 810                 815

Asp Pro Ala Ser Gly Gln Val Pro Leu Pro Ala Arg Arg Ala Pro
                820                 825                 830

Gly Asp Gly Val Lys Ser Asn Arg Ala Ser Gln Asp Tyr Asp Gln Leu
            835                 840                 845

Pro Ser Ser Ser Asp Gly Ser Gln Ala Pro Ala Arg Pro Pro Lys Pro
    850                 855                 860

Arg Pro Arg Arg Thr Ala Pro Glu Ile His His Arg Lys Pro His Gly
865                 870                 875                 880

Pro Glu Ala Ala Leu Glu Asn Val Asp Ala Lys Ile Ala Lys Leu Met
            885                 890                 895

Gly Glu Gly Tyr Ala Phe Glu Glu Val Lys Arg Ala Leu Glu Ile Ala
                900                 905                 910

Gln Asn Asn Leu Glu Val Ala Arg Ser Ile Leu Arg Glu Phe Ala Phe
            915                 920                 925

Pro Pro Pro Val Ser Pro Arg Leu Asn Leu
    930                 935

<210> SEQ ID NO 49
<211> LENGTH: 1446
<212> TYPE: DNA
<213> ORGANISM: Homo sapiens
<220> FEATURE:
<221> NAME/KEY: misc_feature
<222> LOCATION: 4, 10, 12, 13, 58, 74, 136, 206, 222, 237, 254, 385,
      1336, 1344, 1347, 1350, 1380, 1392, 1395, 1400, 1445
<223> OTHER INFORMATION: n = A,T,C or G

<400> SEQUENCE: 49
cgtntttggn anncactaca ggggatgttt aatacacact cacaatgcgc atgatgtnta      60
taactatcta ttcnatgatg taagataccc cactcaaacc cataaaaaag agcatcttta     120
atacgactca ctatanggcg agcgcacgcc atggcaggta cccatacgac gtaccagatt     180
acgctcatat ggccatggag ccagngaat tccacccaag cngtggtatc aacgcanagt      240
ggactctgac ccantgctta tgcggaaaca cagacgccat gatttgcctt tagaaggagc     300
taaggtctct tccaatggtc accttggaag tgaagaatat gatgttcctc cccggctttc     360
tcctcctcct ccagttacca ccctnctccc tagcataaag tgtactggtc cgttagcaaa     420
ttctctttca gagaaaacaa gagacccagt agaggaagat gatgatgaat acaagattcc     480
ttcatcccac cctgtttccc tgaattcaca accatctcat tgtcataatg taaaacctcc     540
tgttcggtct tgtgataatg gtcactgtat gctgaatgga acacatggtc catcttcaga     600
gaagaaatca aacatccctg acttaagcat atatttaaag ggtgaagatg cttttgatgc     660 cctcctcca tctctcccac ctcccccacc tcctgcaagg catagtctca ttgaacattc      720
aaaacctcct ggctccagta gccggccatc ctcaggacag gatcttttc ttcttccttc      780 agatcccttt gttgatctag caagtggcca agttcctttg cctcccgcta aaggttacc     840 aggtgaaaat gtcaaaacta acaggacatc acaggactat gatcagcttc cttcatgttc     900
agatggttca caggcaccag ccagaccccc taaaccacga ccgcgcagga ctgcaccaga     960
```

```
aattcaccac agaaaacccc atgggcctga ggcggcattg gaaaatgtcg atgcaaaaat    1020
tgcaaaactc atgggagagg gttatgcctt tgaagaggtg aagagagcct tagagatagc    1080
ccagaataat gtcgaagttg cccggagcat cctccgagaa tttgccttcc ctcctccagt    1140
atccccacgt ctaaatctat agcagccaga actgtagaca ccaaaatgga aagcaatcga    1200
tgtattccaa gagtgtggaa ataaagagaa ctgagatgga attcaagaga gaagtgtctc    1260
ctcctcgtgt agcagcttga aagaggctt gggagtgcag cttctcaaag aaaaccgatg     1320
cttgctcagg atgtcnacag ctgnggnctn cctgtttttt gctagccatt tttttaaatn    1380
agggttgaac tnganaaaan tatttaaaaa cgtttacctc ccttgaactt tgaacctggg    1440 aaagnc                                                              1446
```

<210> SEQ ID NO 50
<211> LENGTH: 300
<212> TYPE: PRT
<213> ORGANISM: Homo sapiens

<400> SEQUENCE: 50

```
Met Arg Lys His Arg Arg His Asp Leu Pro Leu Glu Gly Ala Lys Val
  1               5                  10                  15

Ser Ser Asn Gly His Leu Gly Ser Glu Glu Tyr Asp Val Pro Pro Arg
             20                  25                  30

Leu Ser Pro Pro Pro Val Thr Thr Leu Leu Pro Ser Ile Lys Cys
         35                  40                  45

Thr Gly Pro Leu Ala Asn Ser Leu Ser Glu Lys Thr Arg Asp Pro Val
 50                  55                  60

Glu Glu Asp Asp Asp Glu Tyr Lys Ile Pro Ser Ser His Pro Val Ser
 65                  70                  75                  80

Leu Asn Ser Gln Pro Ser His Cys His Asn Val Lys Pro Pro Val Arg
                 85                  90                  95

Ser Cys Asp Asn Gly His Cys Met Leu Asn Gly Thr His Gly Pro Ser
            100                 105                 110

Ser Glu Lys Lys Ser Asn Ile Pro Asp Leu Ser Ile Tyr Leu Lys Gly
        115                 120                 125

Glu Asp Ala Phe Asp Ala Leu Pro Pro Ser Leu Pro Pro Pro Pro
130                 135                 140

Pro Ala Arg His Ser Leu Ile Glu His Ser Lys Pro Pro Gly Ser Ser
145                 150                 155                 160

Ser Arg Pro Ser Ser Gly Gln Asp Leu Phe Leu Leu Pro Ser Asp Pro
                165                 170                 175

Phe Val Asp Leu Ala Ser Gly Gln Val Pro Leu Pro Pro Ala Arg Arg
            180                 185                 190

Leu Pro Gly Glu Asn Val Lys Thr Asn Arg Thr Ser Gln Asp Tyr Asp
        195                 200                 205

Gln Leu Pro Ser Cys Ser Asp Gly Ser Gln Ala Pro Ala Arg Pro Pro
    210                 215                 220

Lys Pro Arg Pro Arg Arg Thr Ala Pro Glu Ile His His Arg Lys Pro
225                 230                 235                 240

His Gly Pro Glu Ala Ala Leu Glu Asn Val Asp Ala Lys Ile Ala Lys
                245                 250                 255

Leu Met Gly Glu Gly Tyr Ala Phe Glu Glu Val Lys Arg Ala Leu Glu
            260                 265                 270

Ile Ala Gln Asn Asn Val Glu Val Ala Arg Ser Ile Leu Arg Glu Phe
```

275                 280                 285

Ala Phe Pro Pro Pro Val Ser Pro Arg Leu Asn Leu
    290                 295                 300

<210> SEQ ID NO 51
<211> LENGTH: 1203
<212> TYPE: DNA
<213> ORGANISM: Homo sapiens

<400> SEQUENCE: 51

```
actctgaccc agtgcttatg cggaaacaca gacgccatga tttgccttta gaaggagcta     60
aggtctcttc caatggtcac cttggaagtg aagaatatga tgttcctccc ggctttctc    120
ctcctcctcc agttaccacc ctcctcccta gcataaagtg tactggtccg ttagcaaatt   180
ctctttcaga gaaacaagac acccagtag aggaagatga tgatgaatac aagattcctt   240
catcccaccc tgtttccctg aattcacaac catctcattg tcataatgta aaacctcctg   300
ttcggtcttg tgataatggt cactgtatgc tgaatggaac acatggtcca tcttcagaga   360
agaaatcaaa catccctgac ttaagcatat atttaaaggg tgaagatgct tttgatgccc   420
tccctccatc tctcccacct cccccacctc ctgcaaggca tagtctcatt gaacattcaa   480
aacctcctgg ctccagtagc cggccatcct caggacagga tcttttttctt cttccttcag   540
atcccttttgt tgatctagca agtggccaag ttcctttgcc tcccgctaga aggttaccag   600
gtgaaaatgt caaaactaac aggacatcac aggactatga tcagcttcct tcatgttcag   660
atggttcaca ggcaccagcc agacccccta aaccacgacc cgcgcaggact gcaccagaaa   720
ttcaccacag aaaaccccat gggcctgagg cggcattgga aaatgtcgat gcaaaaattg   780
caaaactcat gggagagggt tatgcctttg aagaggtgaa gagagcctta gagatagccc   840
agaataatgt cgaagttgcc cggagcatcc tccgagaatt tgccttccct cctccagtat   900
ccccacgtct aaatctatag cagccagaac tgtagacacc aaaatggaaa gcaatcgatg   960
tattccaaga gtgtggaaat aaagagaact gagatggaat tcaagagaga agtgtctcct  1020
cctcgtgtag cagcttgaga agaggcttgg gagtgcagct tctcaaagaa aaccgatgct  1080
tgctcaggat gtcgacagct gtggcttcct tgttttttgct agccattttt ttaaatcagg  1140
gttgaactgg aaaaaattat ttaaaaacgt ttacctcccct tgaactttga acctgggaaa  1200
ggc                                                                1203
```

<210> SEQ ID NO 52
<211> LENGTH: 250
<212> TYPE: PRT
<213> ORGANISM: Homo sapiens

<400> SEQUENCE: 52

Ser Asp Pro Val Leu Met Arg Lys His Arg Arg His Asp Leu Pro Leu
1               5                   10                  15

Glu Gly Ala Lys Val Ser Ser Asn Gly His Leu Gly Ser Glu Glu Tyr
            20                  25                  30

Asp Val Pro Pro Arg Leu Ser Pro Pro Pro Val Thr Thr Leu Leu
        35                  40                  45

Pro Ser Ile Lys Cys Thr Gly Pro Leu Ala Asn Ser Leu Ser Glu Lys
    50                  55                  60

Thr Arg Asp Pro Val Glu Glu Asp Asp Glu Tyr Lys Ile Pro Ser
65                  70                  75                  80

Ser His Pro Val Ser Leu Asn Ser Gln Pro Ser His Cys His Asn Val

```
                85                  90                  95
Lys Pro Pro Val Arg Ser Cys Asp Asn Gly His Cys Met Leu Asn Gly
            100                 105                 110

Thr His Gly Pro Ser Ser Glu Lys Lys Ser Asn Ile Pro Asp Leu Ser
            115                 120                 125

Ile Tyr Leu Lys Gly Glu Asp Ala Phe Asp Ala Leu Pro Pro Ser Leu
        130                 135                 140

Pro Pro Pro Pro Pro Ala Arg His Ser Leu Ile Glu His Ser Lys
145                 150                 155                 160

Pro Pro Gly Ser Ser Arg Pro Ser Ser Gly Gln Asp Leu Phe Leu
                165                 170                 175

Leu Pro Ser Asp Pro Phe Val Asp Leu Ala Ser Gly Gln Val Pro Leu
            180                 185                 190

Pro Pro Ala Arg Arg Leu Pro Gly Glu Asn Val Lys Thr Asn Arg Thr
        195                 200                 205

Ser Gln Asp Tyr Asp Gln Leu Pro Ser Cys Ser Asp Gly Ser Gln Ala
        210                 215                 220

Pro Ala Arg Pro Pro Lys Pro Arg Pro Arg Thr Ala Pro Glu Ile
225                 230                 235                 240

His His Arg Lys Pro His Gly Pro Glu Ala
                245                 250

<210> SEQ ID NO 53
<211> LENGTH: 3131
<212> TYPE: DNA
<213> ORGANISM: Mouse

<400> SEQUENCE: 53
gactccctgg gctgcgagcg ccggcggtgg ttgccggaga ggcccctcct tctcgcccgg      60
ctccattccc tcgctcgcgg ccgagcgggc tcccgaccct ccgctggcca tggccggcaa     120
cgtgaagaag agctcgggcg ccggcggcgg cggctctggg ggctcggagc cgggcggcct     180
gatcgggctc atgaaggacg ccttccagcc gcaccaccac caccaccacc tcagcccgca     240
ccctccctgc acggtggaca agaagatggt ggagaagtgc tggaagctca tggacaaggt     300
ggtgcggttg tgtcaaaacc caaagctggc gctcaagaac agcccgcctt atatcttaga     360
cctgctgcct gacacctacc agcacctccg cactgtcttg tcaagatatg aggggaagat     420
ggagacgctt ggagaaaatg agtatttcag ggtgttcatg gaaaatttga tgaagaaaac     480
taagcagact atcagcctct tcaaggaggg aaaagaaagg atgtatgagg agaattccca     540
gcctaggcga aacctgacca aattatccct gatcttcagc cacatgctgg cagaactgaa     600
aggcatcttt ccgagcggac tcttccaagg agacactttc cggattacta aagctgatgc     660
tgccgaattt tggagaaaag cttttggtga aagacgata gtcccgtgga gagctttcg      720 acaggccctg catgaagtgc atcccatcag ttctgggctg gacgccatgg ctctgaagtc     780
cactattgat ctgacctgca atgattatat ttctgtcttt gaatttgata tttttacacg     840
gctgtttcag ccctggtcct ctttgctcag aaattggaac agccttgctg taactcaccc     900
tggttacatg gctttcctga catacgatga agtgaaagcg cgcctgcaga agttcatcca     960
caaacctggc agttacatct tcggctgag ctgtactcgt ttgggtcagt gggctattgg     1020
gtatgttact gccgatggga acattctgca gacaatccca cacaataaac cgctcttcca     1080
agcactgatt gatggcttca gggaaggctt ctatttgttt cctgatggac gaaatcaaaa     1140
tcctgacctg acaggtttat gtgaaccaac tcctcaagat catatcaaag taacccagga     1200
```

-continued

```
acaatatgaa ttatactgtg aaatgggctc cacatttcaa ctgtgtaaga tatgtgctga    1260
gaatgataag gatgtgaaga ttgagccctg tggacacctc atgtgcacat cctgcctcac    1320
gtcgtggcag gaatcagaag gtcagggctg tccttttgc cgatgtgaaa tcaaaggtac     1380
tgagcccatc gtggtggatc cgtttgaccc cagaggcagt ggcagcctat taaggcaagg    1440
agcagaaggt gctccttccc caaattacga cgatgatgat gatgaacgag ctgatgattc    1500
tctcttcatg atgaaggagt tggcaggtgc caaggtggaa aggccttcct ctccattctc    1560
catggcccca caagcttccc ttcctccagt gccaccaaga cttgaccttc tacagcagcg    1620
agcacctgtt cctgccagca cttcagttct ggggactgct tccaaggctg cttctggctc    1680
ccttcataaa gacaaaccat tgccaatacc tcccacactt cgagatcttc caccaccacc    1740
ccctccagac cggccttact ctgttggagc agaaacaagg cctcagagac gccctctgcc    1800
ttgtacacca ggcgattgtc catctagaga caaactgccc cctgtccctt ctagccgccc    1860
aggggactcg tggttgtctc ggccaatccc taaagtacca gtagctactc caaaccctgg    1920
tgatccttgg aatgggagag aattgaccaa tcggcactcg cttccattct cattgccctc    1980
acaaatggaa cccagagcag atgtccctag gcttggaagc acatttagtc tggataccct    2040
tatgactatg aatagcagcc cagtagcagg tccagagagt gagcacccaa agatcaagcc    2100
ttcctcgtct gccaacgcca tttactctct ggctgccagg cctcttccta tgccaaaact    2160
gccacctggg gagcaagggg aaagtgaaga ggacacagaa tatatgactc ccacatctag    2220
gcctgtaggg gttcagaagc cagagcccaa acggccgtta gaggcaaccc agagttcacg    2280
agcatgtgac tgtgaccagc agatcgacag ctgtacctat gaagcgatgt ataacatcca    2340
gtcccaagca ctgtctgtag cagaaaaacag cgcctctggg gaagggaatc tggccacagc    2400
tcacacgagt actggccctg aggaatccga aaacgaggat gatggctatg atgtgcctaa    2460
gccacccgtg ccagctgtac tggcccgccg gaccctgtct gacatctcca atgccagctc    2520
ctcctttggc tggttgtctt tggatggtga ccctacaaac ttcaatgagg gttcccaagt    2580
tcctgagcgg ccccccaaac cattccctcg gagaatcaac tcagaacgaa aagccagtag    2640
ctatcaacaa ggcggaggtg ccactgctaa ccctgtggcc acagcaccct caccgcagct    2700
ctcaagtgag attgaacgcc tcatgagtca gggctattcc taccaggaca ttcagaaagc    2760
tttggtcatt gcccacaaca acattgagat ggctaaaaac atcctccggg aatttgtttc    2820
tatttcttct cctgctcacg tagccaccta gcacatctct ccctgccacg gcttcagagg    2880
acccatgagc caggctctta ctcaaggacc acctaggaaa gcagtggctt cttttgggac    2940
gtcacagtaa ggtcctgcct ttcctgtggg gatcgacaca tatggttcca agatttcaaa    3000
gcagtggaat gaaaatggag cagctgatgt gtttcattgt tgtattggtc ttaagagtgt    3060
ttttgtagtc ctgcagtctc cagtaggaga gagtgggttt ttattaaatg gtaacctacc    3120
ccagaaacag c                                                        3131
```

<210> SEQ ID NO 54
<211> LENGTH: 913
<212> TYPE: PRT
<213> ORGANISM: Mouse

<400> SEQUENCE: 54

```
Met Ala Gly Asn Val Lys Lys Ser Ser Gly Ala Gly Gly Gly Gly Ser
1               5                   10                  15

Gly Gly Ser Gly Ala Gly Gly Leu Ile Gly Leu Met Lys Asp Ala Phe
```

-continued

```
                   20                  25                  30
Gln Pro His His His His His Leu Ser Pro His Pro Pro Cys Thr
            35                  40                  45
Val Asp Lys Lys Met Val Glu Lys Cys Trp Lys Leu Met Asp Lys Val
 50                  55                  60
Val Arg Leu Cys Gln Asn Pro Lys Leu Ala Leu Lys Asn Ser Pro Pro
 65                  70                  75                  80
Tyr Ile Leu Asp Leu Leu Pro Asp Thr Tyr Gln His Leu Arg Thr Val
                 85                  90                  95
Leu Ser Arg Tyr Glu Gly Lys Met Glu Thr Leu Gly Glu Asn Glu Tyr
                100                 105                 110
Phe Arg Val Phe Met Glu Asn Leu Met Lys Lys Thr Lys Gln Thr Ile
                115                 120                 125
Ser Leu Phe Lys Glu Gly Lys Glu Arg Met Tyr Glu Glu Asn Ser Gln
                130                 135                 140
Pro Arg Arg Asn Leu Thr Lys Leu Ser Leu Ile Phe Ser His Met Leu
145                 150                 155                 160
Ala Glu Leu Lys Gly Ile Phe Pro Ser Gly Leu Phe Gln Gly Asp Thr
                165                 170                 175
Phe Arg Ile Thr Lys Ala Asp Ala Ala Glu Phe Trp Arg Lys Ala Phe
                180                 185                 190
Gly Glu Lys Thr Ile Val Pro Trp Lys Ser Phe Arg Gln Ala Leu His
                195                 200                 205
Glu Val His Pro Ile Ser Ser Gly Leu Asp Ala Met Ala Leu Lys Ser
                210                 215                 220
Thr Ile Asp Leu Thr Cys Asn Asp Tyr Ile Ser Val Phe Glu Phe Asp
225                 230                 235                 240
Ile Phe Thr Arg Leu Phe Gln Pro Trp Ser Ser Leu Leu Arg Asn Trp
                245                 250                 255
Asn Ser Leu Ala Val Thr His Pro Gly Tyr Met Ala Phe Leu Thr Tyr
                260                 265                 270
Asp Glu Val Lys Ala Arg Leu Gln Lys Phe Ile His Lys Pro Gly Ser
                275                 280                 285
Tyr Ile Phe Arg Leu Ser Cys Thr Arg Leu Gly Gln Trp Ala Ile Gly
                290                 295                 300
Tyr Val Thr Ala Asp Gly Asn Ile Leu Gln Thr Ile Pro His Asn Lys
305                 310                 315                 320
Pro Leu Phe Gln Ala Leu Ile Asp Gly Phe Arg Glu Gly Phe Tyr Leu
                325                 330                 335
Phe Pro Asp Gly Arg Asn Gln Asn Pro Asp Leu Thr Gly Leu Cys Glu
                340                 345                 350
Pro Thr Pro Gln Asp His Ile Lys Val Thr Gln Glu Gln Tyr Glu Leu
                355                 360                 365
Tyr Cys Glu Met Gly Ser Thr Phe Gln Leu Cys Lys Ile Cys Ala Glu
                370                 375                 380
Asn Asp Lys Asp Val Lys Ile Glu Pro Cys Gly His Leu Met Cys Thr
385                 390                 395                 400
Ser Cys Leu Thr Ser Trp Gln Glu Ser Glu Gly Gln Gly Cys Pro Phe
                405                 410                 415
Cys Arg Cys Glu Ile Lys Gly Thr Glu Pro Ile Val Val Asp Pro Phe
                420                 425                 430
Asp Pro Arg Gly Ser Gly Ser Leu Leu Arg Gln Gly Ala Glu Gly Ala
                435                 440                 445
```

```
-continued

Pro Ser Pro Asn Tyr Asp Asp Asp Asp Glu Arg Ala Asp Asp Ser
    450                 455                 460

Leu Phe Met Met Lys Glu Leu Ala Gly Ala Lys Val Glu Arg Pro Ser
465                 470                 475                 480

Ser Pro Phe Ser Met Ala Pro Gln Ala Ser Leu Pro Val Pro Pro
                485                 490                 495

Arg Leu Asp Leu Leu Gln Gln Arg Ala Pro Val Pro Ala Ser Thr Ser
            500                 505                 510

Val Leu Gly Thr Ala Ser Lys Ala Ala Ser Gly Ser Leu His Lys Asp
        515                 520                 525

Lys Pro Leu Pro Ile Pro Pro Thr Leu Arg Asp Leu Pro Pro Pro
    530                 535                 540

Pro Pro Asp Arg Pro Tyr Ser Val Gly Ala Glu Thr Arg Pro Gln Arg
545                 550                 555                 560

Arg Pro Leu Pro Cys Thr Pro Gly Asp Cys Pro Ser Arg Asp Lys Leu
                565                 570                 575

Pro Pro Val Pro Ser Ser Arg Pro Gly Asp Ser Trp Leu Ser Arg Pro
            580                 585                 590

Ile Pro Lys Val Pro Val Ala Thr Pro Asn Pro Gly Asp Pro Trp Asn
        595                 600                 605

Gly Arg Glu Leu Thr Asn Arg His Ser Leu Pro Phe Ser Leu Pro Ser
            610                 615                 620

Gln Met Glu Pro Arg Ala Asp Val Pro Arg Leu Gly Ser Thr Phe Ser
625                 630                 635                 640

Leu Asp Thr Ser Met Thr Met Asn Ser Ser Pro Val Ala Gly Pro Glu
                645                 650                 655

Ser Glu His Pro Lys Ile Lys Pro Ser Ser Ser Ala Asn Ala Ile Tyr
            660                 665                 670

Ser Leu Ala Ala Arg Pro Leu Pro Met Pro Lys Leu Pro Pro Gly Glu
        675                 680                 685

Gln Gly Glu Ser Glu Glu Asp Thr Glu Tyr Met Thr Pro Thr Ser Arg
    690                 695                 700

Pro Val Gly Val Gln Lys Pro Glu Pro Lys Arg Pro Leu Glu Ala Thr
705                 710                 715                 720

Gln Ser Ser Arg Ala Cys Asp Cys Asp Gln Gln Ile Asp Ser Cys Thr
                725                 730                 735

Tyr Glu Ala Met Tyr Asn Ile Gln Ser Gln Ala Leu Ser Val Ala Glu
            740                 745                 750

Asn Ser Ala Ser Gly Glu Gly Asn Leu Ala Thr Ala His Thr Ser Thr
        755                 760                 765

Gly Pro Glu Glu Ser Glu Asn Glu Asp Asp Gly Tyr Asp Val Pro Lys
    770                 775                 780

Pro Pro Val Pro Ala Val Leu Ala Arg Arg Thr Leu Ser Asp Ile Ser
785                 790                 795                 800

Asn Ala Ser Ser Ser Phe Gly Trp Leu Ser Leu Asp Gly Asp Pro Thr
                805                 810                 815

Asn Phe Asn Glu Gly Ser Gln Val Pro Glu Arg Pro Pro Lys Pro Phe
            820                 825                 830

Pro Arg Arg Ile Asn Ser Glu Arg Lys Ala Ser Ser Tyr Gln Gln Gly
        835                 840                 845

Gly Gly Ala Thr Ala Asn Pro Val Ala Thr Ala Pro Ser Pro Gln Leu
    850                 855                 860
```

```
Ser Ser Glu Ile Glu Arg Leu Met Ser Gln Gly Tyr Ser Tyr Gln Asp
865                 870                 875                 880

Ile Gln Lys Ala Leu Val Ile Ala His Asn Ile Glu Met Ala Lys
            885                 890                 895

Asn Ile Leu Arg Glu Phe Val Ser Ile Ser Ser Pro Ala His Val Ala
        900                 905                 910

Thr

<210> SEQ ID NO 55
<211> LENGTH: 2661
<212> TYPE: DNA
<213> ORGANISM: Drosophila

<400> SEQUENCE: 55
catctcgaaa atattgtgtg ggtttaaaaa acgttaacgt cgccgaaacg cgtagcccca      60
aatgcacacg ccaggtgcaa ggataaagcc gtgaggatcg ggcacccaat cggatagatc     120
gcgtttggtt agcttgtggg ggaaaatcgt acttaagtca ccactactac tacacacggg     180
caccaccagc aacaccaaca acaacaacaa cgagaacagc accagcaaca acaacaacag     240
cagcaagaag gagaagagct gagaagagga agcagaggca gcgcagtcgg cagcgcagcg     300
gcagagagaa aagatggcga cgagaggcag tggaacccgt gtgcaatcgc agccaaagat     360
tttcccatcg ctgctttcca agctgcacgg cgctatctcg gaagcctgcg tctcgcagcg     420
tctgtccacc gacaagaaga cgctggagaa gacctggaag ttgatggaca aggtggtcaa     480
actgtgccag cagccgaaga tgaatcttaa gaatagtcca ccgtttattt tggacatcct     540
gccggatacg taccagcgcc tgagattgat ctactcaaag aaggaggacc agatgcacct     600
gctccatgcc aacgagcact tcaacgtgtt catcaacaac ctgatgcgaa agtgcaagcg     660
ggccatcaag ttgttcaagg agggcaagga agatgttc gacgagaact cccactaccg     720
ccgcaatctc accaagctca gcctggtctt ctcccacatg ctcagcgaac tgaaggccat     780
attccccaac ggtgtctttg ccggggatca atttcggatc accaaagcgg atgcggctga     840
cttttggaag agcaacttcg gtaacagcac attggttccc tggaaaatct ccggcagga     900 gcttagcaaa gtacatccca atctccgg cctggaggcc atgccctaa agaccactat     960 cgatcttacc tgcaacgact tcatttccaa cttcgagttc gacgtcttca cacgcctctt    1020
ccagccttgg gtgacactgc tacgcaactg gcagattctg gccgtcacac atccgggcta    1080
cgtggcgttt ctcacatacg acgaggtgaa ggctcgccta cagcgctaca tcctcaaggc    1140
gggcagctac gttttccggc tctcctgcac gcgattgggc caatgggcca tcggctacgt    1200
aactgccgag ggagagattc tgcagacaat ccctcagaac aagtcgctgt gccaggcgct    1260
gctcgatggc catcgagagg cttctactt gtacccagat ggccaagcgt acaatccgga    1320
tctgtcgtct gccgttcaaa gtcccacaga ggaccacata accgttaccc aagagcaata    1380
cgaactatac tgtgaaatgg gcagcacctt tcagctgtgc aaaatttgtg cggagaacga    1440
caaagatatc cgcatcgagc cctgtggcca cttgttgtgc actccctgcc ttacctcctg    1500
gcaagtggat tccgagggac agggctgccc cttctgtcgg gccgaaatca gggcaccga    1560 acaaatcgtt gtggacgctt tcgatccgcg caagcaacac aaccggaacg tcaccaatgg    1620
gcgacagcag cagcaggaag aagacgacac tgaggtatag ttttgttcac agcctgatca    1680
gcctgatccg cctgctccgc tgccgcctgt gctgctattt atatacatat tactcttatg    1740 attaccttg gttcgtttat acagttatat atgcctatat atacattata tatttttagat    1800
```

-continued

```
tttacaactg ctattgttta tataagttta atgtttagcc tgcagttcgc agtggcagtt      1860
tcgagtttaa ttttgtttgt ttagctgtaa catatttaaa ttattagcca aactcatgca      1920
actaacatcc acagacccac gcacacacgc ccaatcacaa gcacaagtac aaccataacc      1980
attgtccatc catcgagcac atgcataacg tagttaaagt tctttgaccg gaagtcgctc      2040
atcaaccatc gtttgctatc gcttcctctg ttttctctcc gccggtttgg tttggtttgg      2100
tttgtgtgcg ttcgtttagt tgttcgttct tccactctca cgctctctct atctattgat      2160
cacgttcgcc tctgtttatg aatcatattt taatcgattc gattcgccct cgattgcact      2220
tttgtacata ggcactatgg aatttataat tggtaacctt gttcttgtat tattcgggtg      2280
aattttctcc tttcacatcc agcttgatta tcccttgat tatgtatgcc cgccagtaat      2340
ttttgtatct atccctact ctagaatcat tctcttaatc attgtactcc gttatgtgtt      2400
tatttcattt tagtttattg tttaatactt ccaaagatac atttagtttg tagtagcgtg      2460
cgtttacttc cccccatat caattcaatt ttatttgtaa gcagccaayg cgctgcccta      2520
agactgtaat ttattattaa camaaaaaar aaaatcgaaa aagtttaaga aatcaggcta      2580
aacataggag gcctcgaatc gatcgataat ttagttagat tgyatgtaaa ttaattattg      2640
atttcctgtg tcacaaggcc a                                                2661
```

```
<210> SEQ ID NO 56
<211> LENGTH: 448
<212> TYPE: PRT
<213> ORGANISM: Drosophila

<400> SEQUENCE: 56

Met Ala Thr Arg Gly Ser Gly Thr Arg Val Gln Ser Gln Pro Lys Ile
 1               5                  10                  15

Phe Pro Ser Leu Leu Ser Lys Leu His Gly Ala Ile Ser Glu Ala Cys
                20                  25                  30

Val Ser Gln Arg Leu Ser Thr Asp Lys Lys Thr Leu Glu Lys Thr Trp
            35                  40                  45

Lys Leu Met Asp Lys Val Val Lys Leu Cys Gln Gln Pro Lys Met Asn
        50                  55                  60

Leu Lys Asn Ser Pro Pro Phe Ile Leu Asp Ile Leu Pro Asp Thr Tyr
 65                  70                  75                  80

Gln Arg Leu Arg Leu Ile Tyr Ser Lys Lys Glu Asp Gln Met His Leu
                 85                 90                  95

Leu His Ala Asn Glu His Phe Asn Val Phe Ile Asn Asn Leu Met Arg
            100                 105                 110

Lys Cys Lys Arg Ala Ile Lys Leu Phe Lys Glu Gly Lys Glu Lys Met
        115                 120                 125

Phe Asp Glu Asn Ser His Tyr Arg Arg Asn Leu Thr Lys Leu Ser Leu
    130                 135                 140

Val Phe Ser His Met Leu Ser Glu Leu Lys Ala Ile Phe Pro Asn Gly
145                 150                 155                 160

Val Phe Ala Gly Asp Gln Phe Arg Ile Thr Lys Ala Asp Ala Asp
                165                 170                 175

Phe Trp Lys Ser Asn Phe Gly Asn Ser Thr Leu Val Pro Trp Lys Ile
            180                 185                 190

Phe Arg Gln Glu Leu Ser Lys Val His Pro Ile Ile Ser Gly Leu Glu
        195                 200                 205

Ala Met Ala Leu Lys Thr Thr Ile Asp Leu Thr Cys Asn Asp Phe Ile
    210                 215                 220
```

Ser Asn Phe Glu Phe Asp Val Phe Thr Arg Leu Phe Gln Pro Trp Val
225                 230                 235                 240

Thr Leu Leu Arg Asn Trp Gln Ile Leu Ala Val Thr His Pro Gly Tyr
            245                 250                 255

Val Ala Phe Leu Thr Tyr Asp Glu Val Lys Ala Arg Leu Gln Arg Tyr
            260                 265                 270

Ile Leu Lys Ala Gly Ser Tyr Val Phe Arg Leu Ser Cys Thr Arg Leu
            275                 280                 285

Gly Gln Trp Ala Ile Gly Tyr Val Thr Ala Glu Gly Glu Ile Leu Gln
            290                 295                 300

Thr Ile Pro Gln Asn Lys Ser Leu Cys Gln Ala Leu Leu Asp Gly His
305                 310                 315                 320

Arg Glu Gly Phe Tyr Leu Tyr Pro Asp Gly Gln Ala Tyr Asn Pro Asp
            325                 330                 335

Leu Ser Ser Ala Val Gln Ser Pro Thr Glu Asp His Ile Thr Val Thr
            340                 345                 350

Gln Glu Gln Tyr Glu Leu Tyr Cys Glu Met Gly Ser Thr Phe Gln Leu
            355                 360                 365

Cys Lys Ile Cys Ala Glu Asn Asp Lys Asp Ile Arg Ile Glu Pro Cys
370                 375                 380

Gly His Leu Leu Cys Thr Pro Cys Leu Thr Ser Trp Gln Val Asp Ser
385                 390                 395                 400

Glu Gly Gln Gly Cys Pro Phe Cys Arg Ala Glu Ile Lys Gly Thr Glu
            405                 410                 415

Gln Ile Val Val Asp Ala Phe Asp Pro Arg Lys Gln His Asn Arg Asn
            420                 425                 430

Val Thr Asn Gly Arg Gln Gln Gln Glu Glu Asp Asp Thr Glu Val
            435                 440                 445

<210> SEQ ID NO 57
<211> LENGTH: 2274
<212> TYPE: DNA
<213> ORGANISM: C. elegans

<400> SEQUENCE: 57
ctatgatcat tacatcctaa ttaattgcca ctggacttca catcatatca ccgtttcacc    60
gggaatgggt tcaataaaca caattttttca ccggatacat cggtttgtca atggcacagg   120
caataatgcg cgatttgttc ccagcacaaa caactcgacg aagcgttga cactcagtcc    180 gagagctgtt cccagcacag tttcactatt cgaaatccca tcagcttcgg agatgcccgg   240
tttctgcagt gaagaggatc gtcgattttt gctcaaagca tgcaagttta tggatcaagt   300
agtgaagagt tgtcatagcc caagactgaa tttgaaaaat cgccgccctt tcattttgga   360
cattctacct gatacttata cgcatttaat gctgatattc acacaaaaca atgacatact   420
ccaagacaac gactacttga aaatctttct ggagagtatg atcaacaagt gcaaagagat   480
catcaaactg ttcaagacgt cagctatcta caatgaccag tctgaagaac gacggaagct   540
tacgaaaatg tcactaacat tttcacatat gcttttcgag attaaagcat tatttccgga   600
aggtatctat attgaagacc ggtttcggat gacaaagaag gaagccgaaa gcttttggag   660
tcatcatttt acaaaaaaaa acattgtacc ctggtcaaca tttttttactg cattagaaaa   720 gcaccatgga tcaacgatag gaaaaatgga agcagccgaa ttaaaagcta cgatagactt   780
gagcggagat gatttttattt cgaattttga gtttgatgtg tttacaaggt tattctaccc   840

-continued

```
tttcaaaaca ctgatcaaaa attggcaaac actcaccacc gcccatcccg gatactgtgc    900
atttctcaca tacgatgagg tcaaaaaacg gttagaaaaa ttaacgaaaa aacctggaag    960
ctacatcttc cggttatcat gcacacgtcc tggacaatgg gcaataggat acgtagctcc   1020
ggatggaaag atttatcaga caataccaca gaataaaagt ttgattcaag cactacatga   1080
aggccataaa gaaggatttt atatttaccc gaacggtaga gatcaagata ttaacttatc   1140
caaattgatg gatgtgccac aagcggacag agtgcaagtg accagtgaac aatacgagtt   1200
gtattgtgag atgggcacaa cattcgagtt gtgcaaaatt tgtgacgata acgagaagaa   1260
catcaaaatt gagccatgtg gacatttgct ctgcgcaaaa tgtttggcta actggcagga   1320
ttcggatggt ggtggcaaca catgtccatt ctgccgctac gaaatcaaag gaacaaatcg   1380
tgtgattatt gacaggttca agcccactcc ggtagaaatt gaaaaagcga aaaatgtagc   1440
tgctgcggag aagaagctga tctcattagt tcccgacgtg cctcccagaa cgtatgtgtc   1500
ccaatgttct caaagtttgc tgcatgacgc gtcaaactca attccgtcgg tcgacgagtt   1560
gccgttggtg ccgccaccgt tgccaccgaa agcattgggt accctggaca ctttgaattc   1620
gtcacaaaca tcctcttcat acgtgaacat caaagagctg gaaaatgttg aaacaagcgg   1680
agaagcattg gcacaagtgg taaaccggca acgggcgcct tcaatccaag ctccaccact   1740
accgccaagg ttatcagcga gcgagcacca accacaccac ccatacacaa atacgaacag   1800
tgagcgggag tagacttgtg taaatgttca tcttaccgct ttatactgca attttcattc   1860
ccccacttat catagaacta ttcttccaca acaacatatt gccgtgacta gaactggtaa   1920
cactacatca ttctttgtta aaacgttatt atatctctat ttcttttttcg cctactcctt   1980
tccgtttttt tttcaaattt tgtcaattt cctacagcgt tctgactcct attggtaagc   2040
aatcatgtca tatcttgtta aatttcatg ttaatttctt actctcgctg tcccagattt   2100
tacggagttt tcaggaaacg tttgattttg ttctattcta caatttccat cgcccccaac   2160
ctgtcgtgta ttttctatgt gtcactctga agaaaacaag tttagacttt ttaaaaatcg   2220
ttttattact ctaaaactta aaagctgaaa tgtcagctat agtaaaaata cata          2274
```

<210> SEQ ID NO 58
<211> LENGTH: 582
<212> TYPE: PRT
<213> ORGANISM: C. elegans

<400> SEQUENCE: 58

```
Met Gly Ser Ile Asn Thr Ile Phe His Arg Ile His Arg Phe Val Asn
 1               5                  10                  15

Gly Thr Gly Asn Asn Ala Arg Phe Val Pro Ser Thr Asn Asn Ser Thr
            20                  25                  30

Glu Ala Leu Thr Leu Ser Pro Arg Ala Val Pro Ser Thr Val Ser Leu
        35                  40                  45

Phe Glu Ile Pro Ser Ala Ser Glu Met Pro Gly Phe Cys Ser Glu Glu
    50                  55                  60

Asp Arg Arg Phe Leu Leu Lys Ala Cys Lys Phe Met Asp Gln Val Val
65                  70                  75                  80

Lys Ser Cys His Ser Pro Arg Leu Asn Leu Lys Asn Ser Pro Pro Phe
                85                  90                  95

Ile Leu Asp Ile Leu Pro Asp Thr Tyr Thr His Leu Met Leu Ile Phe
            100                 105                 110

Thr Gln Asn Asn Asp Ile Leu Gln Asp Asn Asp Tyr Leu Lys Ile Phe
        115                 120                 125
```

```
Leu Glu Ser Met Ile Asn Lys Cys Lys Glu Ile Ile Lys Leu Phe Lys
    130                 135                 140

Thr Ser Ala Ile Tyr Asn Asp Gln Ser Glu Glu Arg Arg Lys Leu Thr
145                 150                 155                 160

Lys Met Ser Leu Thr Phe Ser His Met Leu Phe Glu Ile Lys Ala Leu
                165                 170                 175

Phe Pro Glu Gly Ile Tyr Ile Glu Asp Arg Phe Arg Met Thr Lys Lys
            180                 185                 190

Glu Ala Glu Ser Phe Trp Ser His His Phe Thr Lys Lys Asn Ile Val
            195                 200                 205

Pro Trp Ser Thr Phe Phe Thr Ala Leu Glu Lys His His Gly Ser Thr
    210                 215                 220

Ile Gly Lys Met Glu Ala Ala Glu Leu Lys Ala Thr Ile Asp Leu Ser
225                 230                 235                 240

Gly Asp Asp Phe Ile Ser Asn Phe Glu Phe Asp Val Phe Thr Arg Leu
                245                 250                 255

Phe Tyr Pro Phe Lys Thr Leu Ile Lys Asn Trp Gln Thr Leu Thr Thr
            260                 265                 270

Ala His Pro Gly Tyr Cys Ala Phe Leu Thr Tyr Asp Glu Val Lys Lys
            275                 280                 285

Arg Leu Glu Lys Leu Thr Lys Lys Pro Gly Ser Tyr Ile Phe Arg Leu
    290                 295                 300

Ser Cys Thr Arg Pro Gly Gln Trp Ala Ile Gly Tyr Val Ala Pro Asp
305                 310                 315                 320

Gly Lys Ile Tyr Gln Thr Ile Pro Gln Asn Lys Ser Leu Ile Gln Ala
                325                 330                 335

Leu His Glu Gly His Lys Glu Gly Phe Tyr Ile Tyr Pro Asn Gly Arg
            340                 345                 350

Asp Gln Asp Ile Asn Leu Ser Lys Leu Met Asp Val Pro Gln Ala Asp
            355                 360                 365

Arg Val Gln Val Thr Ser Glu Gln Tyr Glu Leu Tyr Cys Glu Met Gly
    370                 375                 380

Thr Thr Phe Glu Leu Cys Lys Ile Cys Asp Asp Asn Glu Lys Asn Ile
385                 390                 395                 400

Lys Ile Glu Pro Cys Gly His Leu Leu Cys Ala Lys Cys Leu Ala Asn
                405                 410                 415

Trp Gln Asp Ser Asp Gly Gly Asn Thr Cys Pro Phe Cys Arg Tyr
            420                 425                 430

Glu Ile Lys Gly Thr Asn Arg Val Ile Ile Asp Arg Phe Lys Pro Thr
            435                 440                 445

Pro Val Glu Ile Glu Lys Ala Lys Asn Val Ala Ala Glu Lys Lys
    450                 455                 460

Leu Ile Ser Leu Val Pro Asp Val Pro Pro Arg Thr Tyr Val Ser Gln
465                 470                 475                 480

Cys Ser Gln Ser Leu Leu His Asp Ala Ser Asn Ser Ile Pro Ser Val
                485                 490                 495

Asp Glu Leu Pro Leu Val Pro Pro Leu Pro Pro Lys Ala Leu Gly
            500                 505                 510

Thr Leu Asp Thr Leu Asn Ser Ser Gln Thr Ser Ser Ser Tyr Val Asn
            515                 520                 525

Ile Lys Glu Leu Glu Asn Val Glu Thr Ser Gly Glu Ala Leu Ala Gln
    530                 535                 540
```

```
Val Val Asn Arg Gln Arg Ala Pro Ser Ile Gln Ala Pro Pro Leu Pro
545                 550                 555                 560

Pro Arg Leu Ser Ala Ser Glu His Gln Pro His His Pro Tyr Thr Asn
                565             570             575

Thr Asn Ser Glu Arg Glu
                580
```

UBIQUITIN LIGASE INHIBITORS AND METHODS RELATED THERETO

RELATED APPLICATIONS

This application is a continuation of PCT Application No. PCT/US52004/021900, filed Jul. 9, 2004, which claims the benefit of the filing date of U.S. Provisional Application Nos. 60/486,730, filed Jul. 11, 2003, 60/489,795, filed Jul. 24, 2003, and 60/549,896, filed Mar. 2, 2004. PCT Application No. PCT/US2004/021900 is also a continuation-in-part of PCT International Application No. PCT/US03/35712, filed Nov. 10, 2003. The specifications of all of the above-referenced applications are hereby incorporated by reference in their entirety.

BACKGROUND

Potential drug target validation involves determining whether a DNA, RNA or protein molecule is implicated in a disease process and is therefore a suitable target for development of new therapeutic drugs. Drug discovery, the process by which bioactive compounds are identified and characterized, is a critical step in the development of new treatments for human diseases. The landscape of drug discovery has changed dramatically due to the genomics revolution. DNA and protein sequences are yielding a host of new drug targets and an enormous amount of associated information.

The identification of genes and proteins involved in various disease states or key biological processes, such as inflammation and immune response, is a vital part of the drug design process. Many diseases and disorders could be treated or prevented by decreasing the expression of one or more genes involved in the molecular etiology of the condition if the appropriate molecular target could be identified and appropriate antagonists developed. For example, cancer, in which one or more cellular oncogenes become activated and result in the unchecked progression of cell cycle processes, could be treated by antagonizing appropriate cell cycle control genes. Furthermore many human genetic diseases, such as Huntington's disease, and certain prion conditions, which are influenced by both genetic and epigenetic factors, result from the inappropriate activity of a polypeptide as opposed to the complete loss of its function. Accordingly, antagonizing the aberrant function of such mutant genes would provide a means of treatment. Additionally, infectious diseases such as HIV have been successfully treated with molecular antagonists targeted to specific essential retroviral proteins such as HIV protease or reverse transcriptase. Drug therapy strategies for treating such diseases and disorders have frequently employed molecular antagonists which target the polypeptide product of the disease gene(s). However the discovery of relevant gene or protein targets is often difficult and time consuming.

One area of particular interest is the identification of host genes and proteins that are co-opted by viruses during the viral life cycle. The serious and incurable nature of many viral diseases, coupled with the high rate of mutations found in many viruses, makes the identification of antiviral agents a high priority for the improvement of world health. Genes and proteins involved in a viral life cycle are also appealing as a subject for investigation because such genes and proteins will typically have additional activities in the host cell and may play a role in other non-viral disease states.

Viral maturation involves the proteolytic processing of the Gag proteins and the activity of various host proteins. It is believed that cellular machineries for exo/endocytosis and for ubiquitin conjugation may be involved in the maturation. In particular, the assembly, budding and subsequent release of retroid viruses, RNA viruses and envelope viruses, such as various retroviruses, rhabdoviruses, lentiviruses, and filoviruses may involve the Gag polyprotein. After its synthesis, Gag is targeted to the plasma membrane where it induces budding of nascent virus particles.

The role of ubiquitin in virus assembly was suggested by Dunigan et al. (1988, Virology 165, 310, Meyers et al. 1991, Virology 180, 602), who observed that mature virus particles were enriched in unconjugated ubiquitin. More recently, it was shown that proteasome inhibitors suppress the release of HIV-1, HIV-2 and virus-like particles derived from SIV and RSV Gag. Also, inhibitors affect Gag processing and maturation into infectious particles (Schubert et al 2000, PNAS 97, 13057, Harty et al. 2000, PNAS 97, 13871, Strack et al. 2000, PNAS 97, 13063, Patnaik et al. 2000, PNAS 97, 13069).

It is well known in the art that ubiquitin-mediated proteolysis is the major pathway for the selective, controlled degradation of intracellular proteins in eukaryotic cells. Ubiquitin modification of a variety of protein targets within the cell appears to be important in a number of basic cellular functions such as regulation of gene expression, regulation of the cell-cycle, modification of cell surface receptors, biogenesis of ribosomes, and DNA repair. One major function of the ubiquitin-mediated system is to control the half-lives of cellular proteins. The half-life of different proteins can range from a few minutes to several days, and can vary considerably depending on the cell-type, nutritional and environmental conditions, as well as the stage of the cell-cycle.

Targeted proteins undergoing selective degradation, presumably through the actions of a ubiquitin-dependent proteosome, are covalently tagged with ubiquitin through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and generally also requires auxiliary substrate recognition proteins (E3s). Following the linkage of the first ubiquitin chain, additional molecules of ubiquitin may be attached to lysine side chains of the previously conjugated moiety to form branched multi-ubiquitin chains.

The conjugation of ubiquitin to protein substrates is a multi-step process. In an initial ATP requiring step, a thioester is formed between the C-terminus of ubiquitin and an internal cysteine residue of an E1 enzyme. Activated ubiquitin may then be transferred to a specific cysteine on one of several E2 enzymes. Finally, these E2 enzymes donate ubiquitin to protein substrates, typically with the assistance of an E3 protein, also known as a ubiquitin enzyme. In certain instances, substrates are recognized directly by the ubiquitin-conjugated E2 enzyme.

It is also known that the ubiquitin system plays a role in a wide range of cellular processes including cell cycle progression, apoptosis, and turnover of many membrane receptors. In viral infections, the ubiquitin system is involved not only with assembly, budding and release, but also with repression of host proteins such as p53, which may lead to a viral-induced neoplasm. The HIV Vpu protein interacts with an E3 protein that regulates IκB degradation, and is thought to promote apoptosis of infected cells by indirectly inhibiting NF-κB activity (Bour et al. (2001) J Exp Med 194:1299-311; U.S. Pat. No. 5,932,425). The ubiquitin system regulates protein function by both mono-ubiquitination and poly-ubiquitination, and poly-ubiquitination is primarily associated with protein degradation.

It would be beneficial to identify compounds that target one or more of the proteins involved in these processes for use in, among other things, anti-viral therapy.

SUMMARY

In certain aspects, the application provides compounds that inhibit the ubiquitin ligase activity of one or more proteins, particularly proteins having a RING finger domain ("RING domain"). Compounds disclosed herein may be used, for example, to inhibit the ubiquitin ligase activity of a suitable target protein in vitro or in an ex vivo cell. Compounds disclosed herein may also be used, for example, to inhibit the ubiquitin ligase activity of a suitable target protein in vivo, particularly in a patient suffering from a disease involving an activity of the target protein.

In certain embodiments, compounds disclosed herein may be administered to a subject for the purpose of treating a viral infection, particularly an infection by an envelope virus. Compounds disclosed herein may also be administered to a subject at risk of contracting a viral infection, particularly an infection of an envelope virus, so as to diminish the likelihood that the subject will contract an infection. In a preferred embodiment, compounds disclosed herein are administered to a subject having, or at risk for contracting, a human immunodeficiency virus (HIV) infection.

In certain embodiments, compounds disclosed herein may be formulated as a pharmaceutical composition for administration to a human or animal subject. Optionally, such formulation may include additional active ingredients, such as additional antiviral agents. Additionally, compounds disclosed herein may be administered as part of a combined antiviral therapeutic regimen involving administration of multiple compounds (at different times and doses, as needed).

In certain embodiments, compounds disclosed herein may be used in the formulation of a medicament. The medicament may be formulated for administration to a subject having or at risk for a disease in which a ubiquitin ligase contributes to the causation or pathology. The medicament may be formulated for administration to a subject having or at risk for a viral infection, such as an infection with an envelope virus and preferably a retrovirus. In a preferred embodiment, compounds disclosed herein may be used in the formulation of a medicament for administration to a subject having or at risk for an HIV infection.

In certain embodiments, the application provides agents and methods for inhibiting the ubiquitin ligase activity of a POSH polypeptide in vivo, in an ex vivo cell or in vitro. Agents that inhibit the ubiquitin ligase activity of a POSH polypeptide may be used to treat a disease in which the ubiquitin ligase activity of POSH contributes to the causation and/or pathology. In further embodiments, the application provides numerous methods by which additional agents that inhibit the ubiquitin ligase activity of POSH may be identified.

In certain embodiments, the application relates to a small molecule inhibitor of a POSH polypeptide. In certain embodiments, the POSH polypeptide small molecule inhibitor modulates the activity of a POSH polypeptide. In certain further embodiments, the activity of the POSH polypeptide is ubiquitin ligase activity. In other embodiments, the activity of the POSH polypeptide is binding of the POSH polypeptide to an E2. In certain embodiments, the POSH polypeptide small molecule inhibitor is a compound selected from among the compounds presented in Table 1. In other embodiments, the POSH polypeptide small molecule inhibitor is a compound selected from among the compounds presented in Table 7.

In certain embodiments, the application provides a method of inhibiting the ubiquitin ligase activity of a polypeptide, comprising contacting a cell with a small molecule. In preferred embodiments, the small molecule is a compound selected from among the compounds presented in Table 1. In other embodiments, the small molecule is a compound selected from among the compounds presented in Table 7. In certain further embodiments, the small molecule inhibits the ubiquitin ligase activity of a polypeptide comprising a RING domain. In certain embodiments, the polypeptide is a POSH polypeptide. In further embodiments of the application, a POSH polypeptide is selected from the group consisting of a polypeptide represented by SEQ ID NOs: 2, 5, 7, 9, and 11. In yet further embodiments, the polypeptide is a human POSH polypeptide. In certain embodiments, the polypeptide is a Cbl-b polypeptide. In further embodiments, the polypeptide is a human Cbl-b polypeptide. In yet further embodiments, the polypeptide is selected from the group consisting of a polypeptide represented by SEQ ID NOs: 43-46, 48, 50, 52, 54, 56, and 58. In certain embodiments, the polypeptide is a PEM-3-like polypeptide. In further embodiments, the PEM-3-like polypeptide is a human PEM-3-like polypeptide.

In additional embodiments, the application relates to a method of inhibiting the activity of a POSH polypeptide, comprising contacting a cell with a small molecule. In certain embodiments, the activity of the POSH polypeptide is ubiquitin ligase activity. In other embodiments, the activity of the POSH polypeptide is binding of the POSH polypeptide to a POSH-AP. In certain embodiments, the POSH-AP is an E2. In other embodiments, the POSH-AP is selected from the group consisting of: ARIH2, ASF1, ATP5A1, BANF1, BAT3, BCAR1, BCL9, BIA2, BRD4, C11orf17, C6orf11, C6orf60, CBX4, CDT1, CGI-27, CIC, CL25084, CLK2, COL1A1, DAP, DDX31, DKFZp434B1231, DKFZp761A052, DLG5, DNM2, DRP2, EEF1A1, EGLN2, EIF4EBP1, EVPL, EWSR1, FAT, FL53657, FLJ10120, FLJ13231, FLJ13479, FLJ37147, FSTL1, GC20, GLUL, HEBP2, Hs.31535, Hs.380933, HSPA1B, HSPC016, HSPC142, ITGB, J03930, KHDRBS1, KIAA0191, KLAA1111, KIAA1598, LAMA5, LOC118987, LOC90987, MADH6, MAP1A, MBD2, MRPL36, MT2A, NAP4, NQO2, NUMA1, OPTN, PA1-RBP1, PAWR, PCBP1, PCNT2, PGD, PIASY, POLQ, POLR2J2, PRDX5, PROL4, RAP80, RBAF600, RNH, RPL, RPS20, RPS27A, SETDB1, SF3A2, SH2D2A, SIAH2, SLC2A1, SRPK2, SSR4, STC2, THOC2, TLE1, TPX2, UBB, UBC, VCL, XM_208944, XTP3TPB, ZFM1, ZNF147, and ZNF151. In yet other embodiments, the POSH-AP is selected from the group consisting of: PKA, SNX1, SNX3, ATP6V0C, PTPN12, PPP1CA, GOSR2, CENTB1, DDEF1, ARF1, ARF5, PACS-1, EPS8L2, HERPUD1, UNC84B, MSTP028, GOCAP, EIF3S3, SRA1, CBL-B, RALA, SIAH1, SMN1, SMN2, SYNE1, TTC3, VCY2IP1, UBE2N (UBC13), ARHV (Chp), WASF1, HIP55, SPG20, HLA-A, and HLA-B. In additional embodiments, the small molecule is a compound selected from among the compounds presented in Table 1. In further embodiments, the small molecule is a compound selected from among the compounds presented in Table 7.

In additional embodiments, the application relates to a method of inhibiting maturation of a virus in a cell, comprising contacting the cell with a small molecule that inhibits the ubiquitin ligase activity of a polypeptide. In certain embodiments, the virus is an envelope virus. In further embodiments, the virus is a retrovirus. In yet further embodiments, the virus is a human immunodeficiency virus. In certain embodiments, the polypeptide comprises a RING domain. In further embodiments of the application, the polypeptide is selected from the group consisting of a polypeptide represented by SEQ ID NOs: 2, 5, 7, 9, and 11. In yet further embodiments, the polypeptide is a human POSH polypeptide. In certain embodiments, the polypeptide is a Cbl-b polypeptide. In further embodiments, the polypeptide is a human Cbl-b polypeptide. In yet further embodiments, the polypeptide is selected from the group consisting of a polypeptide represented by SEQ ID NOs: 43-46, 48, 50, 52, 54, 56, and 58. In certain embodiments, the polypeptide is a PEM-3-like polypeptide. In further embodiments, the PEM-3-like polypeptide is a human PEM-3-like polypeptide.

The application further relates to a method of treating a viral infection in a subject in need thereof, comprising administering to the subject a small molecule that inhibits the ubiquitin ligase activity of a polypeptide. In certain embodiments, the viral infection is an infection by an envelope virus. In further embodiments, the viral infection is an infection by a retrovirus. In yet further embodiments, the viral infection is an infection by a human immunodeficiency virus. In certain embodiments, the polypeptide comprises a RING domain. In other embodiments, the polypeptide is selected from among a POSH polypeptide, a Cbl-b polypeptide, a PEM-3-like polypeptide, a SIAH1 polypeptide, and a TTC3 polypeptide. In yet other embodiments of the application, the polypeptide is selected from the group consisting of a polypeptide represented by SEQ ID NOs: 2, 5, 7, 9, and 11. In yet further embodiments, the polypeptide is a human POSH polypeptide. In certain embodiments, the polypeptide is a Cbl-b polypeptide. In further embodiments, the polypeptide is a human Cbl-b polypeptide. In yet further embodiments, the polypeptide is selected from the group consisting of a polypeptide represented by SEQ ID NOs: 43-46, 48, 50, 52, 54, 56, and 58. In certain embodiments, the polypeptide is a PEM-3-like polypeptide. In further embodiments, the PEM-3-like polypeptide is a human PEM-3-like polypeptide.

In certain embodiments, the application provides a composition formulated for administration to a mammal, the composition comprising a compound as described herein and a pharmaceutically acceptable excipient to a small molecule inhibitor of a POSH polypeptide. In further embodiments, the mammal is a rodent.

In additional embodiments, the application provides a method of inhibiting the transport of APP in a cell, comprising contacting the cell with a small molecule that inhibits the ubiquitin ligase activity of a polypeptide. In certain embodiments, the polypeptide comprises a RING domain. In further embodiments, the polypeptide is a human POSH polypeptide.

The application additionally relates to a method of inhibiting the ubiquitin ligase activity of a POSH polypeptide in a subject in need thereof, comprising administrating to the subject an amount of a POSH polypeptide inhibitor effective to inhibit the ubiquitin ligase activity of said POSH polypeptide.

In certain embodiments, the application provides a method of treating a neurological disorder in a subject in need thereof, comprising administrating a small molecule that inhibits the ubiquitin ligase activity of a polypeptide. In certain embodiments, the polypeptide comprises a RING domain. In further embodiments, the polypeptide is a human POSH polypeptide. Examples of neurological disorders include Alzheimer's disease, Parkinson's disease, Huntington's disease, Pick's disease, depression, and schizophrenia.

In additional embodiments, the application provides a method of inhibiting amyloid polypeptide production in a cell, comprising administrating a small molecule that inhibits the ubiquitin ligase activity of a polypeptide. In certain embodiments, the polypeptide comprises a RING domain. In further embodiments, the polypeptide is a human POSH polypeptide.

In other embodiments, the application provides a method of inhibiting cell proliferation, comprising administrating a small molecule that inhibits the ubiquitin ligase activity of a polypeptide. In certain embodiments, the polypeptide comprises a RING domain. In further embodiments, the polypeptide is a human POSH polypeptide.

In preferred embodiments of the application, a small molecule employed in the methods of the application is a compound selected from among the compounds presented in Table 1 or Table 7.

In certain embodiments of the application, a POSH polypeptide is selected from the group consisting of a polypeptide represented by SEQ ID NOs: 2, 5, 7, 9, and 11.

In certain embodiments, the application relates to a method of inhibiting viral budding in a cell, comprising contacting the cell with an agent selected from the group consisting of a compound listed in Table 7.

In certain embodiments, the application provides a composition formulated for administration to a mammal, the composition comprising a compound presented in table 7 and a pharmaceutically acceptable excipient.

The additional embodiments, the application provides a composition formulated for administration to a mammal, the composition comprising a compound selected from the group defined by scaffold no. 2 of table 1 and a pharmaceutically acceptable excipient.

In other embodiments, the application provides a composition formulated for administration to a mammal, the composition comprising a compound selected from the group defined by scaffold no. 3 of table 1 and a pharmaceutically acceptable excipient.

In yet other embodiments, the application provides a composition formulated for administration to a mammal, the composition comprising a compound selected from the group defined by scaffold no. 4 of table 1 and a pharmaceutically acceptable excipient.

In additional embodiments, the application provides a composition formulated for administration to a mammal, the composition comprising a compound selected from the group defined by scaffold no. 5 of table 1 and a pharmaceutically acceptable excipient.

In certain embodiments, the application provides a composition formulated for administration to a mammal, the composition comprising a compound selected from the group defined by scaffold no. 6 of table 1 and a pharmaceutically acceptable excipient.

In other embodiments, the application provides a composition formulated for administration to a mammal, the composition comprising a compound selected from the group defined by scaffold no. 7 of table 1 and a pharmaceutically acceptable excipient.

In yet other embodiments, the application provides a composition formulated for administration to a mammal, the composition comprising a compound selected from the group defined by scaffold no. 8 of table 1 and a pharmaceutically acceptable excipient.

In certain embodiments, the application provides a composition formulated for administration to a mammal, the composition comprising a compound selected from the group defined by scaffold no. 9 of table 1 and a pharmaceutically acceptable excipient.

In other embodiments, the application provides a composition formulated for administration to a mammal, the composition comprising a compound selected from the group defined by scaffold no. 10 of table 1 and a pharmaceutically acceptable excipient.

In yet other embodiments, the application provides a composition formulated for administration to a mammal, the composition comprising a compound selected from the group defined by scaffold no. 11 of table 1 and a pharmaceutically acceptable excipient.

In additional embodiments, the application provides a composition formulated for administration to a mammal, the composition comprising a compound selected from the group defined by scaffold no. 12 of table 1 and a pharmaceutically acceptable excipient.

Other features and advantages of the application will be apparent from the following detailed description, and from the claims.

BRIEF DESCRIPTION OF THE DRAWINGS

FIG. 1: Human POSH Coding Sequence (SEQ ID NO:1)
FIG. 2: Human POSH Amino Acid Sequence (SEQ ID NO:2)
FIG. 3: Human POSH cDNA Sequence (SEQ ID NO:3)
FIG. 4: 5' cDNA fragment of human POSH (public gi:10432611; SEQ ID NO:4)
FIG. 5: N terminus protein fragment of hPOSH (public gi:10432612; SEQ ID NO:5)
FIG. 6: 3' mRNA fragment of hPOSH (public gi:7959248; SEQ ID NO:6)
FIG. 7: C terminus protein fragment of hPOSH (public gi:7959249; SEQ ID NO:7)
FIG. 8: Human POSH full mRNA, annotated sequence
FIG. 9: Domain analysis of human POSH
FIG. 10: Diagram of human POSH nucleic acids. The diagram shows the full-length POSH gene and the position of regions amplified by RT-PCR or targeted by siRNA used in FIG. 11.
FIG. 11: Mouse POSH mRNA sequence (public gi:10946921; SEQ ID NO: 8)
FIG. 12: Mouse POSH Protein sequence (Public gi:10946922; SEQ ID NO: 9)
FIG. 13: *Drosophila melanogaster* POSH mRNA sequence (public gi:17737480; SEQ ID NO: 10)
FIG. 14: *Drosophila melanogaster* POSH protein sequence (public gi:17737481; SEQ ID NO: 11)
FIG. 15: POSH Domain Analysis
FIG. 16: Human POSH has ubiquitin ligase activity
FIGS. 17 A and B: siRNA-Mediated Reduction in Cbl-b Expression Inhibits HIV Virus-like Particle (VLP) Production

DETAILED DESCRIPTION OF THE APPLICATION

1. Definitions

Figure 17B:
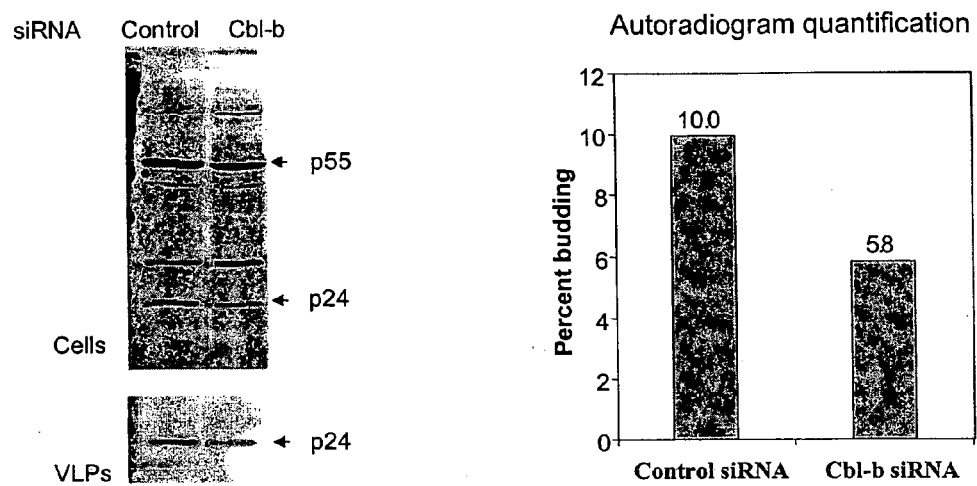

The term "amyloid polypeptide" is used to refer to any of the various polypeptides that are significant components of amyloid plaque as well as precursors thereof. The amyloid beta A4 precursor protein ("APP") gives rise to smaller proteins, such as the roughly 40 amino acid beta amyloid proteins that form a major component of the amyloid plaque associated with Alzheimer's disease, Down's syndrome (in older patients) and certain hereditary cerebral hemorrhage amyloidoses. APP has several isoforms generated by alternative splicing of a 19-exon gene: exons 1-13, 13a, and 14-18 (Yoshikai et al., 1990). The predominant transcripts are APP695 (exons 1-6, 9-18, not 13a), APP751 (exons 1-7, 9-18, not 13a), and APP770 (exons 1-18, not 13a). All of these encode multidomain proteins with a single membrane-spanning region. They differ in that APP751 and APP770 contain exon 7, which encodes a serine protease inhibitor domain. APP695 is a predominant form in neuronal tissue, whereas APP751 is the predominant variant elsewhere. Beta-amyloid is derived from that part of the protein encoded by parts of exons 16 and 17. All of the isoforms of APP and any of the smaller proteins derived therefrom are included in the term "amyloid polypeptide", as well as any of the various naturally occurring variations thereof and any artificially produced variants that retain one or more functional properties of the naturally occurring protein or that are useful as a proxy for monitoring the production of APP or a protein derived therefrom. The subset of amyloid polypeptides that are APP or derived therefrom may be referred to specifically as "APP amyloid polypeptides". Yoshikai et al. Gene 87: 257-263, 1990.

The term "envelope virus" as used herein refers to any virus that uses cellular membrane and/or any organelle membrane in the viral release process.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present application. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid and protein sequences of the present application may be used as a "query sequence" to perform a search against public databases to, for example, identify other family members, related sequences or homologs. Such searches can be performed using the NBLAST and XBLAST programs (version 2.0) of Altschul, et al. (1990) J Mol. Biol. 215:403-10. BLAST nucleotide searches can be performed with the NBLAST program, score=100, wordlength=12 to obtain nucleotide sequences homologous to nucleic acid molecules of the application. BLAST protein searches can be performed with the XBLAST program, score=50, wordlength=3 to obtain amino acid sequences homologous to protein molecules of the application. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and BLAST) can be used.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity.

"Lentiviruses" include primate lentiviruses, e.g., human immunodeficiency virus types 1 and 2 (HIV-1/HIV-2); simian immunodeficiency virus (SIV) from Chimpanzee (SIVcpz), Sooty mangabey (SIVsmm), African Green Monkey (SIVagm), Syke's monkey (SIVsyk), Mandrill (SIVmnd) and Macaque (SIVmac). Lentiviruses also include feline lentiviruses, e.g., Feline immunodeficiency virus (FIV); Bovine lentiviruses, e.g., Bovine immunodeficiency virus (BIV); Ovine lentiviruses, e.g., Maedi/Visna virus (MVV) and Caprine arthritis encephalitis virus (CAEV); and Equine lentiviruses, e.g., Equine infectious anemia virus (EIAV). All lentiviruses express at least two additional regulatory proteins (Tat, Rev) in addition to Gag, Pol, and Env proteins. Primate lentiviruses produce other accessory proteins including Nef, Vpr, Vpu, Vpx, and Vif. Generally, lentiviruses are the causative agents of a variety of disease, including, in addition to immunodeficiency, neurological degeneration, and arthritis. Nucleotide sequences of the various lentiviruses can be found in Genbank under the following Accession Nos. (from J. M. Coffin, S. H. Hughes, and H. E. Varmus, "Retroviruses" Cold Spring Harbor Laboratory Press, 199, 7 p 804): 1) HIV-1: K03455, M19921, K02013, M3843 1, M38429, K02007 and M17449; 2) HIV-2: M30502, J04542, M30895, J04498, M15390, M31113 and L07625; 3) SIV:M29975, M30931, M58410, M66437, L06042, M33262, M19499, M32741, M31345 and L03295; 4) FIV: M25381, M36968 and U1 1820; 5)BIV. M32690; 6)EIAV: M16575, M87581 and U01866; 6) Visna: M10608, M51543, L06906, M60609 and M60610; 7) CAEV: M33677; and 8) Ovine lentivirus M31646 and M34193. Lentiviral DNA can also be obtained from the American Type Culture Collection (ATCC). For example, feline immunodeficiency virus is available under ATCC Designation No. VR-2333 and VR-3112. Equine infectious anemia virus A is available under ATCC Designation No. VR-778. Caprine arthritis-encephalitis virus is available under ATCC Designation No. VR-905. Visna virus is available under ATCC Designation No. VR-779. As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

The term "viral maturation" as used herein refers to the production, post-translational processing, assembly and/or release of proteins and other components that form a viral particle. Accordingly, this includes the processing of viral proteins leading to the pinching off of nascent virion from the cell membrane.

A "POSH nucleic acid" is a nucleic acid comprising a sequence as represented in any of SEQ ID Nos:1, 3, 4, 6, 8, and 10 as well as any of the variants described herein.

A "POSH polypeptide" or "POSH protein" is a polypeptide comprising a sequence as represented in any of SEQ ID Nos: 2, 5, 7, 9 and 11 as well as any of the variations described herein.

A "POSH-associated protein" or "POSH-AP" refers to a protein capable of interacting with and/or binding to a POSH polypeptide. Generally, the POSH-AP may interact directly or indirectly with the POSH polypeptide. Exemplary POSH-APs are provided throughout.

A "RING domain" or "Ring Finger" is a zinc-binding domain with a defined octet of cysteine and histidine residues. Certain RING domains comprise the consensus sequences as set forth below (amino acid nomenclature is as set forth in Table A): Cys Xaa Xaa Cys $Xaa_{10-20}$ Cys Xaa His $Xaa_{2-5}$ Cys Xaa Xaa Cys $Xaa_{13-50}$ Cys Xaa Xaa Cys (SEQ ID NO: 53) or Cys Xaa Xaa Cys $Xaa_{10-20}$ Cys Xaa His $Xaa_{2-5}$ His Xaa Xaa Cys $Xaa_{13-50}$ Cys Xaa Xaa Cys (SEQ ID NO: 54) or Cys Xaa Xaa Cys $Xaa_{9-39}$ Cys $Xaa_{1-3}$ His $Xaa_{2-3}$ Cys Xaa Xaa Cys $Xaa_{4-48}$ Cys Xaa Xaa Cys (SEQ ID NO: 55). Certain RING domains are represented as amino acid sequences that are at least 80% identical to amino acids 12-52 of SEQ ID NO: 2 and is set forth in SEQ ID No: 26. Preferred RING domains are 85%, 90%, 95%, 98% and, most preferably, 100% identical to the amino acid sequence of SEQ ID NO: 26. Preferred RING domains of the application bind to various protein partners to form a complex that has ubiquitin ligase activity. RING domains preferably interact with at least one of the following protein types: F box proteins, E2 ubiquitin conjugating enzymes and cullins.

The term "RNA interference" or "RNAi" refers to any method by which expression of a gene or gene product is decreased by introducing into a target cell one or more double-stranded RNAs which are homologous to the gene of interest (particularly to the messenger RNA of the gene of interest).

"Small molecule" as used herein, is meant to refer to a composition, which has a molecular weight of less than about 5 kD and most preferably less than about 2.5 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures comprising arrays of small molecules, often fungal, bacterial, or algal extracts, which can be screened with any of the assays of the application.

An "SH3" or "Src Homology 3" domain is a protein domain of generally about 60 amino acid residues first identified as a conserved sequence in the non-catalytic part of several cytoplasmic protein tyrosine kinases (e.g., Src, Abl, Lck). SH3 domains mediate assembly of specific protein complexes via binding to proline-rich peptides. Exemplary SH3 domains are represented by amino acids 137-192, 199-258, 448-505 and 832-888 of SEQ ID NO:2 and are set forth in SEQ ID Nos: 27-30. In certain embodiments, an SH3 domain interacts with a consensus sequence of RXaaXaaPXaaX6P (where X6, as defined in table A below, is a hydrophobic amino acid). In certain embodiments, an SH3 domain interacts with one or more of the following sequences: P(T/S)AP, PFRDY, RPEPTAP, RQGPKEP, RQGPKEPFR, RPEPTAPEE and RPLPVAP.

As used herein, a "transgenic animal" is any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant human POSH protein. The "non-human animals" of the application include vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the *Xenopus* genus, and transgenic chickens can also provide important tools for understanding and identifying agents which can affect, for example, embryogenesis and tissue formation. The term "chimeric animal" is used herein to refer to animals in which the recombinant gene is found, or in which the recombinant is expressed in some but not all cells of the animal. The term "tissue specific chimeric animal" indicates that the recombinant human POSH genes is present and/or expressed in some tissues but not others.

As used herein, the term "transgene" means a nucleic acid sequence (encoding, e.g., human POSH polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

TABLE A

Abbreviations for classes of amino acids*

| Symbol | Category | Amino Acids Represented |
|---|---|---|
| X1 | Alcohol | Ser, Thr |
| X2 | Aliphatic | Ile, Leu, Val |
| Xaa | Any | Ala, Cys, Asp, Glu, Phe, Gly, His, Ile, Lys, Leu, Met, Asn, Pro, Gln, Arg, Ser, Thr, Val, Trp, Tyr |
| X4 | Aromatic | Phe, His, Trp, Tyr |
| X5 | Charged | Asp, Glu, His, Lys, Arg |
| X6 | Hydrophobic | Ala, Cys, Phe, Gly, His, Ile, Lys, Leu, Met, Thr, Val, Trp, Tyr |
| X7 | Negative | Asp, Glu |
| X8 | Polar | Cys, Asp, Glu, His, Lys, Asn, Gln, Arg, Ser, Thr |
| X9 | Positive | His, Lys, Arg |
| X10 | Small | Ala, Cys, Asp, Gly, Asn, Pro, Ser, Thr, Val |
| X11 | Tiny | Ala, Gly, Ser |
| X12 | Turnlike | Ala, Cys, Asp, Glu, Gly, His, Lys, Asn, Gln, Arg, Ser, Thr |
| X13 | Asparagine-Aspartate | Asn, Asp |

2. Overview

In part, the present application relates to the discovery of compounds that inhibit the ubiquitin ligase activity of one or more ubiquitin ligase polypeptides, such as polypeptides containing one or more RING domains.

POSH is a ubiquitin ligase comprising a RING domain. As described in PCT patent application PCT/US/02/24589; PCT patent application PCT US/02/36366; U.S. patent application Ser. No. 10/293,965; and European patent application EP02257796, all of which are incorporated by reference herein, the inhibition of POSH inhibits maturation of viruses in infected cells. Many compounds disclosed herein inhibit the ubiquitin ligase activity of POSH and have demonstrated antiviral activity.

Given the functional and structural similarity between proteins having RING domains, it is expected that compounds disclosed herein may be effective for inhibiting the ubiquitin ligase activity of additional ubiquitin ligases.

Ubiquitin ligases contribute to the causation of or the pathology of a wide range of diseases, and compounds disclosed herein may be evaluated and used for treating such diseases, as appropriate.

3. Compounds

In certain embodiments, the present application provides compounds that inhibit the ubiquitin ligase activity of a polypeptide. In certain embodiments, the compounds of the application inhibit the ubiquitin ligase activity of a polypeptide comprising a RING domain. In a preferred embodiment, the application relates to compounds that inhibit the ubiquitin ligase activity of a POSH polypeptide. Many compounds disclosed herein inhibit viral maturation in infected cells.

In certain embodiments, the present application provides compounds described by any of scaffold numbers 1-12 below. Specific examples of compounds are provided in Example 1, below.

TABLE 1

| Scaffold number | General structure | Comments |
| --- | --- | --- |
| 1 | 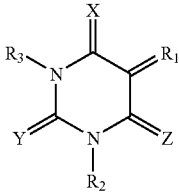 | X, Y, and Z are independently selected from O, S, and $NR_3$; $R_1$ is CRAr, CR(NRAr), CR—CR=CRAr, or CR—CR=CR(NRAr), wherein R is H or lower alkyl, preferably H, and Ar is substituted or unsubstituted aryl or heteroaryl; and $R_2$ and $R_3$ are independently selected for eachoccurrence from H and substituted or unsubstituted lower alkyl, lower alkenyl, cycloalkyl, heterocyclyl, aryl, heteroaryl, cycloalkylalkyl, heterocyclylalkyl, heteroaralkyl, and aralkyl. |
| 2 | 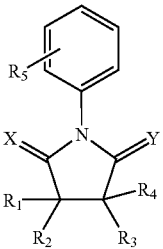 | X and Y are independently selected from O, S, and $NR_6$; $R_1$ and $R_4$ independently represent H or lower alkyl, or, taken together, represent a double bond; $R_2$ and $R_3$ independently represent H, amino, alkylamino, arylamino, aralkylamino, acylamino,$R_2NRN$—, alkylthio, arylthio, aralkylthio, aralkyl, alkoxy, aryloxy, aralkyloxy, or lower alkyl, or, taken together with $R_1$ and $R_4$, represent a benzo ring fused to the maleimide ring; and $R_5$ represents from 0-5 substituents on the ring to which it is attached, selected fromH, halogen, lower alkyl, lower alkenyl, aryl, heteroaryl, carbonyl, thiocarbonyl, ketone, aldehyde, amino, acylamino, cyano, nitro, hydroxyl, acyl, azido, sulfonyl, sulfoxido, sulfate, sulfonate, sulfamoyl, and sulfonamido; and R represents, independently for each occurrence, H,alkyl, alkenyl, alkynyl, aralkyl, aryl, cycloalkyl, heterocyclyl, cycloalkylalkyl, heterocyclylalkyl, heteroaryl, or heteroaralkyl; and $R_6$ is independently selected for each occurrence from H and substituted or unsubstituted lower alkyl, lower alkenyl, cycloalkyl, heterocyclyl, aryl,heteroaryl, cycloalkylalkyl, heterocyclylalkyl, heteroaralkyl, and aralkyl. |

TABLE 1-continued

| Scaffold number | General structure | Comments |
| --- | --- | --- |
| 3 | (structure with $R_1$, X, Y, Z, $R_3$, N) | X is selected from O, S, and $NR_2$; Z and Y are independently selected from O, S, and $NR_3$; $R_1$ is $CR(CR=CR)_nR_6$ or $CR(CR=CR)_nNRR_6$, wherein n is an integer from 0 to 3; $R_2$ and $R_3$ independently represent H or substituted or unsubstituted lower alkyl, lower alkenyl, cycloalkyl, heterocyclyl, aryl, heteroaryl, cycloalkylalkyl, heterocyclylalkyl, heteroaralkyl, or aralkyl; R, independently for each occurrence, represents H or lower alkyl; and $R_6$ is substituted or unsubstituted aryl or heteroaryl. In certain embodiments wherein Z is $NR_3$, $R_3$ represents a substituted or unsubstituted aryl ring (such as a phenyl ring) that is also bound to the adjacent nitrogen (as $R_3$), forming a tricyclic (or higher) ring system. |
| 4 | (structure with $R_1$, X, $R_2$) | V is C=O, C=S, or $SO_2$; X is selected from O, S, and $NR_3$; Y is selected from O, S, and $NR_3$; R is H or lower alkyl; $R_1$ is —$(CR=CR)_n$Ar, wherein Ar is substituted or unsubstituted aryl, heterocyclyl, cycloalkyl, or heteroaryl, and n is an integer from 0 to 2; $R_2$ is $R_6$, $VR_4$ or $CR_3$=N—$N(R)_2$; $R_3$ independently for each occurrence represents H or substituted or unsubstituted lower alkyl, lower alkenyl, cycloalkyl, heterocyclyl, aryl, heteroaryl, cycloalkylalkyl, heterocyclylalkyl, heteroaralkyl, or aralkyl; $R_4$ is substituted aryl, heteroaryl, cycloalkyl, or heterocyclyl, preferably heterocyclyl attached to V through a nitrogen atom; and $R_6$ is CH=(1,3-indandion-2-ylidene). |

TABLE 1-continued

| Scaffold number | General structure | Comments |
| --- | --- | --- |
| 5 | (structure with X, Y, R₁, R₂, and carbonyl) | X is N or CR; Y is O, S, or NR₃; R is H or lower alkyl; R₁ is CRAr, wherein Ar is substituted or unsubstituted aryl or heteroaryl; R₂ is substituted or unsubstituted aryl or heteroaryl; and R₃ independently for each occurrence represents H or substituted or unsubstituted lower alkyl, lower alkenyl, cycloalkyl, heterocyclyl, aryl, heteroaryl, cycloalkylalkyl, heterocyclylalkyl, heteroaralkyl, or aralkyl. |
| 6 | (benzylidene imine structure with R₃ and Ar) | Ar represents a substituted or unsubstituted aryl or heteroaryl ring, optionally attached through —(CR=CR)—, wherein R represents H or lower alkyl; and R₂ represents a substituted or unsubstituted aryl or heteroaryl ring. Preferably, at least one of R₂ and Ar is (or bears as a substituent) a bicyclic ring system. |
| 7 | (five-membered ring with X, R₁, R₂, R₃, R₄, N) | X is O, S, or NR₅; and R₁ represents H, acyl, sulfonyl, or substituted or unsubstituted lower alkyl, lower alkenyl, cycloalkyl, heterocyclyl, aryl, heteroaryl, cycloalkylalkyl, heterocyclylalkyl, heteroaralkyl, or aralkyl; R₂, R₃, R₄, and R₅ independently represent H, halogen, carbonyl, thiocarbonyl, ketone, aldehyde, amino, acylamino, cyano, nitro, hydroxyl, acyl, azido, sulfonyl, sulfoxido, sulfate, sulfonate, sulfamoyl, sulfonamido, or substituted or unsubstituted lower alkyl, lower alkenyl, cycloalkyl, heterocyclyl, aryl, heteroaryl, cycloalkylalkyl, heterocyclylalkyl, heteroaralkyl, or aralkyl. |

TABLE 1-continued

| Scaffold number | General structure | Comments |
| --- | --- | --- |
| 8 | 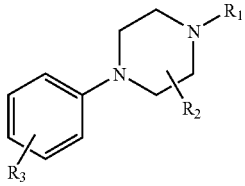 | $R_1$ represents H, acyl, sulfonyl, or substituted or unsubstituted lower alkyl, lower alkenyl, cycloalkyl, heterocyclyl, aryl, heteroaryl, cycloalkylalkyl, heterocyclylalkyl, heteroaralkyl, or aralkyl; $R_2$ represents from 0-4 substituents on the ring to which it isattached, e.g., selected from H, oxo, or substituted or unsubstituted lower alkyl, lower alkenyl, cycloalkyl, heterocyclyl, aralkyl, heteroaralkyl, heteroaryl, or aryl; $R_3$ represents from 0-5 substituents on the ring to which it is attached, e.g., H, halogen, carbonyl, thiocarbonyl, ketone,aldehyde, amino, acylamino, cyano, nitro, hydroxyl, acyl, azido, sulfonyl, sulfoxido, sulfate, sulfonate, sulfamoyl, sulfonamido, or substituted or unsubstituted lower alkyl, lower alkenyl, cycloalkyl, heterocyclyl, aryl, heteroaryl, cycloalkylalkyl, heterocyclylalkyl, heteroaralkyl,or aralkyl. |
| 9 | 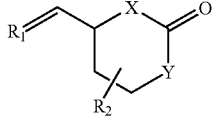 | X and Y independently represent O, S, NR, or $C(R)_2$; R represents, independently for each occurrence, H, lower alkenyl, or lower alkyl; $R_1$ represents CRAr, CR(NRAr), CR—CR═CRAr, or CR—CR═CR(NRAr), wherein R is H or lower alkyl, preferably H, and Ar is substitutedor unsubstituted aryl or heteroaryl; and $R_2$ represents from 0-4 substituents on the ring to which it is attached, e.g., selected from H, oxo, or substituted or unsubstituted lower alkyl, lower alkenyl, cycloalkyl, heterocyclyl, aralkyl, heteroaralkyl, heteroaryl, or aryl |

TABLE 1-continued

| Scaffold number | General structure | Comments |
|---|---|---|
| 10 | 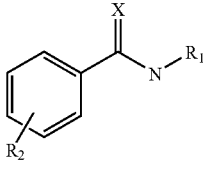 | X represents O or S; $R_1$ represents H or substituted or unsubstituted lower alkyl, lower alkenyl, cycloalkyl, heterocyclyl, aryl, heteroaryl, cycloalkylalkyl, heterocyclylalkyl, heteroaralkyl, or aralkyl $R_2$ represents from 0-5 substituents on the ring to which it isattached, e.g., selected from H, halogen, carbonyl, thiocarbonyl, ketone, aldehyde, amino, acylamino, cyano, nitro, hydroxyl, acyl, azido, sulfonyl, sulfoxido, sulfate, sulfonate, sulfamoyl, sulfonamido, or substituted or unsubstituted lower alkyl, lower alkenyl, cycloalkyl,heterocyclyl, aryl, heteroaryl, cycloalkylalkyl, heterocyclylalkyl, heteroaralkyl, or aralkyl. |
| 11 | 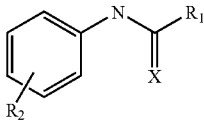 | X represents O or S; $R_1$ represents H or substituted or unsubstituted lower alkyl, lower alkenyl, cycloalkyl, heterocyclyl, aryl, heteroaryl, cycloalkylalkyl, heterocyclylalkyl, heteroaralkyl, or aralkyl $R_2$ represents from 0-5 substituents on the ring to which it isattached, e.g., selected from H, halogen, carbonyl, thiocarbonyl, ketone, aldehyde, amino, acylamino, cyano, nitro, hydroxyl, acyl, azido, sulfonyl, sulfoxido, sulfate, sulfonate, sulfamoyl, sulfonamido, or substituted or unsubstituted lower alkyl, lower alkenyl, cycloalkyl,heterocyclyl, aryl, heteroaryl, cycloalkylalkyl, heterocyclylalkyl, heteroaralkyl, or aralkyl. |

TABLE 1-continued

| Scaffold number | General structure | Comments |
|---|---|---|
| 12 | 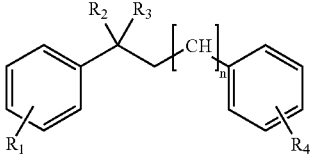 | n represents an even integer from 2 to 6; R$_2$ and R$_3$ independently represent H, halogen, amino, acylamino, cyano, nitro, hydroxyl, or substituted or unsubstituted lower alkyl, lower alkenyl, cycloalkyl, heterocyclyl, aryl,heteroaryl, cycloalkylalkyl, heterocyclylalkyl, heteroaralkyl, or aralkyl, or taken together represent =O or =S; and R$_1$ and R$_4$ independently represent from 0-5 substituents on the ring to which they are attached, e.g., selected from H, halogen, carbonyl,thiocarbonyl, ketone, aldehyde, amino, acylamino, cyano, nitro, hydroxyl, acyl, azido, sulfonyl, sulfoxido, sulfate, sulfonate, sulfamoyl, sulfonamido, or substituted or unsubstituted lower alkyl, lower alkenyl, cycloalkyl, heterocyclyl, aryl,heteroaryl, cycloalkylalkyl, heterocyclylalkyl, heteroaralkyl, or aralkyl. |

The term "acylamino" is art-recognized and refers to a moiety that can be represented by the general formula:

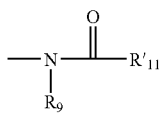

wherein $R_9$ is as defined below, and $R'_{11}$ represents a hydrogen, an alkyl, an alkenyl or —$(CH_2)_m$—$R_8$, where m and $R_8$ are as defined below.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described below.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined below. Representative alkylthio groups include methylthio, ethylthio, and the like.

The terms "amine" and "amino" are art-recognized and refer to both unsubstituted and substituted amines, e.g., a moiety that can be represented by the general formula:

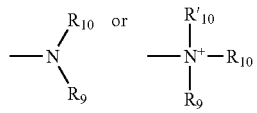

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In still more preferred embodiments, the term 'amine' does not encompass amides, e.g., wherein one of $R_9$ and $R_{10}$ represents a carbonyl. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

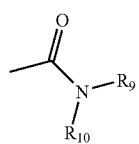

wherein $R_9$, $R_{10}$ are as defined above. Preferred embodiments of the amide will not include imides which may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

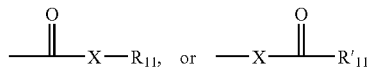

wherein X is a bond or represents an oxygen or a sulfur, and $R_{11}$ represents a hydrogen, an alkyl, an alkenyl, —$(CH_2)_n$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

A "phosphonamidite" can be represented in general formula:

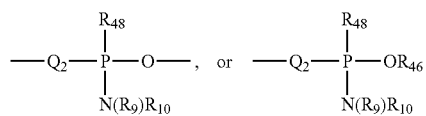

wherein $R_9$ and $R_{10}$ are as defined above, $Q_2$ represents O, S or N, and $R_{48}$ represents a lower alkyl or an aryl, $Q_2$ represents O, S or N.

A "phosphoramidite" can be represented in general formula:

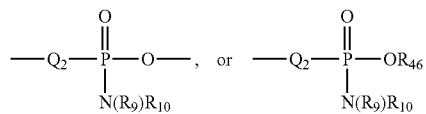

wherein $R_9$ and $R_{10}$ are as defined above, and $Q_2$ represents O, S or N.

A "phosphoryl" can in general be represented by the formula:

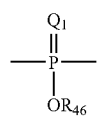

wherein $Q_1$ represented S or O, and $R_{46}$ represents hydrogen, a lower alkyl or an aryl. When used to substitute, for example, an alkyl, the phosphoryl group of the phosphorylalkyl can be represented by the general formula:

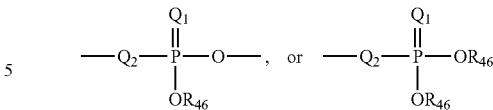

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R$_8$, m and R$_8$ being defined above.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

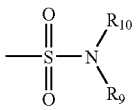

in which $R_9$ and $R_{10}$ are as defined above.

The term "sulfate" is art recognized and includes a moiety that can be represented by the general formula:

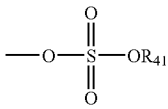

in which $R_{41}$ is as defined above.

The term "sulfonamido" is art recognized and includes a moiety that can be represented by the general formula:

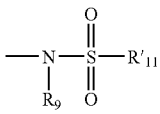

in which $R_9$ and $R'_{11}$ are as defined above.

The term "sulfonate" is art-recognized and includes a moiety that can be represented by the general formula:

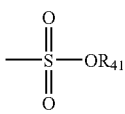

in which $R_{41}$ is an electron pair, hydrogen, alkyl, cycloalkyl, or aryl.

The terms "sulfoxido" or "sulfinyl", as used herein, refers to a moiety that can be represented by the general formula:

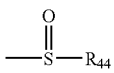

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof, wherein one or more simple variations of substituents are made which do not adversely affect the efficacy of the compound. In general, the compounds of the present invention may be prepared by the methods illustrated in general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

4. Therapeutic Targets

Compounds of the present application may inhibit the ubiquitin ligase activity of a variety of polypeptides. In particular, proteins having RING domains may be inhibited by compounds disclosed herein. A RING domain is a structural component of a subset of ubiquitin ligases, and it is associated with the ubiquitin ligase activity of many E3 polypeptides. Examples of E3 polypeptides containing RING domains include POSH, Cbl-b, and PEM-3-like.

"Selectivity" of a compound of the invention refers to the ability of a compound, such as a small molecule inhibitor of a ubiquitin ligase as described herein, to preferentially interact with one protein over another. For example, in certain instances, a compound will bind to one protein and not bind to another. Also, for example, in other instances, a compound will bind to more than one protein, but will bind one protein more strongly than it binds another. In certain embodiments, a compound of the invention may inhibit one E3 and not inhibit another, different E3. For example, a small molecule inhibitor of the invention may inhibit the ubiquitin ligase activity of one ubiquitin ligase but not inhibit the ubiquitin ligase activity of another, different ubiquitin ligase. In certain embodiments, the invention relates to compounds that inhibit the ubiquitin ligase activity of more than one E3 ligase but inhibit to a greater degree the ubiquitin ligase activity of one E3 over another, different E3. For example, an agent of the invention may inhibit entirely the ubiquitin ligase activity of one E3 but inhibit only partially or not at all the ubiquitin ligase activity of a different E3.

A selective inhibitor of the invention has selectivity for at least one polypeptide over another polypeptide. For example, in certain embodiments, a selective inhibitor of the invention may inhibit the ubiquitin ligase activity of two different E3 polypeptides, but selectively targets only one of them, resulting in selective inhibition of the ubiquitin ligase activity of the targeted E3 polypeptide.

In a preferred embodiment, compounds disclosed herein may be used to inhibit the ubiquitin ligase activity of a POSH polypeptide, and particularly naturally occurring POSH polypeptides, such as the canonical human POSH polypeptide and allelic variants thereof. The term "POSH polypeptide" is intended to include both naturally occurring and modified forms of POSH, including fragments retaining ubiquitin ligase activity. The term POSH polypeptide is specifically intended to include a polypeptide comprising a RING domain, an SH3 domain and having at least 50% sequence identity to the RING domain of a naturally occurring POSH polypeptide. Examples of POSH nucleic acids and polypeptides are prented in the tables below. POSH comprises a RING domain and is a ubiquitin ligase.

In certain instances, inhibiting the activity of a ubiquitin ligase such as an E3 polypeptide results in inhibition of viral budding. For example, inhibition of viral budding by inhibiting POSH has been presented in U.S. Provisional Application No. 60/469,462, filed May 9, 2003, and entitled "Inhibition of Viral Maturation, Methods and Compositions Related Thereto". Furthermore, inhibition of viral budding by inhibiting Cbl-b has been shown and is presented in the Examples of the present application. Additionally, it has been shown and is presented in the Examples of the present application that viral infectivity can be inhibited by inhibiting the ubiquitin ligase, PEM-3-like.

TABLE 2

Exemplary POSH nucleic acids

| Sequence Name | Organism | Accession Number |
|---|---|---|
| cDNA FLJ11367 fis, clone HEMBA1000303 | Homo sapiens | AK021429 |
| Plenty of SH3 domains (POSH) mRNA | Mus musculus | NM_021506 |
| Plenty of SH3s (POSH) mRNA | Mus musculus | AF030131 |
| Plenty of SH3s (POSH) mRNA | Drosophila melanogaster | NM_079052 |
| Plenty of SH3s (POSH) mRNA | Drosophila melanogaster | AF220364 |

TABLE 3

Exemplary POSH polypeptides

| Sequence Name | Organism | Accession Number |
|---|---|---|
| SH3 domains-containing protein POSH | Mus musculus | T09071 |
| plenty of SH3 domains | Mus musculus | NP_067481 |
| Plenty of SH3s; POSH | Mus musculus | AAC40070 |
| Plenty of SH3s | Drosophila melanogaster | AAF37265 |
| LD45365p | Drosophila melanogaster | AAK93408 |
| POSH gene product | Drosophila melanogaster | AAF57833 |
| Plenty of SH3s | Drosophila melanogaster | NP_523776 |

In addition the following Tables provide the nucleic acid sequence and related SEQ ID NOs for domains of human POSH protein and a summary of sequence identification numbers used in this application.

TABLE 4

Nucleic Acid Sequences and related SEQ ID NOs for domains in human POSH

| Name of the sequence | Sequence | SEQ ID NO. |
|---|---|---|
| RING domain | TGTCCGGTGTGTCTAGAGCGCCTTGATGCTTCTGCGAAGGTCTTGCCTTGCCAGC ATACGTTTTGCAAGCGATGTTTGCT GGGGATCGTAGGTTCTCGAAATGAACTCAGATGTCCCGAGT | 31 |
| 1st SH3 domain | CCATGTGCCAAAGCGTTATACAACTATGAAGGAAAAGAGCCTGGAGACCTTAAAT TCAGCAAAGGCGACATCATCATTTT GCGAAGACAAGTGGATGAAAATTGGTACCATGGGGAAGTCAATGGAATCCATGGC TTTTTCCCCACCAACTTTGTGCAGA TTATT | 32 |

TABLE 4-continued

Nucleic Acid Sequences and related
SEQ ID NOs for domains in human POSH

| Name of the sequence | Sequence | SEQ ID NO. |
|---|---|---|
| 2nd SH₃ domain | CCTCAGTGCAAAGCACTTTATGACTTTGAAGTGAAAGACAAGGAAGCAGACAAAG ATTGCCTTCCATTTGCAAAGGATGA TGTTCTGACTGTGATCCGAAGAGTGGATGAAAACTGGGCTGAAGGAATGCTGGCA GACAAAATAGGAATATTTCCAATTT CATATGTTGAGTTTAAC | 33 |
| 3rd SH₃ domain | AGTGTGTATGTTGCTATATATCCATACACTCCTCGGAAAGAGGATGAACTAGAGC TGAGAAAAGGGGAGATGTTTTTAGT GTTTGAGCGCTGCCAGGATGGCTGGTTCAAAGGGACATCCATGCATACCAGCAAG ATAGGGGTTTTCCCTGGCAATTATG TGGCACCAGTC | 34 |
| 4th SH₃ domain | GAAAGGCACAGGGTGGTGGTTTCCTATCCTCCTCAGAGTGAGGCAGAACTTGAAC TTAAAGAAGGAGATATTGTGTTTGT TCATAAAAAACGAGAGGATGGCTGGTTCAAAGGCACATTACAACGTAATGGGAAA ACTGGCCTTTTCCCAGGAAGCTTTG TGGAAAACA | 35 |

TABLE 5

Summary of Sequence Identification Numbers

| Sequence Information | Sequence Identification Number (SEQ ID NO) |
|---|---|
| Human POSH Coding Sequence | SEQ ID No: 1 |
| Human POSH Amino Acid Sequence | SEQ ID No: 2 |
| Human POSH cDNA Sequence | SEQ ID No: 3 |
| 5' cDNA Fragment of Human POSH | SEQ ID No: 4 |
| N-terminus Protein Fragment of Human POSH | SEQ ID No: 5 |
| 3' mRNA Fragment of Human POSH | SEQ ID No: 6 |
| C-terminus Protein Fragment of Human POSH | SEQ ID No: 7 |
| Mouse POSH mRNA Sequence | SEQ ID No: 8 |
| Mouse POSH Protein Sequence | SEQ ID No: 9 |
| Drosophila melanogaster POSH mRNA Sequence | SEQ ID No: 10 |
| Drosophila melanogaster POSH Protein Sequence | SEQ ID No: 11 |
| Human POSH RING Domain Amino Acid Sequence | SEQ ID No: 26 |
| Human POSH 1st SH₃ Domain Amino Acid Sequence | SEQ ID No: 27 |
| Human POSH 2nd SH₃ Domain Amino Acid Sequence | SEQ ID No: 28 |
| Human POSH 3rd SH₃ Domain Amino Acid Sequence | SEQ ID No: 29 |
| Human POSH 4th SH₃ Domain Amino Acid Sequence | SEQ ID No: 30 |
| Human POSH RING Domain Nucleic Acid Sequence | SEQ ID No: 31 |
| Human POSH 1st SH₃ Domain Nucleic Acid Sequence | SEQ ID No: 32 |
| Human POSH 2nd SH₃ Domain Nucleic Acid Sequence | SEQ ID No: 33 |
| Human POSH 3rd SH₃ Domain Nucleic Acid Sequence | SEQ ID No: 34 |
| Human POSH 4th SH₃ Domain Nucleic Acid Sequence | SEQ ID No: 35 |

The following table provides the sequences of the RING domain and the various SH3 domains.

TABLE 6

Amino Acid Sequences and related
SEQ ID NOs for domains in human POSH

| Name of the sequence | Sequence | SEQ ID NO. |
|---|---|---|
| RING domain | CPVCLERLDASAKVLPCQHTFCKRCLLGIVGSRNELRCPEC | 26 |
| 1st SH₃ domain | PCAKALYNYEGKEPGDLKFSKGDIIILRRQVDENWYHGEVNGIHGFFPTNFVQIIK | 27 |
| 2nd SH₃ domain | PQCKALYDFEVKDKEADKDCLPFAKDDVLTVIRRVDENWAEGMLADKIGIFPISYVEFNS | 28 |

TABLE 6-continued

Amino Acid Sequences and related
SEQ ID NOs for domains in human POSH

| Name of the sequence | Sequence | SEQ ID NO. |
|---|---|---|
| 3$^{rd}$ SH$_3$ domain | SVYVAIYPYTPRKEDELELRKGEMFLVFERCQDGWFKGTSMHTSKIGVFPGNYVAPVT | 29 |
| 4$^{th}$ SH$_3$ domain | ERHRVVVSYPPQSEAELELKEGDIVFVHKKREDGWFKGTLQRNGKTGLFPGSFVENI | 30 |

In certain embodiments, compounds disclosed herein may be evaluated for effectiveness in inhibiting the ubiquitin ligase activity of a Cbl-b polypeptide, and, as appropriate, used to inhibit such activity.

Cbl-b polypeptides contain an amino-terminal variant SH2 domain, a RING finger, and a carboxyl-terminal proline-rich domain with potential tyrosine phosphorylation sites. Cbl-b is highly homologous to the mammalian Cbl and the nematode Sli-1 proteins. Examples of Cbl-b are a human Cbl-b (UniGene No.: Hs.3144), an alternative human Cbl-b (UniGene No.: Hs.381921) that may be a splice variant of Cbl-b, a human Cbl-b polypeptide that is a splice variant represented by the amino acid sequence depicted in SEQ ID NO: 50, which is encoded by the nucleic acid sequence depicted in SEQ ID NO: 49, a human Cbl-b polypeptide that is a splice variant represented by the amino acid sequence depicted in SEQ ID NO: 52, which is encoded by the nucleic acid sequence depicted in SEQ ID NO: 51.

Certain Cbl-b polypeptides have been shown to function as adaptor proteins by interacting with other signaling molecules, e.g., interaction with cell surface receptor tyrosine kinases, e.g., EGFR (Ettenberg, S A et al (2001) J Biol Chem 276:77-84) or with proteins such as Syk (Elly, C et al (1999) Oncogene 18:1147-56), Crk-L (Elly, C et al (1999) Oncogene 18:1147-56), PI3K (Fang, D et al. (2001) J Biol Chem 16:4872-8), Grb2 (Ettenberg, S A et al (1999) Oncogene 18:1855-66), or Vav (Bustelo, X R et al. (1997) Oncogene 15:2511-20). Certain Cbl-b polypeptides have been demonstrated to interact directly with the nucleotide exchange factor, Vav (Bustelo, X R et al. (1997) Oncogene 15:2511-20). Certain Cbl-b polypeptides have been shown to function as an E3 ubiquitin ligase that recognizes tyrosine phosphorylated substrates through its SH2 domain and through its RING domain, recruits a ubiquitin-conjugating enzyme, E2 (Joazeiro, C et al. (1999) Science 286:309-312) Additionally, certain Cbl-b polypeptides have been shown to associate directly with the p85 subunit of PI3K and to function as an E3 ligase in the ubiquitination of PI3K (Fang, D et al. (2001) J Biol Chem 16:4872-8).

The term Cbl-b is used herein to refer to full-length, human Cbl-b (UniGene No.: Hs.3144) as well as an alternative Cbl-b (UniGene No.: Hs.381921) composed of two separate Cbl-b sequences (e.g., nucleic acid sequences) that may be a splice variant. The term Cbl-b is used herein to refer as well to the human Cbl-b splice variant represented by the amino acid sequence of SEQ ID NO: 50, which is encoded by the nucleic acid sequence of SEQ ID NO: 49 and to the human Cbl-b splice variant represented by the amino acid sequence of SEQ ID NO: 52, which is encoded by the nucleic acid sequence of SEQ ID NO: 51. The term Cbl-b is used herein to refer as well to various naturally occurring Cbl-b homologs, as well as functionally similar variants and fragments that retain at least 80%, 90%, 95%, or 99% sequence identity to a naturally occurring Cbl-b. The term specifically includes human Cbl-b nucleic acid and amino acid sequences (e.g., SEQ ID NOS: 51 and 52) and the sequences presented in the Examples.

In certain embodiments, compounds disclosed herein may be evaluated for effectiveness in inhibiting the ubiquitin ligase activity of a PEM-3-like polypeptide, and, as appropriate, used to inhibit such activity.

PEM-3-like protein bears a unique composition of KH domains and RING domains and is predicted to localize to the nucleoplasm and to the cytoplasm. The protein, SAM68, and homologous proteins containing a KH domain, play an important role in the post-transcriptional regulation of HIV-1 replication. These proteins are involved in the CRM1 pathway and have been found to interact with viral RNA. CRM1 is a receptor protein normally involved in the nuclear export of certain RNAs and proteins. HIV-1 matrix (MA), the amino-terminal domain of the Pr55 gag polyprotein, is involved in directing unspliced viral RNA from the nucleus to the plasma membrane. Although MA does not contain the canonical leucine-rich nuclear export signal, nuclear export is mediated through the conserved CRM1p pathway (Dupont, S et al. (1999) Nature 402:681-685). Nuclear export of another retroviral Gag polyprotein, the Rous sarcoma virus Gag polyprotein, is mediated by a CRM1-dependent nuclear export pathway (Scheifele, L Z et al. (2002) Proc Natl Acad Sci USA 99:3944-3949). While not wishing to be bound to mechanism, PEM-3-like polypeptides may be involved in the CRM1 pathway and may play a role in the post-transcriptional regulation of HIV-1 and in the replication of other viruses.

The term PEM-3-like is used herein to refer to full-length, human PEM-3-like. The term PEM-3-like is used herein to refer as well to various naturally occurring PEM-3-like homologs, as well as functionally similar variants and fragments that retain at least 80%, 90%, 95%, or 99% sequence identity to a naturally occurring PEM-3-like. The term specifically includes human PEM-3-like nucleic acid and amino acid sequences and the sequences presented in the Examples.

5. Transgenic Animals and Uses Thereof

In certain embodiments, the application further provides methods for using animal models for determining the safety and/or efficacy of virus therapeutics, i.e. compounds which are useful for treating and/or preventing the development of diseases or conditions, which are caused by, or contributed to by viral infection (e.g., AIDS). In addition the assays are useful for further improving known anti-viral compounds, e.g, by modifying their structure to increase their stability and/or activity and/or toxicity. Accordingly, the application features methods of administering a compound disclosed herein to an animal model for viral infection. Animals may be a mammal such as a mouse, rat, rabbit, goat, sheep, dog, cat, cow, or non-human primate. Such an animal may be susceptible to infection with envelope viruses, retroid viruses and RNA viruses such as various rhabdoviruses, lentiviruses, and filoviruses. Retroid viruses include lentiviruses such as HIV. Other RNA viruses include filoviruses such as Ebola virus.

A transgenic animal may carry a construct for expressing a ubiquitin ligase of interest, such as a gene encoding a POSH polypeptide. A transgenic animal may carry a loss of function mutation or knockout of the endogenous copy of a ubiquitin ligase of interest. A transgenic animal may carry one or more human genes involved in HIV infection, such as Cyclin T1, CD34, CCR5, and fusin (CRCX4). In a further embodiment, the additional human transgene is a gene involved in a disease or condition that is associated with AIDS (e.g., hypertension, Kaposi's sarcoma, cachexia, etc.) Such an animal may be an useful animal model for studying HIV infection, AIDS and related disease development.

Another aspect of the present application concerns transgenic animals which are comprised of cells (of that animal) which contain a transgene of the present application and which preferably (though optionally) express an exogenous POSH and/or POSH-AP protein in one or more cells in the animal. A POSH or POSH-AP transgene can encode the wild-type form of the protein, or can encode homologs thereof, as well as antisense constructs. Moreover, it may be desirable to express the heterologous transgene conditionally such that either the timing or the level of gene expression can be regulated. Such conditional expression can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080.

Moreover, transgenic animals exhibiting tissue specific expression can be generated, for example, by inserting a tissue specific regulatory element, such as an enhancer, into the transgene. For example, the endogenous POSH or POSH-AP gene promoter or a portion thereof can be replaced with another promoter and/or enhancer, e.g., a CMV or a Moloney murine leukemia virus (MLV) promoter and/or enhancer.

Alternatively, non-human transgenic animals that only express HIV transgenes in the brain can be generated using brain specific promoters (e.g., myelin basic protein (MBP) promoter, the neurofilament protein (NF-L) promoter, the gonadotropin-releasing hormone promoter, the vasopressin promoter and the neuron-specific enolase promoter, see So Forss-Petter et al., Neuron, 5, 187, (1990). Such animals can provide a useful in vivo model to evaluate the ability of a potential anti-HIV drug to cross the blood-brain barrier. Other target cells for which specific promoters can be used are, for example, macrophages, T cells and B cells. Other tissue specific promoters are well-known in the art, see e.g., R. Jaenisch, Science, 240, 1468 (1988).

Non-human transgenic animals containing an inducible transgene can be generated using inducible regulatory elements (e.g., metallothionein promoter), which are well-known in the art. Transgene expression can then be initiated in these animals by administering to the animal a compound which induces gene expression (e.g., heavy metals). Another preferred inducible system comprises a tetracycline-inducible transcriptional activator (U.S. Pat. No. 5,654,168 issued Aug. 5, 1997 to Bujard and Gossen and U.S. Pat. No. 5,650,298 issued Jul. 22, 1997 to Bujard et al.).

In general, transgenic animal lines can be obtained by generating transgenic animals having incorporated into their genome at least one transgene, selecting at least one founder from these animals and breeding the founder or founders to establish at least one line of transgenic animals having the selected transgene incorporated into their genome.

The present application provides for transgenic animals that carry the transgene in all their cells, as well as animals that carry the transgene in some, but not all cells, i.e., mosaic animals. The transgene can be integrated as a single transgene or in tandem, e.g., head to head tandems, or head to tail or tail to tail or as multiple copies.

The successful expression of the transgene can be detected by any of several means well known to those skilled in the art. Non-limiting examples include Northern blot, in situ hybridization of mRNA analysis, Western blot analysis, immunohistochemistry, and FACS analysis of protein expression.

In a further aspect, the application features non-human animal cells containing a POSH transgene, preferentially a human POSH transgene. For example, the animal cell (e.g., somatic cell or germ cell (i.e. egg or sperm)) can be obtained from the transgenic animal. Transgenic somatic cells or cell lines can be used, for example, in drug screening assays. Transgenic germ cells, on the other hand, can be used in generating transgenic progeny, as described above.

The transgenic animals can be used in in vivo assays to identify viral therapeutics. For example, the animals can be used in assays to identify compounds which reduce or inhibit any phase of the viral life cycle, e.g., expression of one or more viral genes, activity of one or more viral proteins, glycosylation of one or more viral proteins, processing of one or more viral proteins, viral replication, assembly of virions, and/or budding of infectious virions.

In an exemplary embodiment, the assay comprises administering a test compound to a transgenic animal of the application infected with a virus including RNA viruses, DNA viruses, retroidvirus and/or envelope viruses, and comparing a phenotypic change in the animal relative to a transgenic animal which has not received the test compound. For example, where the animal is infected with HIV, the phenotypic change can be the amelioration in an AIDS related complex (ARC), cataracts, inflammatory lesions in the central nervous system (CNV), a mild kidney sclerotic lesion, or a skin lesion, such as psoratic dermatitis, hyperkerstotic lesions, Kaposi's sarcoma or cachexia. The effect of a compound on inhibition of Kaposi's sarcoma can be determined, as described, e.g., in PCT/US97/11202 (WO97/49373) by Gallo et al. These and other HIV related symptoms or phenotypes are further described in Leonard et al. (1988) Science 242:1665.

In another embodiment, the phenotypic change is release/budding of virus particles. In yet another embodiment, the phenotypic change is the number of CD4+ T cells or the ratio of CD4+ T cells versus CD8+ T cells. In HIV infected humans as well as in HIV transgenic mice, analysis of lymph nodes indicate that the number of CD4+ T cells decreases and the number of CD8+ T cells increases. Numbers of CD4+ and CD8+ T cells can be determined, for example, by indirect immunofluorescence and flow cytometry, as described, e.g., in Santoro et al., supra.

Alternatively, a phenotypic change, e.g., a change in the expression level of an HIV gene can be monitored. The HIV RNA can be selected from the group consisting of gag mRNA, gag-pro-pol mRNA, vif mRNA, vpr mRNA, tat mRNA, rev mRNA, vpu/env mRNA, nef mRNA, and vpx mRNA. The HIV protein can be selected from the group consisting of Pr55 Gag and fragments thereof (p17 MA, p24 CA, p7 NC, p1, p9, p6, and p2), Pr160 Gag-Pro-Pol, and fragments thereof (p10 PR, p51 RT, p66 RT, p32 IN), p23 Vif, p15Vpr, p14Tat, p19 Rev, p16Vpu, gPr160 Env or fragments thereof (gp120 SU and gp41TM), p27 Nef, and p14 Vpx. The level of any of these mRNAs or proteins can be determined in cells from a tissue sample, such as a skin biopsy, as described in, e.g., PCT/US97/11202 (WO97/49373) by Gallo et al. Quantitation of HIV mRNA and protein is further described elsewhere herein and also in, e.g., Dickie et al. (1996) AIDS Res. Human Retroviruses 12:1103. In a preferred embodiment, the level of gp120 on the surface of PBMC is determined. This can be done, as described in the examples, e.g., by immunofluorescence on PBMC obtained from the animals.

A further phenotypic change is the production level or rate of viral particles in the serum and/or tissue of the animal. This can be determined, e.g., by determining reverse transcriptase (RT activity) or viral load as described elsewhere herein as well as in PCT/US97/11202 (WO97/49373) by Gallo et al., such as by determining p24 antigen.

Yet another phenotypic change, which can indicate HIV infection or AIDS progression is the production of inflammatory cytokines such as IL-6, IL-8 and TNF-.alpha.; thus, efficacy of a compound as an anti-HIV therapeutic can be assessed by ELISA tests for the reduction of serum levels of any or all of these cytokines.

Cells from the transgenic animals of the application can be established in culture and immortalized to establish cell lines. For example, immortalized cell lines can be established from the livers of transgenic rats, as described in Bulera et al. (1997) Hepatology 25: 1192. Cell lines from other types of cells can be established according to methods known in the art."

In one cell-based assay, cells expressing a POSH transgene can be infected with a virus of interest and incubated in the presence a test compound or a control compound. The production of viral particles is then compared. This assay system thus provides a means of identifying molecular antagonists which, for example, function by interfering with viral release/budding.

Cell based assays can also be used to identify compounds which modulate expression of a viral gene, modulate translation of a viral mRNA, or which modulate the stability of a viral mRNA or protein. Accordingly, a cell which is infected with a virus of interest can be incubated with a test compound and the amount of the viral protein produced in the cell medium can be measured and compared to that produced from a cell which has not been contacted with the test compound. The specificity of the compound for regulating the expression of the particular virus gene can be confirmed by various control analyses, e.g., measuring the expression of one or more control genes. This type of cellular assay can be particularly useful for determining the efficacy of antisense molecules or ribozymes.

6. Drug Screening Assays

The application not only provides compounds which inhibit the ligase activity of a polypeptide and compounds which inhibit viral budding, but in certain aspects, the present application also provides assays for identifying yet additional agents that either interfere with or promote the activity of a ubiquitin ligase, particularly a POSH polypeptide.

In certain embodiments, the application provides assays to identify, optimize or otherwise assess agents that increase or decrease a ubiquitin-related activity of a ubiquitin ligase, such as a POSH polypeptide. Ubiquitin-related activities of POSH polypeptides may include the self-ubiquitination activity of a POSH polypeptide, generally involving the transfer of ubiquitin from an E2 enzyme to the POSH polypeptide, and the ubiquitination of a target protein, generally involving the transfer of a ubiquitin from a POSH polypeptide to the target protein. In certain embodiments, a POSH activity is mediated, at least in part, by a POSH RING domain.

In certain embodiments, an assay comprises forming a mixture comprising a POSH polypeptide, an E2 polypeptide and a source of ubiquitin (which may be the E2 polypeptide pre-complexed with ubiquitin). Optionally the mixture comprises an E1 polypeptide and optionally the mixture comprises a target polypeptide. Additional components of the mixture may be selected to provide conditions consistent with the ubiquitination of the POSH polypeptide. One or more of a variety of parameters may be detected, such as POSH-ubiquitin conjugates, E2-ubiquitin thioesters, free ubiquitin and target polypeptide-ubiquitin complexes. The term "detect" is used herein to include a determination of the presence or absence of the subject of detection (e.g., POSH-ubiqutin, E2-ubiquitin, etc.), a quantitative measure of the amount of the subject of detection, or a mathematical calculation of the presence, absence or amount of the subject of detection, based on the detection of other parameters. The term "detect" includes the situation wherein the subject of detection is determined to be absent or below the level of sensitivity. Detection may comprise detection of a label (e.g., fluorescent label, radioisotope label, and other described below), resolution and identification by size (e.g., SDS-PAGE, mass spectroscopy), purification and detection, and other methods that, in view of this specification, will be available to one of skill in the art. For instance, radioisotope labeling may be measured by scintillation counting, or by densitometry after exposure to a photographic emulsion, or by using a device such as a Phosphorimager. Likewise, densitometry may be used to measure bound ubiquitin following a reaction with an enzyme label substrate that produces an opaque product when an enzyme label is used. In a preferred embodiment, an assay comprises detecting the POSH-ubiquitin conjugate.

In certain embodiments, an assay comprises forming a mixture comprising a POSH polypeptide, a target polypeptide and a source of ubiquitin (which may be the POSH polypeptide pre-complexed with ubiquitin). Optionally the mixture comprises an E1 and/or E2 polypeptide and optionally the mixture comprises an E2-ubiquitin thioester. Additional components of the mixture may be selected to provide conditions consistent with the ubiquitination of the target polypeptide. One or more of a variety of parameters may be detected, such as POSH-ubiquitin conjugates and target polypeptide-ubiquitin conjugates. In a preferred embodiment, an assay comprises detecting the target polypeptide-ubiquitin conjugate. In another preferred embodiment, an assay comprises detecting the POSH-ubiquitin conjugate.

An assay described above may be used in a screening assay to identify agents that modulate a ubiquitin-related activity of a POSH polypeptide. A screening assay will generally involve adding a test agent to one of the above assays, or any other assay designed to assess a ubiquitin-related activity of a POSH polypeptide. The parameter(s) detected in a screening assay may be compared to a suitable reference. A suitable reference may be an assay run previously, in parallel or later that omits the test agent. A suitable reference may also be an average of previous measurements in the absence of the test agent. In general the components of a screening assay mixture may be added in any order consistent with the overall activity to be assessed, but certain variations may be preferred. For example, in certain embodiments, it may be desirable to pre-incubate the test agent and the E3 (e.g., the POSH polypeptide), followed by removing the test agent and addition of other components to complete the assay. In this manner, the effects of the agent solely on the POSH polypeptide may be assessed. In certain preferred embodiments, a screening assay for an antiviral agent employs a target polypeptide comprising an L domain, and preferably an HIV L domain.

In certain embodiments, an assay is performed in a high-throughput format. For example, one of the components of a mixture may be affixed to a solid substrate and one or more of the other components is labeled. For example, the POSH polypeptide may be affixed to a surface, such as a 96-well plate, and the ubiquitin is in solution and labeled. An E2 and E1 are also in solution, and the POSH-ubiquitin conjugate formation may be measured by washing the solid surface to remove uncomplexed labeled ubiquitin and detecting the ubiquitin that remains bound. Other variations may be used. For example, the amount of ubiquitin in solution may be detected. In certain embodiments, the formation of ubiquitin complexes may be measured by an interactive technique, such as FRET, wherein a ubiquitin is labeled with a first label and the desired complex partner (e.g., POSH polypeptide or target polypeptide) is labeled with a second label, wherein the first and second label interact when they come into close proximity to produce an altered signal. In FRET, the first and second labels are fluorophores. FRET is described in greater detail below. The formation of polyubiquitin complexes may be performed by mixing two or more pools of differentially labeled ubiquitin that interact upon formation of a polyubiquitin (see, e.g., US Patent Publication 20020042083). High-throughput may be achieved by performing an interactive assay, such as FRET, in solution as well. In addition, if a polypeptide in the mixture, such as the POSH polypeptide or target polypeptide, is readily purifiable (e.g., with a specific antibody or via a tag such as biotin, FLAG, polyhistidine, etc.), the reaction may be performed in solution and the tagged polypeptide rapidly isolated, along with any polypeptides, such as ubiquitin, that are associated with the tagged polypeptide. Proteins may also be resolved by SDS-PAGE for detection.

In certain embodiments, the ubiquitin is labeled, either directly or indirectly. This typically allows for easy and rapid detection and measurement of ligated ubiquitin, making the assay useful for high-throughput screening applications. As described above, certain embodiments may employ one or more tagged or labeled proteins. A "tag" is meant to include moieties that facilitate rapid isolation of the tagged polypeptide. A tag may be used to facilitate attachment of a polypeptide to a surface. A "label" is meant to include moieties that facilitate rapid detection of the labeled polypeptide. Certain moieties may be used both as a label and a tag (e.g., epitope tags that are readily purified and detected with a well-characterized antibody). Biotinylation of polypeptides is well known, for example, a large number of biotinylation agents are known, including amine-reactive and thiol-reactive agents, for the biotinylation of proteins, nucleic acids, carbohydrates, carboxylic acids; see chapter 4, Molecular Probes Catalog, Haugland, 6th Ed. 1996, hereby incorporated by reference. A biotinylated substrate can be attached to a biotinylated component via avidin or streptavidin. Similarly, a large number of haptenylation reagents are also known.

An "E1" is a ubiquitin activating enzyme. In a preferred embodiment, E1 is capable of transferring ubiquitin to an E2. In a preferred embodiment, E1 forms a high energy thiolester bond with ubiquitin, thereby "activating" the ubiquitin. An "E2" is a ubiquitin carrier enzyme (also known as a ubiquitin conjugating enzyme). In a preferred embodiment, ubiquitin is transferred from E1 to E2. In a preferred embodiment, the transfer results in a thiolester bond formed between E2 and ubiquitin. In a preferred embodiment, E2 is capable of transferring ubiquitin to a POSH polypeptide.

In an alternative embodiment, a POSH polypeptide, E2 or target polypeptide is bound to a bead, optionally with the assistance of a tag. Following ligation, the beads may be separated from the unbound ubiquitin and the bound ubiquitin measured. In a preferred embodiment, POSH polypeptide is bound to beads and the composition used includes labeled ubiquitin. In this embodiment, the beads with bound ubiquitin may be separated using a fluorescence-activated cell sorting (FACS) machine. Methods for such use are described in U.S. patent application Ser. No. 09/047,119, which is hereby incorporated in its entirety. The amount of bound ubiquitin can then be measured.

In certain preferred embodiments, agents that inhibit (or promote) the ubiquitin ligase activity of a ubiquitin ligase, such as POSH, may be identified using a homogenous time resolved fluorescence assay. Such an assay may employ a GST fused to the RING subunit of a ubiquitin ligase (e.g. POSH). Two flurophore-conjugated detection reagents are also used: anti-GSTXL665 and europium cryptate labeled ubiquitn. The ubiqutination of the ubiquitin ligase by ubiqutin cryptate and binding of the anti-GST tagged XL665 brings the fluorophores into close proximity allowing FRET reaction to occur. Accordingly, FRET serves as a measurement of ubiquitination of the ubiquitin ligase. An enzymatic system may be set up to provide activated ubiquitin, e.g., by providing ubiquitin, an E1 and an E2. Compounds that will not allow the FRET reaction are considered to be inhibitors.

In a screening assay, the effect of a test agent may be assessed by, for example, assessing the effect of the test agent on kinetics, steady-state and/or endpoint of the reaction.

The components of the various assay mixtures provided herein may be combined in varying amounts. In a preferred embodiment, ubiquitin (or E2 complexed ubiquitin) is combined at a final concentration of from 5 to 200 ng per 100 microliter reaction solution. Optionally E1 is used at a final concentration of from 1 to 50 ng per 100 microliter reaction solution. Optionally E2 is combined at a final concentration of 10 to 100 ng per 100 microliter reaction solution, more preferably 10-50 ng per 100 microliter reaction solution. In a preferred embodiment, POSH polypeptide is combined at a final concentration of from 1 ng to 500 ng per 100 microliter reaction solution.

Generally, an assay mixture is prepared so as to favor ubiquitin ligase activity and/or ubiquitination activity. Generally, this will be physiological conditions, such as 50-200 mM salt (e.g., NaCl, KCl), pH of between 5 and 9, and preferably between 6 and 8. Such conditions may be optimized through trial and error. Incubations may be performed at any temperature which facilitates optimal activity, typically between 4 and 40 degrees C. Incubation periods are selected for optimum activity, but may also be optimized to facilitate rapid high through put screening. Typically between 0.5 and 1.5 hours will be sufficient. A variety of other reagents may be included in the compositions. These include reagents like salts, solvents, buffers, neutral proteins, e.g., albumin, detergents, etc. which may be used to facilitate optimal ubiquitination enzyme activity and/or reduce non-specific or background interactions. Also reagents that otherwise improve the efficiency of the assay, such as protease inhibitors, nuclease inhibitors, anti-microbial agents, etc., may be used. The compositions will also preferably include adenosine tri-phosphate (ATP). The mixture of components may be added in any order that promotes ubiquitin ligase activity or optimizes identification of candidate modulator effects. In a preferred embodiment, ubiquitin is provided in a reaction buffer solution, followed by addition of the ubiquitination enzymes. In an alternate preferred embodiment, ubiquitin is provided in a reaction buffer solution, a candidate modulator is then added, followed by addition of the ubiquitination enzymes.

In general, a test agent that decreases a POSH ubiquitin-related activity may be used to inhibit POSH function in vivo, while a test agent that increases a POSH ubiquitin-related activity may be used to stimulate POSH function in vivo. Test agent may be modified for use in vivo, e.g., by addition of a hydrophobic moiety, such as an ester.

An additional POSH-AP may be added to a POSH ubiquitination assay to assess the effect of the POSH-AP on POSH-mediated ubiquitination and/or to assess whether the POSH-AP is a target for POSH-mediated ubiquitination.

In certain embodiments, a ubiquitination assay as described above for POSH can similarly be conducted for a Cbl-b, a PEM-3-like, a SIAH1, or a TTC3 polypeptide. In certain embodiments, the application provides assays to identify, optimize or otherwise assess agents that increase or decrease a ubiquitin-related activity of a Cbl-b, a PEM-3-like, a SIAH1, or a TTC3 polypeptide. Ubiquitin-related activities of Cbl-b, PEM-3-like, SIAH1, or TTC3 polypeptides may include the self-ubiquitination activity of a Cbl-b, PEM-3-like, SIAH1, or TTC3 polypeptide, generally involving the transfer of ubiquitin from an E2 enzyme to the respective Cbl-b, PEM-3-like, SIAH1, or TTC3 polypeptide, and the ubiquitination of a target protein, e.g., the p85 subunit of PI3K, e.g, synaptophysin, generally involving the transfer of a ubiquitin from a Cbl-b, PEM-3-like, SIAH1, or TTC3 polypeptide to the target protein, e.g, the p85 subunit of PI3K, e.g., synaptophysin. In certain embodiments, a Cbl-b, a PEM-3-like, a SIAH1, or a TTC3 activity is mediated, at least in part, by a RING domain of a Cbl-b, a PEM-3-like, a SIAH1, or a TTC3 polypeptide, respectively.

Certain embodiments of the application relate to assays for identifying agents that bind to a POSH, optionally a particular domain of POSH such as an SH3 or RING domain or a particular domain of a Cbl-b, such as an SH2 or RING domain of Cbl-b or a RING domain of SIAH1 or TTC3. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions and design of test agents. In one embodiment, an assay detects agents which inhibit interaction of one or more subject POSH polypeptides with a POSH-AP. In another embodiment, the assay detects agents which modulate the intrinsic biological activity of a POSH polypeptide or POSH complex, such as an enzymatic activity, binding to other cellular components, cellular compartmentalization, and the like.

In one aspect, the application provides methods and compositions for the identification of compositions that interfere with the function of ubiquitin ligase polypeptides. In another aspect, the application provides methods and compositions for the identification of compositions that interfere with the function of the RING domain of a polypeptide, e.g., the RING domain of a POSH or a Cbl-b. In an additional embodiment, the application provides methods and compositions for the identification of agents that interact with the RING domain of a polypeptide, e.g., the RING domain of a POSH or a Cbl-b.

In many drug screening programs which test libraries of compounds and natural extracts, high throughput assays are desirable in order to maximize the number of compounds surveyed in a given period of time. Assays of the present application which are performed in cell-free systems, such as may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

In a further embodiment, agents that bind to a ubiquitin ligase may be identified by using an immobilized ubiquitin ligase. In an illustrative embodiment, a fusion protein can be provided which adds a domain that permits the protein to be bound to an insoluble matrix. For example, GST-POSH fusion proteins can be adsorbed onto glutathione sepharose beads (Sigma Chemical, St. Louis, Mo.) or glutathione derivatized microtitre plates, which are then combined with a potential labeled binding agent and incubated under conditions conducive to binding. Following incubation, the beads are washed to remove any unbound agent, and the matrix bead-bound label determined directly, or in the supernatant after the bound agent is dissociated.

As described above, Fluorescence Resonance Energy Transfer (FRET)-based assays may also be used to evaluate the formation of ubiquitin-ubiquitin ligase conjugates. Fluorescent molecules having the proper emission and excitation spectra that are brought into close proximity with one another can exhibit FRET. The fluorescent molecules are chosen such that the emission spectrum of one of the molecules (the donor molecule) overlaps with the excitation spectrum of the other molecule (the acceptor molecule). The donor molecule is excited by light of appropriate intensity within the donor's excitation spectrum. The donor then emits the absorbed energy as fluorescent light. The fluorescent energy it produces is quenched by the acceptor molecule. FRET can be manifested as a reduction in the intensity of the fluorescent signal from the donor, reduction in the lifetime of its excited state, and/or re-emission of fluorescent light at the longer wavelengths (lower energies) characteristic of the acceptor. When the fluorescent proteins physically separate, FRET effects are diminished or eliminated. (U.S. Pat. No. 5,981,200).

For example, a cyan fluorescent protein is excited by light at roughly 425-450 nm wavelength and emits light in the range of 450-500 nm. Yellow fluorescent protein is excited by light at roughly 500-525 nm and emits light at 525-500 nm. If these two proteins are placed in solution, the cyan and yellow fluorescence may be separately visualized. However, if these two proteins are forced into close proximity with each other, the fluorescent properties will be altered by FRET. The bluish light emitted by CFP will be absorbed by YFP and re-emitted as yellow light. This means that when the proteins are stimulated with light at wavelength 450 nm, the cyan emitted light is greatly reduced and the yellow light, which is not normally stimulated at this wavelength, is greatly increased. FRET is typically monitored by measuring the spectrum of emitted light in response to stimulation with light in the excitation range of the donor and calculating a ratio between the donor-emitted light and the acceptor-emitted light. When the donor: acceptor emission ratio is high, FRET is not occurring and the two fluorescent proteins are not in close proximity. When the donor: acceptor emission ratio is low, FRET is occurring and the two fluorescent proteins are in close proximity. In this manner, the interaction between a first and second polypeptide may be measured.

The occurrence of FRET also causes the fluorescence lifetime of the donor fluorescent moiety to decrease. This change in fluorescence lifetime can be measured using a technique termed fluorescence lifetime imaging technology (FLIM) (Verveer et al. (2000) *Science* 290: 1567-1570; Squire et al. (1999) *J. Microsc.* 193: 36; Verveer et al. (2000) *Biophys. J.* 78: 2127). Global analysis techniques for analyzing FLIM data have been developed. These algorithms use the understanding that the donor fluorescent moiety exists in only a limited number of states each with a distinct fluorescence lifetime. Quantitative maps of each state can be generated on a pixel-by-pixel basis.

Suitable fluorescent labels are, in view of this specification, well known in the art. Examples are provided below, but suitable fluorescent labels not specifically discussed are also available to those of skill in the art. Fluorescent labeling may be accomplished by expressing a polypeptide as a fusion protein with a fluorescent protein, for example fluorescent proteins isolated from jellyfish, corals and other coelenterates. Exemplary fluorescent proteins include the many variants of the green fluorescent protein (GFP) of *Aequoria victoria*. Variants may be brighter, dimmer, or have different excitation and/or emission spectra. Certain variants are altered such that they no longer appear green, and may appear blue, cyan, yellow or red (termed BFP, CFP, YFP and RFP, respectively). Fluorescent proteins may be stably attached to polypeptides through a variety of covalent and noncovalent linkages, including, for example, peptide bonds (eg. expression as a fusion protein), chemical cross-linking and biotin-streptavidin coupling. For examples of fluorescent proteins, see U.S. Pat. Nos. 5,625,048; 5,777,079; 6,066,476; 6,124,128; Prasher et al. (1992) *Gene*, 111:229-233; Heim et al. (1994) *Proc. Natl. Acad. Sci., USA*, 91:12501-04; Ward et al. (1982) *Photochem. Photobiol.*, 35:803-808; Levine et al. (1982) *Comp. Biochem. Physiol.*, 72B:77-85; Tersikh et al. (2000) *Science* 290: 1585-88.

Other exemplary fluorescent moieties well known in the art include derivatives of fluorescein, benzoxadioazole, coumarin, eosin, Lucifer Yellow, pyridyloxazole and rhodamine. These and many other exemplary fluorescent moieties may be found in the *Handbook of Fluorescent Probes and Research Chemicals* (2000, Molecular Probes, Inc.), along with methodologies for modifying polypeptides with such moieties. Exemplary proteins that fluoresce when combined with a fluorescent moiety include, yellow fluorescent protein from *Vibrio fischeri* (Baldwin et al. (1990) *Biochemistry* 29:5509-15), peridinin-chlorophyll a binding protein from the dinoflagellate *Symbiodinium* sp. (Morris et al. (1994) *Plant Molecular Biology* 24:673:77) and phycobiliproteins from marine cyanobacteria such as Synechococcus, e.g., phycoerythrin and phycocyanin (Wilbanks et al. (1993) *J. Biol. Chem.* 268:1226-35). These proteins require flavins, peridinin-chlorophyll a and various phycobilins, respectively, as fluorescent co-factors.

FRET-based assays may be used in cell-based assays and in cell-free assays. FRET-based assays are amenable to high-throughput screening methods including Fluorescence Activated Cell Sorting and fluorescent scanning of microtiter arrays.

In general, where the screening assay is a binding assay (whether protein-protein binding, agent-protein binding, etc.), one or more of the molecules may be joined to a label, where the label can directly or indirectly provide a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in a screening assay. These include reagents like salts, neutral proteins, e.g., albumin, detergents, etc that are used to facilitate optimal protein-protein binding and/or reduce nonspecific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° and 40° C. Incubation periods are selected for optimum activity, but may also be optimized to facilitate rapid high-throughput screening.

7. Methods and Compositions for Treatment of Viral Disorders

In a further aspect, the application provides compounds for treatment of viral disorders, and particularly disorders caused by retroid viruses, RNA viruses and/or envelope viruses, including but not limited to retroviruses, rhabdoviruses, lentiviruses, and filoviruses. Certain therapeutics of the application may function by disrupting the biological activity of a POSH polypeptide or POSH complex in viral maturation. Certain therapeutics of the application may function by disrupting the activity of Cbl-b. Certain therapeutics of the application may function by disrupting the activity of PEM-3-like. Certain therapeutics of the application may function as anti-viral agents by inhibiting the RING domain of a polypeptide, for example, by interacting with the RING domain of a polypeptide. In certain embodiments, therapeutics of the invention interact with the RING domain of a POSH or a POSH-AP (e.g., Cbl-b, SIAH1, TTC3). In a further embodiment, therapeutics of the invention may function as anti-viral agents by inhibiting the ligase activity of a polypeptide, for example, by inhibiting the ubiquitin ligase activity of POSH or a POSH-AP (e.g., Cbl-b, SIAH1, TTC3). In additional embodiments, therapeutics of the invention function as anti-viral agents by inhibiting viral maturation (observed as viral budding). Exemplary therapeutics of the application are presented in Table 7.

In view of the teachings herein, one of skill in the art will understand that the methods and compositions of the application are applicable to a wide range of viruses such as for example retroid viruses, RNA viruses, and envelope viruses. In a preferred embodiment, the present application is applicable to retroid viruses. In a more preferred embodiment, the present application is further applicable to retroviruses (retroviridae). In another more preferred embodiment, the present application is applicable to lentivirus, including primate lentivirus group. In a most preferred embodiment, the present application is applicable to Human Immunodeficiency virus (HIV), Human Immunodeficiency virus type-1 (HIV-1), Hepatitis B Virus (HBV) and Human T-cell Leukemia Virus (HTLV).

While not intended to be limiting, relevant retroviruses include: C-type retrovirus which causes lymphosarcoma in Northern Pike, the C-type retrovirus which infects mink, the caprine lentivirus which infects sheep, the Equine Infectious Anemia Virus (EIAV), the C-type retrovirus which infects pigs, the Avian Leukosis Sarcoma Virus (ALSV), the Feline Leukemia Virus (FeLV), the Feline Aids Virus, the Bovine Leukemia Virus (BLV), the Simian Leukemia Virus (SLV), the Simian Immuno-deficiency Virus (SIV), the Human T-cell Leukemia Virus type-I (HTLV-I), the Human T-cell Leukemia Virus type-II (HTLV-II), Human Immunodeficiency virus type-2 (HIV-2) and Human Immunodeficiency virus type-1 (HIV-1).

The method and compositions of the present application are further applicable to RNA viruses, including ssRNA negative-strand viruses and ssRNA positive-strand viruses. The ssRNA positive-strand viruses include Hepatitis C Virus (HCV). In a preferred embodiment, the present application is applicable to mononegavirales, including filoviruses. Filoviruses further include Ebola viruses and Marburg viruses.

Other RNA viruses include picornaviruses such as enterovirus, poliovirus, coxsackievirus and hepatitis A virus, the caliciviruses, including Norwalk-like viruses, the rhabdoviruses, including rabies virus, the togaviruses including alphaviruses, Semliki Forest virus, denguevirus, yellow fever virus and rubella virus, the orthomyxoviruses, including Type A, B, and C influenza viruses, the bunyaviruses, including the Rift Valley fever virus and the hantavirus, the filoviruses such as Ebola virus and Marburg virus, and the paramyxoviruses, including mumps virus and measles virus. Additional viruses that may be treated include herpes viruses.

8. Methods and Compositions for Treatment of Neurological Disorders

In a further aspect, the application provides compounds useful for the treatment of neurological disorders. Treatment or prevention of a neurological disorder includes inhibition of the progression of a neurological disorder.

Certain therapeutics of the application may function by disrupting the biological activity of a POSH polypeptide (e.g., the ubiquitin ligase activity of a POSH polypeptide) or POSH complex involved in the processing of amyloid polypeptides. In certain embodiments, an agent useful in the treatment or prevention of a neurological disorder interferes with the ubiquitin ligase activity of POSH (e.g., POSH ubiquitination of a target protein such as HERPUD1). Certain therapeutics of the application may function by inhibiting aberrant protein processing associated with a neurodegenerative disorder, such as for example, the processing of amyloid beta precursor protein (APP) associated with Alzheimer's disease. Exemplary therapeutics of the application are presented in Table 7.

In certain embodiments, therapeutics of the application inhibit the transport of APP in a cell by inhibiting the ubiquitin ligase activity of a polypeptide. In further embodiments, therapeutics of the application inhibit amyloid polypeptide production in a cell by inhibiting the ubiquitin ligase activity of a polypeptide, such as, for example, by inhibiting the ubiquitin ligase activity of POSH.

In certain embodiments, agents of the application interfere with the trafficking of a protein through the secretory pathway. In other embodiments, agents disclosed herein inhibit or promote POSH and POSH-AP mediated cellular processes such as protein processing in the secretory pathway, for example, processing of amyloid polypeptides.

Neurological disorders include CNS disorders, such as Alzheimer's disease, cerebral vascular disease, and schizophrenia. Neurological disorders further include disorders associated with increased levels of plasma homocysteine, increased levels of amyloid beta production, or aberrant presenilin activity. Examples of neurological disorders are Parkinson's disease, Huntington's disease, Pick's disease, Niemann-Pick's disease, prion-associated diseases (e.g., Mad Cow disease), depression, and schizophrenia.

9. Methods and Compositions for Treatment of Cancer Diseases

In a further aspect, the application provides compounds useful for the treatment or prevention of cancer diseases. In certain embodiments, a therapeutic of the application inhibits cell proliferation by inhibiting the ubiquitin ligase activity of a polypeptide. In certain embodiments, the polypeptide is a POSH polypeptide.

Certain therapeutics of the application may function by disrupting the biological activity of a POSH polypeptide or POSH complex involved in cell proliferation. In certain embodiments, an agent useful in the treatment or prevention of a cancer disease interferes with the ubiquitin ligase activity of POSH. Exemplary therapeutics of the application are presented in Table 7.

The terms "cancer," "tumor," and "neoplasia" are used interchangeably herein. As used herein, a cancer (tumor or neoplasia) is characterized by one or more of the following properties: cell growth is not regulated by the normal biochemical and physical influences in the environment; anaplasia (e.g., lack of normal coordinated cell differentiation); and in some instances, metastasis. Cancer diseases include, for example, anal carcinoma, bladder carcinoma, breast carcinoma, cervix carcinoma, chronic lymphocytic leukemia, chronic myelogenous leukemia, endometrial carcinoma, hairy cell leukemia, head and neck carcinoma, lung (small cell) carcinoma, multiple myeloma, non-Hodgkin's lymphoma, follicular lymphoma, ovarian carcinoma, brain tumors, colorectal carcinoma, hepatocellular carcinoma, Kaposi's sarcoma, lung (non-small cell carcinoma), melanoma, pancreatic carcinoma, prostate carcinoma, renal cell carcinoma, and soft tissue sarcoma. Additional cancer disorders can be found in, for example, Isselbacher et al. (1994) Harrison's Principles of Internal Medicine 1814-1877, herein incorporated by reference.

10. Effective Dose

Toxicity and therapeutic efficacy of such compounds can be determined by standard pharmaceutical procedures in cell cultures or experimental animals, e.g., for determining The $Ld_{50}$ (The Dose Lethal To 50% Of The Population) And The $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the application, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

11. Formulation and Use

Pharmaceutical compositions for use in accordance with the present application may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

An exemplary composition of the application comprises an RNAi mixed with a delivery system, such as a liposome system, and optionally including an acceptable excipient. In a preferred embodiment, the composition is formulated for topical administration for, e.g., herpes virus infections.

For such therapy, the compounds of the application can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the application can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present application are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the application are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

For therapies involving the administration of nucleic acids, the oligomers of the application can be formulated for a variety of modes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, intranodal, and subcutaneous for injection, the oligomers of the application can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the application are formulated into ointments, salves, gels, or creams as generally known in the art.

EXEMPLIFICATION

The application now being generally described, it will be more readily understood by reference to the following examples, which are included merely for purposes of illustration of certain aspects and embodiments of the present application, and are not intended to limit the application.

EXAMPLES

1. Identification of Compounds

Evaluation of POSH-specific inhibitors was conducted as follows:

Step 1: identifying compounds that block POSH autoubiquitnation at 10 micromolar DMSO solution of the compound. Compounds that have shown inhibition rate of 80% and more were designated as good inhibitor.

Step 2: filtering compounds that block E1 and E2 ubiqutination activity in compound concentration of 1 micro molar Step 3: establish IC 50 value measurements. Good inhibitors were designated as having IC 50 with in the range of 1 micromolar-100 nano molar Step 4: specificity of POSH inhibitors was established by determine the ability of POSH inhibitors to inhibit ubiquitination (% A) of different known E3 ligase at concentration of 1 micro molar. We have designates as selective inhibitors compound that fail to inhibit 60% of ubiquitination (% A less than 60%) according to protocol as described for HTS screening assay Compounds were further assessed for effects on maturation of HIV particles in a virus-like particle assay.

The amount of budding in the presence of inhibitors at concentration of 3 micro molar was determined by using RETRO-TEK HIV-1 p24 Antigen ELISA kit. (ZeptoMetrix Corporation, ZMC catalog #: 0801111, Buffalo, N.Y., USA). an enzyme-linked immunoassay used to detect the amount of HIV-1 p24 released during budding process.

A compound was identified as an effective inhibitor when less than 69% budding, relative to control, was observed.

Examples of identified compounds are provided in the following table:

TABLE 7

Exemplary formulas of POSH protein inhibitors.

| Compound ID | Structure |
|---|---|
| 1 | |
| 2 | 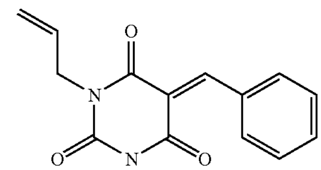 |
| 3 | 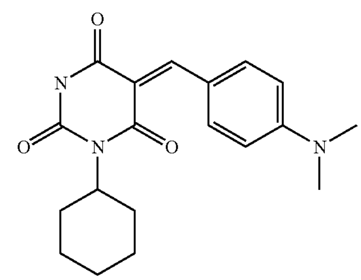 |
| 4 | 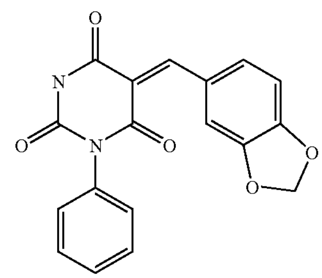 |
| 5 | 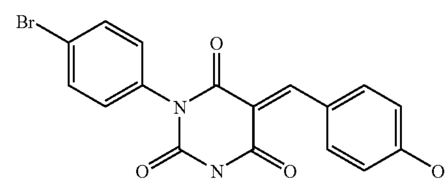 |
| 6 | 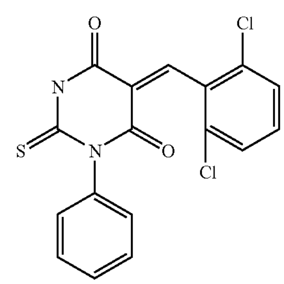 |
| 7 | 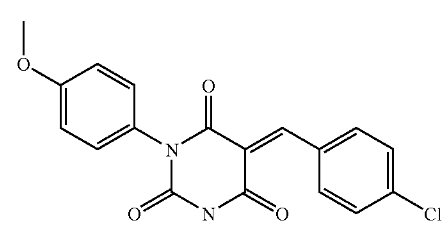 |

TABLE 7-continued

Exemplary formulas of POSH protein inhibitors.

| Compound ID | Structure |
|---|---|
| 8 | (structure) |
| 9 | (structure) |
| 10 | (structure) |
| 11 | (structure) |
| 12 | (structure) |
| 13 | (structure) |
| 15 | (structure) |
| 16 | (structure) |
| 17 | (structure) |
| 18 | (structure) |
| 19 | (structure) |
| 20 | (structure) |

TABLE 7-continued

Exemplary formulas of POSH protein inhibitors.

| Compound ID | Structure |
|---|---|
| 21 | 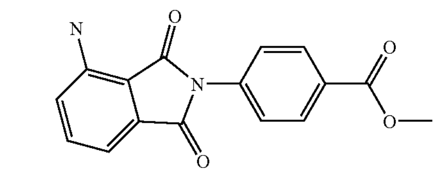 |
| 22 | 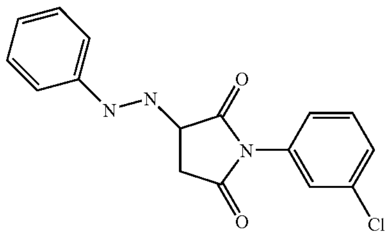 |
| 23 | 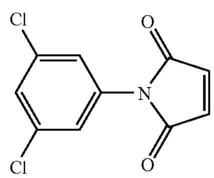 |
| 24 | 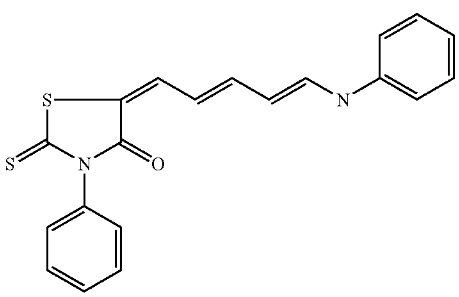 |
| 26 | 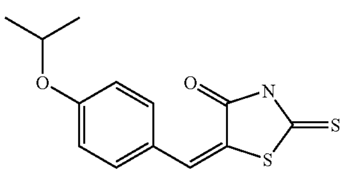 |
| 27 | 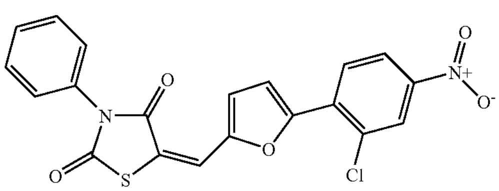 |
| 28 | 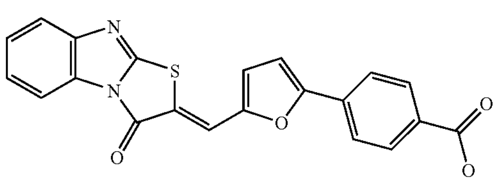 |
| 29 | |
| 30 | |
| 31 | |
| 32 | |
| 34 | |
| 35 | |

TABLE 7-continued

Exemplary formulas of POSH protein inhibitors.

| Compound ID | Structure |
|---|---|
| 36 | (structure) |
| 37 | (structure) |
| 38 | (structure) |
| 39 | (structure) |
| 40 | (structure) |
| 41 | (structure) |
| 42 | (structure) |
| 44 | (structure) |
| 48 | (structure) |
| 49 | (structure) |
| 50 | (structure) |

TABLE 7-continued
Exemplary formulas of POSH protein inhibitors.
| Compound ID | Structure |
|---|---|
| 51 | 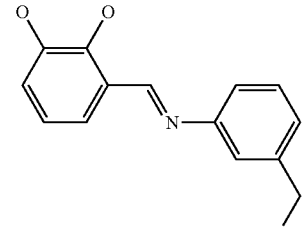 |
| 52 | 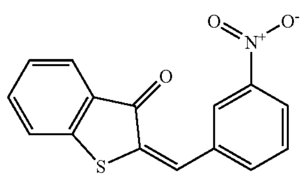 |
| 53 | 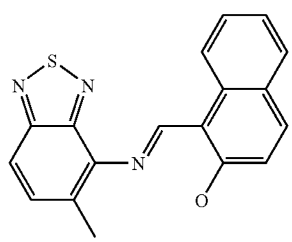 |
| 54 | 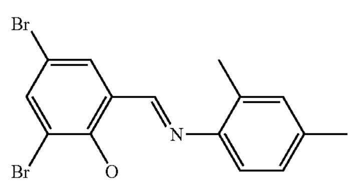 |
| 55 | 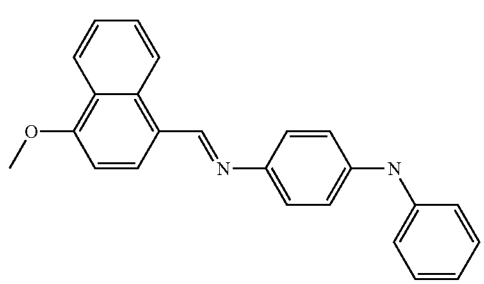 |
| 56 | 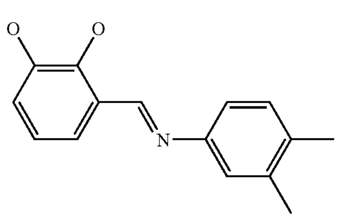 |
| 57 | 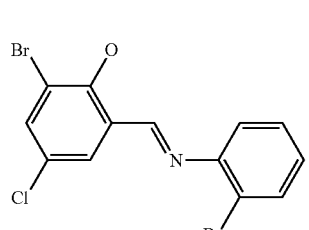 |
| 58 | 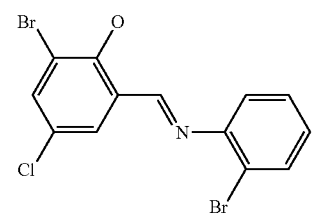 |
| 59 | 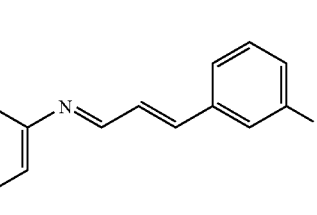 |
| 60 | 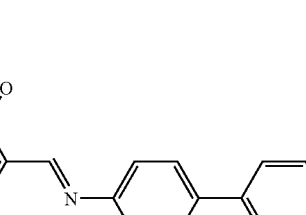 |
| 61 | 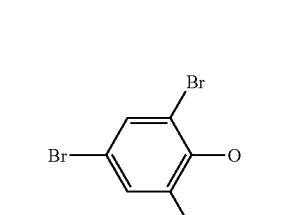 |

TABLE 7-continued

Exemplary formulas of POSH protein inhibitors.

| Compound ID | Structure |
|---|---|
| 62 | |
| 63 | |
| 64 | |
| 65 | |
| 66 | |
| 67 | |
| 68 | 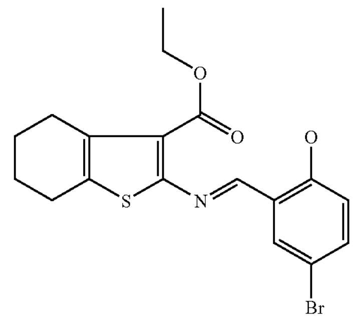 |
| 69 | 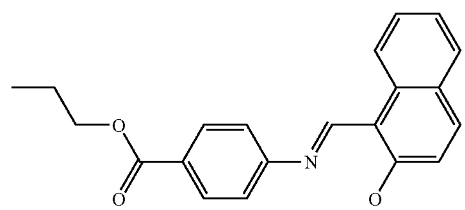 |
| 70 | 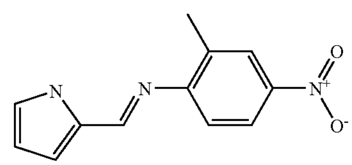 |
| 71 | 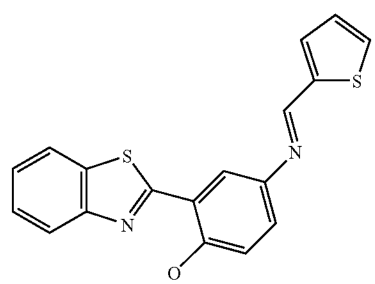 |
| 72 | 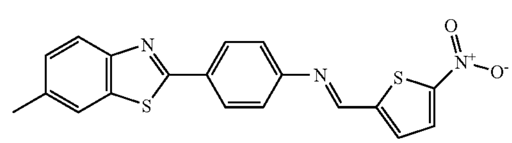 |
| 73 | 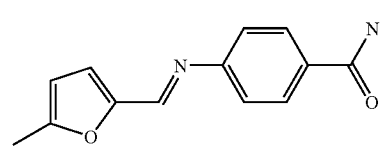 |
| 74 | 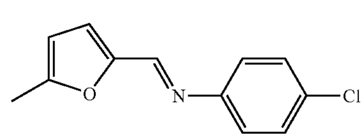 |

TABLE 7-continued

Exemplary formulas of POSH protein inhibitors.

| Compound ID | Structure |
|---|---|
| 75 | *(structure)* |
| 76 | *(structure)* |
| 78 | *(structure)* |
| 79 | *(structure)* |
| 80 | *(structure)* |
| 81 | *(structure)* |
| 82 | *(structure)* |
| 83 | *(structure)* |
| 84 | *(structure)* |
| 85 | *(structure)* |
| 86 | *(structure)* |
| 87 | *(structure)* |
| 88 | *(structure)* |

TABLE 7-continued
Exemplary formulas of POSH protein inhibitors.
| Compound ID | Structure |
|---|---|
| 89 | 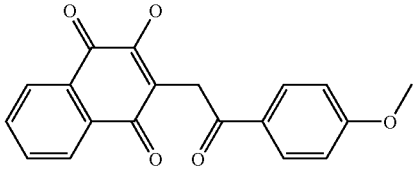 |
| 90 | 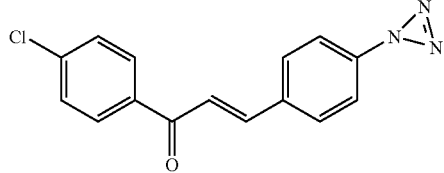 |
| 91 | 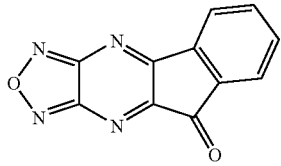 |
| 92 | 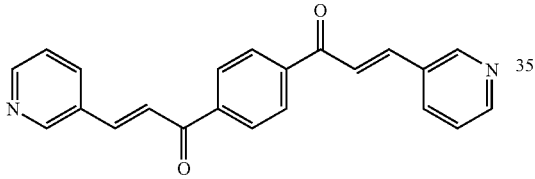 |
| 93 | 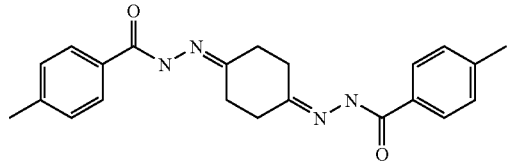 |
| 94 | 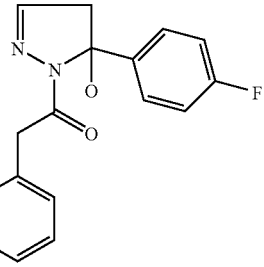 |
| 95 | 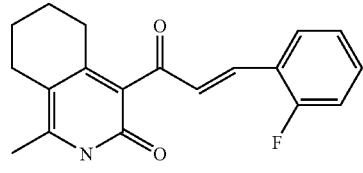 |
| 96 | 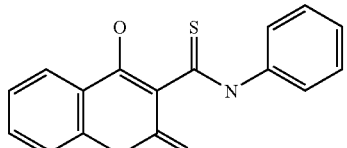 |
| 97 | 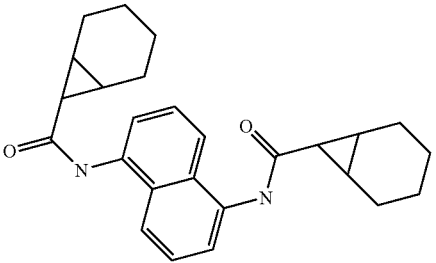 |
| 99 | 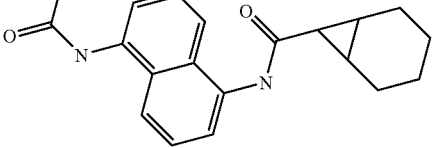 |
| 100 | 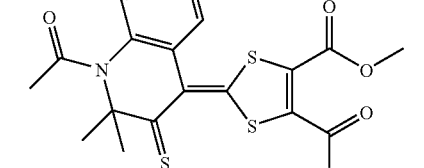 |
| 102 | 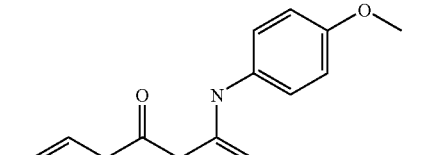 |
| 103 | 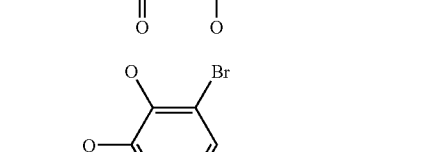 |

TABLE 7-continued

Exemplary formulas of POSH protein inhibitors.

| Compound ID | Structure |
|---|---|
| 104 | 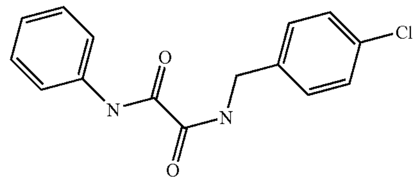 |
| 105 | 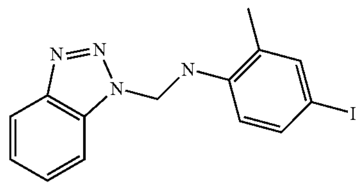 |
| 106 | 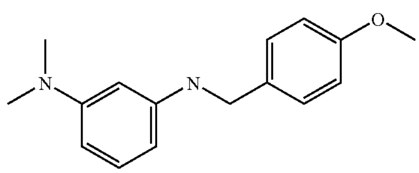 |
| 107 | 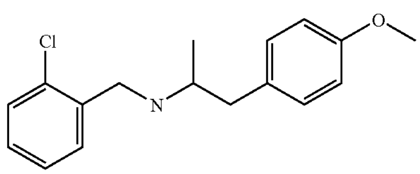 |
| 108 | 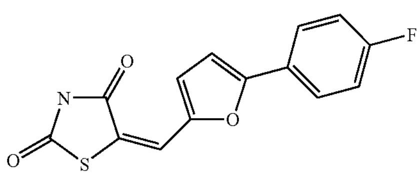 |
| 109 | 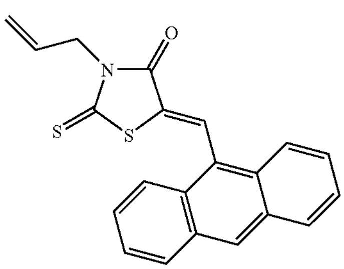 |
| 110 | 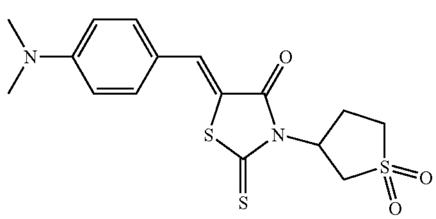 |
| 111 | |
| 112 | |
| 113 | |
| 114 | |
| 115 | |

TABLE 8

| Compound | Scaffold | CAS | Comments |
|---|---|---|---|
| 1 5155605 | 1 | 302563-54-8 | |
| 2 5240764 | 1 | 300804-92-6 | |
| 3 5240815 | 1 | 413611-30-0 | |
| 4 5240820 | 1 | 342014-54-4 | |
| 5 5240887 | 1 | 305867-95-2 | |
| 6 5240904 | 1 | 374541-44-3 | |
| 7 5240912 | 1 | No CAS | |
| 8 5240919 | 1 | No CAS | |

TABLE 8-continued

| Compound | Scaffold | CAS | Comments |
|---|---|---|---|
| 9 5240932 | 1 | 313954-00-6 | |
| 10 5240950 | 1 | No CAS | |
| 11 5240966 | 1 | 112328-79-7 | |
| 12 5241170 | 1 | No CAS | |
| 13 5317140 | 1 | 38307-83-4 | DE 2042663 |
| 14 5321555 | 1 | 27430-18-8 | WO 0193841 WO 0052100 |
| 15 5376633 | 1 | 356792-81-9 | |
| 16 5387991 | 1 | No CAS | |
| 17 5389732 | 1 | No CAS | |
| 18 5133208 | 2 | 1203-24-3 | |
| 19 5133209 | 2 | 1631-29-4 | GB 2376943 |
| 20 5141895 | 2 | 14567-55-4 | DE 2703200 |
| 21 5160537 | 2 | No CAS | |
| 22 5320007 | 2 | No CAS | |
| 23 5323355 | 2 | 24096-52-4 | JP 49124225 |
| 24 5162027 | 3 | 299964-34-4 | |
| 25 5163140 | 3 | 24138-83-8 (Z)74942-64-6 (E)74942-49-7 | |
| 26 5235376 | 3 | No Cas | |
| 27 5376345 | 3 | 3412944-98-2 | |
| 28 5376464 | 3 | No CAS | |
| 29 5376600 | 3 | 331652-34-7 | |
| 30 5377153 | 3 | 503065-65-4 | |
| 31 5377843 | 3 | 312604-25-4 | |
| 32 5378047 | 3 | 329929-55-7 | |
| 33 5378216 | 3 | No CAS | |
| 34 5380357 | 3 | 525569-45-3 | |
| 35 5143713 | 4 | 313959-65-8 | |
| 36 5225235 | 4 | 413595-33-2 | |
| 37 5355212 | 4 | 188123-61-7 | |
| 38 5376806 | 4 | 36376-41-7 | |
| 39 5380107 | 4 | 357158-43-1 | |
| 40 5352924 | 4 | 415715-97-8 | |
| 41 5225231 | 5 | No CAS | |
| 42 5230873 | 5 | 300591-75-7 | |
| 43 5376321 | 5 | No CAS | WO 9845986 |
| 44 5376324 | 5 | 356791-55-4 | |
| 45 5376958 | 5 | No CAS | WO 9845986 |
| 46 5377775 | 5 | No CAS | WO 9845986 |
| 47 5376610 | 5 | No CAS | WO 9845986 |
| 48 5376861 | 5 | 312724-83-7 | |
| 49 5378098 | 5 | No CAS | |
| 50 5378180 | 5 | 299202-78-1 | |
| 51 5378200 | 5 | 339161-23-8 | |
| 52 5378440 | 5 | 307343-52-8 | |
| 53 5202022 | 6 | 362592-42-5 | |
| 54 5271834 | 6 | 329936-50-7 | |
| 55 5273410 | 6 | No CAS | |
| 56 5273595 | 6 | 303766-78-3 | |
| 57 5282570 | 6 | 303058-45-9 | |
| 58 5284259 | 6 | 414899-38-0 | |
| 59 5309557 | 6 | 414908-08-0 | |
| 60 5310558 | 6 | No CAS | |
| 61 5346309 | 6 | 415703-60-5 | |
| 62 5347808 | 6 | 1508-25-4 | |
| 63 5348606 | 6 | No CAS | |
| 64 5349303 | 6 | 415713-27-8 | |
| 65 5353358 | 6 | No CAS | |
| 66 5353532 | 6 | 127926-59-4 | |
| 67 5353724 | 6 | No CAS | |
| 68 5367983 | 6 | No CAS | |
| 69 5375741 | 6 | No CAS | |
| 70 5375945 | 6 | 415940-16-8 | |
| 71 5156933 | 6 | No CAS | |
| 72 5194380 | 6 | No CAS | |
| 73 5321514 | 6 | No CAS | |
| 74 5321883 | 6 | No CAS | |
| 75 5255657 | 7 | 331853-23-7 | |
| 76 5255665 | 7 | 413619-73-5 | |
| 77 5354359 | 7 | 351443-33-9 | |
| 78 5380715 | 7 | 352562-21-1 | |
| 79 5256912 | 8 | 77367-94-3 | EP 23287 |
| 80 5256943 | 8 | 331975-91-8 | |
| 81 5279202 | 8 | 294667-01-9 | |
| 82 5352121 | 8 | 415715-31-0 | |
| 83 5110929 | 9 | 98949-03-2 | |
| 84 5146893 | 9 | 300814-71-5 | |

TABLE 8-continued

| Compound | Scaffold | CAS | Comments |
|---|---|---|---|
| 85 5267979 | 9 | 307524-21-6 | |
| 86 5380107 | 9 | 357158-43-1 | |
| 87 5115737 | 9 | 351371-62-5 | |
| 88 5142456 | 10 | 301158-88-3 | |
| 89 5169036 | 10 | No CAS | |
| 90 5307702 | 10 | 414906-88-0 | |
| 91 5316908 | 10 | 67200-34-4 | WO0179209 A2 |
| 92 5351854 | 10 | 348145-43-7 | |
| 93 5404828 | 10 | 415944-37-5 | |
| 94 5378458 | 10 | 352561-69-4 | |
| 95 5401254 | 10 | 325725-45-9 | |
| 96 5151566 | 11 | 26004-25-1 | |
| 97 5153032 | 11 | 329912-85-8 | |
| 98 5160537 | 11 | 351371-62-5 | |
| 99 5228599 | 11 | 307329-31-3 | |
| 100 5252899 | 11 | 2352-76-3 | |
| 101 5323289 | 11 | 15394-91-9 | |
| 102 5326012 | 11 | 415689-69-9 | |
| 103 5344607 | 11 | 154184-27-7 | |
| 104 5379259 | 11 | 329210-82-4 | |
| 105 5322680 | 12 | 340993-28-4 | |
| 106 5452512 | 12 | 415960-38-2 | |
| 107 5452547 | 12 | 415960-45-1 | |
| 108 5377805 | 3 | No CAS | |
| 109 5376309 | 3 | 498559-85-6 | |
| 110 5365318 | 3 | No CAS | |
| 111 5357074 | 6 | No CAS | |
| 112 5350183 | 6 | 415713-92-7 | |
| 113 5220786 | 13 | 413594-35-1 | |
| 114 5161260 | 10 | 84122-32-7 | |
| 115 5143716 | 4 | No CAS | |

Experimental Protocols:

1. HTS Screening Assay Procedure
   Microplates 10109D to 10114D compounds at 1 mM. (Controls in column 1).
   All compounds were perchase from ChemBridge corporation: ChemBridge corporation 16981 Via Tazon, Suite G San Diego, Calif. 92127 a. Microplates Labeling
      Put labels to 6 PS U-bottom clear microplate.
      Put labels to 18 black microplates (triplicats).

b. Microplates Preparation
      Put 100 μl GST-POSH at 33 nM in wells of the clear PS U-bottom microplates (exept wells A1-D1).
      Negative control: place 100 μl dH$_2$O in wells A1-D1.
      (Positive control: place 100 μl GST-POSH at 33 nM in wells E1-H1).
      Put 8 μl enzymes solution ×4 to black microplates (column 1 to 11).

c. Incubation of E3 with Compounds
      Transfer 5 μl of compounds (at 1 mM) to the microplates containing 100 μl GST-POSH.
      Add 5 μl of DMSO to controls column 1.
      Incubation 30 minutes at RT.

d. Enzymatic (Ubiquitination) and Final Steps
      Distribution of (triplicate) 3×23 μl incubated compounds into 3 black microplates containing enzymatic solution (on splitting apparatus).
      Incubation 30 minutes at 37° C.
      Addition of 8 μl EDTA 0.5 M.
      Incubation 15 (at least) minutes at RT.
      Addition of 30 μl GST XL 665 in reconstitution buffer.
      Incubation 45 (at least) minutes at RT.
      Reading fluorescence.
      Record results in computer.
      Put sealing foil back on original and diluted microplates and keep at −70° C.
      Always the plates must be closed with lids during each step.

2. IC 50Assay Procedure:
   Microplate 301, 302 (redo) containing 50 μl compounds at 91 μM.
   Procedure from column 2 to 12.

e. Microplates Labeling
      Put labels to 4 clear PP clear microplate (18.2 μM, 9.1 uM, 1.82 uM, 910 nM,).
      Put labels to 5 clear PS U-bottom clear microplate 4.44 μM, 909, 444, 91 and 44 nM)
      Put labels to 15 black microplates (triplicates).

f. Original Microplate Dilutions
      Put DMSO 40 μl to (18.2 μM, 1.82 uM plates) and 20 ul to (9.1 uM, 910 nM plates.
      Mix by pipetation the original microplate (3× up and down 45 μl).
      Transfer 10 μl of compounds from the original microplate (at 91 μM) to the next microplate (=18.2 μM) on splitting apparatus.
      Mix by pipetation the 18.2 uM microplate (3× up and down 45 μl).
      Transfer 20 μl of compounds from the 18.2 uM microplate to the next microplate (=9.1 μM) on splitting apparatus.
      Mix by pipetation the 9.1 uM microplate (3× up and down 45 μl).
      Transfer 10 μl of compounds from the 9.1 uM microplate to the next microplate (=1.82 μM) on splitting apparatus.
      Mix by pipetation the 1.82 uM microplate (3× up and down 45 μl).
      Transfer 20 μl of compounds from the 1.82 uM microplate to the next microplate (=910 nM) on splitting apparatus
      Mix by pipetation.

g. Microplates Preparation
      Put 123 μl GST-POSH at 33 nM in wells of the 5 clear PS U-bottom clear microplates.
      Positive control: place 123 μl GST-POSH at 33 nM in well A12-h12 13 μl DMSO.

Negative control: place 123 µl dH$_2$O in well B1 and 13 µl DMSO.

Put 8 µl enzymes solution ×4 to 15 black microplates.

Controls: put 8 µl enzymes solution ×4 to wells A1 to F1.

h. Incubation of POSH with Compounds

Take 7 µl of compounds at original plate (91 µM) and put into the 4.44 µM labeled microplate containing 123 µl GST-POSH, on splitting apparatus.

Mix by pipetation (3× up and down 115 µl), note time.

Take 7 µl of compounds at 18.2 µM and put into the 910 nM labeled microplate containing 123 µl GST-POSH, on splitting apparatus.

Mix by pipetation (3× up and down 115 µl), note time.

Take 7 µl of compounds at 9.1 µM and put into the 444 nM labeled microplate containing 123 µl GST-POSH, on splitting apparatus.

Mix by pipetation (3× up and down 115 µl), note time.

Take 7 µl of compounds at 1.82 nM and put into the 91 nM labeled microplate containing 123 µl GST-POSH, on splitting apparatus.

Mix by pipetation (3× up and down 115 µl), note time.

Take 7 µl of compounds at 91.0 nM and put into the 44 nM labeled microplate containing 123 µl GST-POSH, on splitting apparatus.

Mix by pipetation (3× up and down 115 µl), note time.

Incubation 30 minutes at RT.

i. Enzymatic (Ubiquitination Step)

Distribution of (triplicate) 3×23 µl incubated compounds into 3 black microplates containing enzymatic solution (on splitting apparatus).

Controls: same distribution from A1 to A-C1 and from B1 to D-F1.

Incubation 30 minutes at 37° C.

Addition of 8 µl EDTA 0.5 M.

Incubation 15 (at least) minutes at RT.

Addition of 30 µl GST XL 665 in reconstitution buffer.

Incubation 45 (at least) minutes at RT.

Reading fluorescence.

Record results in computer.

Put sealing foil back on original and diluted microplates and keep at −70° C.

Always the plates must be closed with lids during each step.

Solutions Preparation for Assay 1 and 2

GST-POSH, 33 nM

| Thawing cycles | Material | Lot | Stock conc. | Final conc. | Amount for 140 ml |
|---|---|---|---|---|---|
| | GST-POSH | NB81/p.118 | 3.6 mg/ml | 1.65 mg/L | 64.2 µl |
| | DDW | — | — | — | 140 ml |

Enzymes solution ×4.

| Thawing cycles | Material | Lot | Stock conc. | Final conc. | Amount for 264 ml |
|---|---|---|---|---|---|
| Sigma | Tris pH = 7.2 | T2069, 61K8942 | 1 M | 80 mM | 21.12 ml |
| | ATP | 8.4.03 | 0.1 M | 4 mM | 10.56 ml |
| Sigma | MgCl$_2$ | M1028, 61K8927 | 1 M | 10 mM | 2.640 ml |
| | DTT | 30.3.03 | 1 M | 2 mM | 0.528 ml |
| | Ovalbumin | 8.4.03 | 10% | 0.2% | 5.280 ml |
| | E1 | 26.3.03 | 0.38 mg/ml | 1.76 mg/mL | 1.223 ml |
| | E2 | Vivian 3.4.03 | 0.08 mg/ml | 4.32 mg/L | 14.26 ml |
| | Ubiquitin | 17.2.03 | 1 mg/ml | 0.6 mg/L | 0.158 ml |
| France | Ub-K CisBio | 61UBIKAA, lot 03 | 0.025 mg/ml | 0.125 mg/L | 1.320 ml |
| | ddH$_2$O | — | — | — | 206.9 ml |

GST XL 665 in Rec. buffer

| Thawing cycles | Material | Cat | Lot | Stock conc. | Final conc. | Amount for 1000 ml |
|---|---|---|---|---|---|---|
| France | GST XL 665 | Cis Bio, 61GSTXLD | 15 | 1 mg/ml | 7.5 mg/L | 7.50 ml |
| | Rec. buffer | — | 10.3.03 | — | — | 993 ml |

EDTA 0.5 M pH=8

| | Material | Lot | Stock conc. | Final conc. | Amount for 1000 ml |
|---|---|---|---|---|---|
| Sigma | EDTA, E5134 | 91K0133 | 372.2 g/mol | 0.5 M | 186.1 gr |
| | NaOH | — | 10 N | to pH = 8 | 65 ml |
| | ddH$_2$O | — | — | — | to 1000 ml |

Reconstitution buffer

| Material | Cat | Lot | Stock conc. | Final conc. | Amount for 2 L |
|---|---|---|---|---|---|
| $Na_2HPO_4.12H_2O$ | 6579 | Merck | 358.1 g/mol | 31.2 mM | 22.3 g |
| $KH_2PO_4$ | P-0662 | Sigma | 136.1 g/mol | 18.7 mM | 5.09 g |
| KF, Riedel | 1133 | | 58.1 g/mol | 0.8 M | 93.0 g |
| Ovalbumine | | | (100%) | 0.1% | 2.00 g |

Check pH=7

Sigma DMSO D-8418

Titrated ATP 0.1 M

| | Material | Lot | Stock conc. | Final conc. | Amount for 34 ml |
|---|---|---|---|---|---|
| Sigma | ATP, A8937 | 101K70005 | 583.4 g/mol | 0.1 M | 1.98 gr |
| | NaOH | — | 10 N | To neutrality | 0.60 ml |
| | $ddH_2O$ | — | — | — | to 34 ml |

Checked with pH stick paper.

DTT 1 M

| | Material | Lot | Stock conc. | Final conc. | Amount for 5 ml |
|---|---|---|---|---|---|
| Sigma | DTT, D-5545 | | 154.3 g/mol | 1 M | 772 mg |
| | $ddH_2O$ | — | — | — | to 5 ml |

Ovalbumin 10%

| | Material | Lot | Stock conc. | Final conc. | Amount for 5 ml |
|---|---|---|---|---|---|
| Sigma | Ovalbumine, A-5503 | | 100% | 10% | 500 mg |
| | $ddH_2O$ | — | — | — | to 5 ml |

Ubiquitin 1 mg/ml

| | Material | Lot | Stock conc. | Final conc. | Amount for 300 μl |
|---|---|---|---|---|---|
| Sigma | Ubiquitin, U6253 | 052K7455 | — | 1 mg/ml | 300 μg |
| | $ddH_2O$ | | | | 300 μl |

Results:

The following table presents the IC50 for each compound with respect to the ubiquitin ligase activity of POSH.

TABLE 9

IC 50 results:

| Compound ID | Scaffold | $IC_{50}$ |
|---|---|---|
| 1 | 1 | 200 nM |
| 2 | 1 | 700 nM |
| 3 | 1 | 900 nM |
| 4 | 1 | 800 nM |
| 5 | 1 | 300 nM |
| 6 | 1 | 800 nM |
| 7 | 1 | 1 μM |
| 8 | 1 | 500 nM |
| 9 | 1 | 10 μM |
| 10 | 1 | 1 μM |
| 11 | 1 | 10 μM |
| 12 | 1 | 1 μM |
| 13 | 1 | 1 μM |
| 15 | 1 | 500 nM |
| 16 | 1 | 1 μM |
| 17 | 1 | 700 nM |
| 18 | 2 | 700 nM |
| 19 | 2 | 700 nM |
| 20 | 2 | 900 nM |
| 21 | 2 | 800 nM |
| 22 | 2 | 900 nM |
| 23 | 2 | 200 nM |
| 24 | 3 | 1 μM |
| 26 | 3 | 3 μM |
| 27 | 3 | 700 nM |
| 28 | 3 | 700 nM |
| 29 | 3 | 700 nM |
| 30 | 3 | 2 μM |
| 31 | 3 | 900 nM |
| 32 | 3 | 500 nM |
| 34 | 3 | 1 μM |
| 35 | 4 | 500 nM |
| 36 | 4 | 1 μM |
| 37 | 4 | 1 μM |
| 38 | 4 | 400 nM |
| 39 | 4 | 1 μM |
| 40 | 4 | 1 μM |
| 41 | 5 | 1 μM |
| 42 | 5 | 5 μM |
| 44 | 5 | 650 nM |
| 48 | 5 | 1.3 μM |
| 49 | 5 | 1 μM |
| 50 | 5 | 100 nM |
| 51 | 5 | 700 nM |
| 52 | 5 | 1.3 μM |
| 53 | 6 | 500 nM |
| 54 | 6 | 500 nM |
| 55 | 6 | 500 nM |
| 56 | 6 | 300 nM |
| 57 | 6 | 300 nM |
| 58 | 6 | 800 nM |
| 59 | 6 | 500 nM |
| 60 | 6 | 1 μM |
| 61 | 6 | 700 nM |
| 62 | 6 | 700 nM |
| 63 | 6 | 600 nM |
| 64 | 6 | 900 nM |
| 65 | 6 | 1 μM |
| 66 | 6 | 900 nM |
| 67 | 6 | 1 μM |
| 68 | 6 | 1 μM |
| 69 | 6 | 700 nM |
| 70 | 6 | 600 nM |
| 71 | 6 | 800 nM |
| 72 | 6 | 800 nM |
| 73 | 6 | 1.5 μM |
| 74 | 6 | 1 μM |
| 75 | 7 | 400 nM |
| 76 | 7 | 400 nM |
| 78 | 7 | 900 nM |
| 79 | 8 | 900 nM |
| 80 | 8 | 500 nM |
| 81 | 8 | 100 nM |
| 82 | 8 | 300 nM |

TABLE 9-continued

IC 50 results:

| Compound ID | Scaffold | IC$_{50}$ |
|---|---|---|
| 83 | 9 | 1 μM |
| 84 | 9 | 300 nM |
| 85 | 9 | 700 nM |
| 86 | 9 | 1 μM |
| 87 | 9 | 800 nM |
| 88 | 10 | 250 nM |
| 89 | 10 | 1 μM |
| 90 | 10 | 700 nM |
| 91 | 10 | 300 nM |
| 92 | 10 | 500 nM |
| 93 | 10 | 1.3 μM |
| 94 | 10 | 1 μM |
| 95 | 10 | 1 μM |
| 96 | 11 | 500 nM |
| 97 | 11 | 600 nM |
| 99 | 11 | 1.5 μM |
| 100 | 11 | 700 nM |
| 102 | 11 | 800 nM |
| 103 | 11 | 400 nM |
| 104 | 11 | 1 μM |
| 105 | 12 | 800 nM |
| 106 | 12 | 900 nM |
| 107 | 12 | 1 μM |
| 108 | 3 | 900 nM |
| 109 | 3 | 500 nM |
| 110 | 3 | 600 nM |
| 111 | 6 | 1 μM |
| 112 | 6 | 700 nM |
| 113 | 13 | 400 nM |
| 114 | 10 | 300 nM |
| 115 | 4 | 600 nM |

TABLE 10

Selectivity results:
The following table presents the effects of each compound on the ubiquitin ligase activities of POSH, Hmdm2, c-cbl and an E2 protein.

| | | Selectivity (% A* in 1 μM) | | | |
|---|---|---|---|---|---|
| Compound | Scaffold | POSH | Hmdm2 | c-cbl | E2 |
| 1 | 1 | 19 | 105 | 120 | 100 |
| 2 | 1 | 50 | 108 | 90 | 60 |
| 3 | 1 | 47 | 102 | 82 | 52 |
| 4 | 1 | 48 | 105 | 85 | 63 |
| 5 | 1 | 13 | 61 | 84 | 74 |
| 6 | 1 | 14 | 129 | 116 | 60 |
| 7 | 1 | 108 | 101 | 88 | 84 |
| 8 | 1 | 9 | 78 | 97 | 87 |
| 9 | 1 | 91 | 103 | 88 | 79 |
| 10 | 1 | 15 | 116 | 97 | 93 |
| 11 | 1 | 21 | 95 | 95 | 79 |
| 12 | 1 | 54 | 99 | 102 | 90 |
| 13 | 1 | 7 | 11 | 75 | 54 |
| 15 | 1 | 14 | 90 | 106 | 64 |
| 16 | 1 | 51 | 86 | 166 | 109 |
| 17 | 1 | 71 | 106 | 132 | 107 |
| 18 | 2 | 24 | 101 | 105 | 75 |
| 19 | 2 | 39 | 100 | 107 | 78 |
| 20 | 2 | 33 | 132 | 112 | 83 |
| 21 | 2 | 83 | 80 | 91 | 75 |
| 22 | 2 | 26 | 102 | 64 | 91 |
| 23 | 2 | 9 | 107 | 102 | 112 |
| 24 | 3 | 7 | 69 | 90 | 87 |
| 26 | 3 | 69 | 98 | 85 | 61 |
| 27 | 3 | 6 | 122 | 122 | 112 |
| 28 | 3 | 26 | 90 | 111 | 105 |
| 29 | 3 | 42 | 104 | 159 | 50 |
| 31 | 3 | 105 | 102 | 108 | 104 |

TABLE 10-continued

Selectivity results:
The following table presents the effects of each compound on the ubiquitin ligase activities of POSH, Hmdm2, c-cbl and an E2 protein.

| | | Selectivity (% A* in 1 μM) | | | |
|---|---|---|---|---|---|
| Compound | Scaffold | POSH | Hmdm2 | c-cbl | E2 |
| 32 | 3 | 66 | 141 | 122 | 96 |
| 34 | 3 | 23 | 123 | 135 | 93 |
| 35 | 4 | 44 | 101 | 106 | 118 |
| 36 | 4 | 6 | 71 | 86 | 82 |
| 37 | 4 | 41 | 107 | 93 | 97 |
| 38 | 4 | 17 | 111 | 432 | 89 |
| 39 | 4 | 29 | 108 | 132 | 98 |
| 40 | 4 | 24 | 159 | 95 | 117 |
| 41 | 5 | 17 | 106 | 141 | 82 |
| 42 | 5 | 138 | 111 | 314 | 57 |
| 49 | 5 | 77 | 115 | 127 | 43 |
| 50 | 5 | 39 | 98 | 155 | 103 |
| 51 | 5 | 51 | 80 | 104 | 113 |
| 52 | 5 | 80 | 107 | 124 | 63 |
| 53 | 6 | 12 | 125 | 134 | 99 |
| 54 | 6 | 30 | 124 | 135 | 44 |
| 55 | 6 | 40 | 58 | 70 | 31 |
| 56 | 6 | 27 | 73 | 277 | 88 |
| 57 | 6 | 20 | 80 | 153 | 259 |
| 58 | 6 | 40 | 102 | 115 | 108 |
| 59 | 6 | 26 | 112 | 115 | 90 |
| 60 | 6 | 22 | 90 | 110 | 53 |
| 61 | 6 | 35 | 131 | 133 | 52 |
| 62 | 6 | 37 | 120 | 134 | 94 |
| 63 | 6 | 30 | 102 | 95 | 109 |
| 64 | 6 | 63 | 115 | 118 | 117 |
| 65 | 6 | 8 | 98 | 101 | 65 |
| 66 | 6 | 53 | 120 | 107 | 117 |
| 67 | 6 | 103 | 104 | 92 | 98 |
| 68 | 6 | 72 | 110 | 91 | 57 |
| 70 | 6 | 151 | 125 | 127 | 98 |
| 71 | 6 | 9 | 78 | 84 | 86 |
| 72 | 6 | 39 | 124 | 95 | 77 |
| 73 | 6 | 16 | 96 | 90 | 64 |
| 74 | 6 | 17 | 107 | 110 | 96 |
| 75 | 7 | 103 | 113 | 110 | 77 |
| 76 | 7 | 35 | 110 | 96 | 53 |
| 78 | 7 | 22 | 93 | 151 | 43 |
| 79 | 8 | 120 | 94 | 89 | 55 |
| 80 | 8 | 50 | 95 | 100 | 61 |
| 81 | 8 | 3 | 73 | 66 | 80 |
| 82 | 8 | 60 | 120 | 77 | 47 |
| 84 | 9 | 67 | 102 | 97 | 54 |
| 85 | 9 | 26 | 94 | 88 | 55 |
| 86 | 9 | 29 | 108 | 132 | 98 |
| 87 | 9 | 33 | 119 | 63 | 80 |
| 88 | 10 | 172 | 118 | 112 | 94 |
| 89 | 10 | 45 | 79 | 109 | 70 |
| 90 | 10 | 9 | 119 | 109 | 98 |
| 91 | 10 | 11 | 62 | 151 | 80 |
| 92 | 10 | 21 | 105 | 111 | 125 |
| 93 | 10 | 21 | 106 | 84 | 78 |
| 94 | 10 | 71 | 103 | 106 | 49 |
| 95 | 10 | 12 | 98 | 136 | 100 |
| 96 | 11 | 105 | 90 | 363 | 73 |
| 97 | 11 | 13 | 123 | 148 | 89 |
| 99 | 11 | 36 | 101 | 88 | 89 |
| 100 | 11 | 99 | 75 | 100 | 59 |
| 102 | 11 | 52 | 97 | 111 | 99 |
| 103 | 11 | 102 | 100 | 89 | 92 |
| 104 | 11 | 111 | 145 | 140 | 113 |
| 105 | 12 | 28 | 102 | 117 | 93 |
| 106 | 12 | 27 | 80 | 112 | 88 |
| 107 | 12 | 68 | 113 | 101 | 384 |
| 108 | 3 | 42 | 108 | 135 | 104 |
| 109 | 3 | 67 | 106 | 122 | 113 |
| 110 | 3 | 94 | 51 | 107 | 56 |
| 111 | 6 | 17 | 72 | 98 | 49 |
| 112 | 6 | 27 | 113 | 117 | 84 |
| 113 | 13 | 74 | 101 | 93 | 66 |

TABLE 10-continued

Selectivity results:
The following table presents the effects of each compound on the ubiquitin ligase activities of POSH, Hmdm2, c-cbl and an E2 protein.

| Compound | Scaffold | Selectivity (% A* in 1 μM) | | | |
|---|---|---|---|---|---|
| | | POSH | Hmdm2 | c-cbl | E2 |
| 114 | 10 | 31 | 85 | 96 | 95 |
| 115 | 4 | 8 | 108 | 98 | 87 |

$$\% A = \frac{<sample> - <control>}{<control>}$$

control- is related to 100% activity
The assay was conducted following HTS protocol.

2. Budding Results:
The following table shows the effects of each compound on HIV maturation (assessed as budding) in a VLP assay.

TABLE 11

| Compound | Scaffold | Budding (3 μM) |
|---|---|---|
| 1 | 1 | 46% |
| 2 | 1 | 66% |
| 8 | 1 | 67% |
| 15 | 1 | 52% |
| 18 | 2 | 41% |
| 19 | 2 | 52% |
| 20 | 2 | 60% |
| 27 | 3 | 48% |
| 28 | 3 | 54% |
| 29 | 3 | 63% |
| 32 | 3 | 67% |
| 35 | 4 | 56% |
| 38 | 4 | 38% |
| 42 | 5 | 51% |
| 48 | 5 | 58% |
| 53 | 6 | 64% |
| 54 | 6 | 54% |
| 55 | 6 | 55% |
| 56 | 6 | 59% |
| 57 | 6 | 61% |
| 59 | 6 | 61% |
| 69 | 6 | 41% |
| 70 | 6 | 57% |
| 75 | 7 | 39% |
| 76 | 7 | 48% |
| 80 | 8 | 55% |
| 81 | 8 | 63% |
| 84 | 9 | 47% |
| 85 | 9 | 59% |
| 87 | 9 | 29% |
| 88 | 10 | 57% |
| 90 | 10 | 67% |
| 91 | 10 | 33% |
| 96 | 11 | 56% |
| 97 | 11 | 64% |
| 103 | 11 | 69% |
| 109 | 3 | 60% |
| 110 | 3 | 36% |
| 114 | 10 | 46% |
| 115 | 4 | 48% |

2. In-Vitro Assay of Human Posh Self-Ubiquitination

Recombinant hPOSH was incubated with ATP in the presence of E1, E2 and ubiquitin as indicated in each lane. Following incubation at 37° C. for 30 minutes, reactions were terminated by addition of SDS-PAGE sample buffer. The samples were subsequently resolved on a 10% polyacrylamide gel. The separated samples were then transferred to nitrocellulose and subjected to immunoblot analysis with an anti ubiquitin polyclonal antibody. The position of migration of molecular weight markers is indicated on the right.

Poly-Ub: Ub-hPOSH conjugates, detected as high molecular weight adducts only in reactions containing E1, E2 and ubiquitin. hPOSH-176 and hPOSH-178 are a short and a longer derivatives (respectively) of bacterially expressed hPOSH; C, control E3 preliminary steps in high-throughput screen

Objective

1. Test Ub detection with in a Ub chain as function of an E3 (HRD1) and POSH auto-Ubiquitination.

2. Test Boston Biochem reagents.

Materials

1. E1 recombinant from bacculovirus

2. E2 Ubch5c from bacteria

3. Ubiquitin

4. POSH #178 (1-361) gst fusion-purified but degraded

5. POSH # 176 (1-269) gst fusion-purified but degraded 6. hsHRD1 soluble ring containing region 5. Bufferx12 (Tris 7.6 40 mM, DTT 1 mM, MgCl$_2$ 5 mM, ATP 2 uM)

6. Dilution buffer (Tris 7.6 40 mM, DTT 1 mM, ovalbumin 1 ug/ul) protocol

| | 0.1 ug/ul E1 | 0.5 ug/ul E2 | 5 ug/ul Ub | 0.4 ug/ul 176 | 2.5 ug/ul 178 | 0.8 ug/ul Hrd1 | Bx12 |
|---|---|---|---|---|---|---|---|
| −E1 (E2 + 176) | — | 0.5 | 0.5 | 1 | — | — | 10 |
| −E2 (E1 + 176) | 1 | — | 0.5 | 1 | — | — | 9.5 |
| −ub (E1 + E2 + 176) | 1 | 0.5 | — | 1 | — | — | 9.5 |
| E1 + E2 + 176 + Ub | 1 | 0.5 | 0.5 | 1 | — | — | 9 |
| −E1 (E2 + 178) | — | 0.5 | 0.5 | — | 1 | — | 10 |
| −E2 (E1 + 178) | 1 | — | 0.5 | — | 1 | — | 9.5 |
| −ub (E1 + E2 + 178) | 1 | 0.5 | — | — | 1 | — | 9.5 |
| E1 + E2 + 178 + Ub | 1 | 0.5 | 0.5 | — | 1 | —1 | 9 |
| Hrd1, E1 + E2 + Ub | 1 | 0.5 | 0.5 | — | — | 1 | 8.5* |

1. Incubate for 30 minutes at 37° C.
2. Run 12% SDS PAGE gel and transfer to nitrocellulose membrane
3. Incubate with anti-Ubiquitin antibody.

Results, shown in FIG. 16, demonstrate that human POSH has ubiquitin ligase activity.

3. Cbl-b affects VLP Production

Pulse-Chase Kinetics

A. Transfections
1. One day before transfection plate cells at a concentration of $5*10^6$ cell/plate in four 15 cm plates.
2. Two hours before transfection, replace cell media to 16 ml complete DMEM without antibiotics.
3. siRNA dilution: for each transfection dilute 100 µl siRNA in 2 ml OptiMEM (2 plates with scrambled siRNA (187) and 2 plates with Cbl-b siRNA (275).
4. LF 2000 dilution: for each transfection dilute 50 µl lipofectamine reagent in 2 ml OptiMEM.
5. Incubate diluted siRNA and LF 2000 for 5 minutes at RT.
6. Mix the diluted siRNA with diluted LF2000 and incubated for 25 minutes at RT.
7. Add the mixture to the cells (drop wise) and incubate for 24 hours at 37° C. in $CO_2$ incubator.
8. Next day, perform HIV trasfection (pNLenv-1 #111), 11 µg/plate with the appropriate siRNA at a concentration of 100 nM.

| Plate | Day 2 SiRNA 100 µl/plate | Day 3 Exchange medium | Day 4 SiRNA as in day 2 + 11 µg #111/plate |
|---|---|---|---|
| 1 | 187 | | 187 + 111 |
| 2 | 187 | | 187 + 111 |
| 3 | 275 | | 275 + 111 |
| 4 | 275 | | 275 + 111 |

B. Pulse-Chase
1. Discard medium and wash with PBS. Scrape cells in 12 ml PBS. Wash plate again with 10 ml PBS. Transfer gently cells into 50 ml conical tube. Centrifuge to pellet cells at 1800 rpm for 5-10 minutes at RT.
2. Remove supernatant and resuspend cells in 20 ml of starvation medium. Incubate in the incubator for 1 hour. Invert the tube every 15 minutes. Take 1 plate for checking Cbl-b expression by IP/IB, (30% and 70% respectively) pellet cells and freeze (protocol at section D). Count cells during incubation!

Starvation Medium
RPMI without methionine and no FCS.
5 mM HEPES pH 7.5
Glutamine (1:100)
Pen/Strep (1:100)

3. At the end of incubation pellet cells at 1800 rpm for 5-10 minutes at RT (as in step 1), remove supernatant and resuspend cells gently in 120 µl starvation medium (~1.5 $10^7$ cells in 150 µl RPIM without Met). Transfer cells to an eppendorf tube with an O-ring caps and place in the thermo mixer. If necessary add another 50 µl to splash the rest of the cells out (all specimens should have the same volume of labeling reaction!). First break cell pellet by gentle tapping and vortex and then use cut tips!
4. Pulse: Add 50 µl of $^{35}$S-methionine (specific activity 14.2 µCi/µl), tightly cap tubes and place in thermo mixer. Set the mixing speed to the lowest possible (700-750 rpm), 37° C. and incubate for 25 minutes.
5. Stop the pulse by adding 1 ml ice-cold chase/stop medium. Shake tube very gently three times and pellet cells at 14,000 rpm for 6 sec. Remove supernatant by tip to a 50 ml tube (high radioactivity). Add gently 0.9 ml ice-cold chase/stop medium to the pelleted cells and invert gently. Transfer 200 µl sample (time 0) to a tube containing 1 ml ice-cold stop/chase medium (marked as cell). Place the rest of the samples in the thermomixer and start chase incubation. Pellet the cells immediately (14,000 rpm, 1 min) and transfer sup to a fresh tube (marked as VLP) and freeze the cell pellet at 80° C. Spin the sup (VLPs) for 2 hours, 14,000 at 4° C. and in the end remove the sup carefully by vacuum (leave ~20 µl).
6. Chase: the chase is done at 0, 1, 3 and 6 hours as described in step 5 for the first chase time (time 0).

Chase/Stop Medium
Complete RPMI
10% FCS
10 mM cold methionine
5 mM HEPES pH7.5
Glutamine (1:100)
Pen/Strep \(1:100)
Prepare 50 ml aliquots and freeze at −20° C.
Prior to use, thaw, shake intensively and place on ice.

C. IP with anti-p24
1. Wash protein G beads (calculated below—for preclearing and conjugation of Ab) 3 times with lysis buffer (1 ml). Put the beads for preclearing at 4° C. Centrifuge at 8000 rpm, 1 minute.
2. Conjugate anti-p24 rabbit antibody with protein G beads. Anti-p24 protein G beads conjugation (for 20 samples): Use 40 µl ProG beads (Sigma) and 6 µl anti-p24r (Seramon) per sample.
   a. Add to an ependorff tube: prewashed ProG beads, p24-rabbit antibody and lysis buffer.
   b. Incubate in thermomixer at 25° C. for 2 hours, 1400 rpm.
   c. Wash three times with lysis buffer and resuspend to initial volume of lysis buffer (conjugated beads can be kept up to a week at 4° C.). Centrifuge at 8000 rpm, 1 minute.
3. Lyse cell/VLP pellet by adding 500 µl of lysis buffer (listed below), resuspend well (cells by pipettation and VLP by 10 sec vortex) and incubate on ice for 20 minutes. Spin at 14,000 rpm, at 4° C. for 15 minutes. Remove supernatant to a fresh tube (already contains protein G beads as described in the next step).

Lysis Buffer
50 mM Tris-HCl pH 7.6
1.5 mM $MgCl_2$
150 mM NaCl
10% Glycerol
0.5% NP40
0.5% DOC
1 mM EDTA
1 mM EGTA
Prior to use add 1:200 $PI_3C$.

4. Pre-clear by addition of 10 µl protein G beads (prewashed three times with lysis buffer). Incubate at 4° C. for 1 hour at the orbital shaker. It's possible to freeze the samples after preclearing.
5. Spin samples 1 min at 14000 rpm and transfer supernatant to a fresh tube.
6. Add to all samples 40 µl of anti-p24-protein G conjugated beads and incubate in the orbital shaker for 4 hours at 4° C.
7. At the end of incubation, transfer sup+ beads to fresh tubes, spin down beads and wash twice with 1 ml high salt buffer, once with medium salt buffer and twice with low salt buffer (listed below).

| High salt buffer | Medium salt buffer | Low salt buffer |
| --- | --- | --- |
| 50 mM Tris-HCl, pH 8.0 | 50 mM Tris-HCl, pH 8.0 | 50 mM Tris-HCl, pH 8.0 |
| 500 mM NaCl | 150 mM NaCl | — |
| 0.1% SDS | 0.1% SDS | — |
| 0.1% Triton X-100 | 0.1% Triton X-100 | 0.1% Triton X-100 |
| 5 mM EGTA | — | — |
| 5 mM EDTA | 5 mM EDTA | 5 mM EDTA |

12. Add to each tube 30 μl 2×SDS sample buffer. Heat to 70° C. for 10 minutes.
13. Separate all samples on 1 mm, 12.5% SDS-PAGE. 40 mA/gel
14. Fix gel in 25% ethanol and 10% acetic acid for 15 minutes (minimum).
15. Pour off the fixation solution and soak gels in water until they reach their original size (~20 min).
16. Dry gels on warm plate (80° C.) under vacuum for 2-4 hours.
17. Expose gels to screen for at least 4 hours and scan by typhoon.

Results are presented in FIG. 25A.

D. Check Cbl-b Levels by IP/IB.
1. Resuspend cell pellets from step B2 in 0.5 ml lysis buffer (described in C-7)
2. Incubate on ice for 10 min.
3. Spin in 4° C. for 15 min at 14,000 rpm and transfer the sup into clean tubes.
4. Perform IP Cbl-b:—
   a. Add 4 μg (20 μl) of anti Cbl-b.
   b. Incubate by rotation, in cold, 2.5 hours.
   c. Wash 160 μl of recombinant anti mouse beads three times with 1 ml cold lysis buffer.
   d. Resuspend beads in 160 μl of lysis buffer and add 20 μl (10 μl sepharose) to each IP reaction (mix well between samples and use cut tips).
   e. Rotate IP tubes another 45 minutes.
   f. Pellet in cold centrifuge (30 seconds is sufficient) and wash IP beads 3 times with 1 ml cold HNTG buffer, removing as much as possible between washes.
   g. Add 25 μl 2× Sample buffer, boil 5 minutes, and store −20° C.
   h. Thaw and boil samples additional 3 minute before loading on gel.
   i. Separate on 7.5% gel.
   j. Western Blot: 1 hour blocking TBS-T+skim milk 10%.
   k. 1 hour 1$^{st}$ Ab 1:100, in block solution overnight.
   l. Wash X3, ~7 minutes each wash in TBS-T.
   m. Anti-IgG mouse 1:10,000 in TBS-T-1 hour, RT.
   n. Wash X3, ~7 minutes each wash in TBS-T and perform ECL.

Results are presented in FIG. 17A.

4. Cbl-b Affects the Release of VLP at Steady State
1. Day 1: plate two 6-wells plates with HeLa-SS6 cells at 4×10$^5$ cells/well (50% confluence on the next day).
2. Day 2: transfect as indicate in the table. (0.25 ml OptiMEM+5 μl Lipofectamine2000)+0.25 ml OptiMEM+DNA as indicated in the table).

Plasmid no. 111: pNlenv-1.
Transfections:—

| | Day 2 Transfection with 100 nM siRNA | Day 3 Transfection with 100 nM siRNA + 0.75 ug #111 |
| --- | --- | --- |
| A1 | 187 (Control) | 187 (Control) + 0.75 ug #111 |
| A2 | 275 (Cbl-b) | 275 (Cbl-b) + 0.75 ug #111 |

Steady state VLP Assay

A. Cell Extracts
1. Collect 2 ml medium and pellet floating cells by centrifugation (1 min, 14000 rpm at 4° C.), save sup (continue with sup immediately to step B), scrape cells in ice-cold PBS, add to the corresponding floated cell pellet and centrifuge for 5 min 1800 rpm at 4° C.
2. Wash cell pellet once with ice-cold PBS.
3. Resuspend cell pellet (from 6 well) in 100 μl NP40-DOC lysis buffer and incubate 10 minutes on ice.
4. Centrifuge at 14,000 rpm for 15 min. Transfer supernatant to a clean eppendorf.
5. Prepare samples for SDS-PAGE by adding them sample buffer and boil for 10 min—take the same volume for each reaction (15 μl).

B. Purification of VLP from Cell Media
1. Filtrate the supernatant through a 0.45 μl filter.
2. Centrifuge supernatant at 14,000 rpm at 4° C. for at least 2 h.
3. Resuspend VLP pellet of A1-A7 in 50 1× sample buffer and boil for 10 min. Load 25 μl of each sample.

C. Western Blot Analysis
1. Run all samples from stages A and B on Tris-Gly SDS-PAGE 12.5%.
2. Transfer samples to nitrocellulose membrane (100V for 1.15 h.).
3. Dye membrane with ponceau solution.
4. Block with 10% low fat milk in TBS-t for 1 h.
5. Incubate with anti p24 rabbit 1:500 in TBS-t 2 hour (room temperature)-o/n (4° C.).
6. Wash 3 times with TBS-t for 7 min each wash.
7. Incubate with secondary antibody anti rabbit cy5 1:500 for 30 min.
8. Wash five times for 10 min in TBS-t.
9. View in Typhoon for fluorescence signal (650).

Results are Presented in FIG. 17B

Examples of Cbl-b sequences are presented below.

```
Human CBL-B mRNA sequence -
var1 (public gi: 4757919) (SEQ ID NO: 37)
CTGGGTCCTGTGTGTGCCACAGGGGTGGGGTGTCCAGCGAGCGGTCTCCT
CCTCCTGCTAGTGCTGCTGCGGCGTCCCGCGGCCTCCCCGAGTCGGGCGG
GAGGGGAGAGCGGGTGTGGATTTGTCTTGACGGTAATTGTTGCGTTTCCA
CGTCTCGGAGGCCTGCGCGCTGGGTTGCTCCTTCTTCGGGAGCGAGCTGT
TCTCAGCGATCCCACTCCCAGCCGGGGCTCCCCACACACACTGGGCTGCG
TGCGTGTGGAGTGGGACCCGCGCACACGCGTGTCTCTGGACAGCTACGGC
GCCGAAAGAACTAAAATTCCAGATGGCAAACTCAATGAATGGCAGAAACC
CTGGTGGTCGAGGAGGAAATCCCCGAAAAGGTCGAATTTTGGGTATTATT
GATGCTATTCAGGATGCAGTTGGACCCCCTAAGCAAGCTGCCGCAGATCG
CAGGACCGTGGAGAAGACTTGGAAGCTCATGGACAAAGTGGTAAGACTGT
GCCAAAATCCCAAACTTCAGTTGAAAAATAGCCCACCTATATACTTGAT
ATTTTGCCTGATACATATCAGCATTTACGACTTATATTGAGTTAATATGA
TGACAACCAGAAACTTGCCCAACTCAGTGAGAATGAGTACTTTAAAATCT
ACATTGATAGCCTTATGAAAAAGTCAAAACGGGCAATAAGACTCTTTAAA
GAAGGCAAGGAGAGAATGTATGAAGAACAGTCACAGGACAGACGAAATCT
CACAAAACTCTGCCCTTATCTTCAGTCACATGCTGGCAGAAATCAAAGCAA
TCTTTCCCAATGGTCAATTCCAGGGAGATAACTTTCGTATCACAAAAGCA
GATGCTGCTGAATTCTGGAGAAAGTTTTTTGGAGACAAAACTATCGTACC
ATGGAAAGTATTCAGACAGTGCCTTCATGAGGTCCACCAGATTAGCTCTA
GCCTGGAAGCAATGGCTCTAAAATCAACAATTGATTTAACTTGCAATGAT
```

-continued
TACATTTCAGTTTTTGAATTTTGATATTTTTACCAGGCTGTTTCAGCCTTG
GGGCTCTATTTTGCGGAATTGGAATTTCTTAGCTGTGACACATCCAGGTT
ACATGGCATTTCTCACATATGATGAAGTTAAAGCACGACTACAGAAATAT
AGCACCAAACCCGGAAGCTATATTTTCCGGTTAAGTTGCACTCGATTGGG
ACAGTGGGCCATTGGCTATGTGACTGGGGATGGGAATATCTTACAGACCA
TACCTCATAACAAGCCCTTATTTCAAGCCCTGATTGATGGCAGCAGGGAA
GGATTTTATCTTTATCCTGATGGGAGGAGTTATAATCCTGATTTAACTGG
ATTATGTGAACCTACACCTCATGACCATATAAAGTTACACAGGAACAAT
ATGAATTATATTGTGAAATGGGCTCCACTTTTCAGCTCTGTAAGATTTGT
GCAGAGAATGACAAAGATGTCAAGATTGAGCCTTGTGGGCATTTGATGTG
CACCTCTTGCCTTACGGCATGGCAGGAGTCGGATGGTCAGGGCTGCCCTT
TCTGTCGTTGTGAAATAAAAGGAACTGAGCCCATAATCGTGGACCCCTTT
GATCCAAGAGATGAAGGCTCCAGGTGTTGCAGCATCATTGACCCCTTTGG
CATGCCGATGCTAGACTTGGACGACGATGATGATCGTGAGGAGTCCTTGA
TGATGAATCGGTTGGCAAACGTCCGAAAGTGCACTGACAGGCAGAACTCA
CCAGTCACATCACCAGGATCCTCTCCCCTTGCCCAGAGAAGAAAGCCACA
GCCTGACCCACTCCAGATCCCCACATCTAAGCCTGCCACCCGTGCCTCCT
GCGCCTGGATCTAATTCAGAAAGGCATAGTTAGATCTCCCTGTGGCAGCC
CAACAGGTTCACCAAAGTCTTCTCCTTGCATGGTGAGAAAACAAGATAAA
CCACTCCCAGCACCACCTCCTCCCTTAAGAGATCCTCCTCCACCGCCACC
TGAAAGACCTCCACCAATCCCACCAGACAATAGACTGAGTAGACACATCC
ATCATGTGGAAAGCGTGCCTTCCAGAGACCCGCCAATGCCTCTTGAAGCA
TGGTGCCCTCGGGATGTGTTTGGGACTAATCAGCTTGTGGGATGTCGACT
CCTAGGGGAGGGCTCTCCAAAACCTGGAATCACAGCGAGTTCAAATGTCA
ATGGAAGGCACAGTAGAGTGGGCTCTGACCCAGTGCTTATGCGGAAACAC
AGACGCCATGATTTGCCTTTAGAAGGAGCTAAGGTCTTTTCCAATGGTCA
CCTTGGAAGTGAAGAATATGATGTTCCTCCCCGGCTTTCTCCTCCTCCTC
CAGTTACCACCCTCCTCCCTAGCATAAAGTGTACTGGTCCGTTAGCAAAT
TCTCTTTCAGAGAAAACAAGAGACCCAGTAGAGGAAGATGATGATGAATA
CAAGATTCCTTCATCCCACCCTGTTTCCCTGAATTCACAACCATCTCATT
GTCATAATGTAAAACCTCCTGTTCGGTCCTGTGATAATGGTCACTGTATG
CTGAATGGAACACATGGTCCATCTTCAGAAGAAATCAAACATCCCTGACT
TAAGCATATATTTAAAGGGTACGTATAGAATATAATTTCCTTTGTGATGT
ACATCTTAATGGTCAGAATTTAAAGGCAAAATTTCATGCCATTGTACTGA
AAATACATTAAGGTTTTGTGTTATCCTCTAGGAGATGTTTTTGATTCAGC
CTCTGATCCCGTGCCATTACCACCTGCCAGGCCTCCAACTCGGGACAATC
CAAAGCATGGTTCTTCACTCAACAGGACGCCCTCTGATTATGATCTTCTC
ATCCCTCCATTAGGTTGAAACCTTTAAAAAGTTTTGAACAACCCACCCC
TCCTTCTTTTAATTTCAGAATTTTCAGAATTCAGAGTTCAGTATAACACA
GACTCACTGGGTTGTGAATTTGCCTGAAATTTGAATGGGTTCTCCAGGTG
CCGGTGACTCCCAAGTTCACGAGACCATTACTCCATGTAGATGATTAAGG
TAGTAGTGTAGTAGTTGGGCATCAGTCAGGTTTTAAGCAAGTTGTTTTGT
CCATACTAAATGTAGTCTAAAAACACATGAGAGCTTTGTGCTCTAGTAGT
TTTGAAGTGATGACTTGAAGTGTTGAGATTTTCTTTAAGTATAATAATTC
TTAATAAATATGAACTTGCTTTTCTTGCAGCATGAGCACCAGTTCCACTT
ACGCTAATTAAAATTATGCAAAATTAAATAGTTGTATGTAGAGAACTGATA
ATAAATTCTGTTTTATTCTAATCATTACACTGTAACACATTAAAAAAAAA
AA Human CBL-B mRNA sequence -
var2 (public gi: 23273908) (SEQ ID NO: 38)
AGCGGAGTGCTGCTGCGGCGTCCCGCGGCCTCCCCGAGTCGGGCGGGAGG
GGAGAGCGGGTGTGGATTTGTCTTGACGGTAATTGTTGCGTTTCCACGTC
TCGGAGGCCTGCGCGCTGGGTTGCTCCTTCTTCGGGAGCGAGCTGTTCTC
AGCGATCCCACTCCCAGCCGGGGCTCCCCACACACACTGGGCTGCGTGCG
TGTGGAGTGGGACCCGCGCACACGCGTGTCTCTGGACAGCTACGGCCGAA
AGAACTAAAATTCCAGATGGCAAACTCAATGAATGGCAGAAACCCTGGTG
GTCGAGGAGGAAATCCCCGAAAAGGTCGAATTTTGGGTATTATTGATGCT
ATTCAGGATGCAGTTGGACCCCCTAAGCAAGCTGCCGCAGATCGCAGGAC
CGTGGAGAAGACTTGGAAGCTCATGGACAAAGTGGTAAGACTGTGCCAAA
ATCCCAAACTTCAGTTGAAAAATAGCCCACCATATATACTTGATATTTTG
CCTGATACATATCAGCATTTACGACTTATATTGAGTAAATATGATGACAA
CCAGAAACTTGCCCAACTCAGTGAGAATGAGTACTTTAAAATCTACATTG
ATAGCCTTATGAAAAAGTCAAAACGGGCAATAAGACTCTTTAAAGAAGCA
AGGAGAATGTATGAAGAACAGTCACAGGACAGACGAAATCTCACAAAACT
GTCCCTTATCTTCAGTCACATGCTGGCAGAAATCAAAGCAATCTTTCCCA
ATGGTCAATTCCAGGGAGATAACTTCGTATCACAAAAGCACTGCTGAATT
CTGGAGAAAGTTTTTTGGAGACAAAACTATCGTACCATGGAAAGTATTCA
GACAGTGCCTTCATGAGGTCCACCAGATTAGCTCTGGCCTGGAAGCAATG
GCTCTAAAATCAACAATTGATTTAACTTGCAATGATTACATTTCAGTTTT
TGAATTTGATATTTTTAGCTGTGACACATCCAGGTTACATGGCATTTCTC
ACATATGATGAAGTTAAAGCACGACTACAGAAATATAGCACCAAACCCGG
AAGCTATATTTTCCGGTTAAGTTGCACTCGATTGGGACAGTGGGCCATTG
GCTATGTGACTGGGGATGGGAATATCTTACAGACCATACCTCATAACAAG
CCCTTATTTCAAGCCCTGATTGATGGCAGCAGGGAAGGATTTTATCTTTA
TCCTGATGGGAGGAGTTATAATCCTGATTTAACTGGATTATGTGAACCTA
CACCTCATGACCATATAAAGTTACACAGGAACAATATGAATTATATTGTG
AAATGGGCTCCACTTTTCAGCTCTGTAAGATTTGTGCAGAGAATGACAAA
GATGTCAAGATTGAGCCTTGTGGGCATTTGATGTGCACC -continued
TCTTGCCTTACGGCATGGCAGGAGTCGGATGGTCAGGGCTGCCCTTTCTG
TCGTTGTGAAATAAAAGGAACTGAGCCCATAATCGTGGATCCCTTTGATC
CAAGAGATGAAGGCTCCAGGTGTTGCAGCATCATTGACCCCTTTGGCATG
CCGATGCTCGACTTGGACGACGATGATGATCGTGAGGAGTCCTTGATGAT
GAATCGGTTGGCAAACGTCCGAAAGTGCACTGACAGGCAGAACTCACCAG
TCACATCACCAGGATCCTCTCCCCTTGCCCAGAGAAGAAAGCCACAGCCT
GACCCACTCCAGATCCCCACATCTAAGCCTGCCACCCGTGCCTCCTGCGC
CTGGATCTAATTCAGAAAGGCATAGTTAGATCTCCCTGTGGCAGCCCCGG
GTTCACCAAAGTCTTCTCCTTGCATGGTGAGAAAACAAGATAAACCACTC
CCAGCACCACCTCCTCCCTTAAGGATCCTCCTCCACCGCCACCTGAAAG
ACCTCCACCAATCCCACCAGACAATAGACTGAGTAGACACATCCATCATG
TGGAAAGCGTGCCTTCCAAAGACCCGCCAATGCCTCTTGAAGCATGGTGC
CCTCGGGATGTGTTTGGGACTAATCAGCTTGTGGGATGTCGACTCCTAGG
GGAGGGCTCTCCAAAACCTGGAATCACAGCGAGTTCAAATGTCAATGGAA
GGCACAGTAGAGTGGGCTCTGACCCAGTGCTTATGCGGAAACACAGACGC
CATGATTTGCCTTTAGAAGGAGCTAAGGTCTTTTCCAATGGTCACCTTGG
AAGTGAAGAATATGATGTTCCTCCCCGGCTTTCTCCTCCTCCTCCAGTTA
CCACCCTCCTCCCTAGCATAAAGTGTACTGGTCCGTTAGCAAATTCTCTT
TCAGAGAAAACAAGAGACCCAGTAGAGGAAGATGATGATGAATACAAGAT
TCCTTCATCCCACCCTGTTTCCCTGAATTCACAACCATCTCATTGTCATA
ATGTAAAACCTCCTGTTCGGTCCTGTGATAATGGTCACTGTATGCTGAAT
GGAACACATGGTCCATCTTCAGAGAAGAAATCAAACATCCCTGACTTAAG
CATATATTTAAAGGGAGATGTTTTTGATTCAGCCTCTGATCCCGTGCCAT
TACCACCTGCCAGGCCTCCAACTCGGGACAATCCAAAGCATGGTTCTTCA
CTCAACAGGACGCCCTCTGATTATGATCTTCTCATCCCTCCATTAGGTGA
AGATGTTTTTGATGCCTCCATCTCCATCCCTCCACCCTCCTG
CAAGGCATAGTCTCATTGAACATTCAAAACCTCCTGGCTCCAGTAGCGG
CCATCCTCAGGACAGGATCTTTTTCTTCTTCCTTCAGATCCCTTTGTTGA
TCTAGCAAGTGGCCAAGTTCCTTTGCCTCCCGCTAGAAGGTTACCAGGTG
AAAATGTCAAAACTAACAGAACATCACAGGACTATGATCAGCTTCCTTCA
TGTTCAGATGGTTCACAGGCACCAGCCAGACCCCCTAAACCACGACCGCG
CAGGACTGCACCAGAAATTCACCACAGAAAACCCCATGGGCCTGAGGCGG
CATTGGAAAATGTCGATGCAAAAATTGCAAAACTCATGGAGAGGGTTAT
GCCTTTGCAGAGGTGAAGAGGCCTTTAGAGATAGCCCAGAATAATGTCGA
AGTTGCCCGGAGCAGCTCCTCCGAGAATTTGCCTTCCCTCCTCCAGTATCCC
CACGTCTAAATCTATAGCAGCCAGAACTGTAGACACCAAATGGAAAGCA
ATCGATGTATTCCAAGAGTGTGGAAATAAAGAGAACTGAGATGGAATTCA
AGAGAGAAGTGTCTCCTCCTCGTGTAGCAGCTTGAGAAGAGGCTTGGGAG
TGCAGCTTCTCAAAGGAGACCGATGCTTGCTCAGGATGTCGACAGCTGTG
GCTTCCTTGTTTTGCTAGCCATATTTTAAATCAGGGTTGAACTGACAA
AAATAATTTAAAGACGTTTACTTCCCTTGAACTTTGAACCTGTGAAATGC
TTTACCTTGTTTACAATTTGGCAAAGTTGCAGTTTGTTCTTGTTTTTAGT
TTAGTTTTGTTTTGGTGTTTTGATACCTGTACTGTGTTCTTCACAGATCC
TTTGTAGCGTGGTCAGGTCTGCTGTAACATTTCCCACCAACTCTCTTGCT
GTCCACATCAACAGCTAAATCATTTATTCATATGGATCTCTACCATCCCC
ATGCCTTGCCCAGGTCCAGTTCCATTTCTCTCATTCACAAGATGCTTTGA
AGGTTCTGATTTTCAACTGATCAAACTAATGCAAAAAAAAAAAGTATGTAT
TCTTCACTACTGAGTTTCTTCTTTGGAAACCATCACTATTGAGAGATGGG
AAAAACCTGAATGTATAAAGCATTTATTTGTCAATAAACTGCCTTTTGTA
AGGGGTTTTCACAAAAAAAAAAAAAAAA Human CBL-B mRNA sequence -
var3 (public gi: 862406) (SEQ ID NO: 39)
CTGGGTCCTGTGTGTGCCACAGGGGTGGGGTGTCCAGCGAGCGGTCTCCT
CCTCCTGCTAGTGCTGCTGCGGCGTCCCGCGGCCTCCCCGAGTCGGGCGG
GAGGGGAGAGCGGGTGTGGATTTGTCTTGACGGTAATTGTTGCGTTTCCA
CGTCTCGGAGGCCTGCGCGCTGGGTTGCTCCTTCTTCGGGAGCGAGCTGT
TCTCAGCGATCCCACTCCCAGCCGGGGCTCCCCACACACACTGGGCTGCG
TGCGTGTGGAGTGGGACCCGCGCACACGCGTGTCTCTGGACAGCTACGGC
CGAAAGAACTAAAATTCCAGATGGCAAACTCAATGAATGGCAGAAACC
CTGGTGGTCGAGGAGGAAATCCCCGAAAAGGTCGAATTTTGGGTATTATT
GATGCTATTCAGGATGCAGTTGGACCCCCTAAGCAAGCTGCCGCAGATCG
CAGGACCGTGGAGAAGACTTGGAAGCTCATGGACAAAGTGGTAAGACTGT
GCCAAAATCCCAAACTTCAGTTGAAAAATAGCCCACCATATATACTTGAT
ATTTTGCCTGATACATATCAGCATTTACGACTTATATTGAGTAAATATGA
TGACAACCAGAAACTTGCCCAACTCAGTGAGAATGAGTACTTTAAAATCT
ACATTGATAGCCTTATGAAAAAGTCAAAACGGGCAATAAGACTCTTTAAA
GAAGGCAAGGAGAATGTATGAAGAACAGTCACAGGACAGACGAAATCT
CACAAAACTGTCCCTTATCTTCAGTCACATGCTGGCAGAAATCAAAGCAA
TCTTTCCCAATGGTCAATTCCAGGGAGATAACTTCGTATCACAAAAGCAT
GATGCTGCTGAATTCTGGAGAAAGTTTTTTGGAGACAAAACTATCGTACC
ATGGAAAGTATTCAGACAGTGCCTTCATGAGGTCCACCAGATTAGCTCTA
GCCTGGAAGCAATGGCTCTAAAATCAACAATTGATTTAACTTGCAATGAT
TACATTTCAGTTTTTGAATTTGATATTTTTACCAGGCTGTTTCAGCCTTG
GGGCTCTATTTTGCGGAATTTCTTAGCTGTGACACATCCAGGTT
ACATGGCATTTCTCACATATGATGAAGTTAAAGCACGACTACAGAAATAT
AGCACCAAACCCGGAAGCTATATTTTCCGGTTAAGTTGCACTCGATTGGG
ACAGTGGGCCATTGGCTATGTGACTGGGGATGGGAATATCTTACAGACCA
TACCTCATAACAAGCCCTTATTTCAAGCCCTGATTGATGGCAGCAGGGAA
GGATTTTATCTTTATCCTGATGGGAGGAGTTATAATCCTGATTTAACTGG -continued

```
ATTATGTGAACCTACACCTCATGACCATATAAAAGTTACACAGGAACAAT
ATGAATTATATTGTGAAATGGGCTCCACTTTTCAGCTCTGTAAGATTTGT
GCAGAGAATGACAAAGATGTCAAGATTGAGCCTTGTGGGCATTTGATGTG
CACCTCTTGCCTTACGCATGGCAGGAGTCGGATGGTCAGGGCTGCCCTT
TCTGTCGTTGTGAAATAAAAGGAACTGAGCCCATAATCGTGGACCCCTTT
GATCCAAGAGATGAAGGCTCCAGGTGTTGCAGCATCATTGACCCCTTTGG
CATGCCGATGCTAGACTTGGACGACGATGATGATCGTGAGGAGTCCTTGA
TGATGAATCGGTTGGCAAACGTCCGAAAGTGCACTGACAGGCAGAACTCA
CCAGTCACATCACCAGGATCCTCTCCCCTTGCCCAGAGAAGAAAGCCACA
GCCTGACCCACTCCAGATCCCACATCTAAGCCTGCCACCCGTGCCTCCTC
GCCTGGATCTAATTCAGAAAGGCATAGTTAGATCTCCCTGTGGCAGCCCA
ACAGGTTCACCAAAGTCTTCTCCTTGCATGGTGAGAAAACAAGATAAACC
ACTCCCAGCACCACCTCCTCCCTTAAGAGATCCTCCTCCACCGCCACCTG
AAAGACCTCCACCAATCCCACCAGACAATAGACTGAGTAGACACATCCAT
CATGTGGAAAGCGTGCCTTCCAGAGACCCGCCAATGCCTCTTGAAGCATG
GTGCCCTCGGGATGTGTTTGGGACTAATCAGCTTGTGGGATGTCGACTCC
TAGGGGAGGGCTCTCCAAAACCTGGAATCACAGCGAGTTCAAATGTCAAT
GGAAGGCACAGTAGAGTGGGCTCTGACCCAGTGCTTATGCGGAAACACAG
ACGCCATGATTTGCCTTTAGAAGGAGCTAAGGTCTTTTCCAATGGTCACC
TTGGAAGTGAAGAATATGATGTTCCTCCCCGGCTTTCTCCTCCTCCTCCA
GTTACCACCCTCCTCCCTAGCATAAAGTGTACTGGTCCGTTGCCAAATTC
TCTTTCAGAGAAAACAAGAGACCCAGTAGAGGAAGATGATGATGAATACA
AGATTCTTCATCCCACCCTGTTTCCCTGAATTCACAACCATCTCATTGT
CATAATGTAAAACCTCCTGTTCGGTCCTGTGATAATGGTCACTGTATGCT
GAATGGAACACATGGTCCATCTTCAGAGAAGAAATCAAACATCCCTGACT
TAAGCATATATTTAAAGGGAGATGTTTTTGATTCAGCCTCTGATCCCGTG
CCATTACCACCTGCCAGGCCTCCTACTCGGGACAATCCAAAGCATGGTTC
TTCACTCAACAGGACGCCCTCTGATTATGATCTTCTCATCCCTCCATTAG
GTGAAGATGCTTTTGATGCCCTCCCTCCATCTCTCCCACCTCCCCCACCT
CCTGCAAGGCATAGTCTCATTGAACATTCAAAACCTCCTGGCTCCAGTAG
CCGGCCATCCTCAGGACAGGATCTTTTTCTTCTTCCTTCAGATCCCTTTG
TTGATCTAGCAAGTGGCCAAGTTCCTTTGCCTCCTGCTAGAAGGTTACCA
GGTGAAAATGTCAAAACTAACAGAACATCACAGGACTATGATCAGCTTCC
TTCATGTTCAGATGGTTCACAGGCGATCCTGCACCCCCTAAACTCACGAC
CGCGCAGGACTGCACCAGAAATTCACCACAGAAAACCCCATGGGCCTGAG
GCGGCATTGGAAATGTCGATGCAAAAATTGCAAAACTCATGGGAGAGGG
TTATGCCTTTGAAGAGGTGAAGAGAGCCTTAGAGATAGCCCAGAATAATG
TCGAAGTTGCCCGGAGCATCCTCCGAGAATTTGCCTTTCCCTCCTCCAGTA
TCCCCACGTCTAAATCTATAGCAGCCAGAACTGTAGACACCAAATGGAA
AGCAATCGATGTATTCCAAGAGTGTGGAAATAAAGAGAACTGAGATGGAA
TTCAAGAGAAGTGTCTCCTCCTCGTGTAGCAGCTTGAGAAGAGGCTTG
GGAGTGCAGCTTCTCAAAGGAGACCGATGCTTGCTCAGGATGTCGACAGC
TGTGGCTTCCTTGTTTTTGCTAGCCATATTTTTAAATCAGGGTTGAACTG
ACAAAAATAATTTAAAGACGTTTACTTCCCTTGAACTTTGAACCTGTGAA
ATGCTTTACCTTGTTTACAATTTGGCAAAGTTGCAGTTTGTTCTTGTTTT
TAGTTTAGTTTTGTTTTGGTGTTTTGATACCTGTACTGTGTTCTTCACAG
ACCCTTTGTAGCGTGGTCAGGTCTGCTGTAACATTTCCCACAACTCTCTT
GCTGTCCACATCAACAGCTAAATCATTTATTCATATGGATCTCTACCATC
CCCATGCCTTGCCCAGGTCCAGTTCCATTTCTCTCATTCACAAGATGCTT
TGAAGGTTCTGATTTTCAACTGATCAAACTAATGCAAAAAAAAAGTAT
GTATTCTTCACTACTGAGTTTCTTCTTTGGAAACCATCACTATTGAGAGA
TGGGAAAAACCTGAATGTATAAAGCATTTATTTGTCATAAACTGCCTTTT
GTAAGGGTTTTCACATAAAAAAAAAAAA
```

Human CBL-B mRNA sequence -
var4 (public gi: 862408) (SEQ ID NO: 40)
```
CTGGGTCCTGTGTGTGCCACAGGGGTGGGGTGTCCAGCGAGCGGTCTCCT
CCTCCTGCTAGTGCTGCTGCGCGTCCCGCGGCCTCCCGAGTCGGGCGG
GAGGGGAGACGGGTGTGGATTTGTCTTGACGGTAATTGTTGCGTTTCA
CGTCTCGGAGGCCTGCGCGCTGGGTTGCTCCTTCTTCGGGAGCGAGCTGT
TCTCAGCGATCCCACTCCCAGCCGGGGCTCCCCACACACACTGGGCTGCG
TGCGTGTGGAGTGGGACCCGCGCACACGCGTGTCTCTGGACAGCTACGGC
GCCGAAAGAACTAAAATTCCAGATGGCAAACTCAATGAATGGCAGAAACC
CTGGTGGTCGAGGAGGAAATCCCCGAAAAGGTCGAATTTTGGGTATTATT
GATGCTATTCAGGATGCAGTTGGACCCCCTAAGCAAGCTGCCGCAGATCG
CAGGACCGTGGAGAAGACTTGGAAGCTCATGGACAAAGTGGTAAGACTGT
GCCAAAATCCCAAACTTCAGTTGAAAAATAGCCCACCATATATACTTGAT
ATTTTGCCTGATACATATCAGCATTTACGACTTATATTGAGTAAATATGA
TGACAACCAGAAACTTGCCCAACTCAGTGAGAATGAGTACTTTAAAATCT
ACATTGATAGCCTTATGAAAAAGTCAAAACGGCAATAAGACTCTTTAAA
GAAGGCAAGGAGAGAATGTATGAAGAACAGTCACAGGACAGACGAAATCT
CACAAAACTGTCCCTTATCTTCAGTCACATGCTGGCAGAAATCAAAGCAA
TCTTTCCCAATGGTCAATTCCAGGGAGATAACTTTCGTATCACAAAAGCA
GATGCTGCTGAATTCTGGAGAAAGTTTTTTGGAGACAAAACTATCGTACC
ATGGAAGTATTCAGACAGTGCCTTCATGAGGTCCACCAGATTAGCTCTAG
GCCTGGAAGCAATGGCTCTAAAATCAACAATTGATTTAACTGCAATGATT
ACATTTCAGTTTTGAATTTGATATTTTTACCAGGCTGTTTCAGCCTTG
GGGCTCTATTTTGCGGAATTGGAATTTCTTAGCTGTGACACATCCAGGTT
ACATGGCATTTCTCACATATGATGAAGTTAAAGCACGACTACAGAAATAT
AGCACCAAACCCGGAAGCTATATTTTCCGGTTAAGTTGCACTCGATTGGG
```

-continued
```
ACAGTGGGCCATTGGCTATGTGACTGGGGATGGGAATATCTTACAGACCA
TACCTCATAACAAGCCCTTATTTCAAGCCCTGATTGATGGCAGCAGGGAA
GGATTTATCTTTATCCTGATGGGAGGAGTTATAATCCTGATTTAACTGG
ATTATGTGAACCTACACCTCATGACCATATAAAAGTTACACAGGAACAAT
ATGAATTATATTGTGAAATGGGCTCCACTTTTCAGCTCTGTAAGATTTGT
GCAGAGAATGACAAAGATGTCAAGATTGAGCCTTGTGGGCATTTGATGTG
CACCTCTTGCCTTACGGCATGGCAGGAGTCGGATGGTCAGGGCTGCCCTT
TCTGTCGTTGTGATAAAAGGAACTGAGCCCATAATCGTGGACCCCTTTGA
TCCAAGAGATGAAGGCTCCAGGTGTTGCAGCATCATTGACCCCTTTGGCA
TGCCGATGCTAGACTTGGACGACGATGATCGTGAGGAGTCCTTGATG
ATGAATCGGTTGGCAAACGTCCGAAAGTGCACTGACAGGCAGAACTCACC
AGTCACATCACCAGGATCCTCTCCCCTTGCCCAGAGAAGAAAGCCACAGC
CTGACCCACTCCAGATCCCACATCTAAGCCTGCCACCCGTGCCTCCTCGC
CTGGATCTAATTCAGAAAGGCATAGTTAGATCTCCCTGTGGCAGCCCAAC
AGGTTCACCAAAGTCTTCTCCTTGCATGGTGAGAAAACAAGATAAACCAC
TCCCAGCACCACCTCCTCCCTTAAGAGATCCTCCTCCACCGCCACCTGAA
AGACCTCCACCAATCCCACCAGACAATAGACTGAGTAGACACATCCATCA
TGTGGAAAGCGTGCCTTCCAGAGACCCGCCAATGCCTCTTGAAGCATGGT
GCCCTCGGGATGTGTTTGGGACTAATCAGCTTGTGGGATGTCGACTCCTA
GGGGAGGGCTCTCCAAAACCTGGAATCACAGCGAGTTCAAATGTCAATGG
AAGGCACAGTAGAGTGGGCTCTGACCCAGTGCTTATGCGGAAACACAGAC
GCCATGATTTGCCTTTAGAAGGAGCTAAGGTCTTTTTCCAATGGTCACCTT
GGAAGTGAAGAATATGATGTTCCTCCCCGGCTTTCTCCTCCTCCTCCAGT
TACCACCCTCCTCCCTAGCATAAGTGTACTGGTCCGTTAGCAAATTCTCT
TTCAGAGAAAACAAGAGACCCAGTAGAGGAAGATGATGATGAATACAAGA
TTCTTCATCCCACCCTGTTTCCCTGAATTCACAACCATCTCATTGTCAT
AATGTAAAACCTCCTGTTCGGTCCTGTGATAATGGTCACTGTATGCTGAA
TGGAACACATGGTCCATCTTCAGAGAAGAAATCATTCATCCCTGACTTAA
GCATATATTTAAAGGGAGATGTTTTTGATTCAGCCTCTGATCCCGTGCCA
TTACCACCTGCCAGGCCTCCAACTCGGGACAATCCAAAGCATGGTTCTTC
ACTCAACAGGACGCCCTCTGATTATGATCTTCTCATCCCTCCATTAGGTT
GAAACCTTTAAAAAAGTTTTGAACAACCCACCCCTCCTTCTTTTAATTTC
AGAATTTTCAGAATTCAGAGTTCAGTATAACACAGACTCACTGGGTTGTG
AATTTGCCTGAAATTTGAATTGGGTTCTCCAGGTGCCGGTGACTCCCAAGT
TCACGAGACCATTACTCCATGTAGATGATTAAGGTAGTAGTGTAGTAGTT
GGGCATCAGTCAGGTTTTAAGCAAGTTGTTTTTGTCCATACTAAATGTAG
TCTAAAAACACATGAGAGCTTTGTGCTCTAGTAGTTTTGAAGTGATGACT
TGAAGTGTTGAGATTTTCTTTAAGTATAATAATTCTTAATAAATATGAAC
TTGCTTTTCTTGCAGCATGAGCACCAGTTCCACTTACGCTAATTAAATTA
TGCAAAATTAAATAGTTGTATGTAGAGAACTGATAATAAATTCTGTTTTA
TTTCAATCATTACAACTGTAACACATTCAAAAAAAAAAA
```

Human CBL-B mRNA sequence -
var5 (public gi: 862410) (SEQ ID NO: 41)
```
CTGGGTCCTGTGTGTGCCACAGGGGTGGGGTGTCCAGCGAGCGGTCTCCT
CCTCCTGCTAGTGCTGCTGCGCGTCCCGCGGCCTCCCGAGTCGGGCGG
GAGGGGAGACGGGTGTGGATTTGTCTTGACGGTAATTGTTGCGTTTCA
CGTCTCGGAGGCCTGCGCGCTGGGTTGCTCCTTCTTCGGGAGCGAGCTGT
TCTCAGCGATCCCACTCCCAGCCGGGGCTCCCCACACACACTGGGCTGCG
TGCGTGTGGAGTGGGACCCGCGCACACGCGTGTCTCTGGACAGCTACGGC
GCCGAAAGAACTAAAATTCCAGATGGCAAACTCAATGAATGGCAGAAACC
CTGGTGGTCGAGGAGGAAATCCCCGAAAAGGTCGAATTTTGGGTATTATT
GATGCTATTCAGGATGCAGTTGGACCCCCTAAGCAAGCTGCCGCAGATCGC
AGGACCGTGGAGAAGACTTGGAAGCTCATGGACAAAGTGGTAAGACTGTG
CCAAAATCCCAAACTTCAGTTGAAAAATAGCCCACCATATATACTTGATA
TTTTGCCTGATACATATCAGCATTACGACTTATATTGAGTAAATATGATG
ACAACCAGAAACTTGCCCAACTCAGTGAGAATGAGTACTTTAAAATCTAC
ATTGATAGCCTTATGAAGTCAAACGGCAATAAGACTCTTTAAAGAAGGC
AAGGAGAGAATGTATGAAGAACAGTCACAGGACAGACGAAATCTCACAAA
ACTGTCCCTTATCTCAGTCACATGCTGGCAGAAATCAAAGCAATCTTTC
CCAATGGTCAATTCCAGGGAGATAACTTTCGTATCACAAAAGCAGATGCT
GCTGAATTCTGGAGAAAGTTTTTTGGAGACAAAACTATCGTACCATGGAA
AGTATTCAGACAGTGCCTTCATGAGGTCCACCAGATTAGCTCTAGCCTGG
AAGCAATGGCTCTAAAATCAACAATTGATTTAACTGCAATGATTACATT
TCAGTTTTGAATTTGATATTTTTACCAGGCTGTTTCAGCCTTGGGGCTC
TATTTTGCGGAATTGGAATTTCTTAGCTGTGACACATCCAGGTTACATGG
CATTTCTCACATATGATGAAGTTAAAGCACGACTACAGAAATATAGCACC
AAACCCGGAAGCTATATTTTCCGGTTAAGTTGCACTCGATTGGGACAGTG
GGCCATTGGCTATGTGACTGGGGATGGGAATATCTTACAGACCATACCTC
ATAACAAGCCCTTATTTCAAGCCCTGATTGATGGCAGCAGGGAAGGATTT
TATCTTTATCCTGATGGGAGGAGTTATAATCCTGATTTAACTGGATTATG
TGAACCTACACCTCATGACCATATAAAAGTTACACAGGAACAATATGAAT
TATATTGTGAAATGGGCTCCACTTTTCAGCTCTGTAAGATTTGTGCAGAG
AATGACAAAGATGTCAAGATTGAGCCTTGTGGGCATTTGATGTGCACCTC
TTGCCTTACGGCATGGCAGGAGTCGGATGGTCAGGGCTGCCCTTTCTGTC
GTTGTGAAATAAAAGGAACTGAGCCCATAATCGTGGACCCCTTTGATCCA
AGAGATGAAGGCTCCAGGTGTTGCAGCATCATTGACCCCTTTGGCATGCC
GATGCTAGACTTGGACGACGATGATGATCGTGAGGAGTCCTTGATGATGA
ATCGGTTGGCAAACGTCCGAAAGTGCACTGACAGGCAGAACTCACCAGTC
ACATCACCAGGATCCTCTCCCCTTGCCCAGAGAAGAAAGCCACAGCCTGA
```

```
CCCACTCCAGATCCCACATCTAAGCCTGCCACCCGTGCCTCCTCGCCTGG
ATCTAATTCAGAAAGGCATAGTTAGATCTCCCTGTGGCAGCCCAACAGGT
TCACCAAAGTCTTCTCCTTGCATGGTGAGAAAACAAGATAAACCACTCCC
AGCACCACCTCCTCCCTTAAGAGATCCTCCTCCACCGCCACCTGAAAGAC
CTCCACCAATCCCACCAGACAATAGACTGAGTAGACACATCCATCATGTG
GAAAGCGTGCCTTCCAGAGACCCGCCAATGCCTCTTGAAGCATGGTGCCC
TCGGGATGTGTTTGGGACTAATCAGCTTGTGGGATGTCGACTCCTAGGGG
AGGGCTCTCCAAAACCTGGAATCACAGCGAGTTCAAATGTCAATGGAAGG
CACAGTAGAGTGGGCTCTGACCCAGTGCTTATGCGGAAACACAGACGCCA
TGATTTGCCTTTAGAAGGAGCTAAGGTCTTTTCCAATGGTCACCTTGGAA
GTGAAGAATATGATGTTCCTCCCCGGCTTTCTCCTCCTCCTCCAGTTACC
ACCCTCCTCCCTAGCATAAAGTGTACTGGTCCGTTAGCAAATTCTCTTTC
AGAGAAAACAAGAGACCCAGTAGAGGAAGATGATGATGAATACAAGATTC
CTTCATCCCACCCTGTTTCCCTGAATTCACAACCATCTCATTGTCATAAT
GTAAAACCTCCTGTTCGGTCCTGTGATAATGGTCACTGTATGCTGAATGG
AACACATGGTCCATCTTCAGAGAAGAAATCAAACATCCCTGACTTAAGCA
TATATTTAAAGGGTACGTATAGAATATAATTTCCTTTGTGATGTACATCT
TAATGGTCAGAATTTAAAGGCAAAATTTCATGCCATTGTACTGAAAATAC
ATTAAGGTTTTGTGTTATCCTCTAGGAGATGTTTTTGATTCAGCCTCTGA
TCCCGTGCCATTACCACCTGCCAGGCCTCCAACTCGGGACAATCCAAAGC
ATGGTTCTTCACTCAACAGGACGCCCTCTGATTATGATCTTCTCATCCCT
CCATTAGGTTGAAACCTTTAAAGTTTTGAACAACCCACCCCTCCTTCTTT
TAATTTCAGAATTTTCAGAATTCAGAGTTCAGTATAACACAGACTCACTG
GGTTGTGAATTTGCCTGAAATTTGAATGGGTTCTCCAGGTGCCGGTGACT
CCCAAGTTCACGAGACCATTACTCCATGTAGATGATTAAGGTAGTAGTGT
AGTAGTTGGGCATCAGTCAGGTTTTAAGCAAGTTGTTTTGTCCATACTAA
ATGTAGTCTAAAAACACATGAGAGCTTTGTGCTCTAGTAGTTTTGAAGTG
ATGACTTGAAGTGTTGAGATTTTCTTTAAGTATAATAATTCTTAATAAAT
ATGAACTTGCTTTTCTTGCAGCATGAGCACCAGTTCCACTTACGCTAATT
AAATTATGCAAAATTAAATAGTTGTATGTAGAGAACTGATAATAAATTCT
GTTTTATTCTAATCATTACACTGTAACACATTAAAAAAAAAAA

Human CBL-B mRNA sequence -
var6 (public gi: 21753192) (SEQ ID NO: 42)
AGTGCTGCTGCGGCGTCCCGGCCTCCCCGAGTCGGGCGGGAGGGGAGA
GCGGGTGTGGATTTGTCTTGACGGTAATTGTTGCGTTTCCACGTCTCGGA
GGCCTGCGCGCTGGGTTGCTCCTTCTTCGGGAGCGAGCTGTTCTCAGCGA
TCCCACTCCCAGCCGGGGCTCCCCACACACACTGGGCTGCGTGCGTGTGG
AGTGGGACCCGCGCACACGCGTGTCTCTGGACAGCTACGGCGCCGAAAGA
ACTAAAATTCCAGATGGCAAACTCAATGAATGGCAGAAACCCTGGTGGTC
GAGGAGGAAATCCCCGAAAAGGTCGAATTTTGGGTATTATTGATGCTATT
CAGGATGCAGTTGGACCCCCTAAGCAAGCTGCCGCAGATCGCAAAACCTG
GAATCACAGCGAGTTCAAATGTCAATGGAAGGCACAGTAGAGTGGGCTCT
GACCCAGTGCTTATGCGGAAACACAGACGCCATGATTTGCCTTTAGAAGG
AGCTAAGGTCTTTTCCAATGGTCACCTTGAGTGAAGAATATGATGTTCCT
CCCCGGCTTTCTCCTCCTCCAGTTACCACCCTCCTCCCTAGCATAAA
GTGTACTGGTCCGTTAGCAAATTCTCTTTCAGAGAAAACAAGAGACCCAG
TAGAGGAAGATGATGATGAATACAAGATTCCTTCATCCCACCCTGTTTCC
CTGAATTCACAACCATCTCATTGTCATAATGTAAAACCTCCTGTTCGGTC
TTGTGATAATGGTCACTGTATGCTGAATGGAACACATGGTCCATCTTCAG
AGAAGAAATCAAACATCCCTGACTTAAGCATATATTTAAAGGGAGATGTT
TTTGATTCAGCCTCTGATCCCGTGCCATTACCACCTGCCAGGCCTCCAAC
TCGGGACAATCCAAAGCATGGTTCTTCACTCAACAGGACGCCCTCTGATT
ATGATCTTCTCATCCCTCCATTAGGTGAAGATGCTTTTGATGCCCTCCT
CCATCTCTCCCCACCTCCCCCACCTCCTGCAAGGCATAGTCTCATTGACA
TTCAAAACCTCCTGGCTCCAGTAGCCGGCCATCCTCAGGACAGGATCTTT
TTCTTCTTCCTTCAGATCCCTTTGTTGATCTAGCAAGTGGCCAAGTTCCT
TTGCCTCCTGCTAGAAGGTTACCAGGTGAAAATGTCAAAACTAACAGAAC
ATCACAGGACTATGATCAGCTTCCTTCATGTTCAGATGGTTCACAGGCAT
CAGCCAGACCCCCTAAACCACGACCGCGCAGGACTGCACCAGAAATTCAC
CACAGAAAACCCCATGGGCCTGAGGCGGCATTGGAAAATGTCGATGCAAA
AATTGCAAAACTCATGGGAGAGGGTTATGCCTTTGAAGAGGTGAAGAGAG
CCTTAGAGATAGCCCAGAATAATGTCGAAGTTGCCCGGAGCATCCTCCGA
GAATTTGCCTTCCCTCCCAGTATCCCCACGTCTAAATCTATAGCAGCC
AGAACTGTAGACACCAAATGGAAAGCAATCGATGTATTCCAAGAGTGTG
GAAATAAAGAGAACTGAGATGGAATTCAAGAGAGAAGTGTCTCCTCCTG
TGTAGCAGCTTGAGAAGAGGCTTGGGAGTGCAGCTTCTCAAAGAAACCG
ATGCTTGCTCAGGATGTCGACAGCTGTGGCTTCCTTGTTTTGCTAGCCA
TATTTTTAAATCAGGGTTGAACTGACAAAATAATTTAAAGACGTTTACT
TCCCTTGAACTTTGAACCTGTGAAATGCTTTACCTTGTTTACAGTTTGGC
AAAGTTGCAGTTTGTTCTTGTTTTTAGTTTAGTTTTTGGTTTGTTTTG
TACCTGTACTGTGTTCTTCACAGACCCTTTGTAGCGTGGTCAGGTCTGCT
GTAACATTTCCCACCAACTCTCTTGCTGTCCACATCAACAGCTAAATCAT
TTATTCATATGGATCTCTACCATCCCCATGCCTTGCCCAGGTCCAGTTCC
ATTTCTCCATTCACAAGATGCTTTGAAGGTTCTGATTTTCAACTGATCA
AACTAATGCAAAAAAAAAAAAAAAAAAAAAAAAA Human Cbl-b mRNA sequence -
var7 (SEQ ID NO: 49)
CGTNTTTGGNANNCACTACAGGGGATGTTTAATACACACTCACAATGCGC
ATGATGTNTATAACTATCTATTONATGATGTAAGATACCCCACTCAAACC
CATAAAAAGAGCATCTTTAATACGACTCACTATANGGCGAGCGCACGCC
ATGGCAGGTACCCATACGACGTACCAGATTACGCTCATATGGCCATGGAG
GCCAGNGAATTCCACCCAAGCNGTGGTATCAACGCANAGTGGACTCTGAC
CCANTGCTTATGCGGAAACACAGACGCCATGATTTGCCTTTAGAAGGAGC
TAAGGTCTCTTCCAATGGTCACCTTGGAAGTGAAGAATATGATGTTCCTC
CCCGGCTTTCTCCTCCTCCAGTTACCACCCTNCTCCCTAGCATAAAG
TGTACTGGTCCGTTAGCAAATTCTCTTTCAGAGAAAACAAGAGACCCAGT
AGAGGAAGATGATGATGAATACAAGATTCCTTCATCCCACCCTGTTTCCC
TGAATTCACAACCATCTCATTGTCATAATGTAAAACCTCCTGTTCGGTCT
TGTGATAATGGTCACTGTATGCTGAATGAACACATGGTCCATCTTCAGA
GAAGAAATCAAACATCCCTGACTTAAGCATATATTTAAAGGGTGAAGATG
CTTTTGATGCCCTCCCTCCATCTCTCCCACCTCCCCCACCTCCTGCAAGG
CATAGTCTCATTGAACATTCAAAACCTCCTGGCTCCAGTAGCCGGCCATC
CTCAGGACAGGATCTTTTTCTTCTTCCTTCAGATCCCTTTGTTGATCTAG
CAAGTGGCCAAGTTCCTTTGCCTCCCGCTAGAAGGTTACCAGGTGAAAAT
GTCAAAACTAACAGGACATCACAGGACTATGATCAGCTTCCTTCATGTTC
AGATGGTTCACAGGCACCAGCCAGACCCCCTAAACCACGACCGCGCAGGA
CTGCACCAGAAATTCACCACAGAAAACCCCATGGGCCTGAGGCGGCATTG
GAAAATGTCGATGCAAAAATTGCAAAACTCATGGGAGAGGGTTATGCCTT
TGAAGAGGTGAAGAGAGCCTTAGAGATAGCCCAGAATAATGTCGAAGTTG
CCCGGAGCATCCTCCGAGAATTTGCCTTCCCTCCTCCAGTATCCCCCACGT
CTAAATCTATAGCAGCCAGAACTGTAGACACCAAATGGAAAGCAATCGA
TGTATTCCAAGAGTGTGGAAATAAAGAGAACTGAGATGGAATTCAAGAGA
GAAGTGTCTCCTCCTCGTGTAGCAGCTTGAGAAGAGGCTTGGGAGTGCAG
CTTCTCAAAGAAAACCGATGCTTGCTCAGGATGTCNACAGCTGNGGNCTN
CCTTGTTTTTGCTAGCCATTTTTTAAATNAGGGTTGAACTNGANAAAAN
TATTTAAAAACGTTTACCTCCCTTGAACTTTGAACCTGGGAAAGNC Human Cbl-b Protein sequence -
var5 (SEQ ID NO: 50)
MRKHRRHDLPLEGAKVSSNGHLGSEEYDVPPRLSPPPPVTTLLPSIKCTG
PLANSLSEKTRDPVEEDDDEYKIPSSHPVSLNSQPSHCNVKPPVRSCDN
GHCMLNGTHGPSSEKKSNIPDLSIYLKGEDAFDALPPSLPPPPPPARRSL
IEHSKPPGSSSRPSSGQDLFLLPSDPFVDLASGQVPLPPARRLPGENVKT
NRTSQDYDQLPSCSDGSQAPARPPKPRPRRTAPEIHHRKPHGPEAALENV
DAKIAXLMGEGYAEEEVKRALEIAQNNVEVARSILREFAFPPPVSPRLNL Human cbl-B clone3Gd114
(partial sequence) (SEQ ID NO: 51)
ACTCTGACCCAGTGCTTATGCGGAAACACAGACGCCATGATTTGCCTTTA
GAGGAGCTAAGGTCTCTTCCAATGGTCACCTTGGAAGTGAAGAATATGAT
GTTCCTCCCCGGCTTTCTCCTCCTCCAGTTACCACCCTCCTCCCTAG
CATAAAGTGTACTGGTCCGTTAGCAAATTCTCTTTCAGAGAAAACAAGAG
ACCCAGTAGAGGAAGATGATGATGAATACAAGATTCCTTCATCCCACCCT
GTTTCCCTGAATTCACAACCATCTCATTGTCATAATGTAAAACCTCCTGT
TCGGTCTTGTGATAATGGTCACTGTATGCTGAATGGAACACATGGTCCAT
CTTCAGAGAAGAAATCAAACATCCCTGACTTAAGCATATATTTAAAGGGT
GAAGATGCTTTTGATGCCCTCCCTCCATCTCTCCCACCTCCCCCACCTCC
TGCAAGGCATAGTCTCATTGAACATTCAAAACCTCCTGGCTCCAGTAGCC
GGCCATCCTCAGGACAGGATCTTTTTCTTCTTCCTTCAGATCCCTTTGTT
GATCTAGCAAGTGGCCAAGTTCCTTTGCCTCCCGCTAGAAGGTTACCAGG
TGAAAATGTCAAAACTAACAGGACATCACAGGACTATGATCAGCTTCCTT
CATGTTCAGATGGTTCACAGGCACCAGCCAGACCCCCTAAACCACGACCG
CGCAGGACTGCACCAGAAATTCACCACAGAAAACCCCATGGGCCTGAGG
CGGCATTGGAAAATGTCGATGCAAAAATTGCAAAACTCATGGGAGAGGGT
TATGCCTTTGAAOAGGTGAAGAGAGCCTTAGAGATAGCCCAGAATAATGT
CGAAGTTGCCCGGAGCATCCTCCGAGAATTTGCCTTCCCTCCTCCAGTAT
CCCCACGTCTAAATCTATAGCAGCCAGAACTGTAGACACCAAATGGAAAT
GCAATCGATGTATTCCAAGAGTGTGGAAATAAAGAGAACTGAGATGGAAT
TCAAGAGAAGTGTCTCCTCCTCGTGTAGCAGCTTGAGAAGAGGCTTGG
GAGTGCAGCTTCTCAAAGAAAACCGATGCTTGCTCAGGATGTCGACAGCT
GTGGCTTCCTTGTTTTTGCTAGCCATTTTTTAAATCAGGGTTGAACTGG
AAAAAATTATTTAAAAACGTTTACCTCCCTTGAACTTTGAACCTGGGAAA
GGC Human CblB protein in 3Gd114 Translation of cbl-B
clone3Gd114 starting at base pair 3 (SEQ ID NO:
52)
SDPVLMRKHRRHDLPLEGAKVSSNGHLGSEEYDVPPRLSPPPPVTTLLPS
IKCTGPLANSLSEKTRDPVEEDDDEYKIPSSHPVSLNSQPSHCNVKPPV
RSCDNGHCMLNGTHGPSSEKKSNIPDLSIYLKGEDAFDALPPSLPPPPPP
ARHSLIEHSKPPGSSSRPSSGQDLFLLPSDPFVDLASGQVPLPPARRLPG
ENVKTNRTSQDYDQLPSCSDGSQAPARPPKPRPRRTAPEIHHRKPHGPEA Human CBL-B Protein sequence -
van (public gi: 4757920) (SEQ ID NO: 43)
MANSMNGRNPGGRGGNPRICGRILGIIDAIQDAVGPPKQAAADRRTVEKT
WKLMDKVVRLCQNPKLQLKNSPPYILDILPDTYQHLRLILSKYDDNQKLA
QLSENEYFKIYIDSLMKKSKRAIRLFKEGKERMYEEQSQDRRNLTKLSLI
```

-continued

```
PSEMLABINAIFPNGQFQGDNFRITICADAAEFWRKFFGDKTIVPWKVFR
QCLHEVHQISSSLEAMALKSTIDLTCNDYISVFEFDIFTRLFQPWGSILR
NWNFLAVTHPGYMAFLTYDEVKARLQKYSTKPGSYIFRLSCTRLGQWAIG
YVTGDGNILQTIPHNKPLFQALIDGSREGFYLYPDGRSYNPDLTGLCEPT
PHDMIICVTQEQYELYCEMGSTFQLCKICAENDKDVKIEPCGHLMCTSCL
TAWQESDGQGCPFCRCEIKGTEPIIVDPFDPRDEGSRCCSIIDPFGMPML
DLDDDDDREESLMMNRLANVRKCTDRQNSPVTSPGSSPLAQRRKPQPDPL
QIPHLSPPVPPRLDLIQKGIVRSPCGSPTGSPKSSPCMVRKQDKPLPAP
PPPLRDPPPPPPERPPPIPPDNRLSRHIHHVESVPSRDPPMPLEAWCPRD
VFGTNQLVGCRLLGEGSPKPGITASSNVNGRHSRVGSDPVLMRKHRRHDL
PLEGAKVFSNGHLGSEEYDVPPRLSPPPPVTTLLPSIKCTGPLANSLSEK
TRDPVEEDDDEYKIPSSHPVSLNSQPSHCHNVKPPVRSCDNGHCMLNGTH
GPSSEKKSNIPDLSIYLKGTYRI

Human CBL-B Protein sequence -
var2 (public gi: 23273909) (SEQ ID NO: 44)
MANSMNGRNPGGRGGNPRKGRILGIIDAIQDAVGPPKQAAADRRTVEKTW
KLMDKVVRLCQNPKLQLKNSPPYILDILPDTYQHLRLILSKYDDNQKLAQ
LSENEYFKIYIDSLMKICSKRAIRLFKEGKERMYEEQSQDRRNLTKLSLI
PSEMLABIKAIFPNGQFQGDNFRITKADAAEFWRKFFGDKTIVPWKVFRQ
CLHEVHQISSGLEAMAIJKSTIDLTCNDYISVFEFDIFTRLFQPWGSILR
NWNFLAVTHPGYMAFLTYDEVKARLQKYSTKPGSYIFRLSCTRLGQWAIG
YVTGDGNILQTIPHNKPLFQALIDGSREGFYLYPDGRSYNPDLTGLCEPT
PHDHIKVTQEQYELYCEMGSTFQLCKICAENDKDVKIEPCGHLMCTSCLT
AWQESDGQGCPFCRCEIKGTEPIIVDPFDPRDEGSRCCSIIDPFGMPMLD
LDDDDDREESLDWSLRLARVRKCTDRQNSPVTSPGSSPLAQRRKPQPDPL
QIPHLSPPVPPRLDLIQKGIVRSPCGSPTGSPKSSPCMVRKQDKPLPAP
PPPLRDPPPPPPERPPPIPPDNRLSRHIHHVESVPSKDPPMPLEAWCPRD
VFGTNQLVGCRLLGEGSPKPGITASSNVNGRHSRVGSDPVLMRKHRRHDL
PLEGAKVFSNGHLGSEEYDVPPRLSPPPPVTTLLPSIKCTGPLANSLSEK
TRDPVEEDDDEYKIPSSHPVSLNSQPSHCHNVKPPVRSCDNGHCMLNGTH
GPSSEKKSNIPDLSIYLKGDVFDSASDPVPLPPARPPTRDNPKHGSSLNR
TPSDYDLLIPPLGEDAFDALPPSLPPPPPPARHSLIEHSKPPGSSSRPSS
GQDLFLLPSDPFVDLASGQVPLPPARRLPGENVPLTNRTSQDYDQLPSCSD
GSQAPARPPKPRPRRTAPEIMHRKPHGPEAALENVDAKIAKLMGEYAFE
EVKMALEIAQNNVEVARSILREFAPPPPVSPRLNL Human CBL-B Protein sequence -
var3 (public gi: 862407) (SEQ ID NO: 45)
MANSMNGRNPGGRGGNPRKGRILGIIDAIQDAVGPPKQAAADRRTVEKTW
KLMDKVVRLCQNPKLQLKNSPPYILDILPDTYQHLRLILSKYDDNQKLAQ
LSENEYFKIYIDSLMKICSKRAIRLFKEGKERMYEEQSQDRRNLTKLSLI
FSMMLAEIKAIFPNGQFQGDNFRITKADAAEFWRKFPGDKTIVPWKVFRQ
CLMEVHQISSSLEAMAKSTIDLTOUDYISVFEFDIFTRLFQPWGSILRN
WNFLAVTHPGYMAFLTYDEVKARLQKYSTKPOSYIFRLSCTRLGQWAIGY
VTGDGNILQTIPHNKPLFQALIDGSREGFYLYPDGRSYNPDLTGLCEPT
HDMIICVTQEQYELYCEMGSTFQLCKICAENDKiDVKIEPCGHLMCTSCL
TAWQESDGQGCPFCRCEIKGTEPIIVDPFDPRDEGSRCCSIIDPFGMPML
DLDDDDDREESLMMNRLANVRKCTDRQNSPVTSPGSSPLAQRRKPQPDPL
QIPHLSPPVPPRLDLIQKGIVRSPCGSPTGSPKSSPCMVRKQDKPLPAP
PPPLRDPPPPPPERPPPIPPDNRLSRMIHHVESVPSRDPPMPLEAWCPRD
VFGTNQLVGCRLLGEGSPKPGITASSNVNGRHSRVGSDPVLMRKHRRHDL
PLEGAKVFSNGHLGSEEYDVPPRLSPPPPVTTLLPSIKCTGPLANSLSEK
TRDPVEEDDDEYKIPSSMPVSLNSQPSMCMNVKPPVRSCDNGHCMLNGTH
GPSSEKKSNIPDLSIYLKGDVFDSASDPVPLPPARPPTRDNPKHGSSLNR
TPSDYDLLIPPLGEDAFDALPPSLPPPPPPARHSLIEMSKPPGSSSRPSS
GQDLFLLPSDPFVDLASGQVPLPPARRLPGENVKNRTSQDYDQLPSCSDG
SQAPARPPKPRPRRTAPEIHHRKPHGPEAALENVDAKIAKLMGEYAFEE
VKRALEIAQNNVEVARSILREFAFPPPVSPRLNL Human CBL-B Protein sequence -
var4 (public gi: 862409) (SEQ ID NO: 46)
MANSMNGRNPGGRGGNPRKGRILGIIDAIQDAVGPPKQAAADRRTVEKTW
KLMDKVVRLCQNPKLQLKNSPPYILDILPDTYQHLRLILSKDDNQKLAQL
SENEYFKIYIDSLMKKSKRAIRLFKEGKERMYEEQSQDRRNLTKLSLIFS
HKHLAEIKAIFPNGQFQGDNFRITKADAAEFWRKFFGDKTIVPWKVFRQC
LHEVMQISSSLEAMALKSTIDLTCNDYISVFEFDIFTRLFQPWGSILRNP
LAVTHPGYMAFLTYDEVKARLQKYSTKPGSYIFRLSCTRLGQWAIGYVTG
DGNILQTIPHNKPLFQALIDGSREGFYLYPDGRSYNPDLTGLCEPTPHDH
IKVTQEQYELYCEMGSTFQLCKICAENDKDVKIEPCGHLMCTSCLTAWQE
SDGQGCPFCRCEIKGTEPIIVDPFDPRDEGSRCCSIIDPFGMPMLDLDDD
DDKEESLMMNRLANVRKCTDRQNSPVTSPGSSPLAQRRKPQPDPLQIPHL
SLPPVPPRLDLIQKGIVRSPCGSPTGSPKSSPCMVRKQDKPLPAPPPLR
DPPPPPPERPPPIPPDNRLSRIHHVESVPSRDPPMPLEAWCPRDVFGTNQ
LVGCRLLGEGSPKPGITASSNVNGRHSRVGSDPVLMRKHRRHDLPLEGAK
VFSNGHLGSEEYDVPPRLSPPPPVTTLLPSIKCTGPLANSLSEKTRDPV
EEDDDEYKIPSSHPVSLNSQPSHCHNVKPPVRSCDNGIICMLNGTMGPSS
EKKSNIPDLSIYLKGDVFDSASDPVPLPPARPPTRDNPKHGSSLNRTPSD
YDLLIPPLG
```

Rat CBL-B mRNA sequence
(public gi: 21886623) (SEQ ID NO: 47)
```
CGGGCGGGCGTGGAGCTGTCTGCACGAAAGGACTAAGATTCCAGATGGCA
AATTCTATGAATGGCAGAAATCCTGGTGGTCGAGGAGGGAAACCCCCGCAA
AGGTCGAATTTTGGGGATTATTGATGCCATTCAGGATGCAGTTGGACCCC
CAAAGCAAGCTGCAGCTGACCGCAGGACAGTGGAGAAGACTTGGAAACTC
ATGGACAAAGTGGTAAGACTGTGCCAAAATCCGAAACTTCAGTTGAAAAA
CAGCCCACCATATATCCTCGACATTTTACCTGATACGTATCAGCATTTGC
GGCTTATATTGAGTAAGTATGACGACAACCAGAAGCTGGCTCAACTGAGC
GAGAATGAGTACTTTAAAATCTACATCGACAGTCTCATGAAGAAGTCAAA
GCGAGCGATCCGGCTCTTCAAAGAAGGCAAGGAGAGGATGTACGAGGAGC
AGTCGCAGGACAGACAGAATCTCACAAAGCTGTCCCTTATCTTCAGTCAC
ATGCTGGCAGAAATCAAGGCGATCTTTCCCAATGGCCAGTTCCAGGGAGA
TAACTTCCGGATCACCAAAGCAGATGCTGCCGAATTCTGGAGGAAGTTTT
TTGGAGACAAAACTATCGTACCATGGAAAGTCTTCAGACAGTGCCTGCAT
GAGGTCCATCAGATCAGCTCTGGCCTGGAGGCCATGGCTCTGAAGTCAAC
CATTGACTTAACTTGTAATGATTACATCTCCGTGTTTGAATTTGATATTT
TTACCAGGCTATTTCAGCCCTGGGGCTCTATTTTACGGAATTGGAACTTC
TTAGCTGTGACACACCCGGGGTACATGGCATTTCTCACATATGATGAAGT
TAAAGCTCGACTACAGAAATACAGCACCAAGCCTGGAAGCTACATTTTCC
GGTTAAGCTGCACTCGGCTGGGACAATGGGCCATTGGCTATGTGACTGGG
GACGGCAATATCCTACAGACCATACCTCATAACAAGCCCCTGTTCCAAGC
CCTGATTGATGGTAGCAGGGAAGGCTTTTACCTTTATCCAGATGGACGAA
GCTATAACCCTGATTTAACCGGATTGTGAACCTACACCTCATGATCAT
ATAAAAGTTACACAGGACAATATGAACTGTATTGTGAAATGGGCTCCAT
TTTTCAGCTGTCAAGATCTGTCAGAGAATGACAAAGATGTCAAGATCG
AGCCTTGTGGGCATCTCATGTGCACTTCGTGCCTTACCGCGTGGCAGGAG
TCTGATGGCCAAGGCTGCCCCTTCTGTCGCTGTGAGATAAAAGGAACCGA
ACCTATCATCGTGGATCCCTTTGACCCCAGAGACGAAGGCTCCAGGTGCT
GCAGCATCATCGACCCTTTCAGCATCCCATGCTGCACTTGGATGATGAC
GATGATGAGAGGAGTCTCTGATGATGAACCGGCTGGCGAGTGTTCGCAA
GTGCACAGACAGGCAGAACTCGCCAGTCACATCGCCAGGATCCTCACCCC
TTGCCCAGGAGAAAAGCCTCAGCCAGACCCTCTCCAGATCCCCCACCTC
AGCCTGCCACCAGTGCCTCCCCGCCTGGACCTCATTCAGAAAGGCATCGT
GCGCTCTCCCTGTGGCAGCCCCACGGGCTCCCCGAAGTCTTCTCCATGCA
TGGTTAGAAAACAAGACAAACCACTCCCAGCACCCCCTCCTCCCCTTGCGA
GATCCTCCGCCTCCACCAGAGCGGCCTCTCCAATCCCGCCTGACAGTAG
ACTGAGCAGACACTTCCACCACGGAGAGAGTGTGCCTTCCAGGGACCAGC
CAATGCCTCTTGAAGCCTGGTGCCCTCGGGATGCCTCGGGACTAATCAG
GTGATGGGATGTCGCATCCTAGGGGATGGCTCTCCAAAGCCTGGCGTCAC
AGCAGACTCCAACTTAAATGGACGTCACAGTCGAATGGGCTCTGACCAGG
TTCTTATGAGGAAAACAGACGCCACGATTTGCCTTCAGAAGGCCCAAG
GTCTTTTCCAATGGACACCTTGCCCCTGAAGAATACGACGTTCCTCCTCG
GCTTTCCCCTCCTCCTCCAGTCACTGCCCCTTCTCCCTAGCATAAAGTGTA
CTGGTCCAATAGCAAATTGTCTCTCCGAGAAACAAGAGACACAGTAGAA
GAAGATGATGATGAATAACAAGATTCCTTCATCCCATCCTGTTTCCTGAA
TTCACAACCATCTCATTGTCATAATGTCAAACCTCCTCGGTCTTGTG
ATAATGGTCACTGTATACTGAATGGAACTCATGGTACGCCTTCAGAGATG
AAGAAATCAAACATCCCAGATTTAGGCATCTATTTGAAGGGGTGAAGATGC
TTTTGATGCCTCCCCCCATCCCTTCCTCCTCCCCCACCTCCTGCAAGAC
ATAGTCTCATCGAGCATTCAAAACCTCCAGGCTCCAGTAGCCGGCCTTCC
TCAGGACAGGACCTTTTCCTTCTTCCTTCAGATCCCTTTTTTGACCCAGC
AAGTGGCCAAGTTCCATTGCCTCCGGCCAGGAGAGCACCAGGAGATGGTG
TCAAATCCAACAGAGCCTCCCAGGACTATGACCAGCTCCCTTCATCTTCC
GATGGTTCGCAAGCACCAGCTACACCCCCAAACCACGACCCCGAAGGAC
TGCACCAGAAATTCATCACAGAAAGCCCCATGGGCCGAGGCGGCACTGG
AAAAATGTGGATGCGAAAATTGCAAAACTCATGGGAGAGGGGTATGCCTTT
GAAGAGGTGAGAGAGCCTTAGAGATCGCCCAGAATAACCTGGAAGTGGC
CAGGAGCATACTTCGAGAATTCGCCTTTCCCTCCTCCCGTCTCGCCACGTC
TCAATCTATAGCAGCCCAGACTGCAAACACCAAAGGGTAAAACAGTTAAC
AAATATTCCAGGAGTATGGGAACAGAAGGACTGAGAGGGAATGCAGGAGCC
ATGGTGTCTTTTCATGTGGCGTCTCCAGAAGGCAGCCTTGAGTCCAGCTT
CTCTGGTACTCACAGCTCCCTGAGGATGCCCCACGCTGCACGTTCTGTGTTT
GTGCTAGCACATACTTTTAAATCAGGGTTGAACTGAGAAATAATTTAAAG
ACGTTTACTCCCCCTTGAACTTTGAATCTGTGAAATGCTTTCCTTGTTTA
CACGTTGCAGAATTGCAGTTTGTCTCTGTTTTTGATTCCTGCTACTGTGT
TCCTGACAGGCCCTTGGCGAGTTGGTCAGGTCTGCTGTAAGTTTGTCCA
TGCCCACCCTGCTGCCCACATTGGCAGCTAAAGCATCTCTTCGTGTTGCT
GTCTATCCGGGCCCCACCTCATGTGTCCACGTCCAGTTCATTTCTCTCAT
TCACACAGCATGCTAGTCTGAGG
```

Rat CBL-B Protein sequence
(public gi: 21886624) (SEQ ID NO: 48)
```
MANSMNGRNPGGRGGNPRKGRILGIIDAIQDAVGPPKQAAADRRTVEKTW
KLMDKVVRLCQNPKLQLKNSPPYILDILPDTYQHLRLILSKYDDNQKLAQ
LSENEYFKIYIDSLMKKSKRAIRLFKEGKERMYEEQSQDRRNLTKLSLIF
SHMLAEIKAIFPNGQFQGDNFRITKADAAEFWRKFPGDKTIVPWKVFRQC
LHEVMQISSGLEAMALKSTIDLTCNDYISVFEFDIFTRLFQPWGSILRNW
NFLAVTHPGYMAPLTYDEVKARLQKYSTKPGSYIFRLSCTRLGQWAIGYV
```

-continued

TGDGNILQTIPMNKPLFQALIDGSREGFYLYPDGRSYNPDLTGLCEPTPH
DHIKVTQEQYELYCEMGSTFQLCKICAENDKDVKIEPCGHLMCTSCLTAW
QESDGQGCPFCRCEIKGTEPIIVDPFDPRDEGSRCCSIIDPFSIPMLDLD
DDDDREESLMNNRLASVRKCTDRQNSPVTSPGSSPLAQRRKPQPDPLQIP
HLSLPPVPPRLDLIQKGIVRSPCGSPTGSPKSSPCMVRKQDKPLPAPPPP
LRDPPPPPERPPPIPPDSRLSHFHHGESVPSRDQPMPLEAWCPRDAFGTN
QVMGCRILGDGSPKPGVTANSNLNGRHSRMGSDQVLMRIRRHDLPSEGAK
VFSNGHLAPEEYDVPPRLSPPPPVTALLPSIKCTGPThNCLSEKTRDTVE
EDDDEYKIPSSHPVSLNSQPSHCHNVKPPVRSCDNGHCILNGTMGTPSEM
KKSNIPDLGIYLKGEDAFDALPPSLPPPPPPARHSLIEHSKPPGSSSRPS
SGQDLFLLPSDPFFDPASGQVPLPPARRAPGDGVKSNRASQDYDQLPSSS
DGSQAPARPPKPRPRRTAPEIHMRKPHGPEAALENVDAKIAKLMGEGYAF
EEVKRALEIAQNNLEVARSILREFAFPPPVSPRLNL

Mouse CBL-B mRNA sequence
(public gi: 26324665) (SEQ ID NO: 53)
GACTCCCTGGGCTGCGAGCGCCGGCGGTGGTTGCCGGAGAGGCCCCTCCT
TCTCGCCCGGCTCCATTCCCTCGCTCGCGCCGAGCGGGCTCCCGACCCTC
CGCTGCCITGCCGGCAACGTGAAGAAGAGCTCGGGCGCCGGCGGCGGCGG
CTCTGGGGGCTCGGGAGCGGGCGGCCTGATCGGGCTCATGAAGGACGCCT
TCCAGCCGCACCACCACCACCACCTCAGCCCGCACCCTCCCCTGCACG
GTGGACAAGAAGATGGTGGAGAAGTGCTGGAAGCTCATGGACAAGGTGGT
GCGGTTGTGTCAAAACCCAAAGCTGGCGCTCAAGAACAGCCCGCCTTATA
TCTTAGACCTGCTGCCTGACACCTACCAGCACCTCCGCACTGTCTTGTCA
AGATATGAGGGGAAGATGGAGAGCGCTTGGAGAAATGAGTATTTCAGGGTG
TTCATGGAAAATTTGATGAAGAAAACTAAGCAGACTATCAGCCTCTTCAA
GGAGGGAAAAGAAAGGATGTATGAGGAGAATTCCCAGCTAGGCGAAACC
TGACCAAATTATCCCTGATCTTCAGCCACATGCTGGCAGAACTGAAAGGC
ATCTTTCCGAGCGGGACTCTTCAAGGAGCACTTTCCGGATTACTAAAGC
TGATGCTGCCGAATTTTGGAGAAAAGCTTTTGGTGAAAAGACGATAGTCC
CGTGGAAGAGCTTTCGACAGGCCCTGCATGAAGTGCATCCCATCAGTTCT
GGGCTGGACGCCATGGCTCTGAGTCCACTATTGATCTGACCTGCAATGAT
TATATTTCTGTCTTTGAATTTGATATTTTTACACGGCTGTTTCAGCCCTG
GTCCTCTTTGCTCAGAAATTGGAACAGCCTTGCTGTAACTCACCCTCAGG
ACATGGCTTTCCTGACATACGATGAAGTGAAAGCGCCTCAGAAGTTC
ATCCACAAACCTGGCAGTTACATCTTTCGGCTGAGCTGTACTCGTTTGGG
TCAGTGGGCTATTGGGTATGTTACTGCCGATGGGAACATTCTGCAGACAA
TCCCACACAATAAACCGCTCTTCCAACACTGATTGATGGCTTCAGGGAA
GGCTTCTATTTGTTTCCTGATGGACGAAATCAAATCCTGACCTGACAGG
TTTATGTGAACCAACTCCTCAAGATCATATCAAAGTAACCCAGGAACAAT
ATGAATTATACTGTGAAATGGGCTCCACATTTCAACTGTGTAAGATATGT
GCTGAGAATGATAAGGATGTGAAGATTGAGCCCTGTGGACACCTCATGTG
CACATCCTGCCTCACGTCGTGGCAGGAATCAGAAGGTCAGGGCTGTCCTT
TTTGCCGATGTGAAATCAAAGGTACTGAGCCCATCGTGGTGGATCCGTTT
GACCCCAGAGGCAGTGGCAGCCTATTAAGGCAAGGAGCAGAAGGTGCTCC
TTCCCCAAATTACGACGATGATGATGAACGAGCTGATGATTCTCTCTT
TCATGATGAAGGAGTTGGCAGGTGCCAAGGTGGAAAGGCCTTCCTCTCCA
TTCTCCATGGCCCCACAAGCTTCCCTTCCTCCAGTGCCACCAAGACTTGA
CCTTCTACAGCAGCGAGCACCTGTTCCTGCCAGCACTTCAGTTCTGGGGA
CTGCTTCCAAGGCTGCTTCTGGCTCCCTTCATAAAGACAAAACATTGCCA
ATACCTCCCACACTTCTGAGATCTTCCACCACCACCCCCTCCAGACCGCC
TTACTCTGTTGGAGCAGAAACAAGGCCTCAGAAGCGCCCTCTGCCTTGTA
CACCAGGCGATTGTCCATCTAGAGACAAACTGCCCCCTGTCCCTTCTAGC
CGCCCAGGGGACTCGTGGTTGTCTCGGCCAATCCCTAAAGTACCAGTAGC
TACTCCAAACCCTGGTGATCCTTGGAATGGGAGAGAATTGACCAATCGAC
ACTCGCTTCCATTCTCATTGCCCTCACAAATGGAACCCAGACAGATGTC
CCTAGGCTTGGAAGCACATTTAGTCTGGATACCTCTATGACTATGAATAG
CAGCCCAGTAGCAGGTCAGAGAGTGAGCACCCAAAGATCAAGCCTTCCT
CGTCTGCCAACGCCATTTACTCTCTGGCTGCCAGGCCTCTTCCTATGCCA
AAACTGCCACCTGGGGAGCAAGGGGAAAGTGAAGAGGACACAGAATATAT
GACTCCCACATCTAGGCCTGTAGGGGTTCAGAAGCCAGAGCCCAAACGGC
CGTTAGAGGCAACCCAGAGTTCACGAGCATGTGACTGTGACCAGCAGATC
GACAGCTGTACCTATGAGCGATGATGTAACATCCAGTCCCAAGCACTGCT
TGTAGCAGAAAACAGCGCCTCTGGGGAAGGGAATCTGGCCACAGCTCACA
CGAGTACTGGCCCTGAGGAATCCGAAAACGAGGATGATGGCTATGATGTG
CCTAAGCCACCCGTGCCAGCTGTACTGGCCCGCCGGACCCTGTCTGACAT
CTCCAATGCCAGCTCCTCCTTTGGCTGGTTGTCTTTGGATGGTGACCCTA
CAAACTTCAATGAGGGTTCCCAAGTTCCTGAGCGGCCCCCCAAACCATTC
CCTCGGAGAATCAACTCAGAACGAAAGCCCAGTAGCTATCAACAAGGCGG
AGGTGCCACTGCTAACCCTGTGGCCACAGCACCCTCACCGCAGCTCTCAA
GTGAGATTGAACGCCTCATGAGTCAGGGCTATTCCTACCAGGACATTCAG
AAAGCTTTGGTCATTGCCCACAACAACATTGAGATGGCTAAAAACATCCT
CCGGGAATTTGTTTCATTTCTTCCTCCTGCTCACGTAGCCACCTAGCACA
TCTCTCCCTGCCACGGCTTCAGAGGACCCATGAGCCAGGCTCTTACTCAA
GGACCACCTAGGAAAGCAGTGGCTTCTTTTGGGACGTCACAGTAAGGTCC
TGCCTTTCCTGTGGGGATCGACACATATGGTTCCAAGATTTCAAAGCAGT
GGAATGAAAATGGAGCAGCTGATGTGTTTCATTGTTGTATTGGTCTTAAG
AGTGTTTTTGTAGTCCTGCAGTCTCCAGTAGGAGAGAGTGGGTTTTTATT
AAATGGTAACCTACCCCAGAAACAGC Mouse CBL-B Protein sequence
(public gi: 26324666) (SEQ ID NO: 54)
MAGNVICSSGAGGGGSGGSGAGGLIGLMKDAFQPHHHHHHLSPHPPCTVD
KKMVEKCWKLMDKVVRLCQNPKALKNSPPYILDLLPDTYQHLRTVLSRYE
GKMETLGENEYFRVFMENLMKKTKQTISLFKEGKERNYEENSQPRRNLTK
LSLIFSHMLAELKGIFPSGLFQGDTFRITKADAAEFWRKAFGEKTIVPWK
SFRQALHEVHPISSGLDAMALKSTIDLTCNDYISVFEFDIFTRLFQPWSS
LLRCNSLAVTHPGYMAFLTYDEVKARLQKFIHKPGSYIFRLSCTRLGQWA
IGYVTADGNILQTIPMNKPLFQALIDGFREGFYLFPDGRNQNPDLTGLCE
PTPQDHIKVTQEQYELYCEMGSTFQLCKICAENDKDVKIEPCGHLMCTSC
LTSWQESEGQGCPFCRCEIKGTEPIVVDPFDPRGSGSLLRQGAEGAPSPN
YDDDDDERADDSLFMMKELAGAKVERPSSPFSMAPQASLPPVPPRLDLLQ
QRAPVPASTSVLGTASKAASGSLMKDKPLPIPPTLRDLPPPPPDRPYSV
GAETRPQRRPLPCTPGDCPSRDKLPPVPSSRPGDSWLSRPIPKVPVATPN
PGDPWNGRELTNRHSLPFSLPSQMEPRADVPRLGSTFSLDTSMTMNSSPV
AGPESEHPKIKPSSSANAIYSLAARPLPMPKLPPGEQGESEEDTEYMTPT
SRPVGVQKPEPKRPLEATQSSRACDCDQQIDSCTYEANYNIQSQALSVAE
NSASGEGNLATAHTSTGPEESENEDDGYDVPKPPVPAVLARRTLSDISNA
SSSFGWLSLDGDPTNFNEGSQVPERPPKPFPRRINSERKASSYQQGGGAT
ANPVATAPSPQLSSEIERLMSQGYSYQDIQKALVIAHNNIEMAKNILREF
VSISSPAHVAT Drosophila CBL-B mRNA sequence
(public gi: 1842452) (SEQ ID NO: 55)
CATCTCGAAAATATTGTGTGGGTTTAAAAAACGTTAACGTCGCCGAAACG
CGTAGCCCCAAATGCACACGCCAGGTGCAAGGATAAAGCCGTGAGGATCG
GGCACCCAATCGGATAGATCGCGTTTGGTTAGCTTGTGGGGGAAAATCGT
ACTTAAGTCACCACTACTACTACACACGGGCACCACCAGCAACACCAACA
ACAACAACAACGAGAACAGCACCAGCAACAACAACAACAGCAGCAAGAA
GAGAGAAGCTGAGAAGAGGAAGCAGAGGCAGCGCAGTCGGCAGCGCAGCG
GCAGAGAGAAAAGATGGCGACGAGAGGCAGTGGAACCCGTGTGCAATCGC
AGCCAAAGATTTTCCCATCGCTGCTTTCCAAGCTGCACGGCGCTATCTCG
GAAGCCTGCGTCTCGCAGCGTCTGTCCACCGACAAGAAGACGCTGGAGAA
GACCTGGAAGTTGATGGACAGCTTGGTGAAACTGTGCCAGAGCCGAAGAT
GATCTTAAGAATAGTCCACCGTTTATTTTGGACATCCTGCCGGATACGTA
CCAGCGCCTGAGATTGATCTACTCAAAGAAGGAGGACCAGATGCACCTGC
TCCATGCCAACGAGCACTTCAACGTGTTCATCAACAACCTGATGCGAAAG
TGCACGCGGGCCATCAATGGTTGTCAAGGAGGGCAAGGAGAAGATGTTCGA
CGAGAACTCCCACTACCGCCGCAATCTCACCAAGCTCAGCCTGGTCTTCT
CCCACATGCTCAGCGAACTGAAGGCCATATTCCCCAACGGTGTCTTTGCC
GGGGATCAATTTCGGATCACCAAAGCGGATGCGGCTGACTTTTGGAAGAG
CAACTTCGGTAACAGCACATTGGTTTCCCTGGAAAATCTTCCGGCAGGAGC
TTAGCAAAGTACATCCCATAATCTTCCGGCTGGAGGCCATGGCCCTAAAG
ACCACTATCGATCTTACCTGCAACGACTTCATTTCCAACTTCGAGTTCGA
CGTCTTCACACGCCTCTTCCAGCCTTGGGTGACACTGCTACGCAACTGGC
AGATTCTGGCCGTCACACATCCGGGCTACGTGGCGTTTCTCACATACGAC
GAGGTGAAGGCTCGCCTACACGCTACATCCTCAAGGCGGGCAGCTACGT
TTTCCGGCTCTCCTGCACGCGATTGGGCCAATGGGCCATCGGCTACGTAA
CTGCCGAGGGAGAGATTCTGCAGACAATCCCTCAGAACAAGTCGCTGTGC
CAGGCGCTGCTCGATGGCCATCGAGAGGCTTCTACTTGTACCCAGATGGC
CAAGCGTACAATCCGGATCTGTCGTCTGCCGTTCAAAGTCCCACAGAGGA
CCACATAACCGTTACCCAAGAGCAATACGAACTATACTGTGAAATGGGCA
GCACCTTTCAGCTGTGCAAAATTTGTGCGGAGAACGACAAAGATATCCGC
ATCGAGCCCGTGGCCACTTGTTGTGCACTCCCTGCCTTACCTCCTGGCA
AGTGGATTCCGAGGGACAGGGCTGCCCCTTCGTCGGGCCGAAATCAAGG
GCACCGAACAAATCGTTGTGGACGCTTTCGATCCGCGCAAGCAACACAAC
CGGAACGTCACCAATGGCGACAGCAGCACGAGGAAGACGACGAAGACGAGG
TATAGTTTTGTTCACAGCCTGATCAGCCTGATCCGCCTGCTCCGCTGCCG
CCTGTGCTGCTATTTATATACATATTACTCTTATGATTACCTTTGGTTCG
TTTATACAGTTATATATGCCTATATATACATTATATATTTTAGATTTTAC
AACTGCTATTGTTTATATAAGTTTAATGTTTAGCCTGCAGTTCGCAGTGG
CAGTTTCGAGTTTAATTTTGTTTGTTTAGCTGTAACATATTTAAATTATT
AGCCAAACTCATGCAACTAACATCCACAGACCCACGCACACACACGCCAAT
CACAAGCACAAGTACAACCAThACCATTGTCCATCCATCGAGCACATGCA
TAACGTAGTTAAAGTTCTTTGACCGGAAGTCGCTCATCAACCATCGTTTG
CTATCGCTTCCTCTGTTTTCTCTCCGCCGGTTTGGTTTGGTTTTGGTTTG
TGTGCGTTCGTTTAGTTGTTCGTTCTTCCACTCTCACGCTCTCTCTATCT
ATTGATCACGTTCGCCTCTGTTTATGAATCATATTTTAATCGATTCGATT
CGCCCTCGATTGCACTTTTGTACATAGGCACTATGGAATTTATAATTGGT
AACCTTGTTCTTGTATTATTCGGGTGAATTTTCTCCTTTCACATCCAGCT
TGATTATCCCCTTGATTATGTATGCCCGCCAGTAATTTTGTATCTATCC
CCTACTCTAGAATCATTCTCTTAATCATTGTACTCCGTTATGTGTTTATT
TCATTTTAGTTTATTGTTTAATACTTCCAAAGATACATTTAGTTTGTAGT
AGCGTGCGTTTACTTCCCCCCATATCAATTCAATTTTATTTGTAAGCAGC
CAAYGCGCTGCCCTAAGACTGTAATTTATTATTAACAMAAAAATAAAT
CGAAAAAGTTTAAGAAATCAGGCTAAACATAGGAGGCCTCGAATCGATCG
ATAATTTAGTTAGATTGYATGTAAATTAATTATTGATTTCCTGTGTCACA
AGGCCA -continued

```
Drosophila CBL-B Protein sequence
(public gi: 1842453) (SEQ ID NO: 56)
MATRGSGTRVQSQPKIFPSLLSKLHGAISEACVSQRLSTDKXTLEKTWKL
MDKVKLCQQPKMNLKNSPPFILDILPDTYQRLRLIYSKKEDQMHLLHANE
HFNVFINNLMRKCKRAILKLFKEGKEKMFDENSHYRRNLTKLSLVFSHML
SELKAIFPNGVFAGDQPRITKADAADFWKSNFGNSTLVPWKIFRQELSKV
HPIISGLEAMALKTTIDLTCNDFISNFEFDVFTRLFQPWVTLLRNWQILA
VTHPGYVAFLTYDEVKARLQRYILKAGSYVFRLSCTRLGQWAIGYVTAEG
EILQTIPQNKSLCQALLDGHREGFYLYPDGQAYNPDLSSAVQSPTEDHIT
VTQEQYELYCEMGSTFQLCKICAENDKDIRIEPCGHLLCTPCLTSWQVDS
EGQGCPFCRAEIKGTEQIVVDAFDPRXQHNRNVTNGRQQQQEEDDTEV C. elegans CBL-B mRNA sequence
(public gi: 25150544) (SEQ ID NO: 57)
CTATGATCATTACATCCTAATTAATTGCCACTGGACTTCACATCATATCA
CCGTTTCACCGGGAATGGGTTCAATAAACACAATTTTTCACCGGATACAT
CGGTTTGTCAATGGCACAGGCAATAATGCGCGATTTGTTCCCAGCACAAA
CAACTCGACGGAAGCGTTGACACTCAGTCCGAGAGCTGTTCCCAGCACAG
TTTCACTATTCGAAATCCCATCAGCTTCGGAGATGCCCGGTTTCTGCAGT
GAAGAGGATCGTCGATTTTGCTCAAAGCATGCAAGTTTATGGATCAAGT
AGTGAAGAGTTGTCATAGCCCAAGACTGAATTTGAAAAATTCGCCGCCTT
TCATTTTGGACATTCTACCTGATACTTATACGCATTTAATGCTGATATTC
ACACAAAACAATGACATACTCCAAGACAACGACTACTTGAAAATCTTTCT
GGAGAGTATGATCAACAAGTGCAAAGAGATCATCAAACTGTTCAAGACGT
CAGCTATCTACAATGACCAGTCTGAAGAACGACGGAAGCTTACGAAAATG
TCACTAACATTTTCAQCATATGCTTTTCGAGATTAAAGCATTATTTCCGG
AAGGTATCTATATTGAAGACCGGTTTCGGATGACAAAGAAGGAAGCCGAA
AGCTTTTGGAGTCATCATTTTACAAAAAAAACATTGTACCCTGGTCAAC
ATTTTTTACTGCATTAGAAAAGCACCATGGATCAACGATAGGAAAATGG
AAGCAGCCGAATTAAAAGCTACGATAGACTTGAGCGGAGATGATTTATT
TCGAATTTTGAGTTTGATGTGTTTACAAGGTTATTCTACCCTTTCAAAAC
ACTGATCAAAAATTGGCAAACACTCACCACCGCCCATCCCGGATACTGTG
CATTTCTCACATACGATGAGGTCAAAAATCGGTTAGAAAAATTAACGAAA
AAACCTGGAAGCTACATCTTCCGGTTATCATGCACACGTCCTGGACAATG
GGCAATAGGATACGTAGCTCCGGATGGAAAGATTTATCAGACAATACCAC
AGAATAAAAGTTTGATTCAAGCACTACATGAAGGCCATAAAGAAGGATTT
TATATTTACCCGAACGGTAGAGATCAAGATATTAACTAATCCAAATTGAT
GGATGTGCCACAAGCGGACAGAGTGCAAGTGACCAGTGAACAATACAGTT
GTATTGTGAGATGGGCACAACATTCGAGTTGTGCAAAATTTGTGACGATA
ACGAGAAGAACATCAAAATTGAGCCATGTGGACATTTGCTCTGCGCAAAA
TGTTTGGCTAACTGGCAGGATTCGGATGGTGGTGGCAACACATGTTCCAT
TCTGCCGCTACGAAATCAAAGGAACAAATCGTGTGATTATTGACAGGTTC
AAGCCCACTCCGGTAGAAATTGAAAAAGCGAAAATGTAGCTGCTGCGGAG
AAGAAGCTGATCTCATTAGTTCCCCGACGTGCCTCCCAGAACGTATGTGC
CCAATGTTCTCAAAGTTTGCTGCATGACGCGTCAAACTCAATTCCGTCGG
TCGACGAGTTGCCGTTGGTGCCGCCACCGTTGCCACCGAAAGCATTGGGT
ACCCTGGACACTTTGAATTCGTCACAAACATCCTCTTCATACGTGAACAT
CAAAGACTGGAAAATGTTGAAACAAGCGGAGAAGCATTGGCACAAGTGG
TAAACCGGCAACGGGCGCCTTCAATCCAAGCTCCACCACTACCGCCAAGG
TTATCAGCGAGCGAGCACCAACCACACCACCCATACACAAATACGAACAG
TGAGCGGGAGTAGACTTGTGTAAATGTTCATCTTACCGCTTTATACTGCA
ATTTTCATTCCCCCACTTATCATAGAACTATTCTTCCACAACAACATATT
GCCGTGACTAGAACTGGTAACACTACATCATTCTTTGTTAAAACGTTATT
ATATCTCTATTTCTTTTCGCCACTCCTTTCCGTTTTTTTTCAAATTTTG
TCAATTTTCCTACAGCGTTCTGACTCCTATTGGTAAGCAATCATGTCATA
TCTTGTTAAATTTTCATGTTAATTTCTTACTCTCGCTGTCCCAGATTTTA
CGAGTTTTCAGGAAACGTTTGATTTTGTTCTATTCTACAATTTCCATCGC
CCCCAACCTGTCGTGTATTTTCTATGTGTCACTCTGAAGAAAACAAGTTT
AGACTTTTTAAAAATCGTTTTATTACTCTAAAACTTAAAAGCTGAAATGT
CAGCTATAGTAAAAATACATA C. elegans CBL-B Protein sequence
(public gi: 25150545) (SEQ ID NO: 58)
MGSINTIFNRIHRFVNGTGNNARFVPSTNNSTEALTLSPRAVPSTVSLFE
IPSASEMPGFCSEEDRRFLLKACKFMDQVVKSCHSPRLNLKNSPPFILDI
LPDTYTHLMLIPTQNNDILQDNDYLKIFLESMINKCKEIIKLFKTSAIYN
DQSEERRKLTKMSLTFSHMLFEIKALFPEGIYIEDRFRMTKKEAESFWSH
HFTKKNIVPWSTPFTALEHGSTIGIEAELKATIDLSGDDPISNFEPDVFT
RLFYPFKTLIKNWQTLTTAHPGYCAFLTYDEVKKRLEKLTKKPGSYIFRL
SCTRPGQWAIGYVAPDGKIYQTIPQNKSLIQALMEGHKEGFYIYPNGRDQ
DINLSKLMDVPQADRVQVTSEQYELYCEMGTTFELCKICDDNEKNIKIEP
CGMLLCAKCLANWQDSDGGGNTCPFCRYEIKGTNEVIIDRFKPTPVEIEK
AXNVAAAEKXLISLVPDVPPRTYVSQCSQSLLHDASNSIPSVDELPLVPP
PLPPKALGTLDTLHSSQTSSSYVNIKELENVETSGEALQVVNRQRAPSIQ
APPLPPRLSASEHQPHMPYTNTNSERE
```

Example 5

POSH Modulates HeLa Cell Growth

HeLa cells subject to siRNA knockdown of POSH expression showed a reversible decrease in cell growth.

Protocol:

Day 1: Plate two 6-well plates with HeLa SS6 cells ($5 \times 10^5$) cells/well.

Day 2: Change medium to medium without antibiotics.

Day 3: Perform the same transfection as noted below.

Transfection: 10 nM RNAi: A2=RNAi #153; A3=RNAi#187 (see Example 2 for RNAi information)

Prepare mix of LF2000+OptiMEM: 3.25 ml optimem with 65 ul LF2000, incubate together for 5 min. Add to reactions as noted above. Incubate for 25 min. Add 500 ul to the corresponding well.

| Reaction name | No. of reactions | RNAi oligo # | RNAi (ul) | OptiMEM (ul) | Mix (LF2000 + OptiMEM) |
|---|---|---|---|---|---|
| A2 | 4 | 153 | 10 nM = 5 ul | 1000 | 1000 |
| A3 | 4 | 187 | 10 nM = 5 ul | 1000 | 1000 |

Day 4: Harvest one of each reaction for both protein extraction and RNA. (#153 day 4 and #187 day 4). For the other set of reactions: count and split each well into ($5 \times 10^5$ cells) for transfection next day.

Day 5: Perform the same transfection as noted above.

Day 6: Harvest one plate for protein and RNA extraction and the other split to ($5 \times 10^5$ cells) and ($2.5 \times 10^5$ cells)

Day 8: Harvest and count and to the ($5 \times 10^5$ cells) plate form day six.

Day 10: Harvest and count the ($2.5 \times 10^5$ cells) plate from day 6.

Protein extract: for POSH expression evaluation

1. Wash cells twice with cold PBS on ice.

2. Add PBS and scrape cells off to eppendorf tubes.

3. Centrifuge at 40 deg. C. at 1800 rpm for 5 min.

4. Add 100 ul of RIPA Buffer+protease inhibitors (PI3K) (1:200)+EDTA (1:100) to the remaining cells on plate.

5. Incubate on ice for 15 minutes.

6. Centrifuge for 10 min in 40 deg. C. at maximum speed.

7. Proteins (15 ug/lane) were loaded onto a 10% tris glycine gel, resolved by electrophoresis, transferred to nitrocellulose membrane and probed with anti POSH antibody for 1 h (1:2000 dilution). Detected was by ECL.

Figure 18:
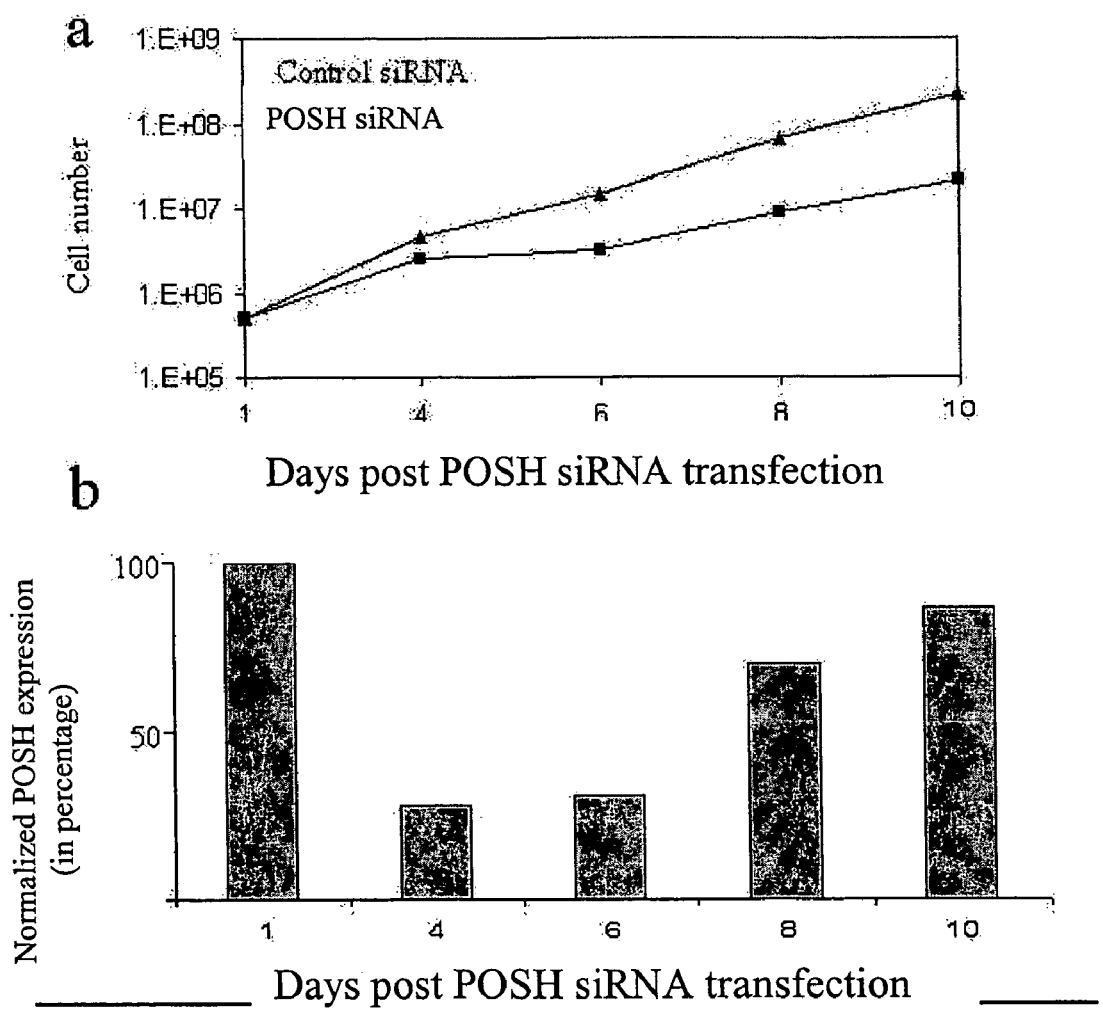
FIG. 18: (A) Growth curve of HeLa SS cells as a function of time. Control siRNA (triangles), POSH siRNA (squares). (B) Levels of POSH expression as a function of time after POSH siRNA transfection.

8. Evaluations of protein levels were performed using an ImageQuant analyzer. Results are shown in FIG. 18.

Example 6

Figure 19:
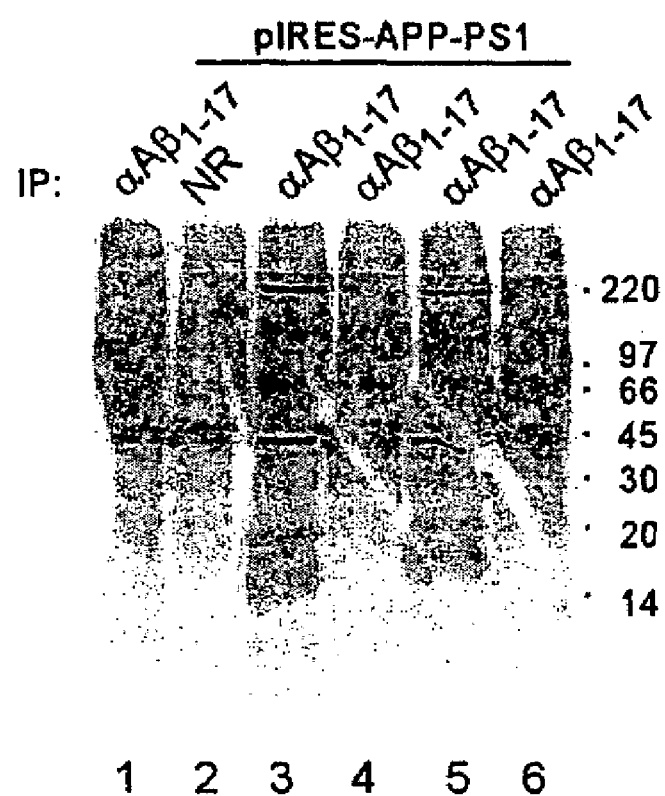
FIG. 19 shows that amyloid precursor protein levels are reduced in cells that have reduced levels of POSH. HeLa SS6 cells that express reduced levels of POSH (H153) and control cells expressing scrambled RNAi (H187) were transfected with a plasmid expressing amyloid precursor protein (APP) and presenilin 1 (PS1). Cells were metabolic labeled and protein extracts were immunoprecipitated with anti-amyloid beta specific antibody, which recognize an epitope common to APP, C199 and Aβ polypeptides. A labeled protein was specifically precipitated by the antibody in H187-transfected cells (see Lanes 3 and 5). However, this polypeptide was not recognized in H153 cells (see Lanes 4 and 6) indicating that APP steady state levels are reduced in H153 and may be rapidly degraded in these cells.

Amyloid Precursor Protein Levels are Reduced in Cells that have Reduced Levels of POSH HeLa SS6 cells that express reduced levels of POSH (H153) and control cells expressing scrambled RNAi (H187)

were transfected with a plasmid expressing amyloid precursor protein (APP) and presenilin 1 (PS1). Cells were metabolic labeled and protein extracts were immunoprecipitated with anti-amyloid beta specific antibody, which recognize an epitope common to APP, C199 and Aβ polypeptides. A labeled protein was specifically precipitated by the antibody in H187-transfected cells (see FIG. 19, Lanes 3 and 5). However, this polypeptide was not recognized in H153 cells (see FIG. 19, Lanes 4 and 6) indicating that APP steady state levels are reduced in H153 and may be rapidly degraded in these cells.

Methods

Cloning of pIRES-APP-PS1

Cloning was performed in two steps: Presenilin 1 (PS1) was first cloned from human brain library into pIREs (pIREs-PS1). Then APP-695 was obtained from amplifying two image clones (3639599 and 5582406) and mixing their PCR products in an additional PCR reaction to yield full-length APP695 that was further ligated into pIREs-PS1 to generate pIREs-APP-PS1.

Transfection, Metabolic Labeling and Immunoisolation of Amyloid Beta (Aβ)

Hela SS6 cells expressing POSH-specific RNAi or scrambled RNAi (H153 and H187, respectively) were transfected with pIREs-APP-PS1 (24 μg) using lipofectamin 2000 reagent (Invitrogen, LTD). Twenty-four hours post-transfection, cells were metabolic labeled with 1 mCi of $^{35}$S-methionine at 37° C. for an additional twenty-four hours. Media was collected from cells and spun at 3000 rpm for 10 min to pellet cell debris. Protease inhibitors and 2 mM 1, 10-phenanthroline were added to the cleared cell media. Cells were lysed in lysis buffer (50 mM Tris-HCl, pH7.8, 150 mM sodium chloride, 1 mM EDTA, 0.5% NP-40, 0.5% sodium deoxycholate and protease inhibitors). Cell media and lysate were immunoprecipitated with anti-Aβ (1-17) antibody (6E10) (Chemicon) or a non-relevant (NR) antibody. Precipitated proteins were separated on 16% Tris-Tricine gel. Gel was dried and bands detected by phoshoimager (Typhoon instrument, Amersham Biosciences, Corp.).

Example 7

PEM-3-Like Reduction Inhibits Viral Release and Infectivity

Figure 20:
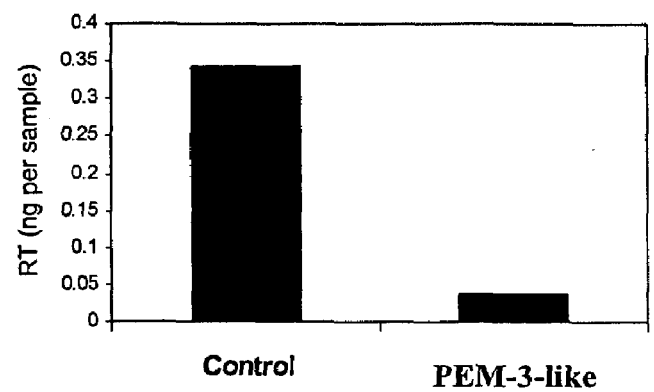
FIG. 20: Reverse transcriptase ("RT") activity in VLP secreted from cells treated with indicated siRNAs. HeLa SS6 cell cultures (in triplicates) were transfected with siRNA targeting PEM-3-like protein or with a control siRNA. Following gene silencing by siRNA, cells were transfected with pNLeny1, encoding an envelope-deficient subviral Gag-Pol expression system and RT activity in VLP released into the culture medium was determined. Cells treated with PEM-3-like-specific siRNA reduced RT activity by 90 percent.

PEM-3-like reduction reduces reverse transcriptase (RT) activity in release virus-like-particles (VLP):

HeLa SS6 cell cultures (in triplicates) were transfected with siRNA targeting PEM-3-like or with a control siRNA. Following gene silencing by siRNA, cells were transfected with pNLeny1, encoding an envelope-deficient subviral Gag-Pol expression system (Schubert, U., Clouse, K. A., and Strebel, K. (1995). Augmentation of virus secretion by the human immunodeficiency virus type 1 Vpu protein is cell type independent and occurs in cultured human primary macrophages and lymphocytes. J Virol 69, 7699-7711) and RT activity in VLP released into the culture medium was determined (FIG. 20). Cells treated with PEM-3-like-specific siRNA reduced RT activity by 90 percent.

Cell Culture and Transfections:

Hela SS6 cells were grown in Dulbecco's modified Eagle's medium (DMEM) supplemented with 10% heat-inactivated fetal calf serum and 100 units/ml penicillin and 100 μg/ml streptomycin. For transfections, HeLa SS6 cells were grown to 50% confluency in DMEM containing 10% FCS without antibiotics. Cells were then transfected with the relevant double-stranded siRNA (50-100 nM) using lipofectamin 2000 (Invitrogen, Paisley, UK). On the day following the initial transfection, cells were split 1:3 in complete medium and co-transfected 24 hours later with HIV-1NLenv1 (2 μg per 6-well) (Schubert, U., Clouse, K. A., and Strebel, K. (1995). Augmentation of virus secretion by the human immunodeficiency virus type 1 Vpu protein is cell type independent and occurs in cultured human primary macrophages and lymphocytes. J Virol 69, 7699-7711) and a second portion of double-stranded siRNA.

Assays for Virus Release by RT Activity:

Virus and virus-like particle (VLP) release was determined one day after transfection with the pro-viral DNA as previously described (Adachi, A., Gendelman, H. E., Koenig, S., Folks, T., Willey, R., Rabson, A., and Martin, M. A. (1986) Production of acquired immunodeficiency syndrome-associated retrovirus in human and nonhuman cells transfected with an infectious molecular clone. J Virol 59:284-291; Fukumori, T., Akari, H., Yoshida, A., Fujita, M., Koyama, A. H., Kagawa, S., and Adachi, A. (2000). Regulation of cell cycle and apoptosis by human immunodeficiency virus type 1 Vpr. Microbes Infect 2, 1011-1017; Lenardo, M. J., Angleman, S. B., Bounkeua, V., Dimas, J., Duvall, M. G., Graubard, M. B., Hornung, F., Selkirk, M. C., Speirs, C. K., Trageser, C., et al. (2002). Cytopathic killing of peripheral blood CD4(+) T lymphocytes by human immunodeficiency virus type 1 appears necrotic rather than apoptotic and does not require env. J Virol 76, 5082-5093). The culture medium of virus-expressing cells was collected and centrifuged at 500×g for 10 minutes. The resulting supernatant was passed through a 0.45 μm-pore filter and the filtrate was centrifuged at 14,000×g for 2 hours at 4° C. The resulting supernatant was removed and the viral-pellet was re-suspended in cell solubilization buffer (50 mM Tris-HCl, pH7.8, 80 mM potassium chloride, 0.75 mM EDTA and 0.5% Triton X-100, 2.5 mM DTT and protease inhibitors). The corresponding cells were washed three times with phosphate-buffered saline (PBS) and then solubilized by incubation on ice for 15 minutes in cell solubilization buffer. The cell detergent extract was then centrifuged for 15 minutes at 14,000×g at 4° C. The sample of the cleared extract (normally 1:10 of the initial sample) were resolved on a 12.5% SDS-polyacrylamide gel, then transferred onto nitrocellulose paper and subjected to immunoblot analysis with rabbit anti-CA antibodies. The CA was detected after incubation with a secondary anti-rabbit antibody conjugated to Cy5 (Jackson Laboratories, West Grove, Pa.) and detected by fluorescence imaging (Typhoon instrument, Molecular Dynamics, Sunnyvale, Calif.). The Pr55 and CA were then quantified by densitometry. A colorimetric reverse transcriptase assay (Roche Diagnostics GmbH, Mannenheim, Germany) was used to measure reverse transcriptase activity in VLP extracts. RT activity was normalized to amount of Pr55 and CA produced in the cells.

Scanning Electron Microscopy:

HeLa cells were fixed for two hours in 0.1M phosphate buffer (PB) (pH 7.2) containing 2.5% glutaraldehyde and then washed three times with PB. The cells were then dehydrated by gradual increase of the ethanol concentration (25%, 75%, 95%, 100%). The samples at 100% ethanol were dried in a critical point dryer BIO-RAD (C.P.D750) and then coated with gold. Images were taken on a Jeol 5410 LV scanning electron microscope at 25 kV.

REFERENCES

Naldini, L., Blomer, U., Gage, F. H., Trono, D., and Verma, I. M. (1996a). Efficient transfer, integration, and sustained long-term expression of the transgene in adult rat brains injected with a lentiviral vector. Proc Natl Acad Sci USA 93, 11382-11388.

Naldini, L., Blomer, U., Gallay, P., Ory, D., Mulligan, R., Gage, F. H., Verma, I. M., and Trono, D. (1996b). In vivo gene delivery and stable transduction of nondividing cells by a lentiviral vector. Science 272, 263-267.

Example 8

PEM-3-Like is Required for HIV-1 Infectivity

Figure 21:
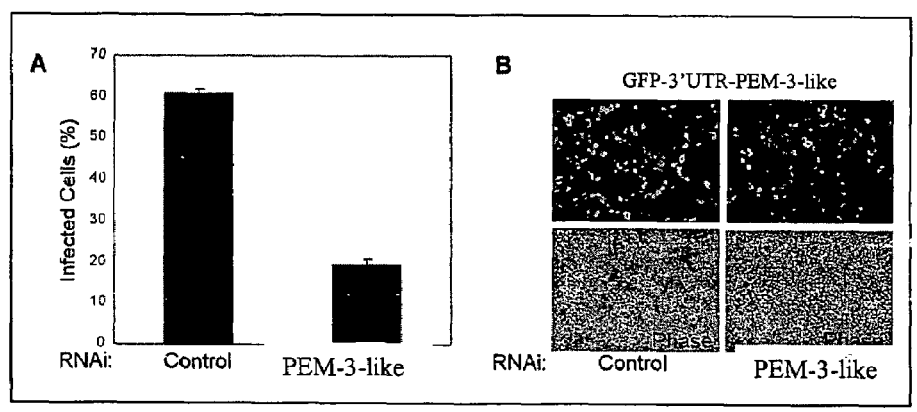
FIG. 21: PEM-3-like is important for HIV-1 infectivity. A. Hela SS6 cells were co-transfected with plasmids encoding HIV-1 (see materials and methods) and RNAi directed against PEM-3-like or control RNAi. Twenty four hours post transfection viruses were collected and used to infect target HEK 293T cells. Percent infection was determined by FACS analysis of GFP-positive cells. B. Hela SS6 cells were co-trasnfected with control or PEM-3-like specific RNAi and a plasmid encoding GFP-PEM-3-like tester plasmid to detect the efficiency of PEM-3-like reduction. The upper panels depict GFP fluorescence and the lower panel phase microscopy.

The production of infectious virus over a single cycle of HIV-1 replication, in the presence of normal or reduced levels of PEM-3-like was compared (FIG. 21A). To this end, cells were initially transfected with either a control or PEM-3-like specific siRNA (225) and then co-transfected with three plasmids encoding HIV-1 gag-pol, HIV-LTR-GFP and VSV-G-. Hence, the virus-producing cells release pseudotyped virions that contain VSV-G but do not by themselves encode an envelope protein and therefore, can infect target cells only once. Viruses were collected twenty-four hours post-transfection and used to infect HEK-293T cells. Infected target cells are detected by FACS analysis of GFP-positive cells. PEM-3-like reduction resulted in 60% reduction of virus infectivity (FIG. 21A), which correlated with the reduction in PEM-3-like levels as detected in parallel cultures co-transfected with RNAi and GFP-PEM-3-like tester plasmid (FIG. 21B), indicating that PEM-3-like is important for HIV-1 release.

Examples of PEM-3-like sequences are presented below. Additional examples of PEM-3-like sequences are presented in the PCT patent application, International Application No. PCT/US04/16865, filed on May 28, 2004 and entitled "PEM-3-like Compositions and Related Methods Thereof".

```
Human PEM-3-LIKE mRNA sequence -
var1 (public gi: 21755617)
AGAGGAGGAGGACCGGTCGTCGCTGCTGCTGCTGTCGCCGCCCGCGGCCA
CCGCCTCTCAGACCCAGCAGATCCCAGGCGGGTCCCTGGGGTCTGTGCTG
CTGCCAGCCGCCAGGTTCGATGCCCGGGAGGCGGCGGCCGCGGCGGCGGC
GGCGGGGGTGCTTACGGAGGGGACGATGCCCAGGGCATGATGGCGGCGAT
GCTGTCCCACGCCTACGGCCCCGGCGGTTGTGGGGCGGCGGCGGCCGCCC
TGAACGGGGAGCAGGCGGCCCTGCTCCGGAGAAAGAGCGTCAACACCACC
GAGTGCGTCCCGGTGCCCAGCTCCGAGCACGTCGCCGAGATCGTCGGCCG
CCAGGGTTGTAAAATTAAAGCACTGAGAGCCAAGACAAACACGTATATCA
AGACTCCTGTTCGTGGTGAAGAGCCCATTTTTGTTGTCACTGGAAGGAAA
GAAGATGTTGCCATGGCCAAAAGAGAGATCCTCTCAGCTGCAGAGCACTT
CTCCATGATTCGTGCATCTCGAAACAAAAATGGGCCTGCCCTGGGAGGAT
TATCATGTAGTCCTAATCTGCCCGGTCAAACCACCGTCCAAGTCAGGGTC
CCTTATCGTGTGGTAGGATTAGTGGTTGGACCCAAAGGAGCAACTATTAA
AAGAATTCAGCAGCAGACCCACACCTACATAGTAACTCCGAGCAGAGATA
AGGAACCTGTCTTTGAAGTGACAGGGATGCCTGAAAATGTTGACCGAGCA
CGGGAAGAAATAGAAATGCATATTGCCATGCGTACAGGAAACTATATAGA
GCTCAATGAAGAGAATGATTTTCCATTACAATGGTACCGATGTAAGCTTTG
AAGGTGGCACTCTTGGCTCTGCGTGGCTCTCCTCCAATCCTGTTCCTCCT
AGCCGCGCAAGAATGATATCCAATTATCGAAATGATAGTTCCAGTTCTCT
AGGAAGTGGCTCTACAGATTCCTACTTTGGAAGCAATAGGCTGGCTGACT
TTAGTCCAACAAGCCCATTTAGCACAGGAAACTTCTGGTTTGGAGATACA
CTACCATCTGTAGGCTCAGAAGACCTAGCAGTTGACTCTCCTGCCTTTGA
CTCTTTACCAACATCTGCTCAAACTATCTGGACTCCATTTGAACCAGTTA
ACCCACTCTCTGGCTTTGGGAGTGATCCTTCTGGTAACATGAAGACTCAG
CGCAGAGGAAGTCAGCCATCTACTCCTCGTCTGTCTCCTACATTTCCTGA
GAGCATAGAACATCCACTTGCTCGGAGGGTTAGGAGCGACCCACCTAGTA
CAGGCAACCATGTTGGCCTTCCAATATATCCCTGCTTTTTCTAATGGT
ACCAATAGTTACTCCTCTTCCAATGGTGGTTCCACCTCTAGCTCACCTCC
AGAATCAAGACGAAAGCATGACTGTGTGATTTGCTTTGAGAATGAGGTTA
TTGCTGCCCTAGTTCCATGTGGCCACAACCTCTTCTGCATGGAATGTGCC
AACAAGATCTGTGAAAAGAGAACGCCATCATGTCCAGTTTGCCAGACAGC
TGTTACTCAGGCAATCCAAATTCACTCTTAACTATATATATACATAAA
TACTATATCTCTATATGGACTCGTAAAGGCATGGGTATAATGGTACCCCC
CAGTAAACTTCCTAATGATTTCTTATGACTGTTATCAGGCTTTATTGGGA
TTAGGCTAAAGTTGTTAGTAAACTTATAAAAGGCTGCTATGGTAACACTA
AACCTAAGTGGTCTCTTGTCTATTAGTTTGGTTTGAATTATTAGTACTAT
CCTGTAGACCCAGAGACATAGTTTATATAAGAATTGCTAAAGCTGAAGTT
CAACTTGGCTGAGTGAAGATAATCATAGGTTGTGTGAGCCTATGAAAAAG
TGTATACGTCTAAGATTTCAAAACAATGGGTCCCAAAGCCTAACCACTTT
AAGAGTTTATGGAGGGTACTTGGCATTACAGACGATTCATACACTTCCAG
TGCTGCCTTCTTTACACTGCCAGTTTTGACAAAACAGGTTTGTTTTTAT
TTTACAACAACATATGCCTAATTCTGCAGGATTGCAAGTAACTTTTTAAT
GCATTGTGATTACTTATTGGTAATGATAGGGCTGATGGCAGTTTACTAGA
TCACTGGTTATAATTTGGGACAAAAACTGCTACATCAACTTTCATCTCGC
CCAGAGTGCTCAAGGCTGGTATGATCAGTGGATCAGGAATGCAATTGTGA
ATTCCTGCCCATTGCCTCTCTTGGTGAATGTGGAAATGGCCACCTGGGTT
TTCCCATATCAGGAAGGGCTTTGGGATGGCACCTATATTGGCTGATAATT
GAGGATGCAAACATTCCATTCATTAGTGTGATCGAGCTGTTAATTTTTAG
ACTATAGATCAAAATGTGAAACATTTTATGTTCAATCCATATTTGTCTTG
CACATTATAAATATATTTTTATTTTTTAGTAATTTAGGGGAGGGAGGAGG
GAGAAAGGGATAATGATGCCCTTGGCATAATTCACAAAAACAGCTGTGAC
AACCTCCAATCAGTTTACTTCATTTCAAAACTATTTCCAATCACAAGGAA
AGATTTATTTAAAATATACTCGTACATTTCACCTGTGGATGTCTATAACT
TCATCCTCAGTATGTTCCCAAATCTGTGCTGGCATTGAAAGGACAAAACA
TTATACTAGTGGGTTTTTCTACTAATTATTTTTTGAAGCATTATTTTCCC
AACACAAAAGAGCTTTTTCTCGGTATAATGAAAATTGAAATCCTATGTG
TATTCAATAGTAAATAGACAAATTTTATTTTTTATTTCCACTTGAAGAGT
TACATTTCGTATAAAAGTTTACAAATAACGGTTTTTATTTTGATTTTTC
AGTATAAAAAAAGTTGCCTTGATGGCATATTATGATGTAATGCTAATTGC
TTGTAGGATAGTAAATGGTCAGTATTGAAACCTAATCTCTAGCTGCCGTC
TTGTAGATATGAACGAATGTTCACCAAGCATGTATTTTGTATTTTGTTGC
ATTGTACACTGCAACTAATAAGCCAAGCAATCGACATATATTAGGTGCGT
GTACTGTTTCTAAAAACCACAAACTAAGAATGATAAATTATCAATATAGT
TTAGTATTTGCTAATTTTACTACACTCTTTTGTTATGTATATGTAGGGAA
GTCATAGGGATTATAAATTCAATTTGAGTAAAATTTAAAACCATATATTT
TATGATAAAGGGCCTTTAACTTAAGATGGCCAAAGCACTGATATTATATA
TTTGCTGTAAAGAGAATTATAAGAGTTTTATTTTTCTGATATTTAAAAGTT
ACTTAATAAAGACTTGTTTCCATTAACTTG Human PEM-3-LIKE protein sequence -
var1 (predicted)
MMAANLSHAYGPGGCGAAAAALNGEQAALLRRKSVNTTECVPVPSSEHVA
EIVGRQGCKIKALRAXTNTYIKTPVRGEEPIFVVTGRKEDVAMAKREILS
AAEHFSMIRASRNKNGPALGGLSCSPNLPGQTTVQVRVPYRVVGLVVGPK
GATIKRIQQQTHTYIVTPSRDKEPVFEVTGMPEVDREEIEMHIAMRTGNY
IELNEENDFHYNGTDVSFEGGTLGSAWLSSNPVPPSRARMISNYRNDSSS
SLGSGSTDSYFGSNRLADFSPTSPFSTGNFWFGDTLPSVGSEDLAVDSPA
FDSLPTSAQTIWTPFEPVNPLSGFGSDPSGNMKTQRRGSQPSTPRLSPTF
PESIEMPLARRVRSDPPSTGNMVGLPIYIPAFSNGTNSYSSSNGGSTSSS
PPESRRKHDCVICFENEVIAALVPCGHNLFCMECANKICEKRTPSCPVCQ
TAVTQAIQIHS Human PEM-3-LIKE mRNA sequence -
var2 (public gi: 21734163)
CAAGACAAACACGTATATCAAGACTCCTGTTCGTGGTGAAGAGCCCATTT
TTGTTGTCACTGGAAGGAAAGAAGATGTTGCCATGGCCAAAAGAGAGATC
CTCTCAGCTGCAGAGCACTTCTCCATGATTCGTGCATCTCGAAACAAAAA
TGGGCCTGCCCTGGGAGGATTATCATGTAGTCCTAATCTGCCCGGTCAAA
CCACCGTCCAAGTCAGGGTCCCTTATCGTGTGGTAGGATTAGTGGTTGGA
CCCAAAGGAGCAACTATTAAAAGAATTCAGCAGCAGACCCACACCTACAT
AGTAACTCCGAGCAGAGATAAGGAACCTGTCTTTGAAGTGACAGGGATGC
CTGAAAATGTTGACCGAGCACGGGAAGAAATAGAAATGCATATTGCCATG
CGTACAGGAAACTATATAGAGCTCAATGAAGAGAATGATTTTCCATTACAA
TGGTACCGATGTAAGCTTTGAAGGTGGCACTCTTGGCTCTGCGTGGCTCT
CCTCCAATCCTGTTCCTCCTAGCCGCGCAAGAATGATATCCAATTATCGA
AATGATAGTTCCAGTTCTCTAGGAAGTGGCTCTACAGATTCCTACTTTGG
AAGCAATAGGCTGGCTGACTTTAGTCCAACAAGCCCATTTAGCACAGGAA
ACTTCTGGTTTGGAGATACACTACCATCTGTAGGCTCAGAAGACCTAGCA
GTTGACTCTCCTGCCTTTGACTCTTTACCAACGTCTGCTCAAACTATCTG
GACTCCATTTGAACCAGTTAACCCACTCTCTGGCTTTGGGAGTGATCCTT
CTGGTAACATGAAGACTCAGCGCAGGGGAAGTCAGCCATCTACTCCTCGT
CTGTCTCCTACATTTCCTGAGAGCATAGAACATCCACTTGCTCGGAGGGT
TAGGAGCGACCCACCTAGTACAGGCAACCATGTTGGCCTTCCAATATATA
TCCCTGCTTTTTCTAATGGTACCAATAGTTACTCCTCTTCCAATGGTGGT
TCCACCTCTAGCTCACCTCCAGAATCAAGACGAAAGCATGACTGTGTGAT
TTGCTTTGAATGAGGTTATTGCTGCCCTAGTTCCATGTGGCCACAACC
TCTTCTGCATGGAATGTGCCAACAAGATCTGTGAAAAGAGAACGCCATCA
TGTCCAGTTTGCCAGACAGCTGTTACTCAGGCAATCCAAATTCACTCTTA
ACTATATATATACATAAATACTATCTCTATATGGACTCGTAAAGGCATGG
ATGGGTATAATGGTACCCCCCAGTAAACTTCCTAATGATTTCTTATGACT
GTTATCAGGCTTTATTGGGATTAGGCTAAAGTTGTTAGTAAACTTATAAA
AGGCTGCTATGGTAACACTAAACCTAAGTGGTCTCTTGTCTATTAGTTTG
GTTTGAATTATTAGTACTATCCTGTAGACCCAGAGACATAGTTTATATAA
GAATTGCTAAAGCTGAAGTTCAACTTGGCTGAGTGAAGATAATCATAGGT
TGTGTGAGCCTATGAAAAAGTGTATACGTCTAAGATTTCAAAACAATGGG
TCCCAAAGCCTAACCACTTTAAGAGTTTATGGAGGGTACTTGGCATTACA
GACGATTCATACACTTCCAGTGCTGCCTTCTTTACACTGCCAGTTTTGAC
AAAACAGGTTTGTTTTTATTTTACAACAATATGCCTAATTCTGCAGATT
GCAAGTAACTTTTTAATGCATTGTGATTACTTATTGGTAATGATAGGGCT
GATGGCAGTTTACTAGATCACTGGTTATAATTTGGGACAAAAACTGCTAC
ATCAACTTTCATCTCGCCCAGAGTGCTCAAGGCTGGTATGATCAGTGGAT
CAGGAATGCAATTGTGAATTCCTGCCCATTGCCTCTCTTGGTGAATGTGG
```

-continued
AAATGGCCACCTGGGTTTTCCCATATCAGGAAGGGCTTTGGGATGGCACC
TATATTGGCTGATAATTGAGGATGCAAACATTCCATTCATTAGTGTGATC
GAGCTGTTAATTTTTAGACTATAGATCAAAATGTGAAACATTTTATGTTC
AATCCATATTTGTCTTGCACATTATAAATATATTTTTATTTTTTAGTAAT
TTAGGGGAGGGAGGAGGGAGAAAGGGATAATGATGCCCTTGGCATAATTC
ACAAAAGCAGCTGTGACAACCTCCAATCAGTTTACTTCATTTCAAAACTA
TTTCCAATCACAAGGAAAGATTTATTTAAAATATACTCGTACATTTCACC
TGTGGATGTCTATAACTTCATCCTCAGTATGTTCCCAAATCTGTGCTGGC
ATTGAAAGGACAAAACATTATACTAGTGGGTTTTTCTACTAATTATTTTT
TGAAGCATTATTTTCCCAACACAAAAGAGCTTTTTTCTCGGTATAATGAA
AATTGAAATCCTATGTGTATTCAATAGTAAATAGACAAATTTTATTTTTT
ATTTCCACTTGAAGAGTTACATTTCGTATAAAAGTTTACAAATAACGGTT
TTTATTTTGATTTTTTCAGTATAAAAAAAGTTGCCTTGATGGCATATTAT
GATGTAATGCTAATTGCTTGTAGGATAGTAAATGGTCAGTATTGAAACCT
AATCTCTAGCTGCCGTCTTGTAGATATGAACGAATGTTCACCAAGCATGT
ATTTTGTATTTTGTTGCATTGTACACTGCAACTAATAAGCCAAGGAATCG
ACATATATTAGGTGCGTGTACTGTTTCTAAAAACCACAAACTAAGAATGA
TAAATTATCAATATAGTTTAGTATTTGCTAATTTTACTACACTCTTTTGT
TATGTATATGTAGGGAAGTCATAGGGATTATAAATTCAATTTGAGTAAAA
TTTAAAACCATATATTTTATGATAAAGGGCCTTTAACTTAAGATGGCCAA
AGCACTGATATTATATATTTGCTGTAAAGAGAATTATAAGAGTTTTATTT
TTCTGATATTAAAAGTTACTTGATAAAGACTTGTTTCCATTAACTTG Human PEM-3-LIKE protein sequence - 
var2 (predicted)
MAKREILSAAEHFSMIRASRNKNGPALGGLSCSPNLPGQTTVQVRVPYRV
VGLVVGPKGATIKRIQQQTHTYIVTPSRDKEPVFEVTGMPENVDRAREEI
EMHIAMRTGNYIELNEENDFHYNGTDVSFEGGTLGSAWLSSNPVPPSRAR
NISNYRNDSSSSLGSGSTDSYFGSNRLADFSPTSPFSTGNFWFGDTLPSV
GSEDLAVDSPAFDSLPTSAQTIWTPFEPVNPLSGFGSDPSGNMKTQRRGS
QPSTPRLSPTFPESIEHPLARRVRSDPPSTGNXVGLPIYIPAFSNGTNSY
SSSNGGSTSSSPPESRRKHDCVICFENEVIAALVPCGHNLFCMECANKIC
EKRTPSCPVCQTAVTQAIQIHS Human PEM-3-LIKE mRNA sequence - 
var3 (public gi: 21438819)
CCTGAACGGGGAGCAGGCGGCCCTGCTCCGGAGAAAGAGCGTCAACACCA
CCGAGTGCGTCCCGGTGCCCAGCTCCGAGCACGTCGCCGAGATCGTCGGC
CGCCAGGGTTGTAAAATTAAAGCACTGAGAGCCAAGACAAACACGTATAT
CAAGACTCCTGTTCGTGGTGAAGAGCCCATTTTTGTTGTCACTGGAAGGA
AAGAAGATGTTGCCATGGCCAAAAGAGAGATCCTCTCAGCTGCAGAGCAC
TTCTCCATGATTCGTGCATCTCGAAACAAAAATGGGCCTGCCCTGGGAGG
ATTATCATGTAGTCCTAATCTGCCCGGTCAAACCACCGTCCAHGTCAGGG
TCCCTTATCGTGTGGTAGGATTAGTGGTTGGACCCAAAGGAGCAACTATT
AAAAGAATTCAGCAGCAGACCCACACCTACATAGTAACTCCGAGCAGAGA
TAAGGAACCTGTCTTTGAAGTGACAGGGATGCCTGAAAATGTTGACCGAG
CACGGGAAGAAATAGAAATGCATATTGCCATGCGTACAGGAAACTATATA
GAGCTCAATGAAGAGAATGATTTCCATTACAATGGTACCGATGTAAGCTT
TGAAGGTGGCACTCTTGGCTCTGCGTGGCTCTCCTCCAATCCTGTTCCTC
CTAGCCGCGCAAGAATGATATCCAATTATCGAAATGATAGTTCCAGTTCT -continued
CTAGGAAGTGGCTCTACAGATTCCTACTTTGGAAGCAATAGGCTGGCTGA
CTTTAGTCCAACAAGCCCATTTAGCACAGGAAACTTCTGGTTTGGAGATA
CACTACCATCTGTAGGCTCAGAAGACCTAGCAGTTGACTCTCCTGCCTTT
GACTCTTTACCAACATCTGCTCAAACTATCTGGACTCCATTTGAACCAGT
TAACCCACTCTCTGGCTTTGGGAGTGATCCTTCTGGTAACATGAAGACTC
AGCGCAGAGGAAGTCAGCCATCTACTCCTCGTCGTCTCCTACATTTCCT
GAGAGCATAGAACATCCACTTGCTCGGAGGGTTAGGAGCGACCCACCTAG
TACAGGCAACCATGTTGGCCTTCCAATATATATCCCTGCTTTTTCTAATG
GTACCAATAGTTACTCCTCTTCCAATGGTGGTTCCACCTCTAGCTCACCT
CCAGAATCAAGACGAAAGCACGACTGTGTGATTTGCTTTGAGAATGAGGT
TATTGCTGCCCTAGTTCCATGTGGCCACAACCTCTTCTGCATGGAATGTG
CCAACAAGATCTGTGAAAAGAGAACGCCATCATGTCCAGTTTGCCAGACA
GCTGTTACTCAGGCAATCCAAATTCACTCTTAACTATATATATATACATA
AATACTATATCTCTATATGGACTCGTAAAGGCATGGGTATAATGGTACCC
CCCAGTAAACTTCCTAATGATTTCTTATGACTGTTATCAGGCTTTATTGG
GATTAGGCTAAAGTTGTTAGTAAACTTATAAAAGGCTGCTATGGTAACAC Human PEM-3-LIKE protein sequence - 
var3 (public gi: 21438820)
MAKREILSAAEHPSMIRASRNKNGPALGGLSCSPNLPGQTTVQVRVPYRV
VGLVVGPKGATIKRIQQQTHTYIVTPSRDKEPVFEVTGMPENVDRAREEI
EMHIANRTGNYIELNEENDFHYNGTDVSFEGGTLGSAWLSSNPVPPSRAR
MISNYRNDSSSSLGSGSTDSYFGSNRLADFSPTSPFSTGNFWfGDTLPSV
GSEDLAVDSPAFDSLPTSAQTIWTPFEPVNPLSGFGSDPSGNMKTQRRGS
QPSTPRLSPTFPESIEHPLARRVRSDPPSTGNHVGLPIYIPAFSNGTNSY
SSSNGGSTSSSPPESRRKMDCVICFENEVIAALVPCGHNLFCMECANKIC
EKRTPSCPVCQTAVTQAIQIHS

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject applications have been discussed, the above specification is illustrative and not restrictive. Many variations of the applications will become apparent to those skilled in the art upon review of this specification and the claims below. The full scope of the applications should be determined by reference to the claims, along with their full scope of equivalents, and the specification, along with such variations.

We claim:

1. A pharmaceutical composition, comprising a small molecule inhibitor of a POSH (Plenty of SH3 domains) polypeptide and at least one physiologically acceptable carrier or excipient, wherein the POSH polypeptide small molecule inhibitor is a compound having a structure of formula

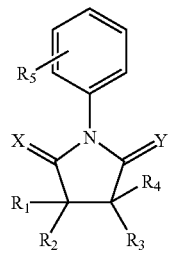

X and Y are independently selected from O, S, and $NR_6$;

$R_1$ and $R_4$ independently represent H or lower alkyl, or, taken together, represent a double bond;

$R_2$ and $R_3$ independently represent H, amino, alkylamino, arylamino, aralkylamino, acylamino, $R_2NRN$—, alkylthio, arylthio, aralkylthio, aralkyl, alkoxy, aryloxy, aralkyloxy, or lower alkyl, or, taken together with $R_1$ and $R_4$, represent a benzo ring fused to the maleimide ring;

$R_5$ represents from 0-5 substituents on the ring to which it is attached, selected from H, halogen, lower alkyl, lower alkenyl, aryl, heteroaryl, carbonyl, thiocarbonyl, ketone, aldehyde, amino, acylamino, cyano, nitro, hydroxyl, acyl, azido, sulfonyl, sulfoxido, sulfate, sulfonate, sulfamoyl, and sulfonamido;

R represents, independently for each occurrence, H, alkyl, alkenyl, alkynyl, aralkyl, aryl, cycloalkyl, heterocyclyl, cycloalkylalkyl, heterocyclylalkyl, heteroaryl, or heteroaralkyl; and $R_6$ is independently selected for each occurrence from H and substituted or unsubstituted lower alkyl, lower alkenyl, cycloalkyl, heterocyclyl, aryl, heteroaryl, cycloalkylalkyl, heterocyclylalkyl, heteroaralkyl, and aralkyl;

provided that the POSH polypeptide small molecule inhibitor is not a compound having the structure

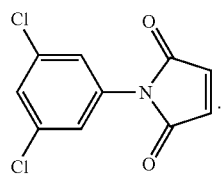

2. The pharmaceutical composition of claim 1, wherein the POSH polypeptide small molecule inhibitor is a compound selected from

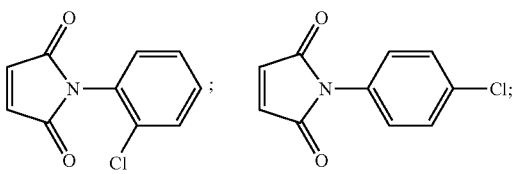

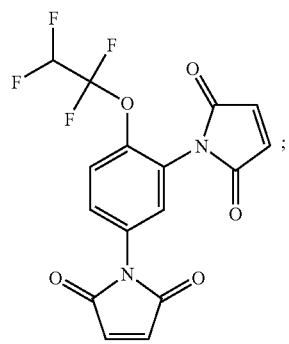

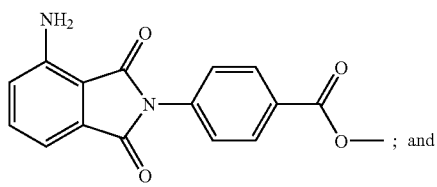

; and

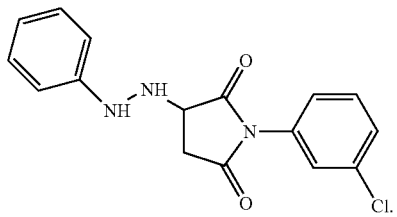

* * * * *